US011464854B2

(12) United States Patent
Levy et al.

(10) Patent No.: US 11,464,854 B2
(45) Date of Patent: Oct. 11, 2022

(54) METHODS AND COMPOSITIONS RELATING TO ADJUVANTS

(71) Applicants: Children's Medical Center Corporation, Boston, MA (US); University of Montana, Missoula, MT (US)

(72) Inventors: Ofer Levy, Cambridge, MA (US); David Dowling, Brighton, MA (US); Helene Bazin-Lee, Stevensville, MT (US); David Burkhart, Missoula, MT (US); Jay Evans, Corvallis, MT (US); Alyson Jessica Smith, Bonner, MT (US)

(73) Assignees: Children's Medical Center Corporation, Boston, MA (US); University of Montana, Missoula, MT (US)

(*) Notice: Subject to any disclaimer, the term of this patent is extended or adjusted under 35 U.S.C. 154(b) by 0 days.

(21) Appl. No.: 16/495,901

(22) PCT Filed: Mar. 23, 2018

(86) PCT No.: PCT/US2018/023970
§ 371 (c)(1),
(2) Date: Sep. 20, 2019

(87) PCT Pub. No.: WO2018/175854
PCT Pub. Date: Sep. 27, 2018

(65) Prior Publication Data
US 2020/0108139 A1 Apr. 9, 2020

Related U.S. Application Data

(60) Provisional application No. 62/475,430, filed on Mar. 23, 2017, provisional application No. 62/512,308, filed on May 30, 2017.

(51) Int. Cl.
| | |
|---|---|
| *A61K 39/39* | (2006.01) |
| *A61K 47/54* | (2017.01) |
| *A61K 47/60* | (2017.01) |
| *A61P 31/04* | (2006.01) |
| *A61K 31/4745* | (2006.01) |
| *A61K 31/685* | (2006.01) |
| *A61K 39/09* | (2006.01) |
| *A61K 39/00* | (2006.01) |

(52) U.S. Cl.
CPC .......... *A61K 39/39* (2013.01); *A61K 31/4745* (2013.01); *A61K 31/685* (2013.01); *A61K 39/092* (2013.01); *A61K 47/543* (2017.08); *A61K 47/60* (2017.08); *A61P 31/04* (2018.01); *A61K 2039/55* (2013.01); *A61K 2039/55511* (2013.01); *A61K 2039/55561* (2013.01)

(58) Field of Classification Search
CPC ...... A61K 39/39; A61K 47/543; A61K 47/60; A61K 31/4745; A61K 31/685; A61K 39/092; A61K 2039/55; A61K 2039/55511; A61K 2039/55561; A61K 39/395; A61K 31/522; A61P 31/04
See application file for complete search history.

(56) References Cited

U.S. PATENT DOCUMENTS

| | | | |
|---|---|---|---|
| 7,799,800 B2 | 9/2010 | Wightman | |
| 2008/0193468 A1 | 8/2008 | Levy et al. | |
| 2012/0237546 A1* | 9/2012 | Singh | A61K 33/42 424/211.1 |
| 2012/0294885 A1 | 11/2012 | David et al. | |
| 2013/0315831 A1 | 11/2013 | Shi et al. | |
| 2014/0093525 A1 | 4/2014 | Pentel et al. | |
| 2014/0322271 A1 | 10/2014 | Garcon-Johnson et al. | |

FOREIGN PATENT DOCUMENTS

| | | | |
|---|---|---|---|
| WO | WO-2015082905 A1 * | 6/2015 | ............. A61P 31/00 |
| WO | WO 2016142880 * | 9/2016 | |
| WO | WO 2021/076906 | 4/2021 | |

OTHER PUBLICATIONS

Philbin et al. Journal of Allergy and Clinical Immunology 2012, 130, 195-204. (Year: 2012).*
Burdin et al., "What is wrong with pertussis vaccine immunity? The problem of waning effectiveness of pertussis vaccines." Cold Spring Harbor perspectives in biology 9(12):a029454 pp. 1-20 (2017).
Cortez et al., "Incorporation of Phosphonate into Benzonaphthyridine Toll-like Receptor 7 Agonists for Adsorption to Aluminum Hydroxide." Journal of Medicinal Chemistry 59(12):5868-5878 (2016).
Szeimies et al., "A phase II dose-ranging study of topical resiquimod to treat actinic keratosis." British Journal of Dermatology 159(1): 205-210 (2008).
Bazin et al. "Phospholipidation of TLR7/8-active imidazoquinolines using a tandem phosphoramidite method." Tetrahedron Letters 57(19): 2063-2066 (2016).
Buonsanti et al., "Novel adjuvant Alum-TLR7 significantly potentiates immune response to glycoconjugate vaccines." Scientific reports 6(29063): 1-12 (2016).
Delany et al., "Vaccines for the 21st century." EMBO Molecular Medicine 6(6): 708-720 (2014).
Dowling et al., "The ultra-potent and selective TLR8 agonist VTX-294 activates human newborn and adult leukocytes." PLoS One 8(3): 1-11 e58164 (2013).

(Continued)

*Primary Examiner* — Noble E Jarrell
(74) *Attorney, Agent, or Firm* — Wolf, Greenfield & Sacks, P.C.

(57) ABSTRACT

The methods and compositions described herein relate to methods of immunization or stimulating an immune response, e.g., using agonists of TLR7 and/or TLR8 as antigens. The methods and compositions described herein have particular relevance to use in infants.

19 Claims, 88 Drawing Sheets

(56) References Cited

OTHER PUBLICATIONS

Dowling et al., "TLR7/8 adjuvant overcomes newborn hyporesponsiveness to pneumococcal conjugate vaccine at birth." JCI Insight 2(6): 1-18 e91020 (2017).

Dowling et al., "Toll-like receptor 8 agonist nanoparticles mimic immunomodulating effects of the live BCG vaccine and enhance neonatal innate and adaptive immune responses." Journal of Allergy and Clinical Immunology 140(5): 1339-1350 (2017).

Holbrook et al., "A Novel R848-Conjugated Inactivated Influenza Virus Vaccine Is Efficacious and Safe in a Neonate Nonhuman Primate Model." The Journal of Immunology 197(2): 555-564 (2016).

Holbrook et al., "An R848 adjuvanted influenza vaccine promotes early activation of B cells in the draining lymph nodes of non-human primate neonates." Immunology 153(3): 357-367 (2018).

Levy et al., "Selective impairment of TLR-mediated innate immunity in human newborns: neonatal blood plasma reduces monocyte TNF-alpha induction by bacterial lipopeptides, lipopolysaccharide, and imiquimod, but preserves the response to R-848." J Immunol 173(7): 4627-4634 (2004).

Levy et al., "Unique efficacy of Toll-like receptor 8 agonists in activating human neonatal antigen-presenting cells." Blood 108(4): 1284-1290 (2006).

Maisonneuve et al., "Unleashing the potential of NOD-and Toll-like agonists as vaccine adjuvants." PNAS 111(34): 12294-12299 (2014).

Misiak et al., "Addition of a TLR7 agonist to an acellular pertussis vaccine enhances Th1 and Th17 responses and protective immunity in a mouse model." Vaccine 35(39): 5256-5263 (2017).

Pettengill et al., "Distinct TLR-mediated cytokine production and immunoglobulin secretion in human newborn naive B cells." Innate Immunity 22(6): 433-443 (2016).

Philbin et al., "Imidazoquinoline Toll-like receptor 8 agonists activate human newborn monocytes and dendritic cells through adenosine-refractory and caspase-1-dependent pathways." J Allergy Clin Immunol 130(1): 195-204 (2012).

Sauder et al., "Randomized, single-blind, placebo-controlled study of topical application of the immune response modulator resiquimod in healthy adults." Antimicrobial Agents and Chemotherapy 47(12): 3846-3852 (2003).

Smirnov et al., "Vaccine adjuvant activity of 3M-052: an imidazoquinoline designed for local activity without systemic cytokine induction." Vaccine 29(33): 5434-5442 (2011).

Smith et al., "Evaluation of novel synthetic TLR7/8 agonists as vaccine adjuvants." Vaccine 34(36): 4304-4312 (2016).

Vasilakos et al., "The use of Toll-like receptor 7/8 agonists as vaccine adjuvants." Expert review of vaccines 12(7): 809-819 (2013).

Wu et al., "Rational design of small molecules as vaccine adjuvants." Science Translational Medicine 6(263): 1-12 263ra160 (2014).

* cited by examiner

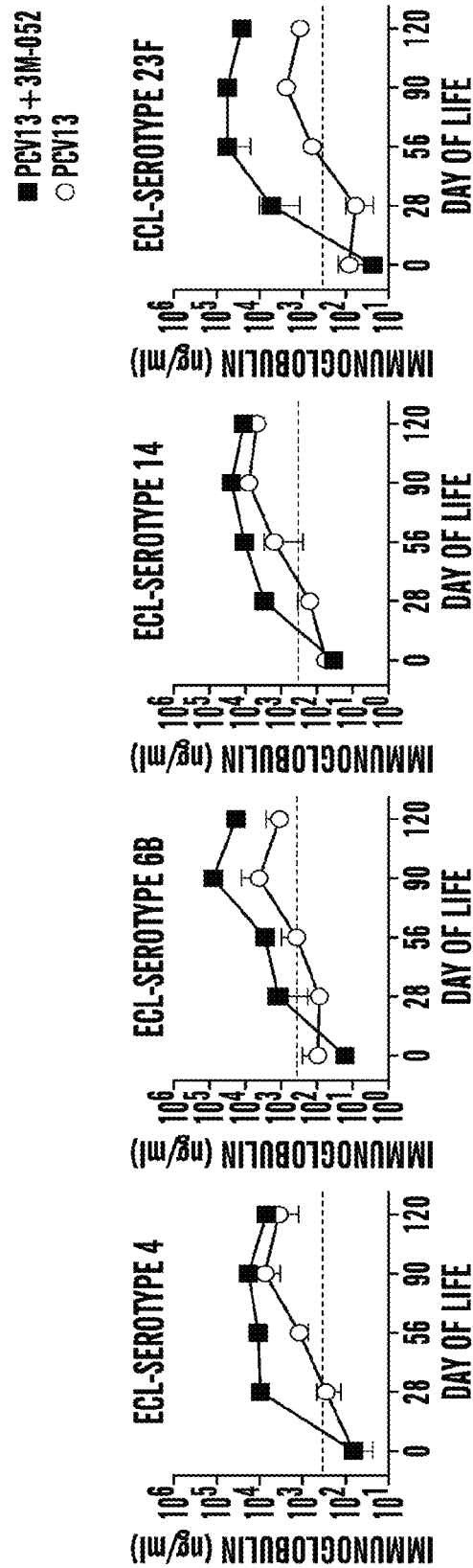
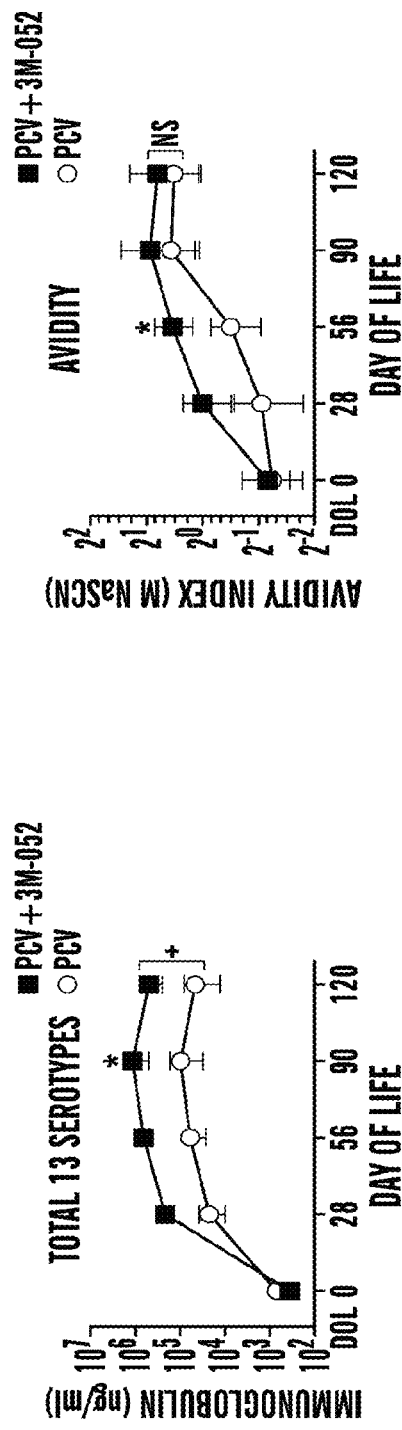
FIG. 23B
FIG. 23C
FIG. 23D

| Core compound | Class | TLR selectivity/potency |
|---|---|---|
| CRX-648 | IMQ | TLR8 selective, low potency |
| CRX-649 | IMQ | TLR8 selective |
| CRX-664 | IMQ | TLR7 selective |
| CRX-672 | OA | TLR7 selective |
| CRX-677 | OA | Slightly TLR8 selective |
| CRX-748 | OA | Slightly TLR8 selective |

IMQ: Imidazoquinoline; OA: Oxoadenines; TLR: Toll-like receptor.

*FIG. 25A*

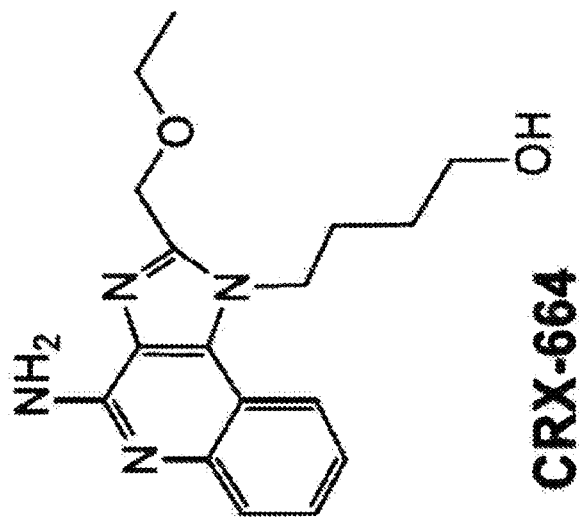
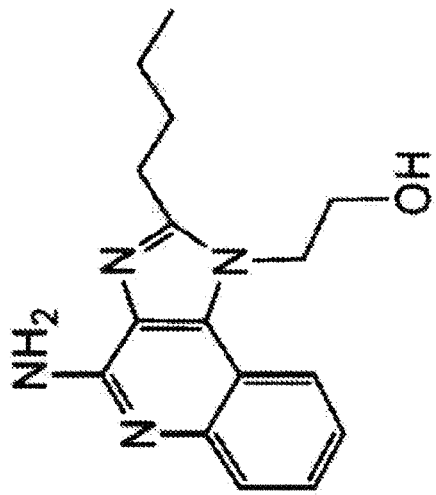
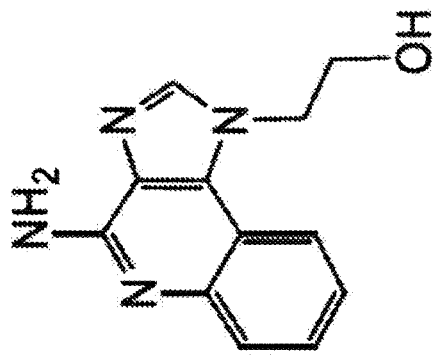
FIG. 25B

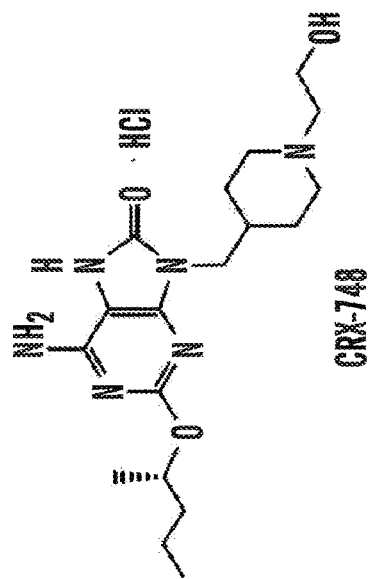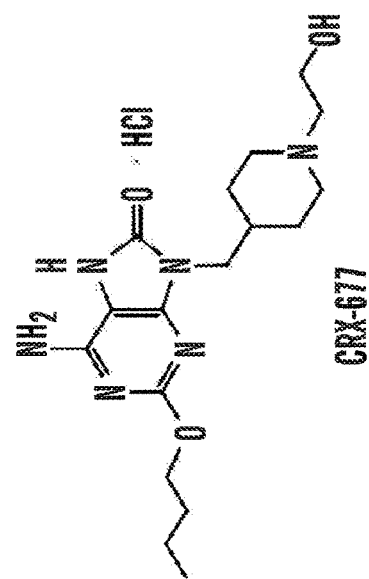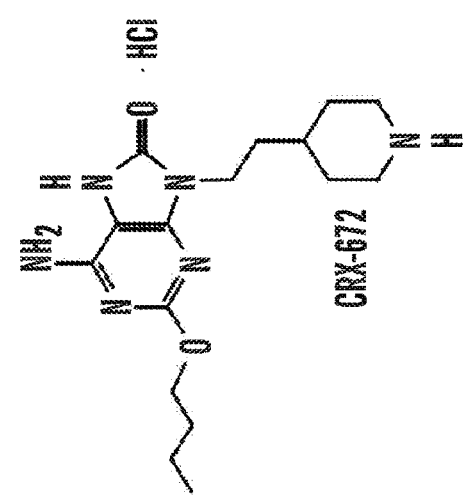
FIG. 25C

|  | EC50 (µM) | | TLR7:TLR8 |
|---|---|---|---|
|  | TLR7 | TLR8 | Ratio |
| CRX-649 | 1.64 | 0.98 | 1.67 |
| CRX-648 | 49.46 | 16.28 | 3.04 |
| CRX-748 | 12.09 | 1.98 | 6.11 |
| CRX-664 | 2.94 | 202.40 | 0.01 |
| CRX-677 | 79.04 | 8.69 | 9.10 |
| CRX-672 | 3.03 | 16.10 | 0.19 |

*FIG. 26C*

Basic Pharmacophore of
TLR7/8 agonist

Optimized core
imidazoquinoline CRX-649

Lead TLR7/8 agonist
CRX-727

| CRX-727 + Infanrix | | |
|---|---|---|
| Time point | Peak Area (mAU) | % Adsorbed to Alum |
| 1 hour | 1.35 | 96.12 |
| 2 hours | 0.00 | 100.00 |
| 24 hours | 0.23 | 99.34 |
| Ag Control (no 727) | 0.00 | NA |
| 727 Control (no Ag) | 34.80 | |
| CRX727 + alum + Infanrix | | |
| Time point | Peak Area (mAU) | % Adsorbed to Alum |
| 1 hour | 0.22 | 99.37 |
| 2 hours | 0.19 | 99.45 |
| 24 hours | 0.16 | 99.54 |
| Ag Control (no 727) | 0.00 | NA |
| 727 Control (no Ag) | 34.80 | |
| CRX-649 + Infanrix | | |
| Time point | Peak Area (mAU) | % Adsorbed to Alum |
| 1 hour | 114.30 | -5.35 |
| 2 hours | 101.20 | 6.73 |
| 24 hours | 112.20 | -30.92 |
| Ag Control (no 649) | 0.00 | NA |
| 649 Control (no Ag) | 108.50 | |
| 650 Control (no Ag)-24 hrs | 85.70 | |
| CRX649 + alum + Infanrix | | |
| Time point | Peak Area (mAU) | % Adsorbed to Alum |
| 1 hour | 104.20 | 3.96 |
| 2 hours | 107.80 | 0.65 |
| 24 hours | 88.30 | -3.03 |
| Ag Control (no 649) | 0.00 | NA |
| 649 Control (no Ag) | 108.50 | |
| 650 Control (no Ag) 24 hrs | 85.70 | |

*FIG. 30*

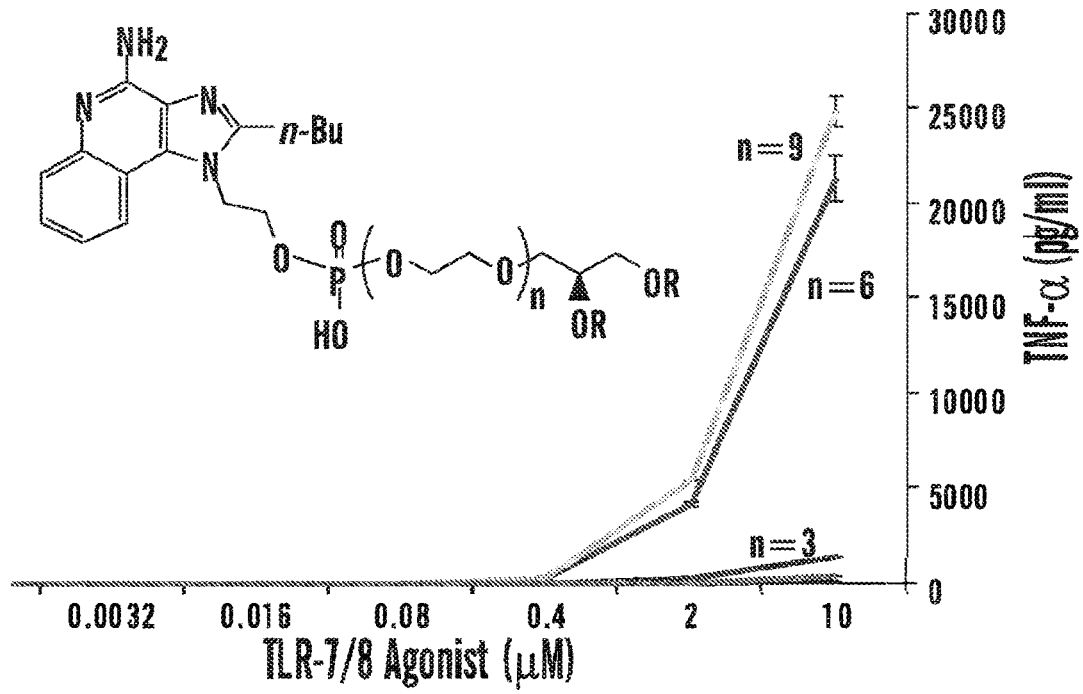
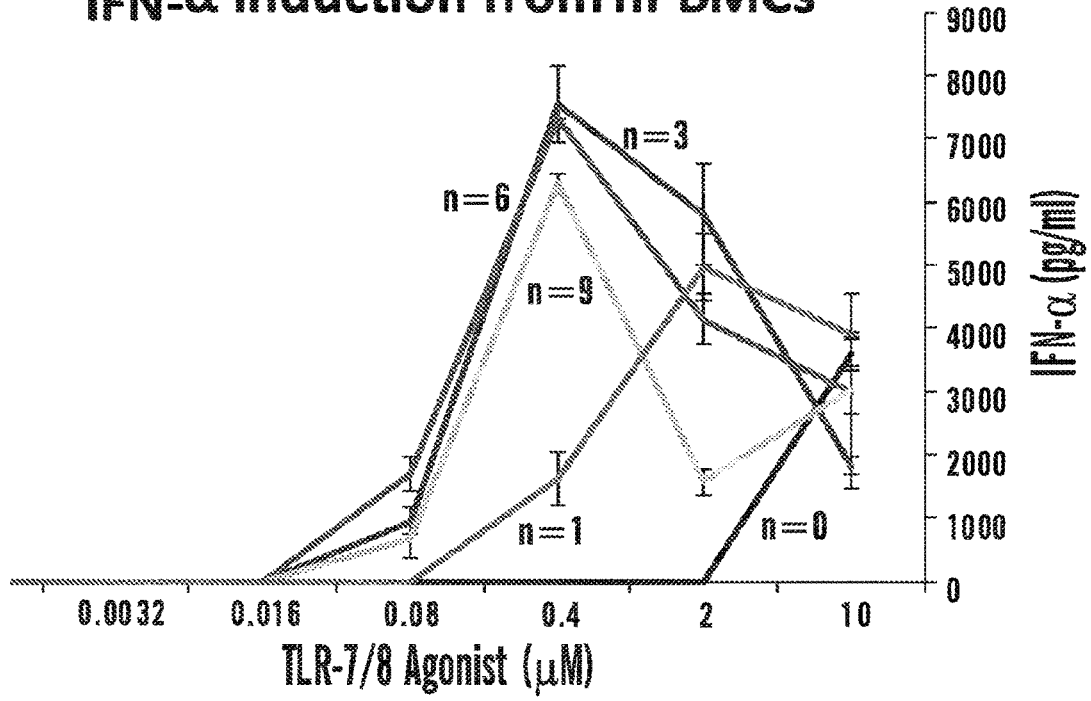
FIG. 34

| Group | No. of rhesus macaques | Treatment |
|---|---|---|
| 1 | 5 | Saline |
| 2 | 5 | PCV13 |
| 3 | 5 | 3M-052 |
| 4 | 5 | PCV13 + 3M-052 |

*FIG. 35*

| Serotype | PCV13 - DOL | | | | PCV13 + 3M-052 (0.01 mg/kg) | | | | PCV13 + 3M-052 (0.1 mg/kg) | | | |
|---|---|---|---|---|---|---|---|---|---|---|---|---|
| | 0 | 28 | 56 | 120 | 0 | 28 | 56 | 120 | 0 | 28 | 56 | 120 |
| 4 | 12 | 123 | 2,913 | 787 | 12 | 391 | 1,461 | 1,467 | 12 | 929 | 3,723 | 1,556 |
| 6B | 12 | 12 | 317 | 596 | 12 | 12 | 32,195 | 13,032 | 12 | 12 | 2,980 | 4,838 |
| 9V | 12 | 19 | 2,177 | 970 | 12 | 379 | 5,513 | 6,617 | 12 | 785 | 8,155 | 7,115 |
| 14 | 12 | 51 | 4,492 | 1,707 | 12 | 1,769 | 4,104 | 1,568 | 12 | 9,258 | 12,141 | 4,884 |
| 18C | 18 | 50 | 2,264 | 340 | 12 | 922 | 586 | 2,454 | 288 | 2,659 | 2,714 | 1,530 |
| 19F | 12 | 189 | 2,720 | 596 | 12 | 22 | 4,594 | 1,566 | 12 | 353 | 13,983 | 4,219 |
| 23F | 12 | 12 | 1,097 | 850 | 12 | 180 | 20,285 | 15,657 | 12 | 56 | 15,790 | 3,477 |
| 1 | 12 | 12 | 83 | 41 | 12 | 12 | 51 | 28 | 12 | 31 | 89 | 120 |
| 5 | 12 | 12 | 373 | 264 | 12 | 832 | 865 | 493 | 12 | 597 | 352 | 641 |
| 7F | 12 | 805 | 11,090 | 2,065 | 83 | 4,668 | 10,024 | 10,386 | 12 | 8,293 | 12,324 | 6,823 |
| 3 | 12 | 21 | 170 | 219 | 12 | 151 | 247 | 88 | 12 | 490 | 302 | 167 |
| 6A | 12 | 12 | 3,296 | 562 | 12 | 369 | 12,309 | 3,674 | 12 | 196 | 3,848 | 2,362 |
| 19A | 12 | 12 | 1,490 | 179 | 12 | 12 | 5,930 | 2,023 | 12 | 61 | 13,369 | 5,022 |

Mean titers of serotype-specific opsonophagocytic killing activity in serum derived from infant rhesus macaques immunized with PCV13 or (PCV13 + 3M-052). Samples identified as negative in the assay (i.e., samples having no functional activity detected) were assigned a titer of 12. n = 5 infants per group for PCV13 and PCV13 + 0.1 mg/kg 3M-052. n = 3 infants per group for PCV13 + 0.01 mg/kg 3M-052. DOL, day of life.

*FIG. 36*

| Name | TLR | Ave. Diameter (nm) | Pdi Index | Endotoxin-LAL Assay (EU/ml) |
|---|---|---|---|---|
| O/W (vehicle) | N/A | 129 | 0.23 | < 1 |
| 3M-052 (0.01 mg/kg) O/W | 7/8 | 134 | 0.18 | < 1 |
| 3M-052 (0.1 mg/kg) O/W | 7/8 | 141 | 0.19 | < 1 |

Pdi: Polydispersity; TLR: Toll-like receptor; LAL: Limulus amebocyte lysate; EU: Endotoxin Units; O/W: Oil-in-Water.

*FIG. 37*

| DOL | 0 | 2 | 7 | 14 | 28 | 30 | 35 | 42 | 56 | 58 | 63 | 70 | 90 | 120 | 150 | 180 | 360 |
|---|---|---|---|---|---|---|---|---|---|---|---|---|---|---|---|---|---|
| Vaccination | [x] | | | | [x] | | | | [x] | | | | | | | | |
| Micro-chipping/Tattooing | x | | | | | | | | | | | | | | | | |
| Weight monitoring | x | x | x | x | x | x | x | x | x | | x | | x | x | x | x | x |
| Physical Exam | x | x | x | x | x | x | x | x | x | | x | x | x | x | x | x | x |
| Representative Photography | x | x | | | | | x | x | x | | x | x | | | | | |
| Phlebotomy | x | x | x | x | x | x | x | x | x | | x | | x | x | x | x | x |
| Muscle Biopsy* | x | | | | | x | | | | x | | | | | | | |
| LN Biopsy* | | | x | | | | | | | | x | | | | | | |

Neonatal and infant NHP were vaccinated on DOL0 (within 24 hours of birth), DOL28, and DOL56. Phlebotomy, routine physical exams, weight measurements were performed up to DOL360. Representative photography for each animal was performed up to DOL70. * Indicates sub study group of animals (n = 8) that underwent muscle and lymph node biopsies.

METHODS AND COMPOSITIONS RELATING TO ADJUVANTS

CROSS-REFERENCE TO RELATED APPLICATIONS

This application claims benefit under 35 U.S.C. § 119(e) of U.S. Provisional Application No. 62/512,308 filed May 30, 2017 and 62/475,430 filed Mar. 23, 2017, the contents of which are incorporated herein by reference in their entirety.

GOVERNMENT SUPPORT

This invention was made with government support under Grant Nos. 1R01AI100135-01 and 3R01AI067353-05S1 awarded by the National Institutes of Health and Grant No. HHSN272201400052C awarded by the Department of Health and Human Services. The government has certain rights in the invention.

TECHNICAL FIELD

The technology described herein relates to adjuvants, e.g, for use in immunization.

BACKGROUND

Vaccines typically rely upon adjuvants to stimulate the immune system and generate an effective response to the vaccine. Existing adjuvants, while effective in adults, often give poor performance or are even counterproductive in infants and newborns. In order to successfully immunize infants and newborns, and reduce the number of vaccine doses such patients receive, effective adjuvants are necessary.

SUMMARY

The inventors have found that agonists of TLR7 and/or TLR8 provide surprisingly effective adjuvant activity in newborns, improving the efficacy of vaccination and lowering the number of doses required. Moreover, such adjuvants permit effective vaccination at or within days of birth of the subject, providing earlier protection, reducing the number of vaccine doses required to achieve protection, and making vaccination more plausible for many at-risk populations. Such adjuvants also enhance vaccine responses during infancy, reducing the number of vaccine doses required to achieve protection.

In one aspect, described herein is a method of immunizing a subject, the method comprising administering to the subject i) an adjuvant comprising an agonist of TLR7 and/or TLR8; and ii) at least one antigen; wherein the adjuvant and the at least one antigen are not conjugated to each other.

In some embodiments of any of the aspects, the adjuvant is lipidated. In some embodiments of any of the aspects, the adjuvant is 3M-052.

In some embodiments of any of the aspects, the adjuvant comprising an agonist of TLR7 and/or TLR8 is selected from the group consisting of: a single sstranded (ss) RNA; an imidazoquinoline; a thiazoquinoline; an oxoadinine; and a benzazepine. In some embodiments of any of the aspects, the adjuvant comprising an agonist of TLR7 and/or TLR8 comprises a compound having the structure of Formula IX:

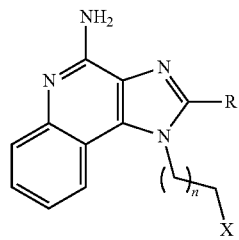

Formula IX wherein n is from 0 to 20,
R is R is selected from H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino and C1-6alkoxyC1-6alkoxy; wherein the C1-6alkyl, C1-6alkylamino, C1-6alkoxy, C3-6cycloalkylC1-6alkyl, C3-6cycloalkylC1-6alkylamino, 20 C3-6cycloalkylC1-6alkoxy, C1-6alkoxyC1-6alkyl, C1-6alkoxyC1-6alkylamino or C1-6alkoxyC1-6alkoxy is branched or unbranched and optionally terminally substituted with a hydroxyl, amino, thio, hydrazino, hydrazido, azido, acetylenyl, carboxyl, or maleimido group and
X is a phospholipid, lipid, lipidation, and/or PEG moiety.
In some embodiments of any of the aspects, the adjuvant comprising an agonist of TLR7 and/or TLR8 comprises a compound having the structure of Formula X:

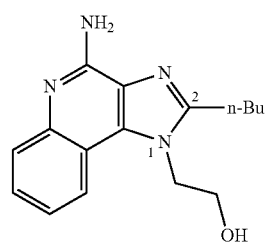

Formula X

In some embodiments of any of the aspects, wherein the adjuvant comprising an agonist of TLR7 and/or TLR8 comprises a compound having the structure of Formula XI:

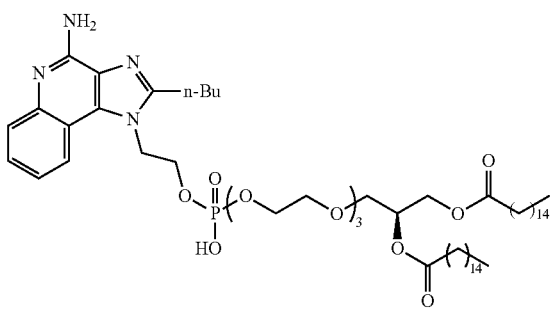

Formula XI

In some embodiments of any of the aspects, the adjuvant comprising an agonist of TLR7 and/or TLR8 comprises a compound selected from the group consisting of: 3M-052; CRX-648; CRX-649; CRX-664; CRX-672; CRX-677; and CRX-748. In some embodiments of any of the aspects, the adjuvant comprising an agonist of TLR7 and/or TLR8 comprises CRX-649.

In some embodiments of any of the aspects, the adjuvant comprising an agonist of TLR7 and/or TLR8 further comprises a lipid moiety. In some embodiments of any of the aspects, the adjuvant further comprises a phosphorylation or phospholipid moiety. In some embodiments of any of the aspects, the moiety is located at the ethanol group of 3M-052; CRX-648; CRX-649; CRX-664; CRX-672; CRX-677; or CRX-748. In some embodiments of any of the aspects, the moiety is located at an N position corresponding to the N1 of Formula X. In some embodiments of any of the aspects, the moiety is conjugated to the adjuvant via a PEG linker. In some embodiments of any of the aspects, the PEG linker comprises from 3 to 9 repeats of PEG. In some embodiments of any of the aspects, the PEG linker comprises 3 repeats of PEG.

In some embodiments of any of the aspects, the administration of the adjuvant and antigen causes a greater immune response, increased rate of an immune response and/or greater protection than the same dose of the antigen administered without the adjuvant. In some embodiments of any of the aspects, the administration of the adjuvant and antigen provides protection at a lower dose or with fewer doses than the antigen administered without the adjuvant.

In some embodiments of any of the aspects, the at least one antigen is comprised by an attenuated vaccine. In some embodiments of any of the aspects, the antigen is comprised by a subunit vaccine or recombinant subunit vaccine. In some embodiments of any of the aspects, the antigen is comprised by a conjugate vaccine. In some embodiments of any of the aspects, the antigen is a polysaccharide. In some embodiments of any of the aspects, the antigen is bound to or adsorbed to alum.

In some embodiments of any of the aspects, the antigen is comprised by a vaccine selected from the group consisting of a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine. In some embodiments of any of the aspects, the vaccine is pneumococcal conjugate vaccine (PCV)13. In some embodiments of any of the aspects, the vaccine is alum-adjuvanted.

In some embodiments of any of the aspects, the method further comprises administering a second adjuvant. In some embodiments of any of the aspects, the second adjuvant is alum.

In some embodiments of any of the aspects, the subject is a human infant at the time of administration. In some embodiments of any of the aspects, the subject is a human of less than 28 days of age at the time of administration. In some embodiments of any of the aspects, the subject is a human of less than 4 days of age at the time of administration. In some embodiments of any of the aspects, the subject is a human of less than 2 days of age at the time of administration. In some embodiments of any of the aspects, the subject is a human of less than 24 hours of age at the time of administration. In some embodiments of any of the aspects, the administration occurs at birth.

In some embodiments of any of the aspects, the adjuvant is administered at a dose of from about 0.01 mg per kilogram of a subject's body mass to about 1.0 mg per kilogram of the subject's body mass. In some embodiments of any of the aspects, the adjuvant is administered at a dose of about 0.1 mg per kilogram of the subject's body mass.

In some embodiments of any of the aspects, the adjuvant is administered intramuscularly or subcutaneously.

In some embodiments of any of the aspects, the method further comprises at least a second administration of the adjuvant and antigen. In some embodiments of any of the aspects, the first administration occurs when the subject is less than 1 day of age. In some embodiments of any of the aspects, the first administration occurs at the birth of the subject. In some embodiments of any of the aspects, the first administration occurs when the subject is less than 28 days of age. In some embodiments of any of the aspects, the first and/or second administration occur when the subject is less than 6 months of age. In some embodiments of any of the aspects, the first and/or second administration occur when the subject is less than 28 days of age. In some embodiments of any of the aspects, the first and/or second administration occur when the subject is from 28 days to 6 months of age. In some embodiments of any of the aspects, the second administration occurs within 28 days of the first administration.

In some embodiments of any of the aspects, the adjuvant and the antigen are administered in the same formulation. In some embodiments of any of the aspects, the adjuvant and the antigen are administered in different formulations and/or at different times.

In some embodiments of any of the aspects, the antigen is administered only once. In some embodiments of any of the aspects, the antigen and adjuvant are administered only once. In some embodiments of any of the aspects, the antigen is administered no more than twice. In some embodiments of any of the aspects, the antigen and adjuvant are administered no more than twice each. In some embodiments of any of the aspects, the antigen is administered no more than three times. In some embodiments of any of the aspects, the antigen and adjuvant are administered no more than three times each.

In one aspect of any of the embodiments, described herein is a method of stimulating an immune response of a subject, the method comprising administering to the human an adjuvant comprising an agonist of TLR7 and/or TLR8. In some embodiments of any of the aspects, the immune response is T helper 1-cytokine production. In some embodiments of any of the aspects, the immune response is an increase in the level of Th1 CRM-197-specific neonatal CD4+ cells.

In some embodiments of any of the aspects, the adjuvant is selected from the group consisting of a single sstranded (ss) RNA; an imidazoquinoline; a thiazoquinoline; and a benzazepine. In some embodiments of any of the aspects, the adjuvant is lipidated. In some embodiments of any of the aspects, the adjuvant is 3M-052.

In some embodiments of any of the aspects, the method further comprises administering a second adjuvant. In some embodiments of any of the aspects, the second adjuvant is alum.

In some embodiments of any of the aspects, the subject is a human infant at the time of administration. In some embodiments of any of the aspects, the subject is a human of less than 28 days of age at the time of administration. In some embodiments of any of the aspects, the subject is a human of less than 4 days of age at the time of administration. In some embodiments of any of the aspects, the subject is a human of less than 2 days of age at the time of administration. In some embodiments of any of the aspects, the subject is a human of less than 24 hours of age at the time of administration. In some embodiments of any of the aspects, the administration occurs at birth.

In some embodiments of any of the aspects, the adjuvant is administered at a dose of from about 0.01 mg per kilogram of a subject's body mass to about 1.0 mg per kilogram of the subject's body mass. In some embodiments of any of the aspects, the adjuvant is administered at a dose of about 0.1 mg per kilogram of the subject's body mass.

In some embodiments of any of the aspects, the adjuvant is administered intramuscularly or subcutaneously.

In some embodiments of any of the aspects, the method further comprises at least a second administration of the adjuvant and antigen and/or the subject is administered at least a second administration of the adjuvant and antigen, and/or the composition or kit further comprises a second dose of the adjuvant and antigen. In some embodiments of any of the aspects, the first administration occurs when the subject is less than 1 day of age. In some embodiments of any of the aspects, the first administration occurs at the birth of the subject. In some embodiments of any of the aspects, the first administration occurs when the subject is less than 28 days of age. In some embodiments of any of the aspects, the first and/or second administration occur when the subject is less than 6 months of age. In some embodiments of any of the aspects, the first and/or second administration occur when the subject is less than 28 days of age. In some embodiments of any of the aspects, the first and/or second administration occur when the subject is from 28 days to 6 months of age. In some embodiments of any of the aspects, the second administration occurs within 28 days of the first administration.

In one aspect of any of the embodiments, described herein is a composition for use in immunizing a subject or stimulating an immune response in a subject, the composition comprising an adjuvant comprising an agonist of TLR7 and/or TLR8. In one aspect of any of the embodiments, described herein is a composition comprising an adjuvant comprising an agonist of TLR7 and/or TLR8.

In some embodiments of any of the aspects, the composition further comprises at least one antigen, wherein the adjuvant and the at least one antigen are not conjugated to each other.

In one aspect of any of the embodiments, described herein is a composition or kit comprising a first formulation comprising an adjuvant comprising an agonist of TLR7 and/or TLR8 and a second formulation comprising at least one antigen, wherein the formulations are for use in immunizing a subject or stimulating an immune response in a subject. In one aspect of any of the embodiments, described herein is a composition or kit comprising a first formulation comprising an adjuvant comprising an agonist of TLR7 and/or TLR8 and a second formulation comprising at least one antigen.

In one aspect of any of the embodiments, described herein is a kit comprising an adjuvant comprising an agonist of TLR7 and/or TLR8. In some embodiments of any of the aspects, the composition or kit can further comprise at least one antigen.

In some embodiments of any of the aspects, the at least one antigen is comprised by an attenuated vaccine. In some embodiments of any of the aspects, the antigen is comprised by a subunit vaccine or recombinant subunit vaccine. In some embodiments of any of the aspects, the antigen is comprised by a conjugate vaccine. In some embodiments of any of the aspects, the antigen is a polysaccharide. In some embodiments of any of the aspects, the antigen is bound to or adsorbed to alum. In some embodiments of any of the aspects, the antigen is comprised by a vaccine selected from the group consisting of a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine. In some embodiments of any of the aspects, the vaccine is pneumococcal conjugate vaccine (PCV)13. In some embodiments of any of the aspects, the vaccine is alum-adjuvanted.

In some embodiments of any of the aspects, the composition or kit further comprises a second adjuvant. In some embodiments of any of the aspects, the second adjuvant is alum.

In some embodiments of any of the aspects, the adjuvant is formulated at a dose of from about 0.01 mg per kilogram of a subject's body mass to about 1.0 mg per kilogram of the subject's body mass. In some embodiments of any of the aspects, the adjuvant is formulated at a dose of about 0.1 mg per kilogram of the subject's body mass.

BRIEF DESCRIPTION OF THE DRAWINGS

FIG. 1A depicts the structure of R848 (Resiquimod) and 3M-052, a TLR7/8 activating imidazoquinoline bearing a C18 lipid moiety and designed for slow dissemination from the site of injection. FIGS. 1B and 1C demonstrate rodent pharmacokinetic and pharmacodynamic studies. Serum drug levels were measured by LC-MS/MS at the indicated times pre- or post-dose in rats following a single intramuscular (IM, to quadriceps) or subcutaneous (SC, to scruff of neck) administration of 3M-052 or R848 formulated in oil-in-water (O/W) emulsion (vehicle). The results represent median serum drug levels and induced TNF at each time-point for each dose (n=5). FIG. 1D depicts evaluation of SC mouse serum cytokine kinetics post-single dose of 3M-052 or R848 (both 1 mg/kg, (20 µg/mouse)) formulated in O/W emulsion (vehicle) (n=3).

FIG. 3A depicts the rhesus macaque study groups and their enrollment/immunization timeline. Neonatal and infant rhesus macaques were immunized at day of life (DOL)-0, 28, and 56 (the three immunization time-points are indicated by boxes) with either PCV13 alone or PCV13 co-administered with 3M-052 (a lipidated TLR7/8A). Peripheral blood was collected at the indicated time-points for measurement of anti-pneumococcal serotype titers by polysaccharide-IgG binding microarray. FIG. 3B demonstrates a total of 13 tested serotypes, infant n=5 per group. Horizontal broken line indicates the WHO-recommended reference Ab concentration of IgG used as a correlate of protection levels in humans (0.35 jag/ml). Numbers refer to p values approaching significant for that group. For comparisons between overall groups (e.g., PCV13 vs. (PCV13+

3M-052)), statistical significance denoted as +p<0.05, ++p<0.01 or NS (not significant). For comparison at individual time-points (e.g., PCV13 vs. (PCV13+3M-052) at DOL28), statistical significance denoted as *p<0.05, p<0.01, *p<0.001. Results represent means±SEM.

Figure 4A:
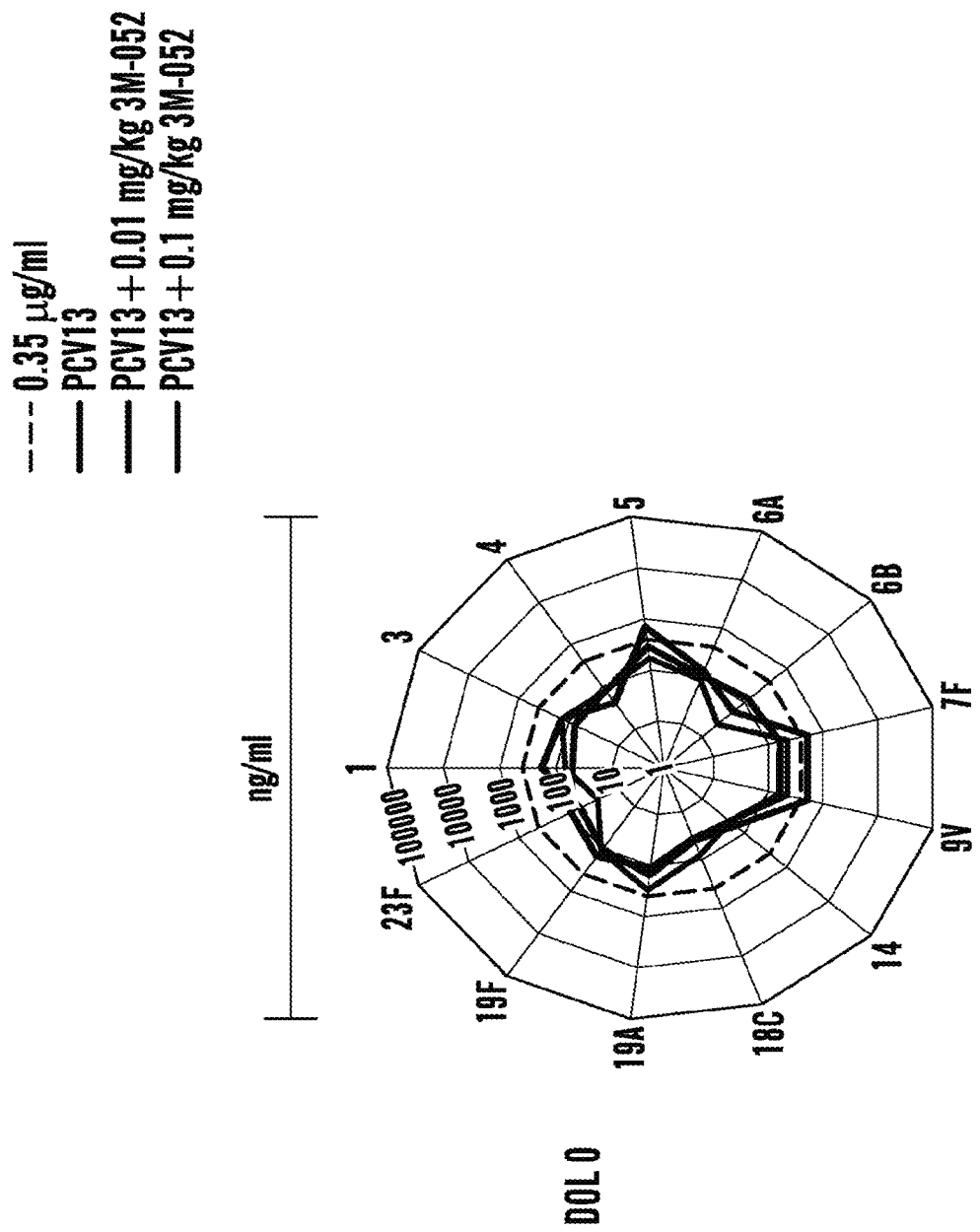
Figure 4A:
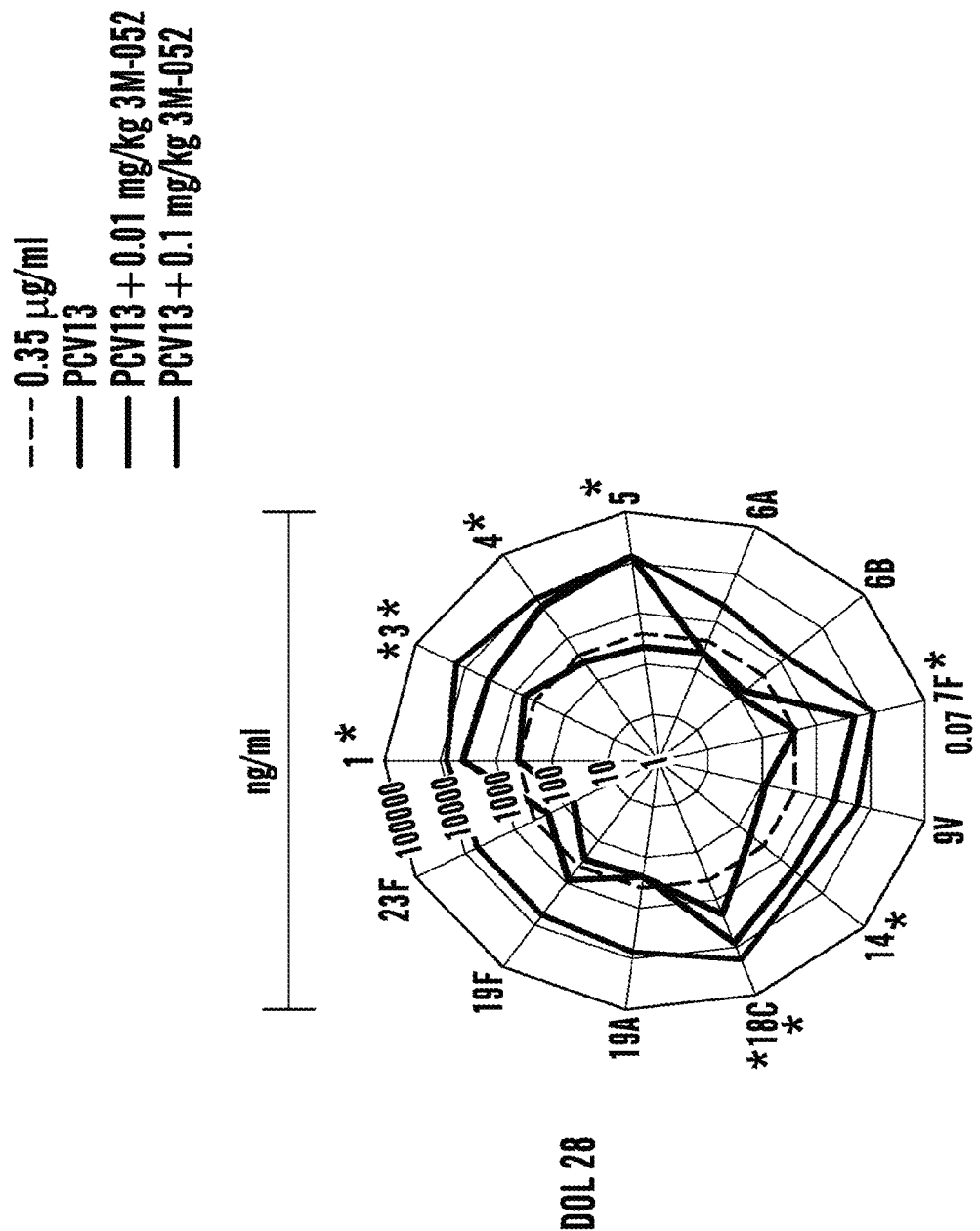
Figure 4A:
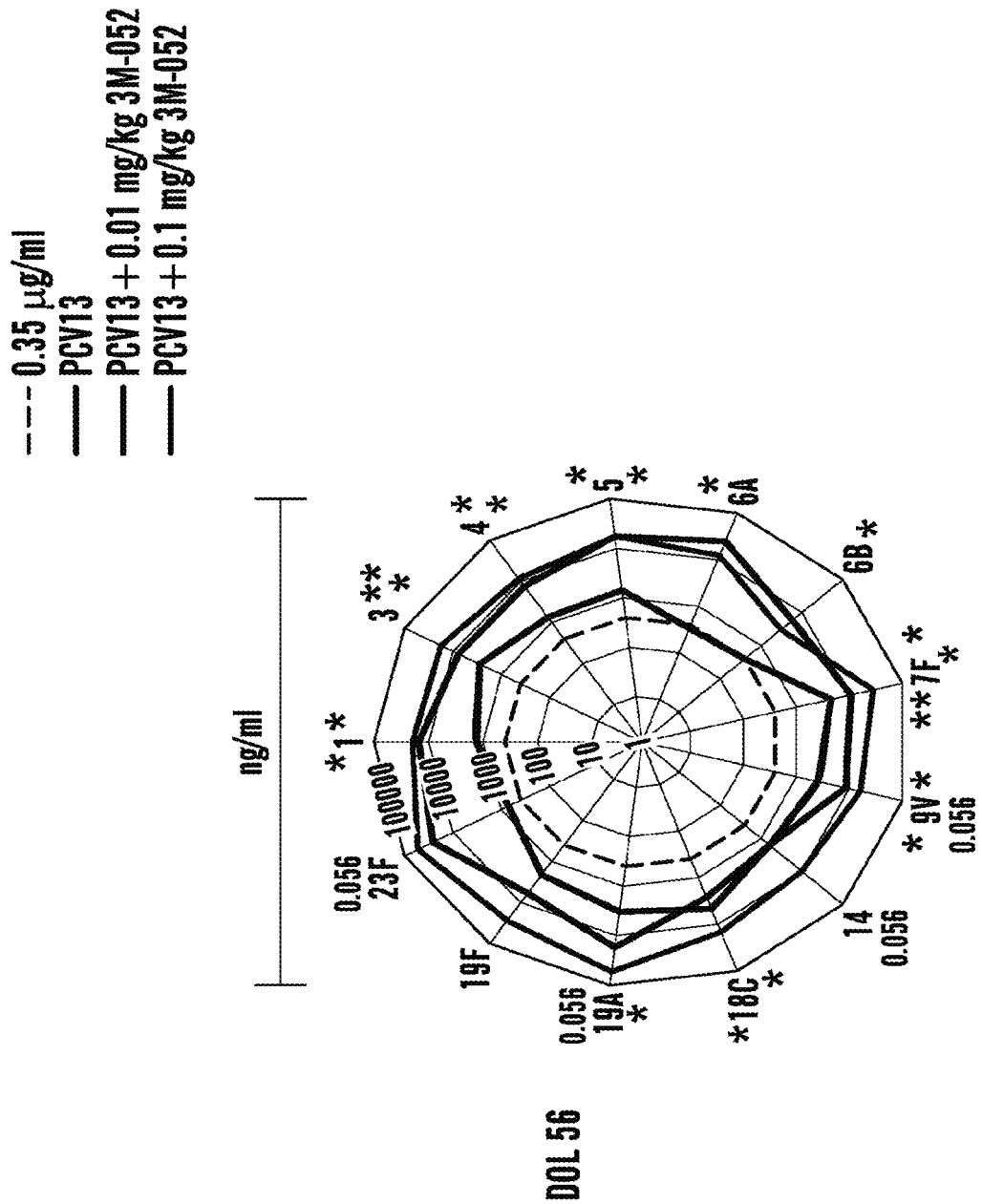
Figure 4A:
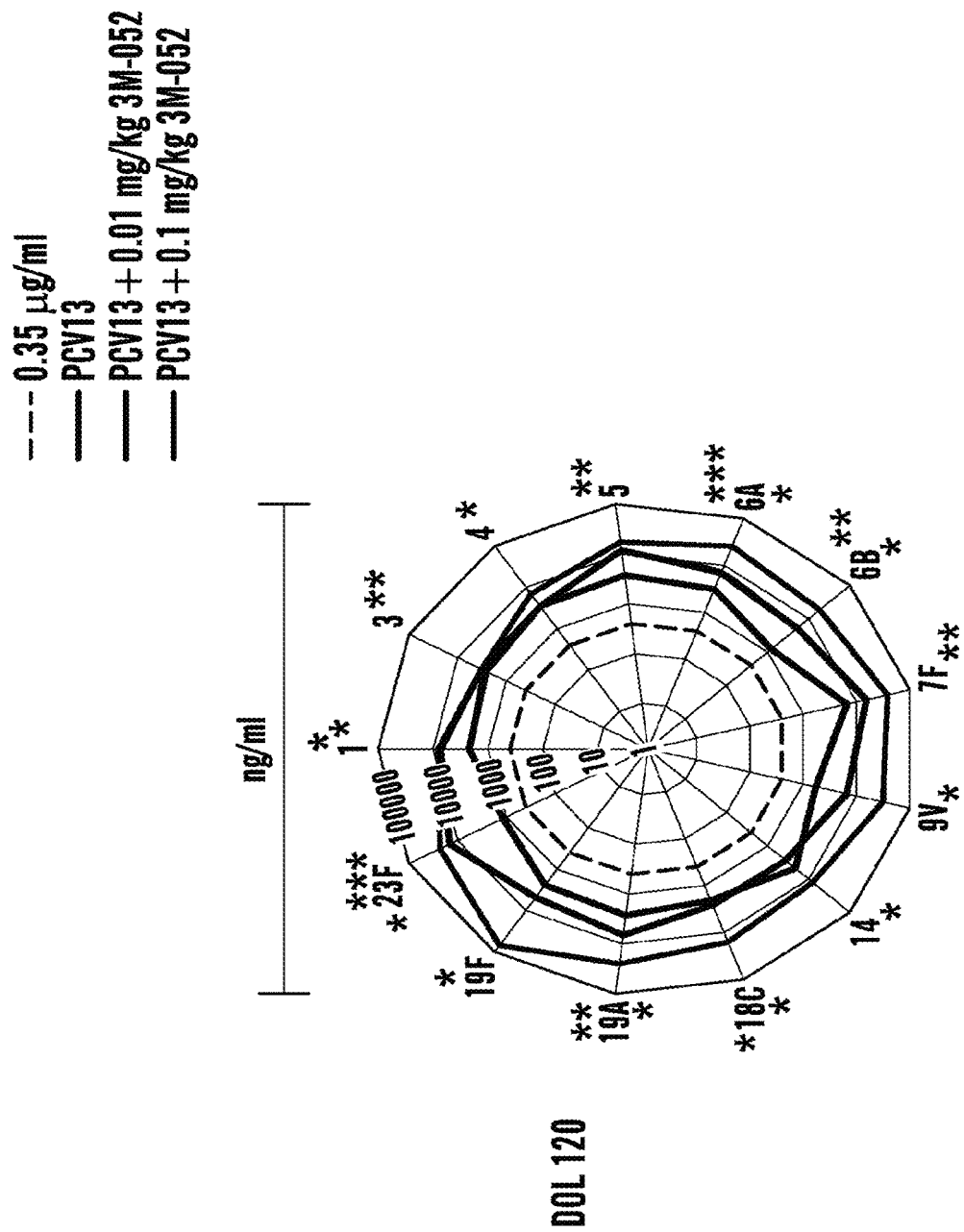
Figure 4B:
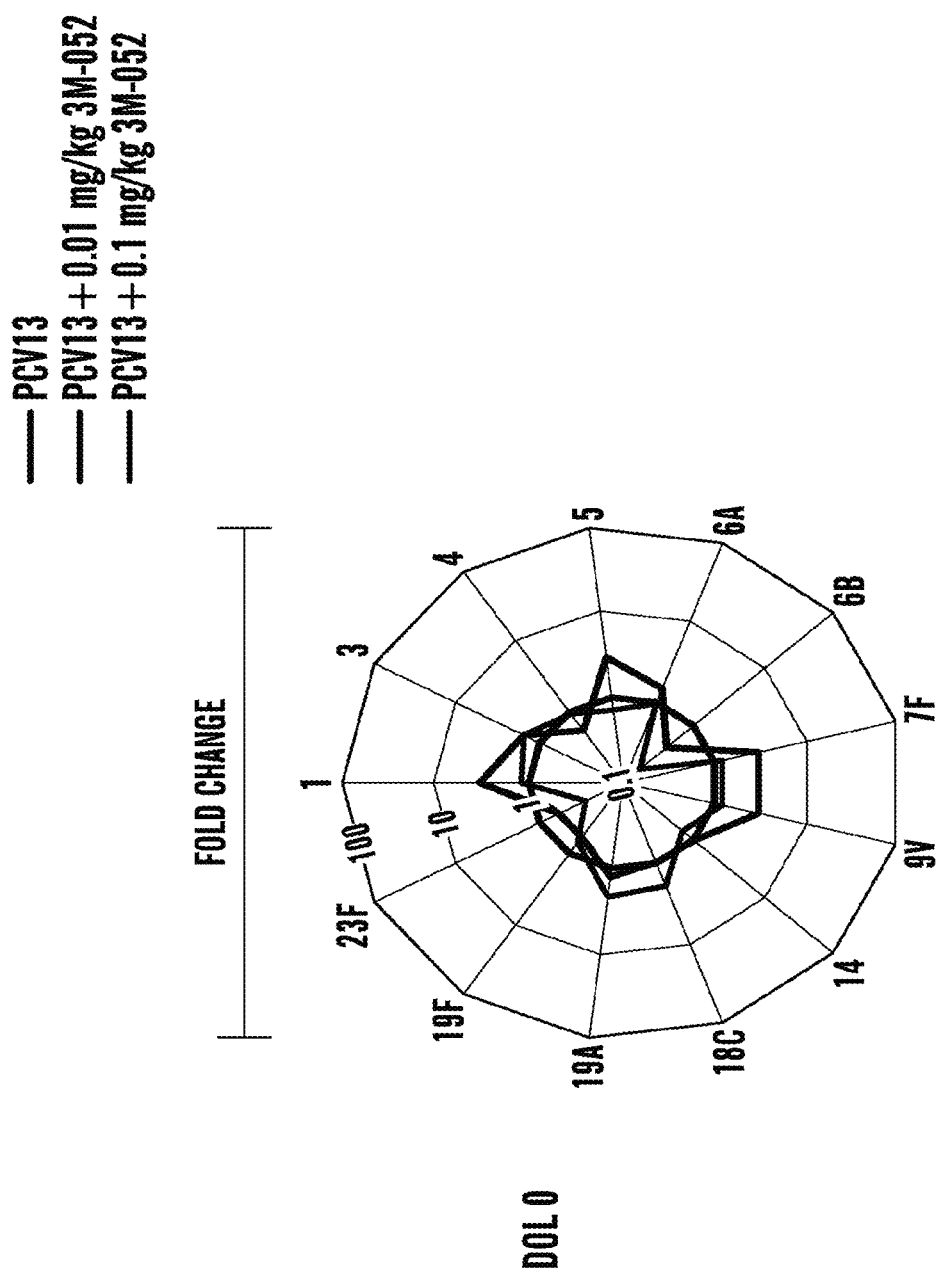
Figure 4B:
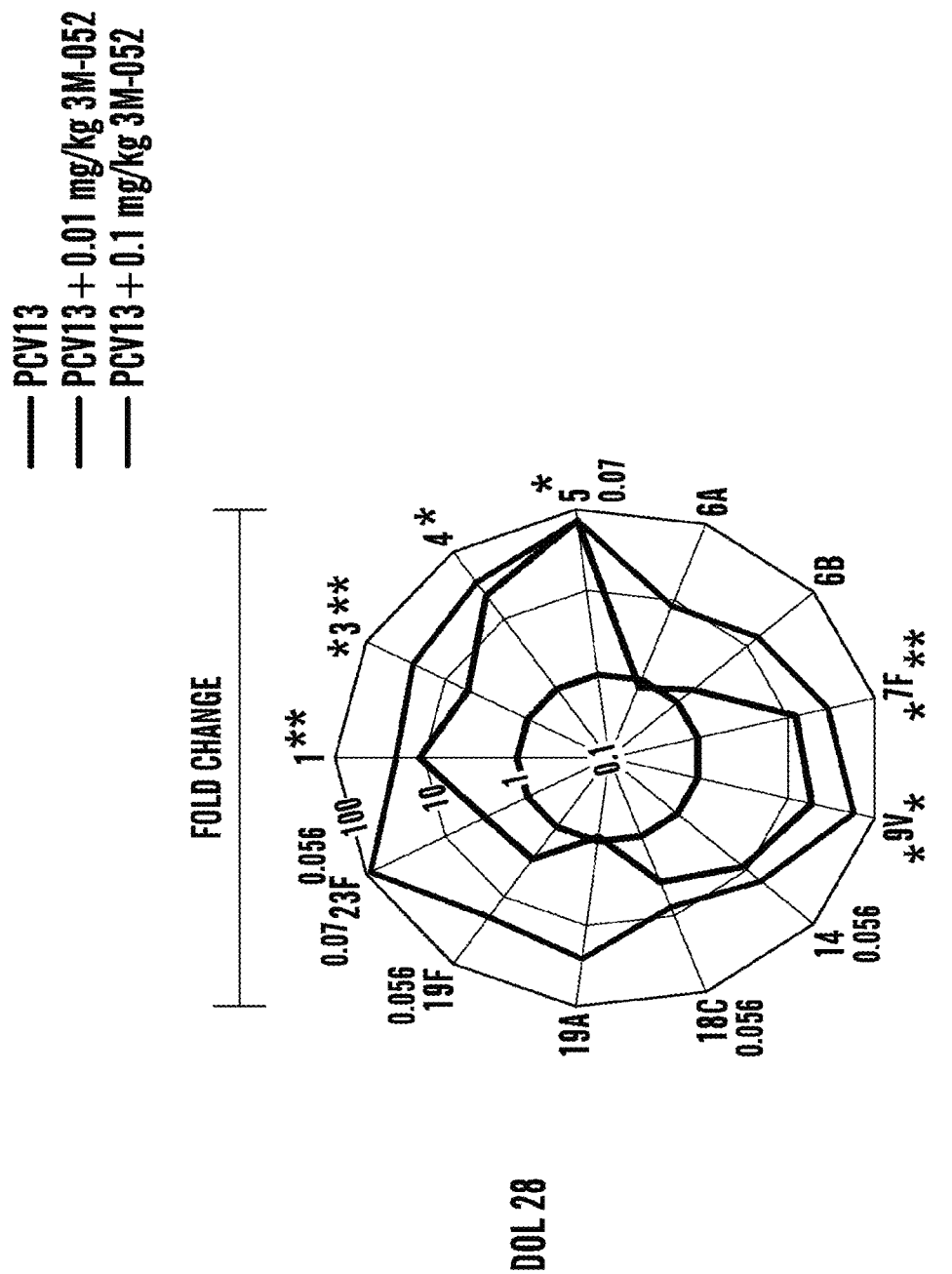
Figure 4B:
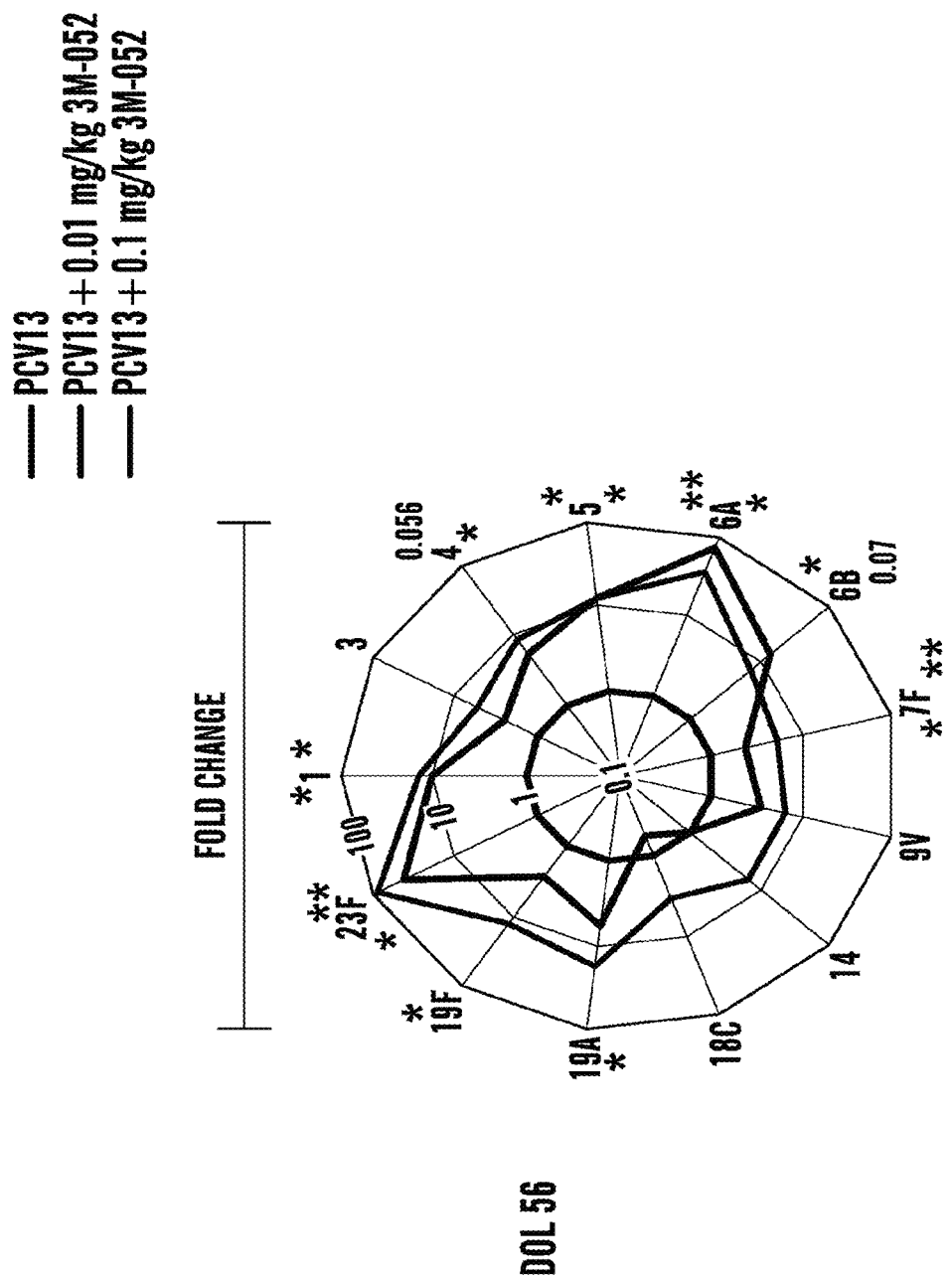
Figure 4B:
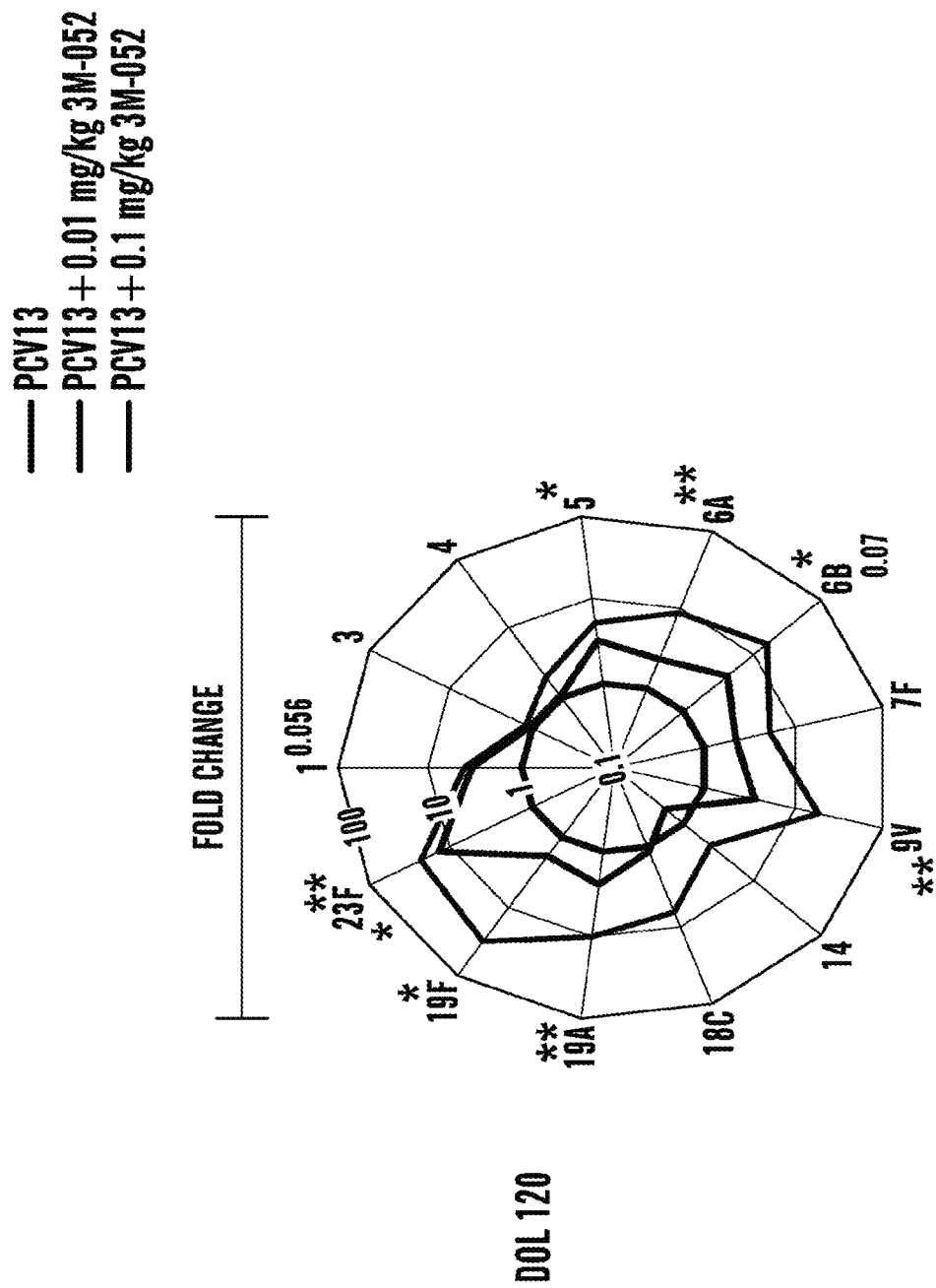

FIGS. 4A-4B demonstrate that in vivo adjuvanticity of 3M-052 is dose dependent. Radar plot analysis of all 13 serotypes tested, including raw ng/ml (FIG. 4A) and fold-change analysis (FIG. 4B) at DOL0, 28, 56 and 120. After 3 doses of (PCV13+3M-052), all immunized infants significantly exceeded protection level for all 13 serotypes tested. Broken black line indicates WHO-recommended reference. Numbers refer to p values approaching significant for that group. Infant n=5 per group for PCV13 and (PCV13+0.1 mg/kg 3M-052), n=3 for (PCV13+0.01 mg/kg 3M-052). For comparisons between overall groups (e.g., PCV13 vs. (PCV13+3M-052)), statistical significance denoted as +p<0.05, ++p<0.01 or NS (not significant). For comparison at individual time-points (e.g., PCV13 vs. (PCV13+3M-052) at DOL28), statistical significance denoted as *p<0.05, p<0.01, *p<0.001. Results represent means±SEM.

Figures 5A, 5B:
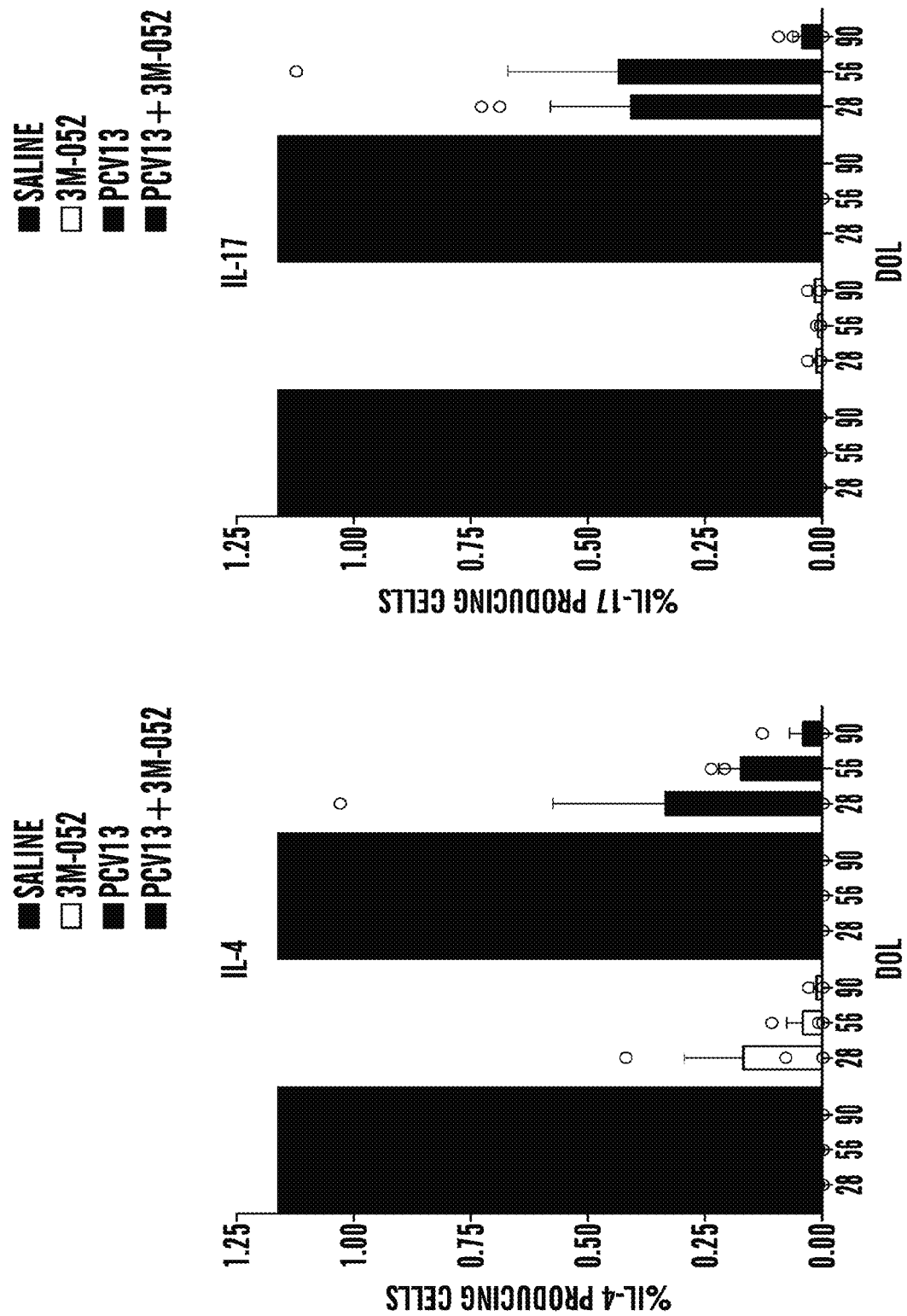
Figures 5C, 5D:
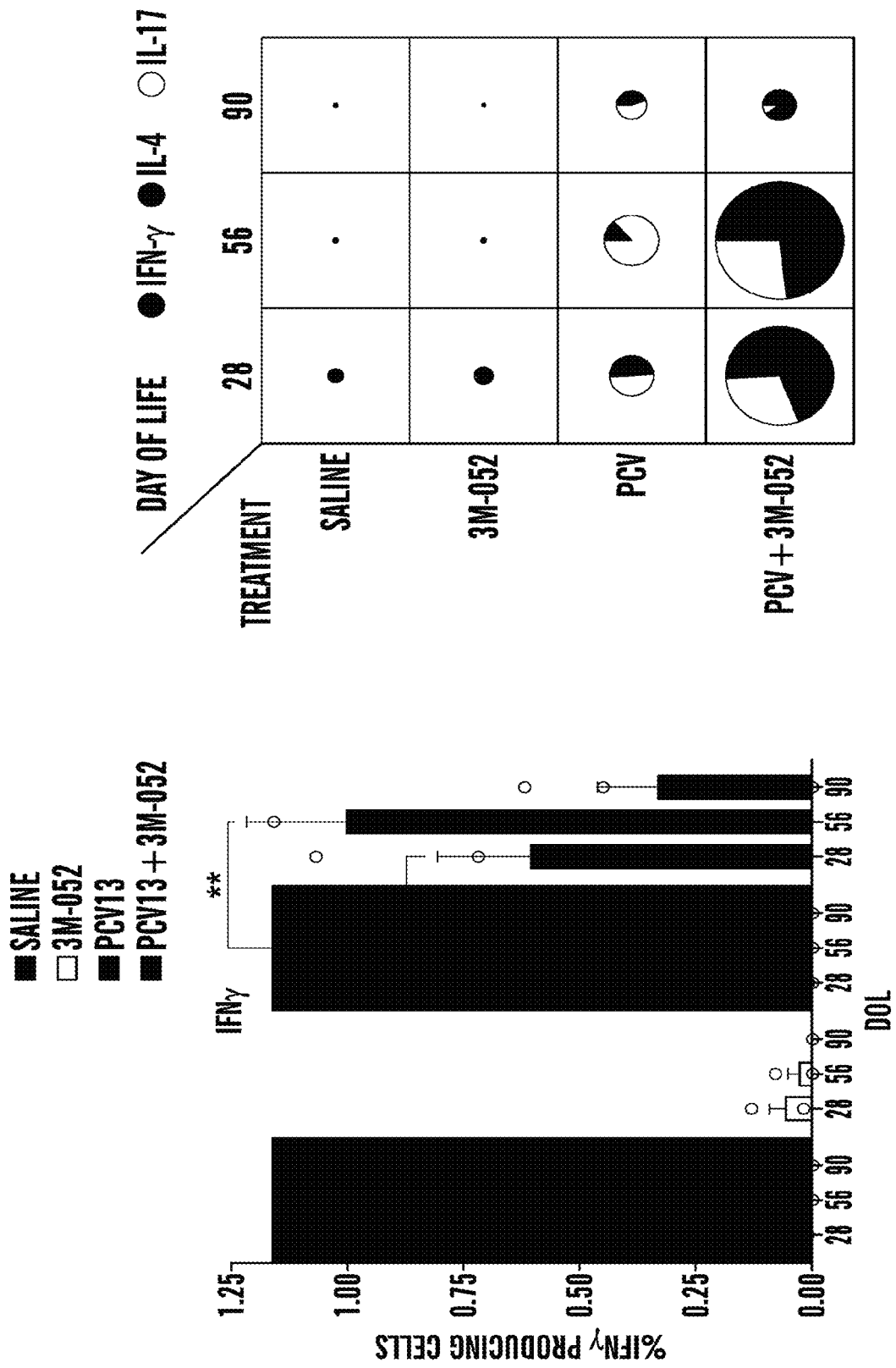

FIGS. 5A-5D demonstrate that (PCV13+3M-052) activates both Th17 and Th1 CRM-197-specific CD4+ cells. FIGS. 5A-5C depict the percentage of IL-4-, IL-17-, and IFNγ-producing CRM197-specific CD4+ T cells post-ex vivo recall assays with CRM197-pulsed autologous rhesus DCs. FIG. 5D depicts pie charts representing scale and frequencies of cytokine producing CRM197-specific CD4+ T cells, indicating that neonatal PCV13 alone treatment enhances CRM197-specific Th17-responses, while (PCV13+3M-052) enhances and accelerates a mixed Th1/Th17-response. Results represent mean±SEM (n=3-4), with statistical significance denoted as *p<0.05, **p<0.01.

Figure 6B:
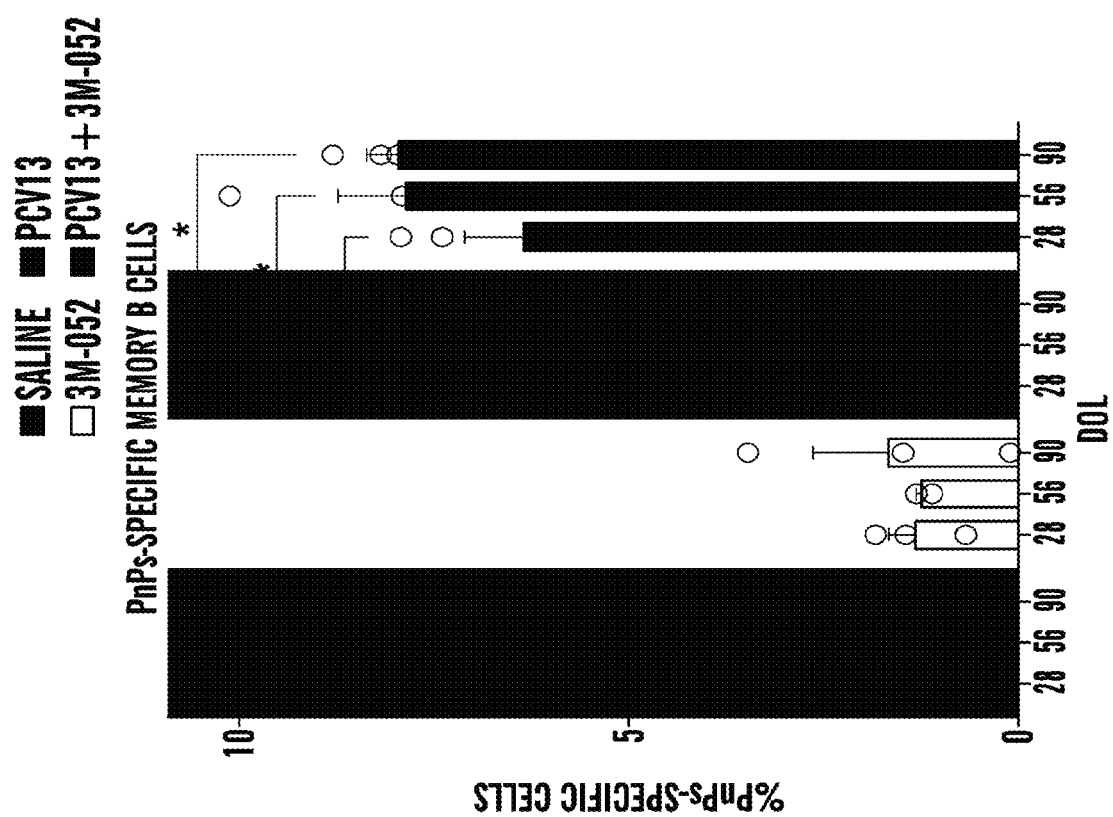
Figure 6A:
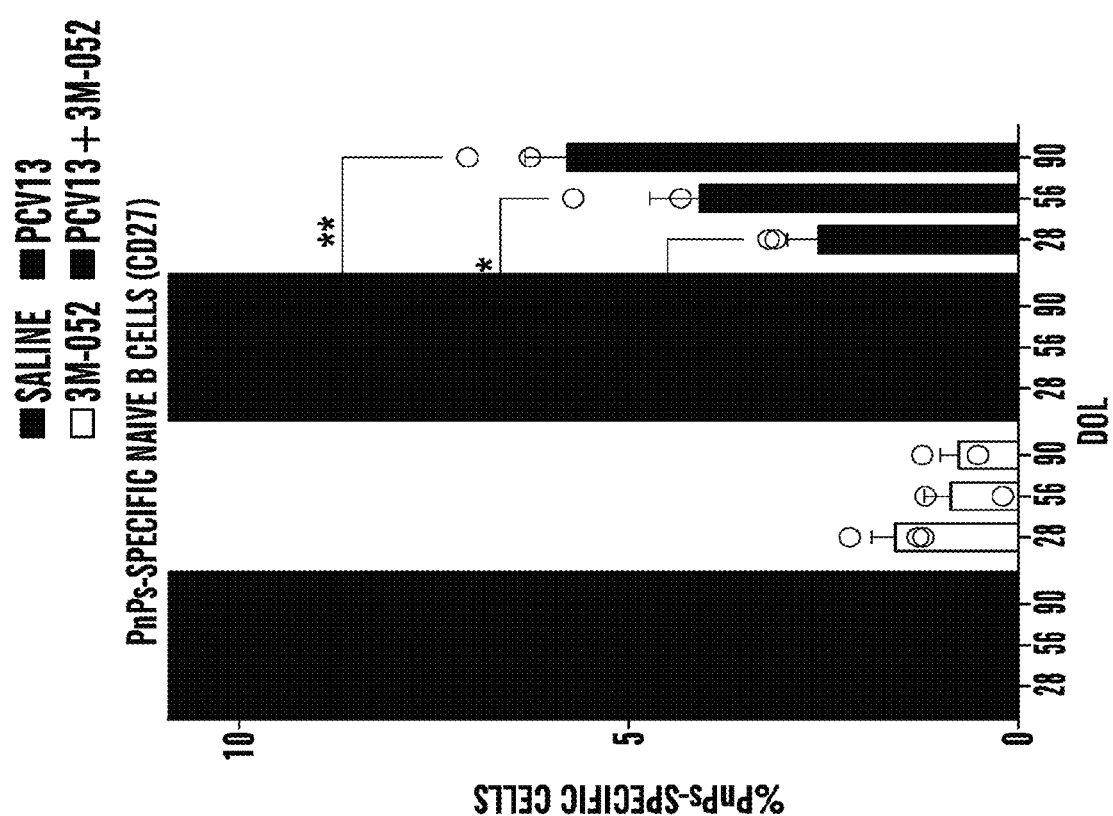
Figure 6C:
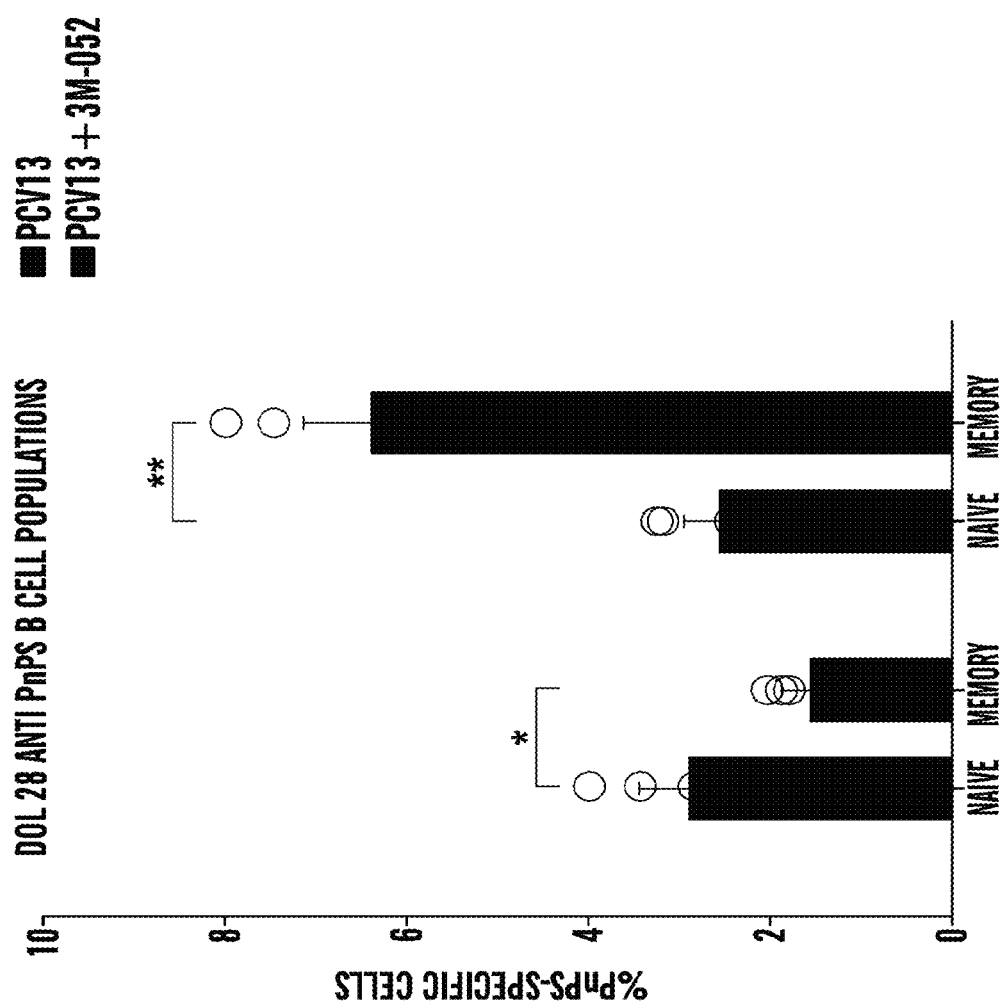

FIGS. 6A-6C demonstrate that 3M-052 enhances and accelerates activation of early life PnPS-specific B cells. FIGS. 6A-6B depict anti-pneumococcal polysaccharide (PnPS) IgG/IgM-producing rhesus naïve and memory B cell quantification. Higher frequencies of PnPS-specific B cells were noted in the (PCV13+3M-052) animals vs. the PCV13 group (n=3-4). FIG. 6C demonstrates that co-administration of 3M-052 with PCV13 to newborn rhesus macaques dramatically accelerated the transition of anti-PnPS B-cells from naïve to memory phenotype. Anti-pneumococcal polysaccharide (PnPS) IgG producing naïve (CD27−) and memory (CD27+) B cells were measured by flow cytometry. At DOL28, the switch from naïve to memory phenotype occurred earlier in (PCV13+3M-052) vs. PCV13 only-immunized animals. Non-specific polysaccharide in vitro activation in the control conditions (i.e., saline or 3M-052 alone) or specific CRM-197 treatment of B cells from all treatment groups never exceeded ~1.0%. Results represent means±SEM (n=4 per group), with statistical significance denoted as *p<0.05, **p<0.01.

Figure 7A:
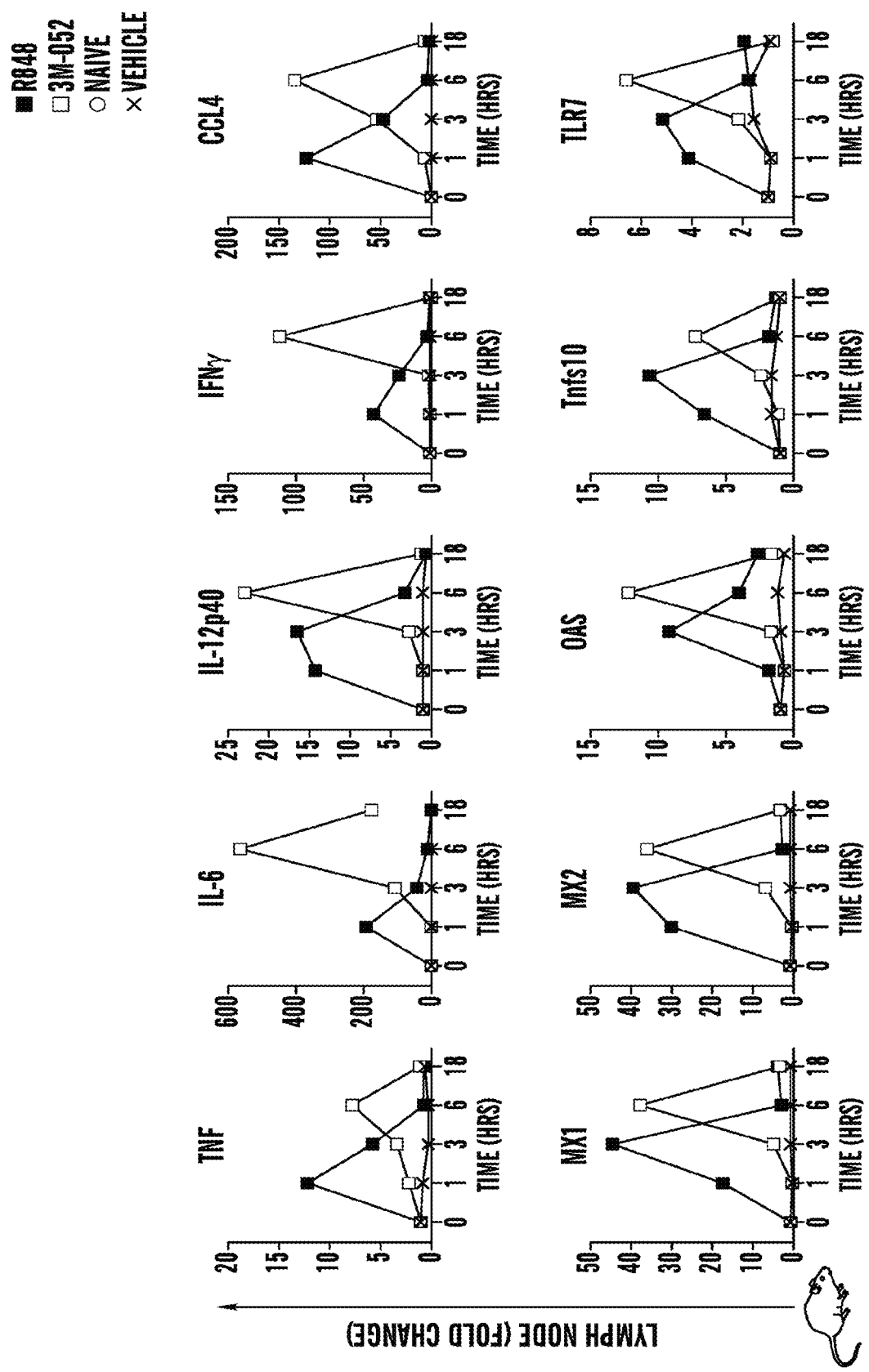
Figure 7B:
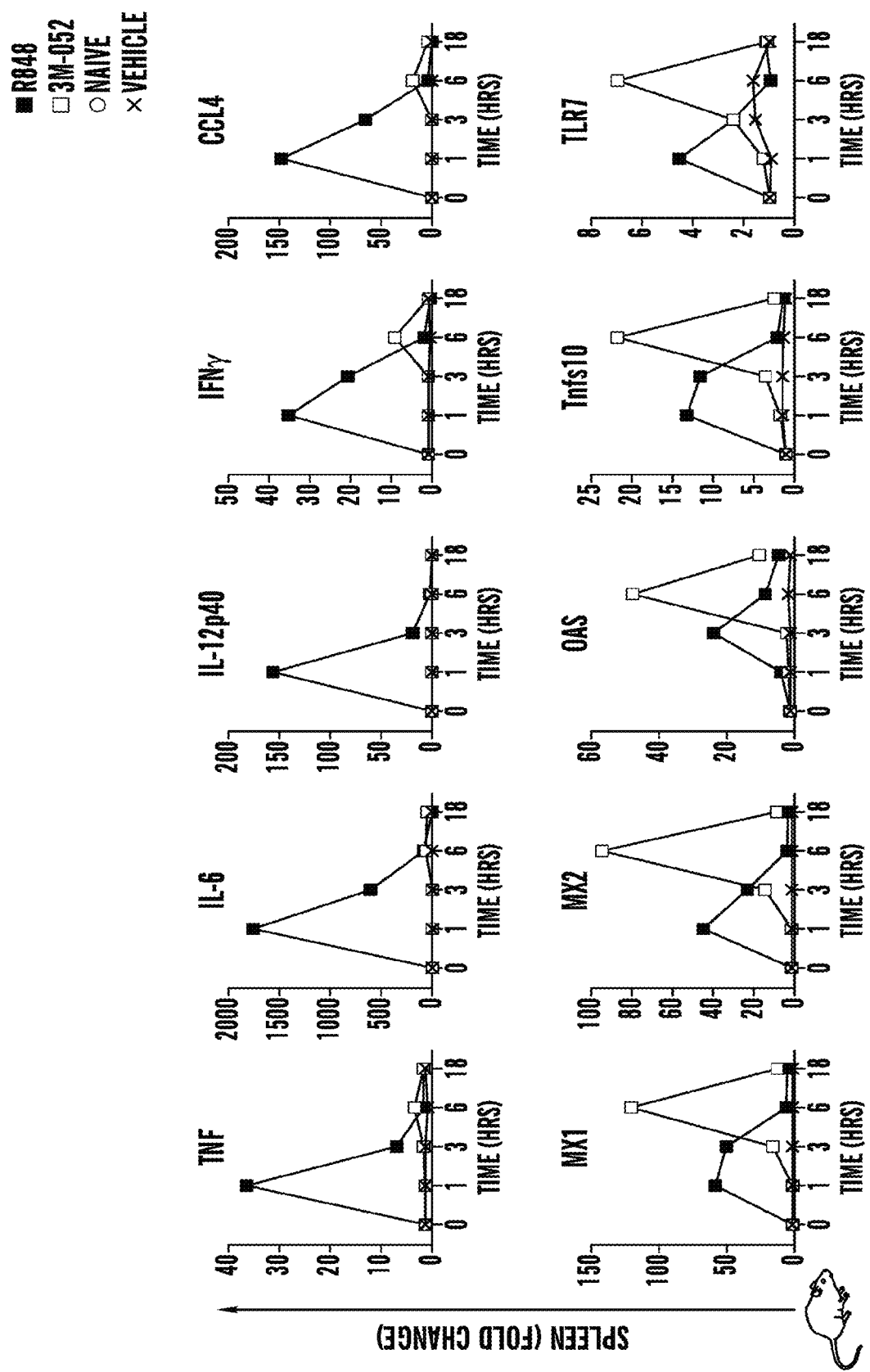

FIGS. 7A-7B demonstrate Cytokine and IFN-inducible gene expression following free or lipidated TLR7/8 imidazoquinoline subcutaneous injection. Mouse mRNA expression is depicted in (FIG. 7A) draining lymph nodes (brachial and axillary), and (FIG. 7B) spleen post a single subcutaneous injection of 3M-052 or R848 formulated (both 1 mg/kg, (20 μg/mouse)) in oil-in-water emulsion (O/W) (vehicle) to the scruff of the neck. Data represents relative fold-change gene expression (i.e., treatment relative expression/untreated relative expression) (n=3).

Figure 8A:
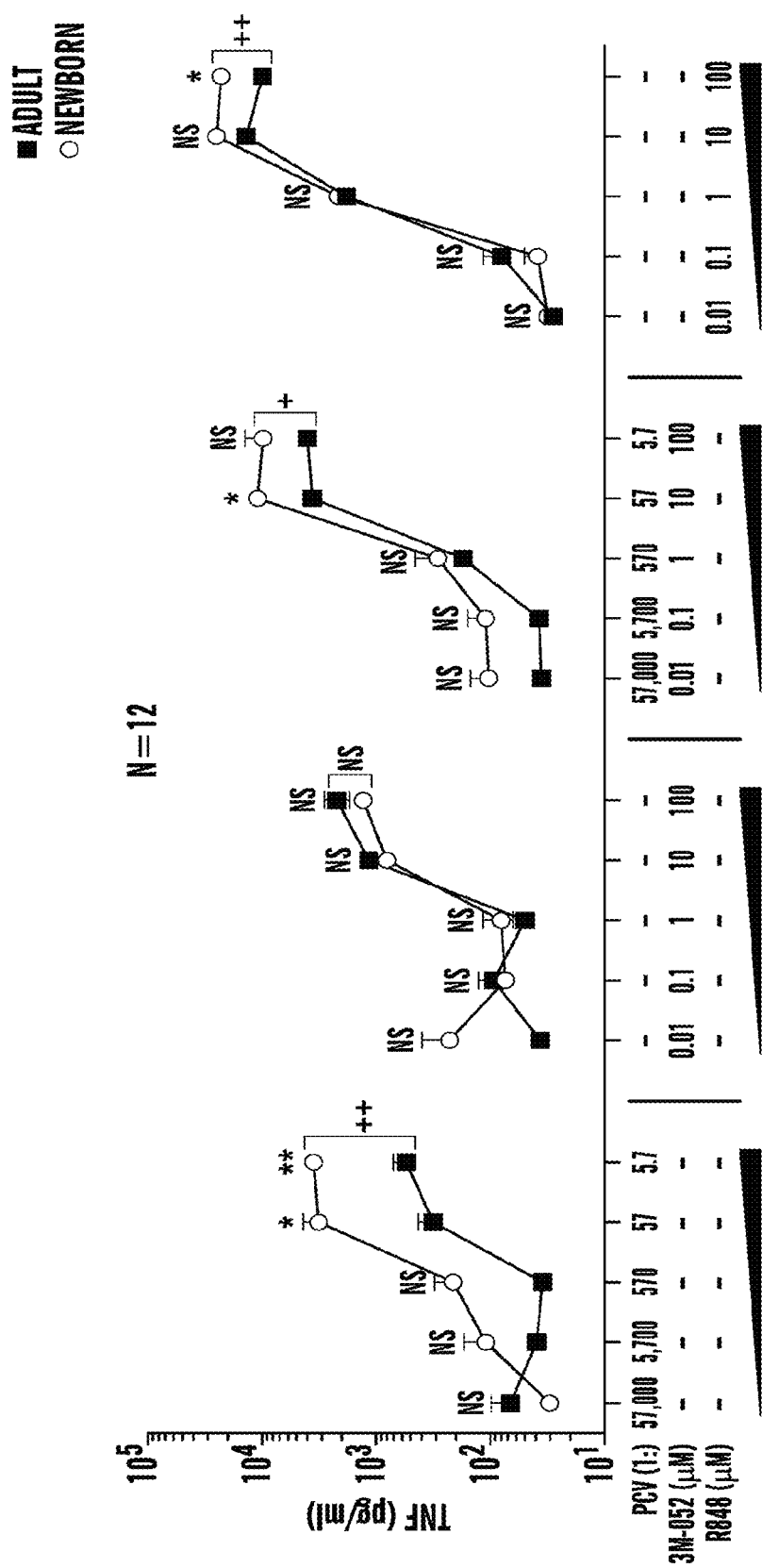
Figure 8B:
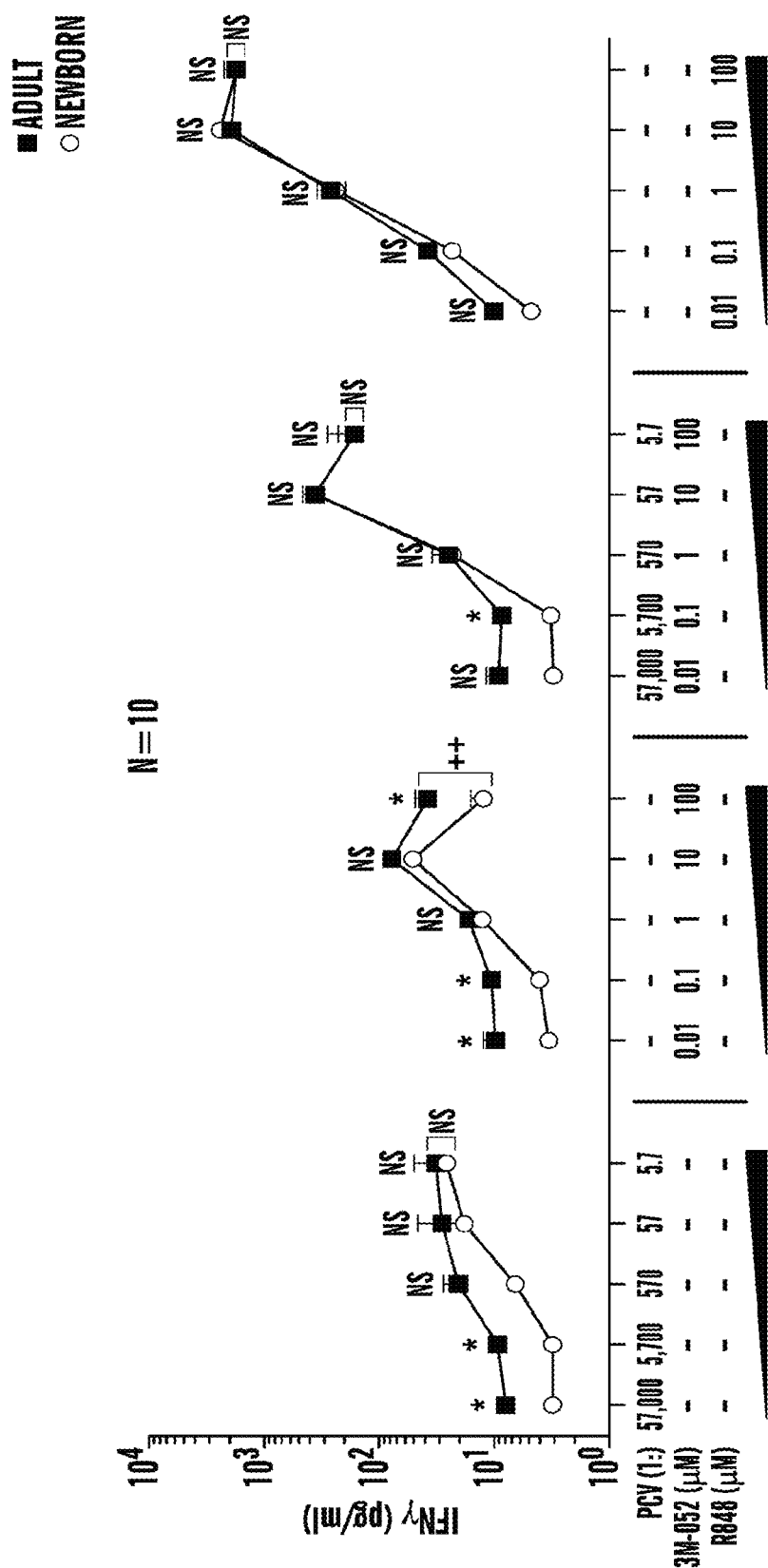

FIGS. 8A-8B demonstrate that addition of 3M-052 to PCV13 enhances TNF and IFN responses in newborn cord blood. Human neonatal and adult blood was cultured for 6 hours with sterile buffer control (RPMI, not shown), PCV13 (1:5.7-57,000 v/v), 3M-052 or R848 (both 0.01, 0.1, 1, 10, 100 μM), or (PCV13+3M-052). Supernatants were collected for ELISA and multiplex assay. Mean±SEM of agonist-induced cytokine production are shown for (FIG. 8A) TNF (n=12) and (FIG. 8B) IFNγ (n=10). For comparisons between overall groups (e.g., newborn vs. adult), twoway repeated measures ANOVA for non-parametric sample populations were applied and statistical significance denoted as +p<0.05, ++p<0.01. For comparison at individual concentrations, the unpaired Mann-Whitney test was applied and statistical significance denoted as *p<0.05, **p<0.01, or NS (not significant). Results represent means±SEM.

Figure 9:
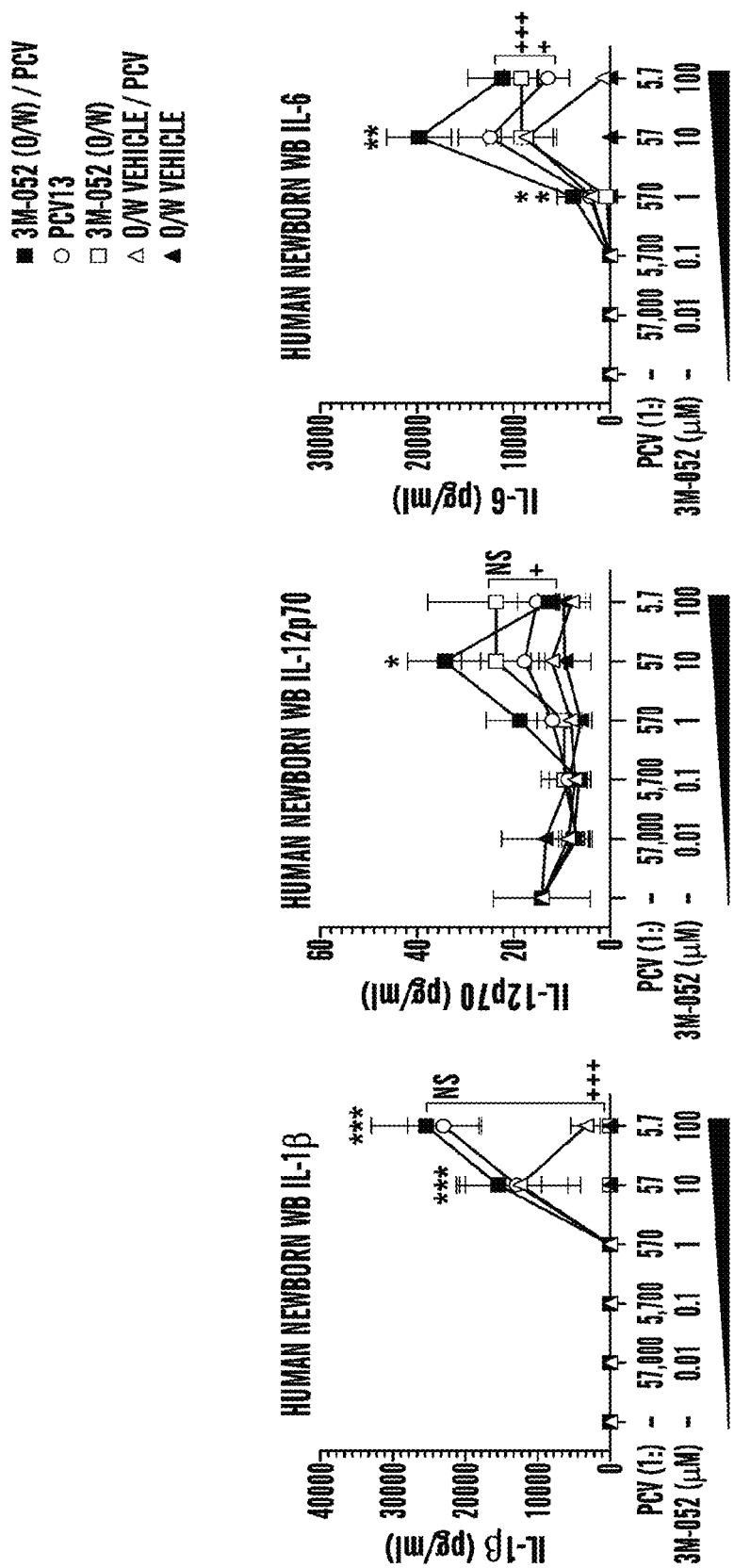
Figure 9:
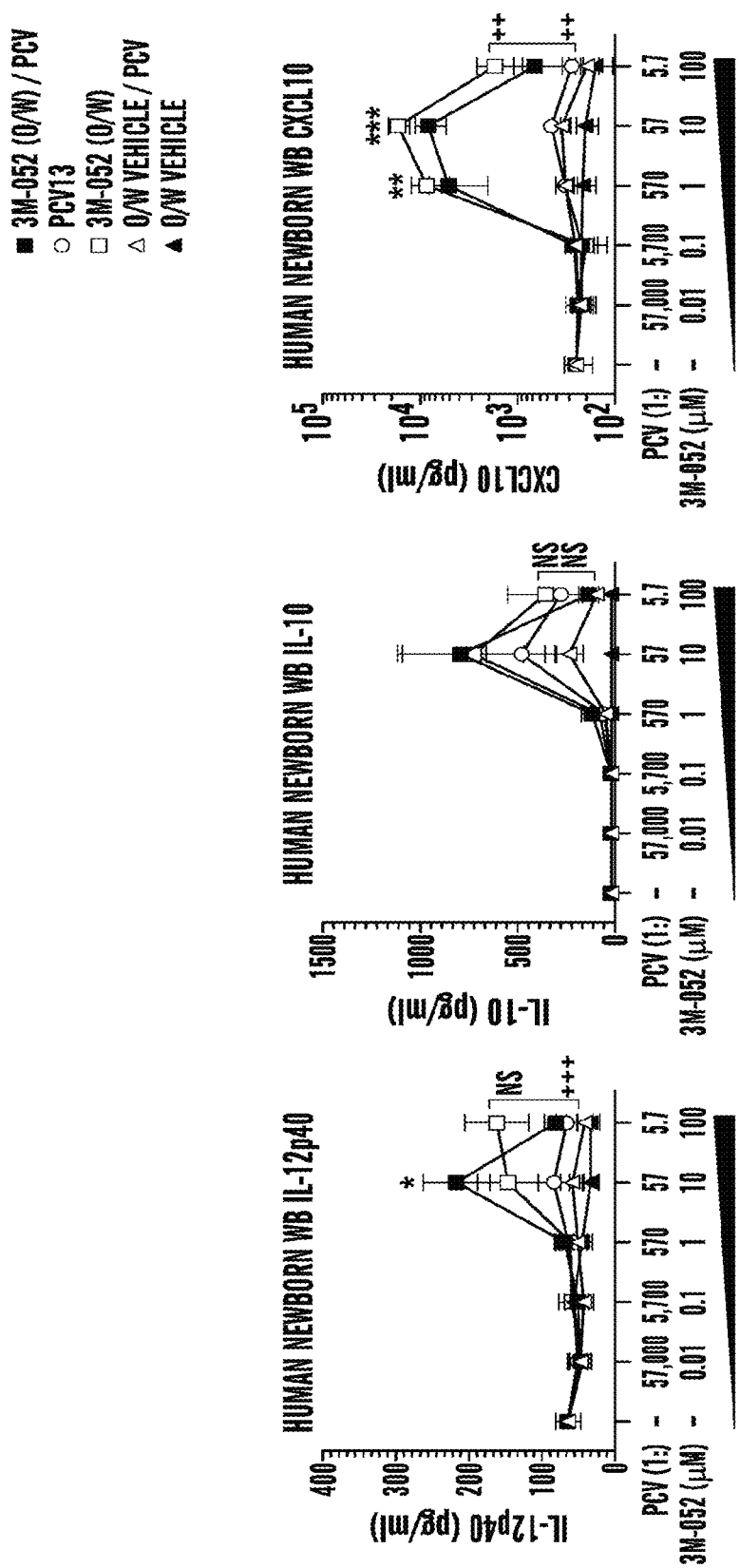
Figure 9:
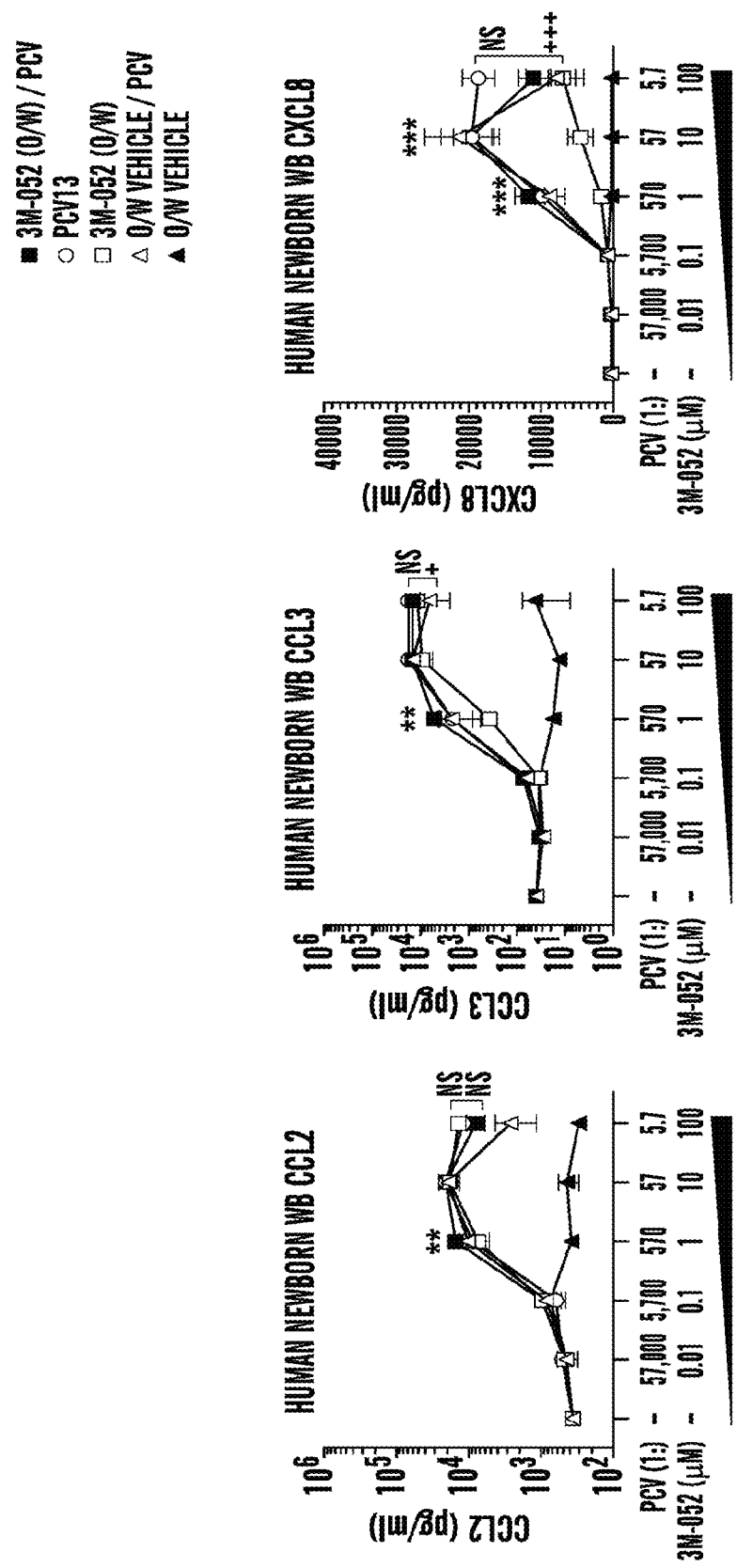

FIG. 9 demonstrates that human newborn whole blood cytokine responses to 3M-052, PCV13, and (PCV13+3M-052). Human cord blood cultured for 6 hours with O/W vehicle, PCV13 alone (1:5.7-57,000 v/v), 3M-052 alone (0.01, 0.1, 1, 10, 100 μM) and concentration dependent combinations of each. Supernatants were collected for ELISA and multiplex assay. Mean±SEM of agonist-induced cytokine production are shown (n=8-10). For comparisons between overall groups (e.g., PCV13 vs. (PCV13+3M-052)), two-way repeated measures ANOVA for non-parametric sample populations were applied and statistical significance denoted as +p<0.05, ++p<0.01, +++p<0.001. For comparison at individual concentrations, the unpaired Mann-Whitney test was applied and statistical significance denoted as *p<0.05, p<0.01, *p<0.001. Results represent means±SEM, with p values indicating significance as compared to that group.

Figure 10:
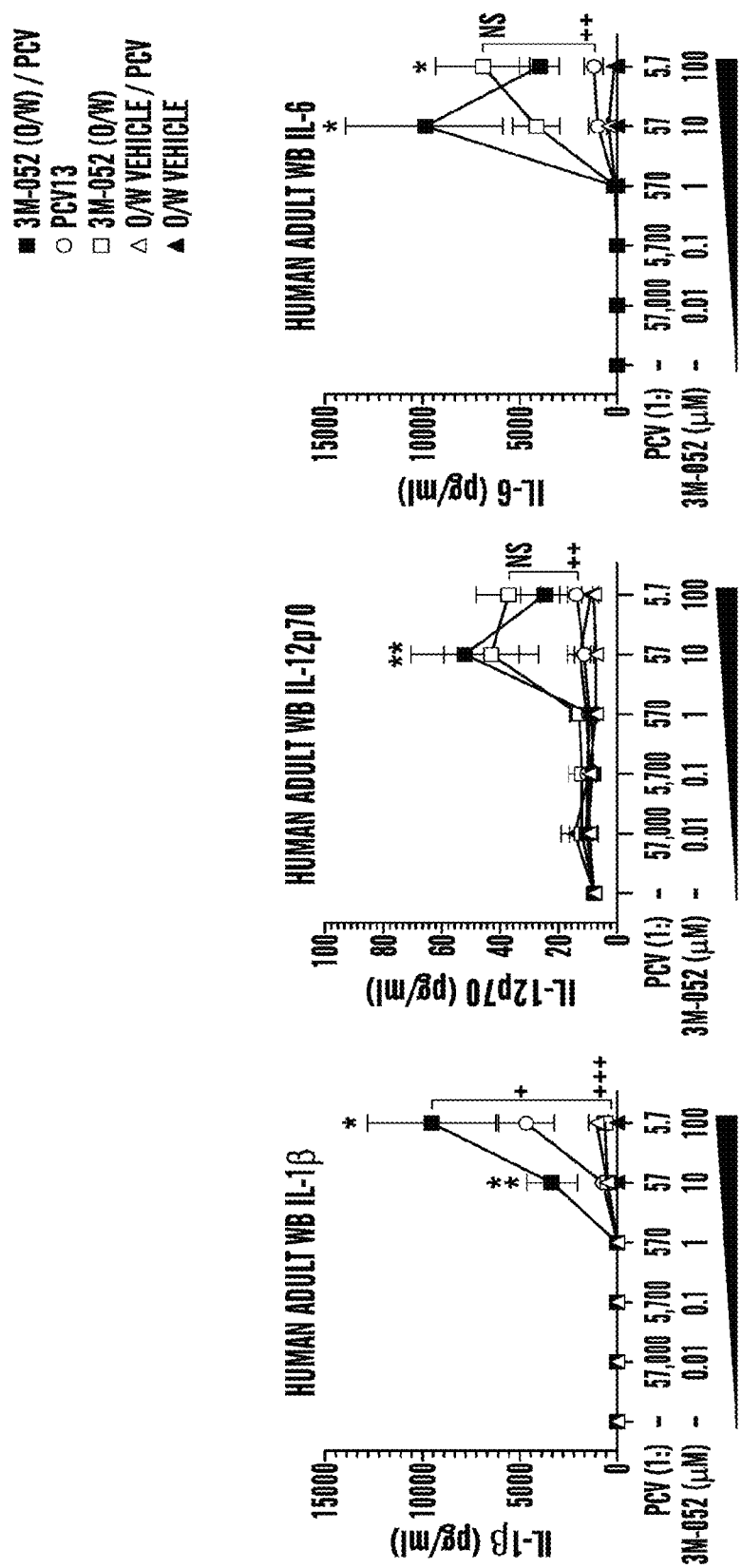
Figure 10:
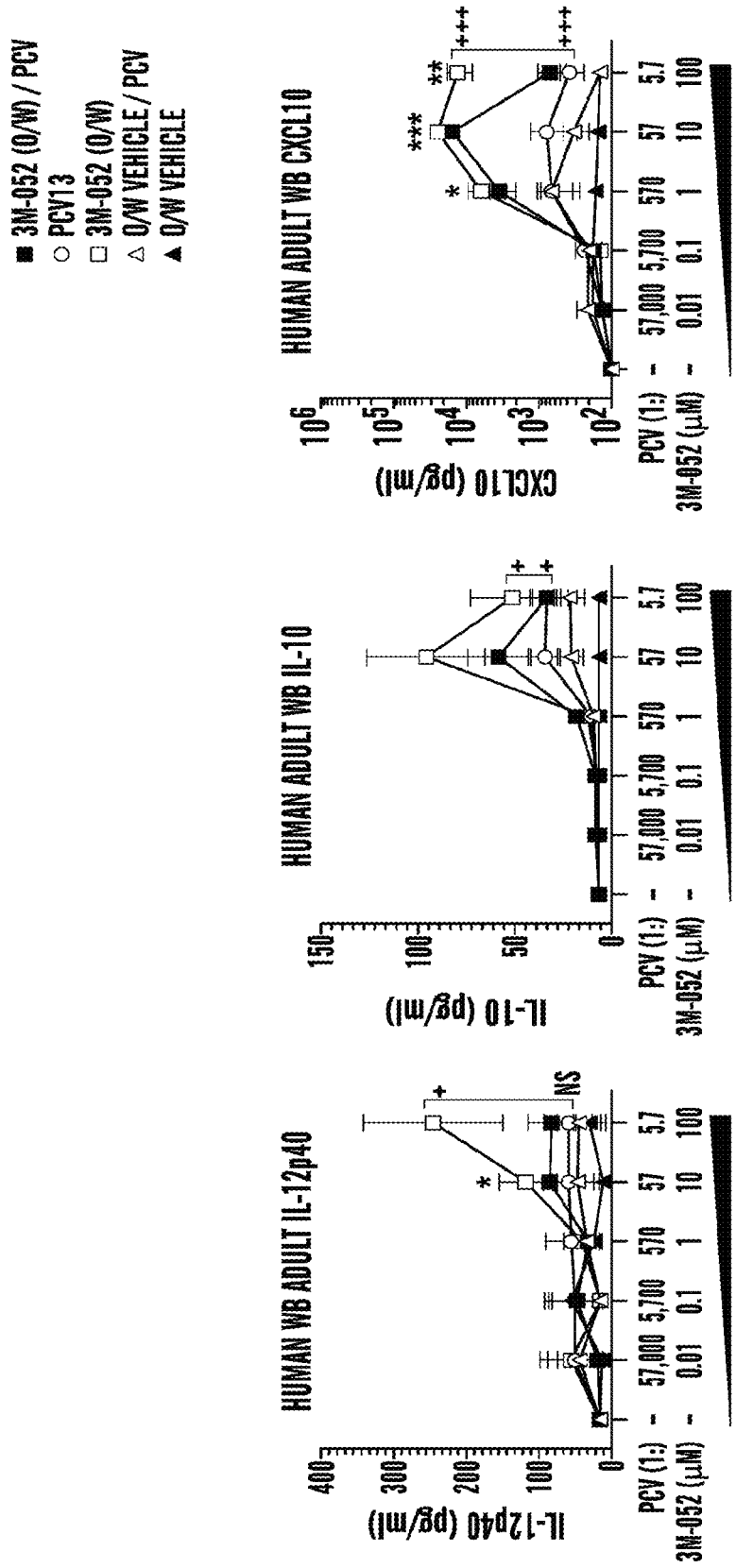
Figure 10:
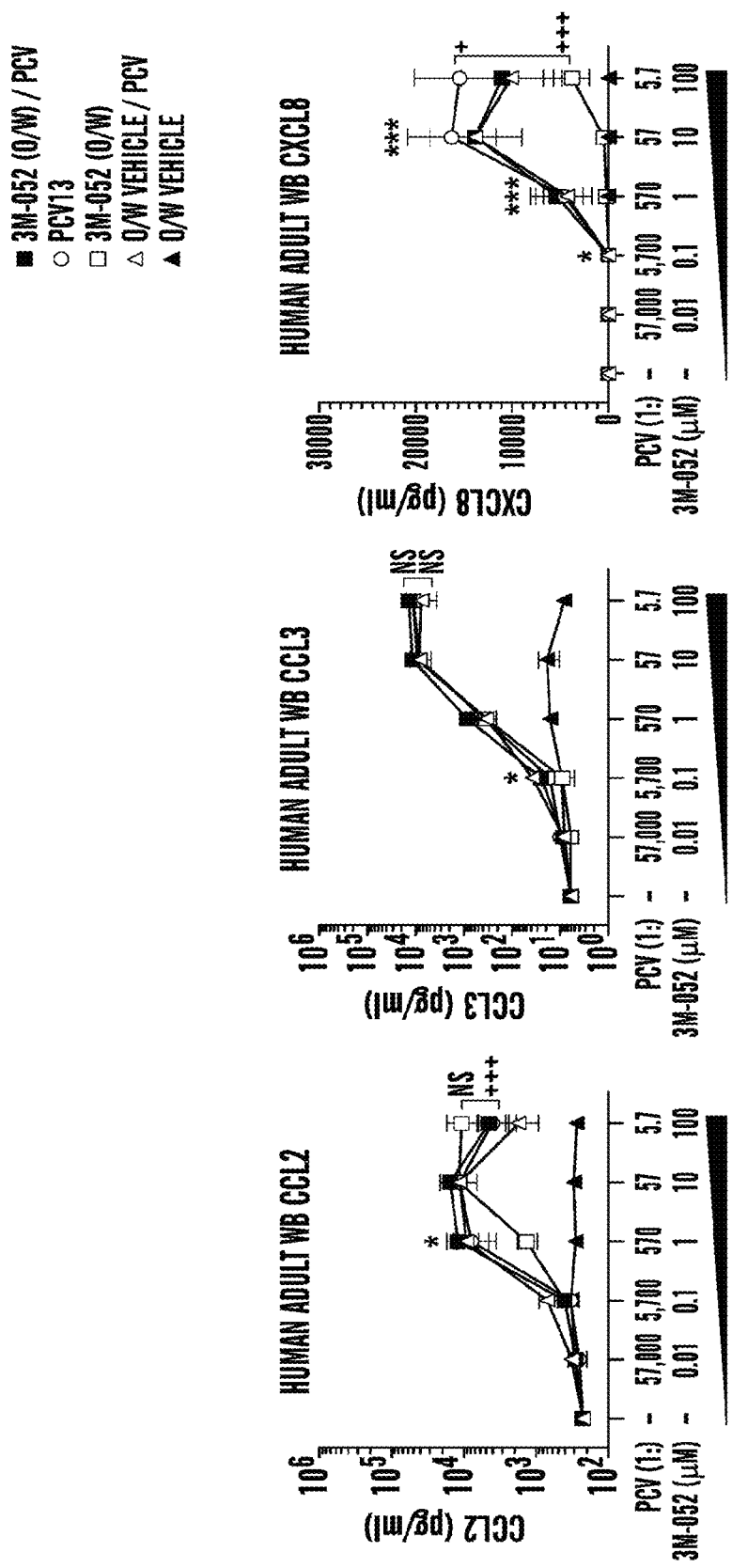

FIG. 10 demonstrates that human adult whole blood cytokine responses to 3M-052, PCV13 and (PCV13+3M-052). Human adult blood cultured for 6 hours with O/W vehicle, PCV13 alone (1:5.7-57,000 v/v), 3M-052 alone (0.01, 0.1, 1, 10, 100 μM) and concentration dependent combinations of each. Supernatants were collected for ELISA and multiplex assay. Mean±SEM of agonist-induced cytokine production are shown (n=8-10). For comparisons between overall groups (e.g., PCV13 vs. (PCV13+3M-052)), two-way repeated measures ANOVA for non-parametric sample populations were applied and statistical significance denoted as +p<0.05, ++p<0.01, +++p<0.001. For comparison at individual concentrations, the unpaired Mann-Whitney test was applied and statistical significance denoted as *p<0.05, p<0.01, *p<0.001. Results represent means±SEM, with p values indicating significance as compared to that group.

Figure 11B:
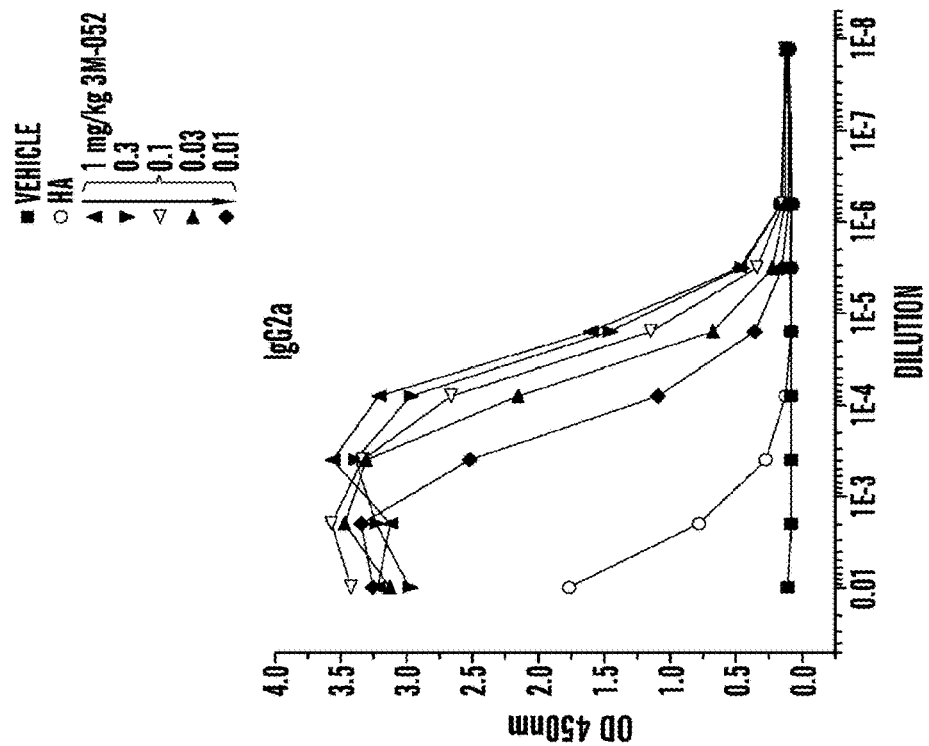
Figure 11A:
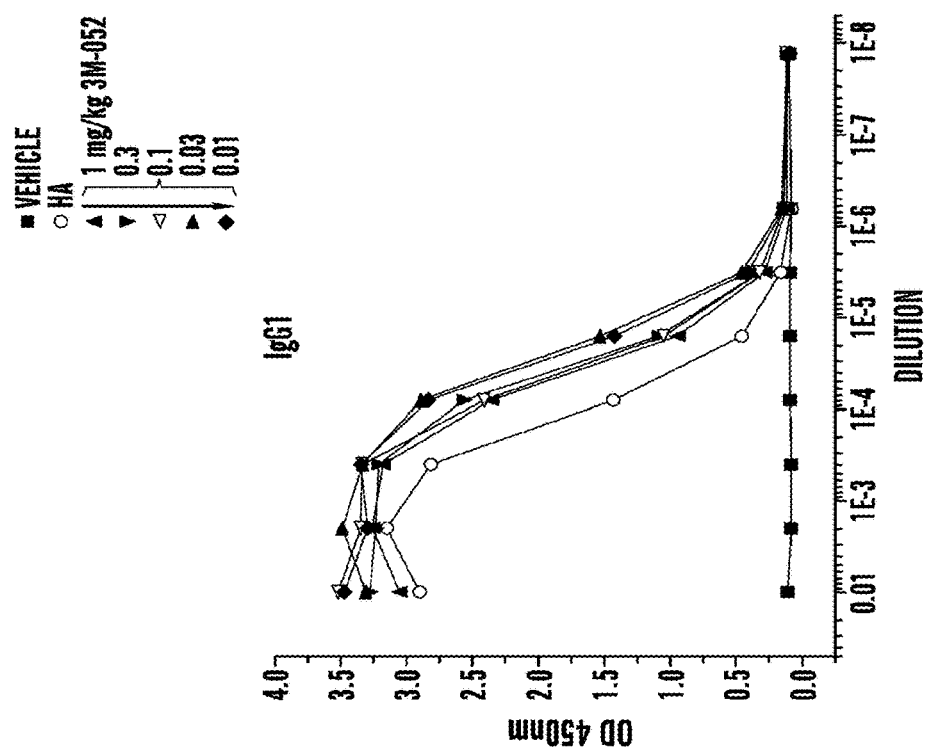

FIGS. 11A-11B demonstrate that 3M-052 enhances antigen-specific IgG levels while also skewing the response towards Th1 (IgG2a induction). Balb/c mice were immunized by subcutaneous injection (scruff of neck) with a 10 μg dose of influenza hemagglutinin (HA) alone, or in combination with 0.01, 0.03, 0.1, 0.3, or 1 mg/kg 3M-052 three times (prime, boost, boost) 14 days apart. Serum was collected at Day 77 (21 days after the final immunization) for measurement of HA-specific serum Ig levels by ELISA. Production of both serum (FIG. 11A) IgG1 and (FIG. 11B) IgG2a, indicate induction of a mixed Th1/Th2-response following immunization (n=5).

Figures 12A, 12B, 12C:
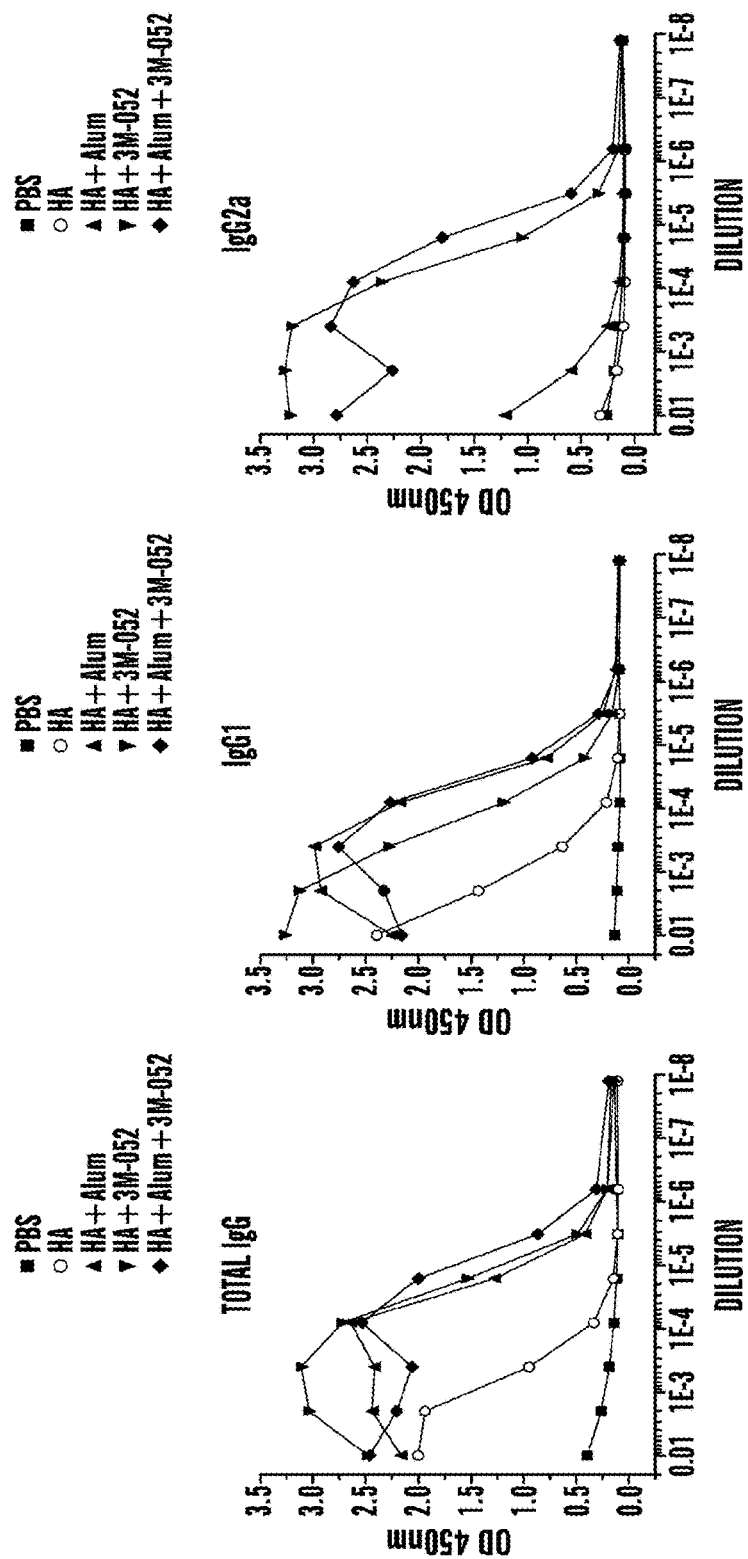

FIGS. 12A-12C demonstrate that addition of 3M-052 augments Th1-responses to alum adjuvanted influenza hemagglutinin antigen. Addition of 3M-052 to Alumadjuvanted HA antigen markedly enhances IgG2a Ab production. Balb/c mice were immunized by subcutaneous injection (scruff of neck) with a 10 μg dose of influenza hemagglutinin (HA) alone or in combination with Alum or 0.1 mg/kg 3M-052 three times (prime, boost, boost) 14 days apart. The results depict median HA-specific serum (FIG.

12A) IgG, (FIG. 12B) IgG1, and (FIG. 12C) IgG2a levels measured by ELISA on Day 77, which was 21 days after the final immunization (n=5).

Figure 13:
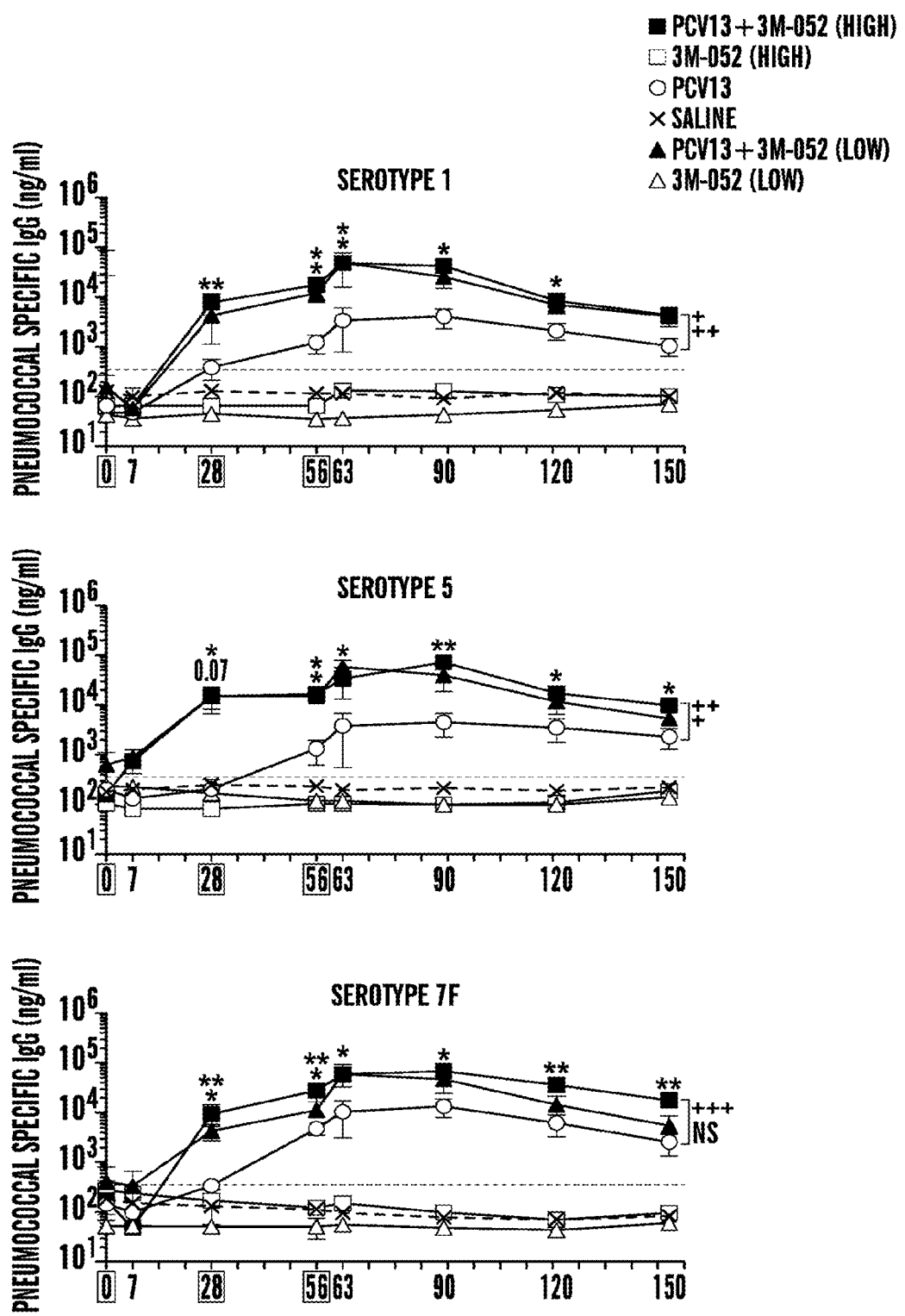
Figure 13:
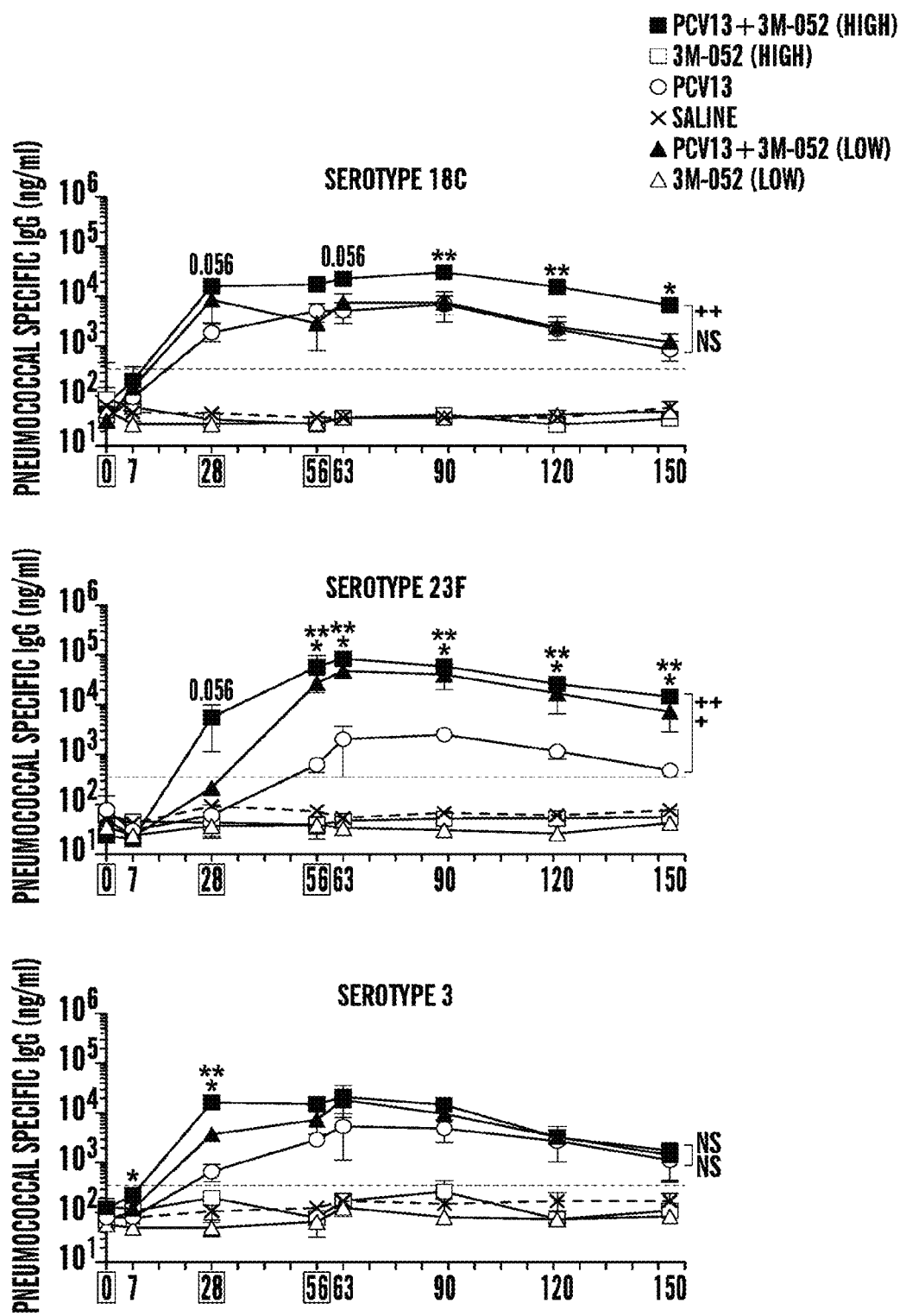
Figure 13:
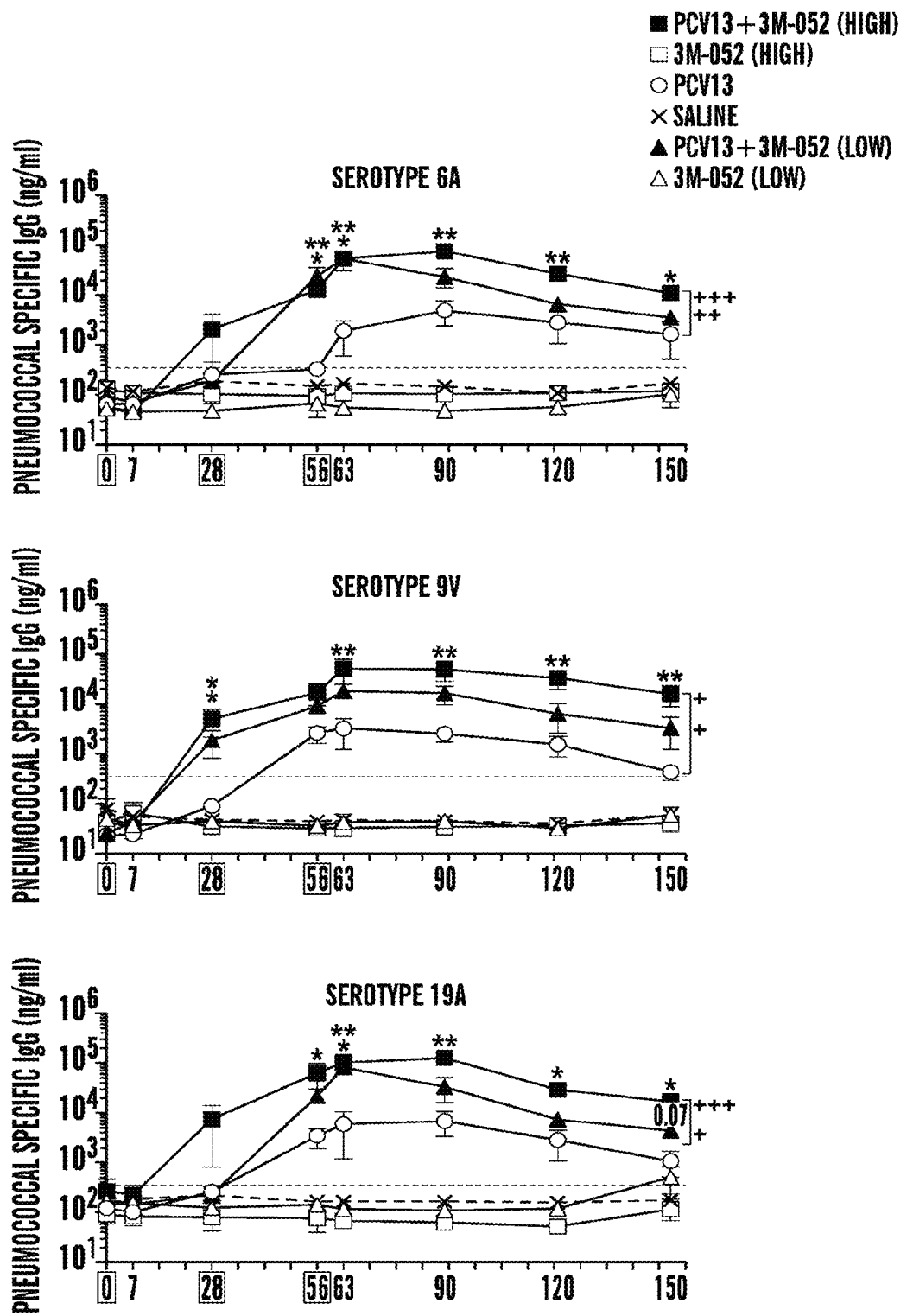
Figure 13:
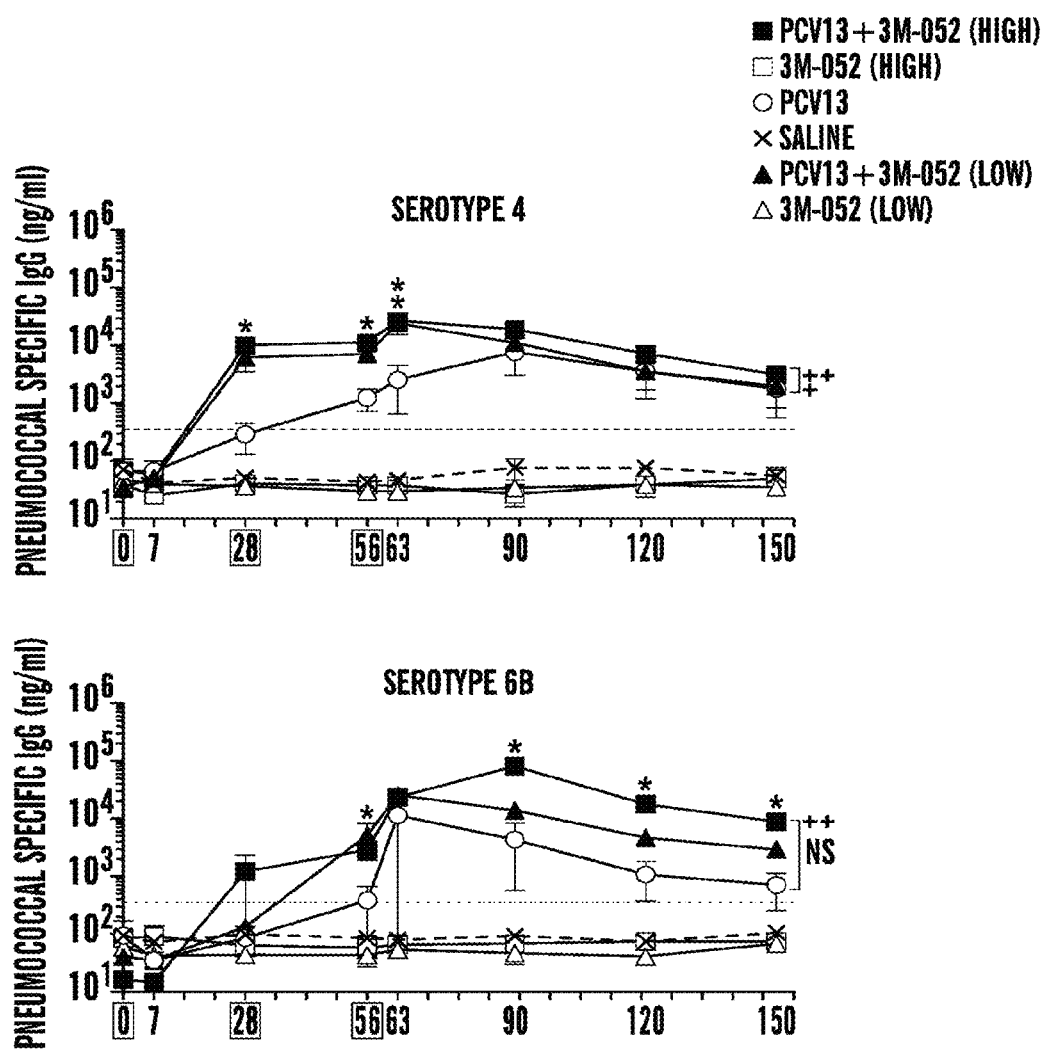
Figure 13:
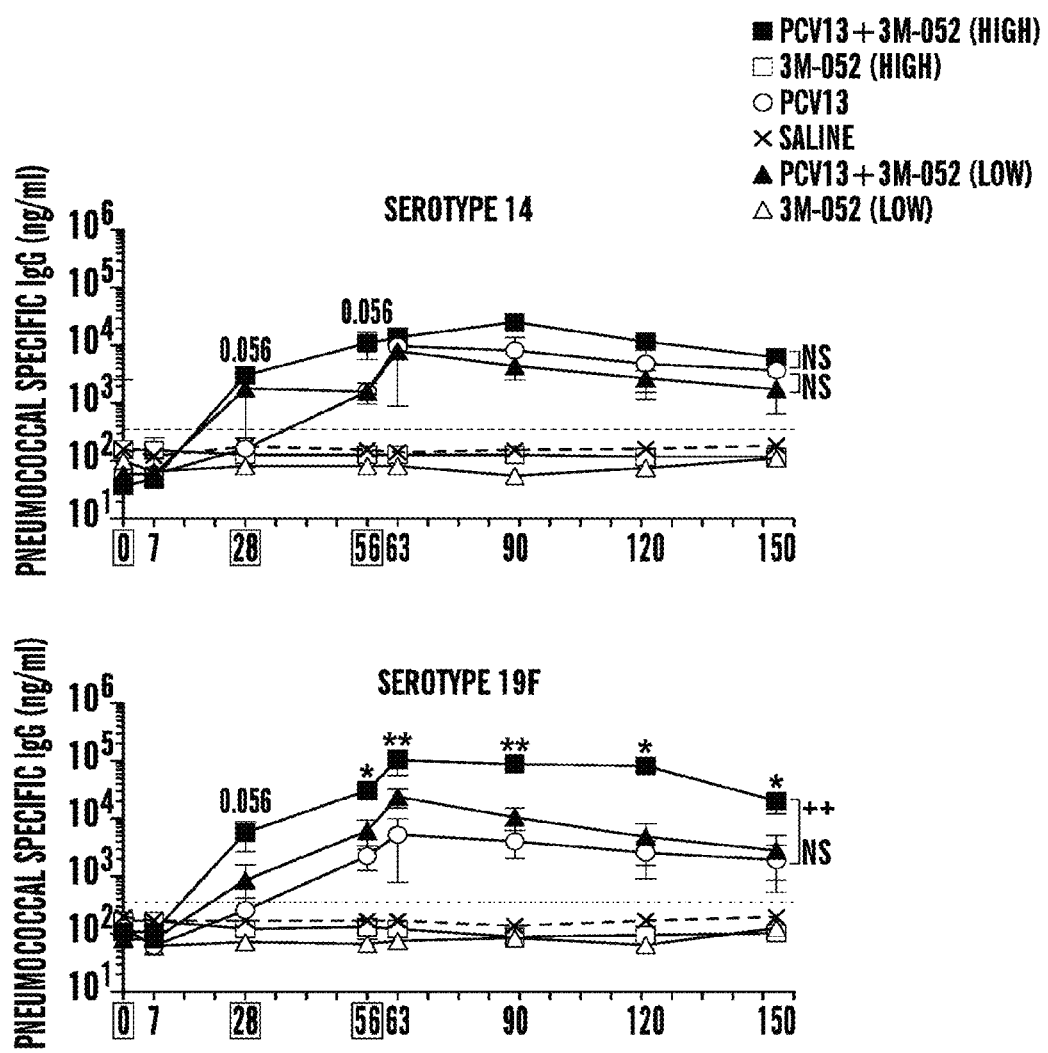

FIG. 13 demonstrates that Addition of a TLR7/8 agonist accelerates serotype-specific antibody responses to PCV13 in a dose dependent manner. Thirteen PCV13 serotypes are shown. Neonatal and infant rhesus macaques were immunized at DOL0, 28, and 56 with saline control, PCV13 alone, 3M-052 alone (0.01 or 0.1 mg/kg), or (PCV13+3M-052 (0.01 or 0.1 mg/kg)). Peripheral blood was collected at the indicated time-points to obtain serum for anti-pneumococcal serotype titers by polysaccharide-IgG binding microarray (n=3-5 per group) run in triplicate. Horizontal broken line indicates 0.35 µg/ml, the WHO recommended reference Ab concentration of IgG used as a correlate of protective levels in humans. For comparisons between overall groups (i.e., PCV13 vs. (PCV13+3M-052)), two-way repeated measures ANOVA for non-parametric sample populations were applied and statistical significance denoted as $+p<0.05$, $++p<0.01$, or NS (not significant). For comparison at individual time-points (i.e. PCV13 vs. (PCV13+3M-052) at DOL28), unpaired Mann-Whitney test was applied at each time-point. Results represent means±SEM, with statistical significance denoted as $*p<0.05$, $p<0.01$, $*p<0.001$.

Figure 14:
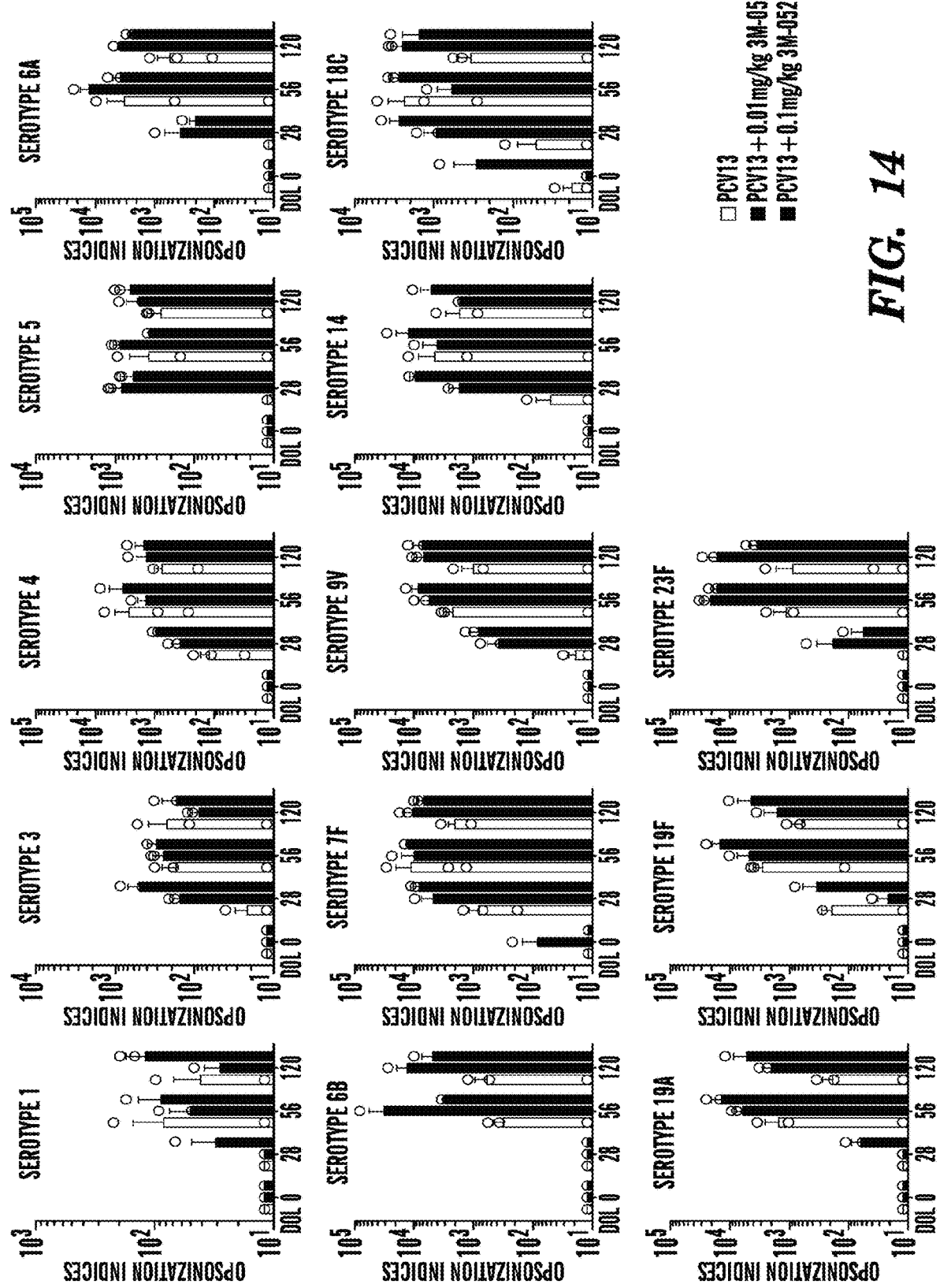

FIG. 14 demonstrates that TLR7/8 adjuvantation markedly accelerates and enhances serotype-specific pneumococcal opsonophagocytic killing capacity in neonatal serum. Neonatal and infant rhesus macaques were immunized at DOL0, 28, and 56 with either PCV13 alone or (PCV13+3M-052). Peripheral blood was collected at the indicated time-points to obtain serum for measurement of IgG concentrations and opsonization indicies (OIs) as described in Example 1. Geometric mean titers of serotype-specific opsonophagocytic killing activity from n=3 rhesus macaques per treatment group are shown. Samples with undetectable OIs were assigned an OI of 12. Results represent means±SEM.

Figure 15A:
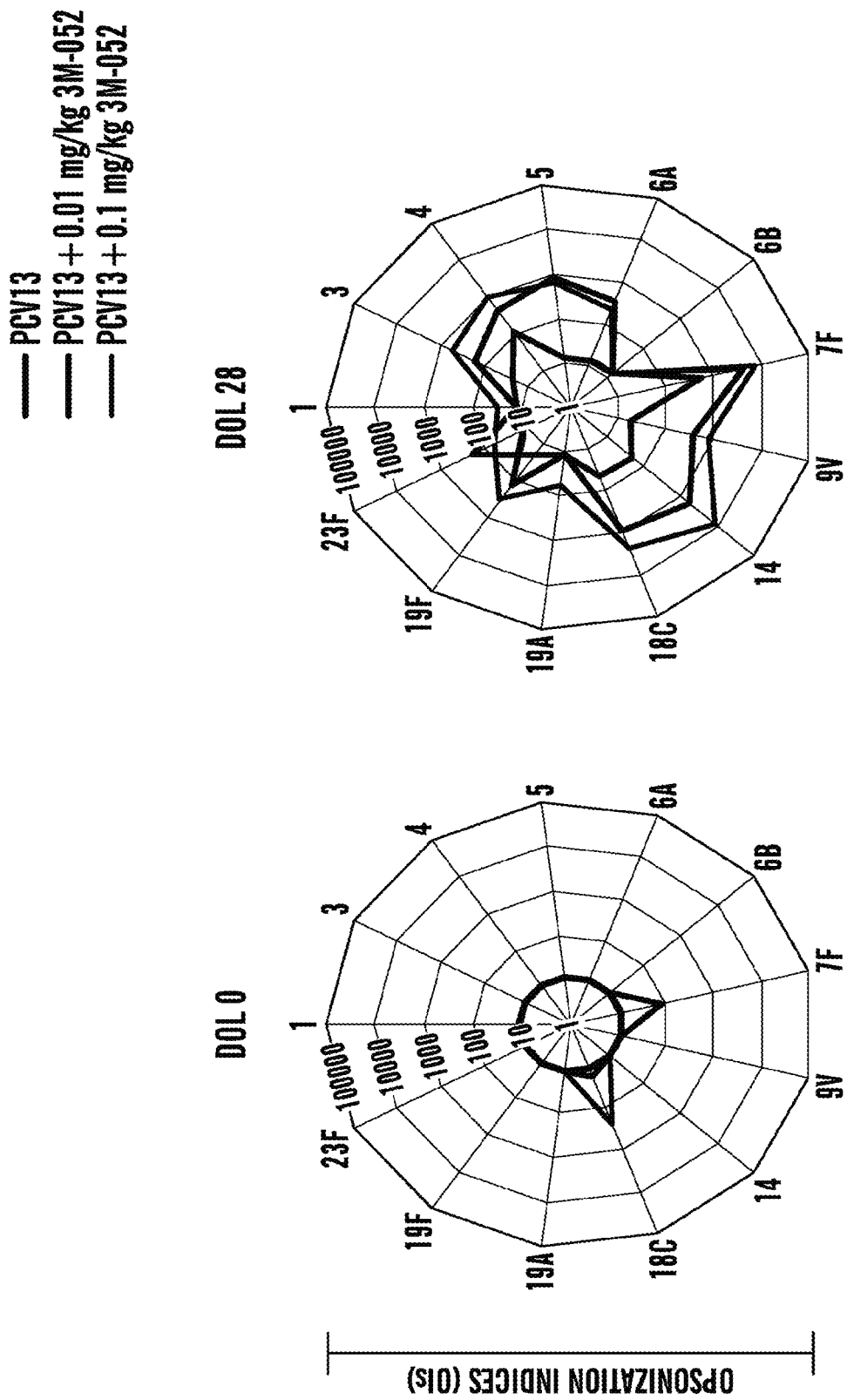
Figure 15A:
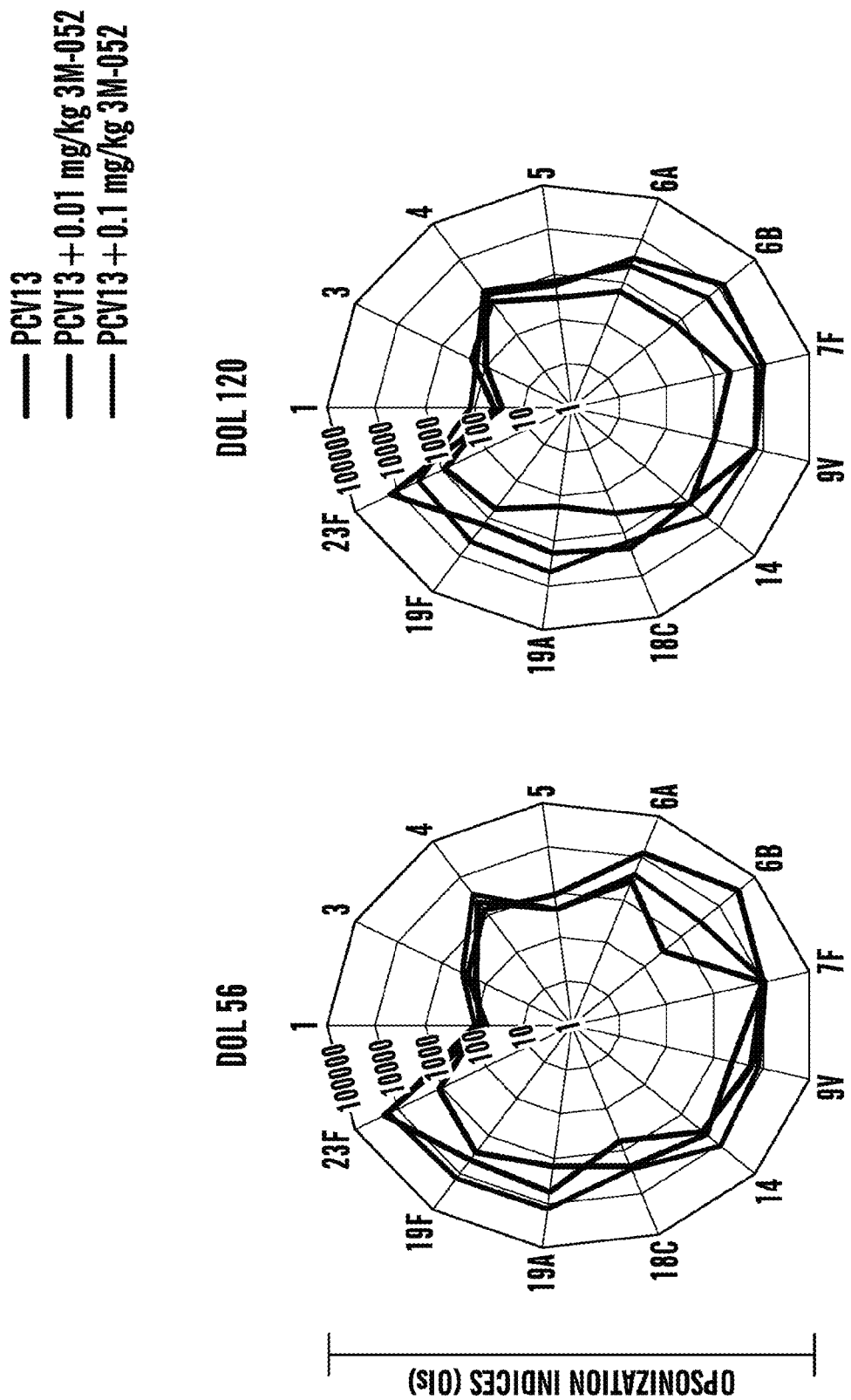
Figure 15B:
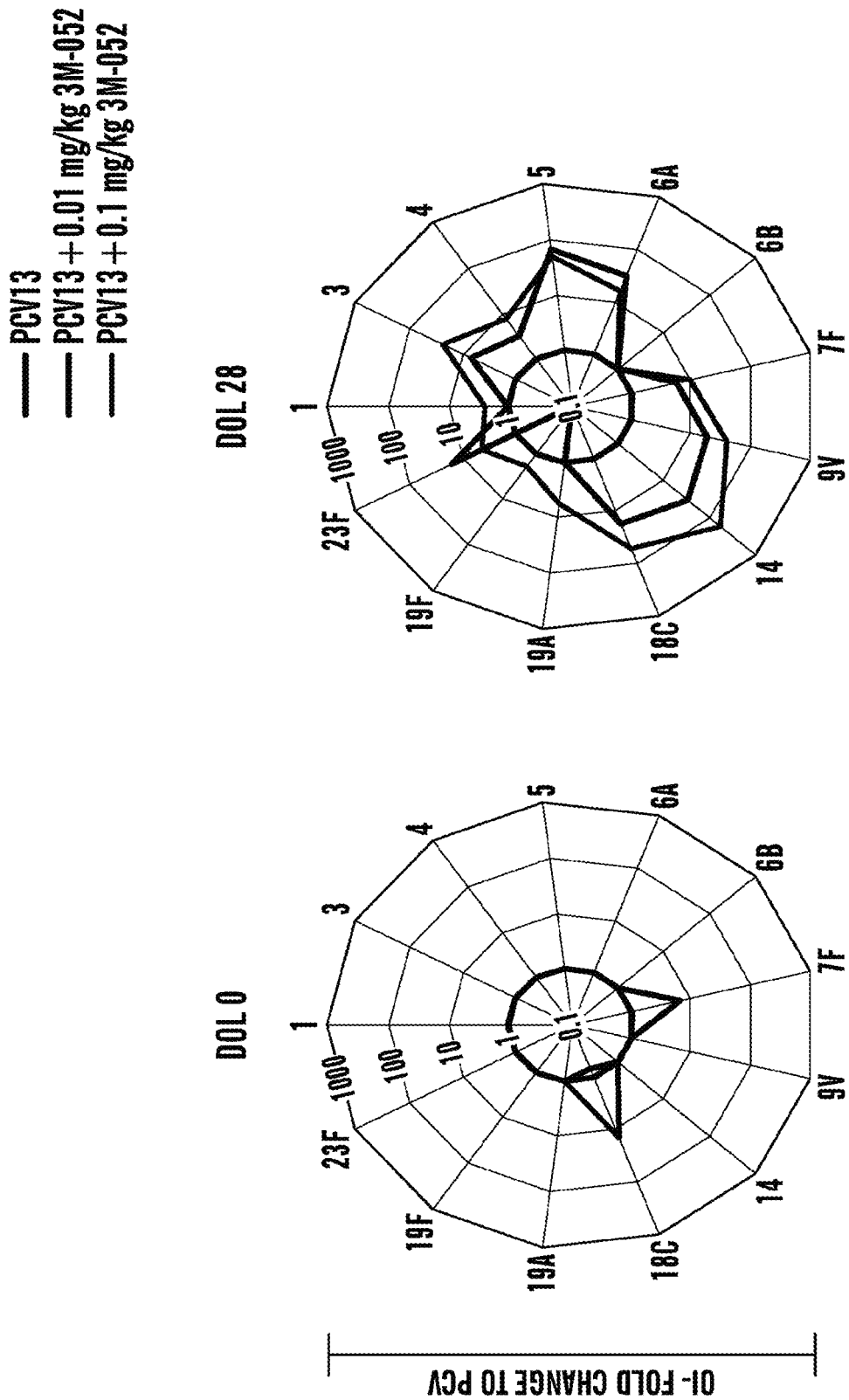
Figure 15B:
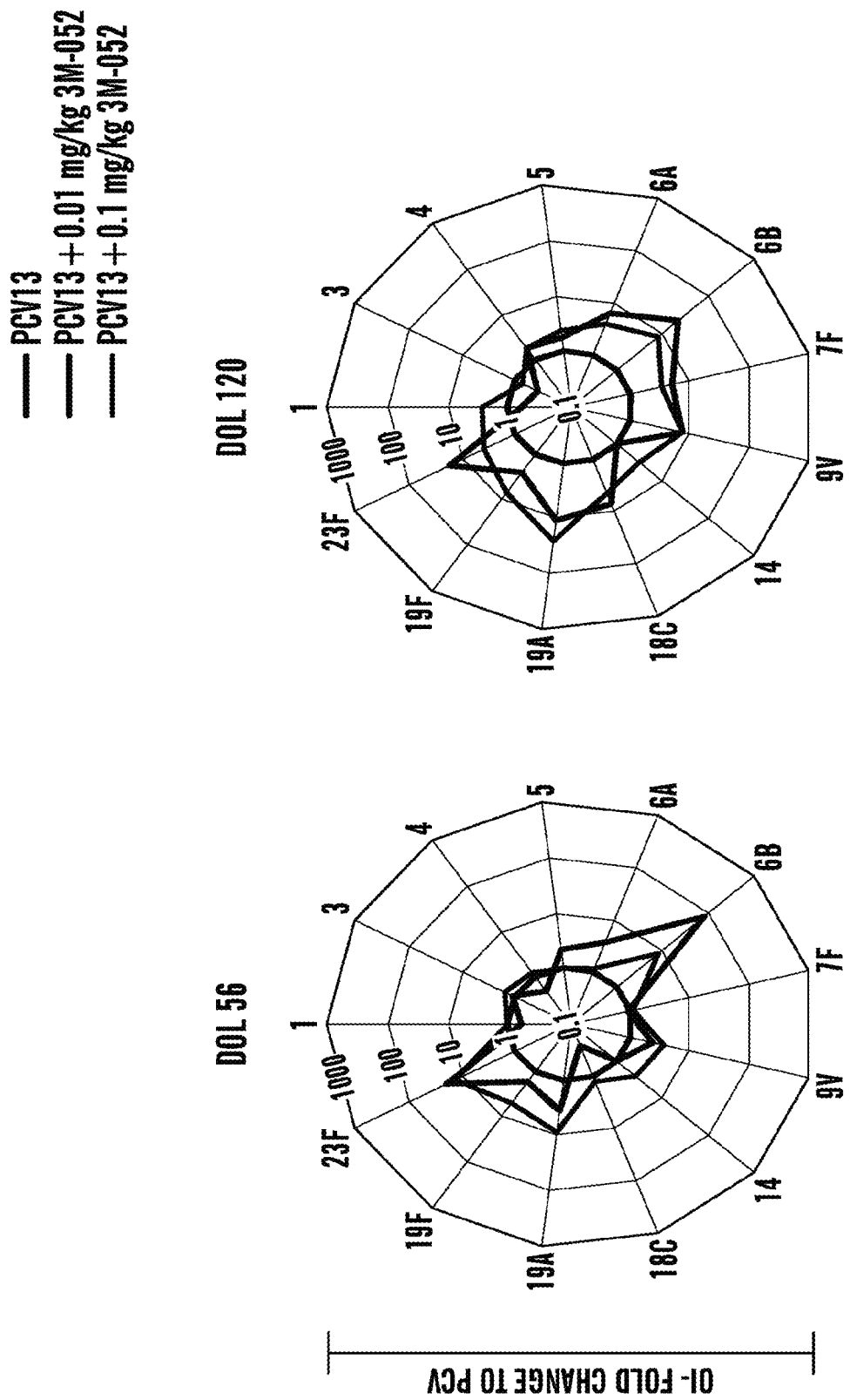

FIGS. 15A-15B demonstrate that TLR7/8 adjuvantation dramatically accelerates and enhances serotype-specific pneumococcal opsonophagocytic killing capacity in neonatal serum. Neonatal and infant rhesus macaques were immunized at DOL0, 28, and 56 days with either PCV13 alone or PCV13 co-administered with 3M-052. Peripheral blood was collected at the indicated time-points to obtain serum. Average geometric mean titers of serotype-specific opsonophagocytic killing activity from rhesus macaques per treatment group (n=3). The results are expressed as opsonization indices (OIs), defined as the interpolated dilution of serum that kills 50% of bacteria. Samples identified as negative in the assay (i.e., samples having no functional activity detected) were assigned an OI of 12. Radar plot analysis of all 13 serotypes tested, including raw OI (FIG. 15A) and fold-change analysis (FIG. 15B) at DOL0, 28, 56, and 120. After a single dose of (PCV13+3M-052), all immunized infants exceeded this level for all 13 serotypes tested.

Figure 16:
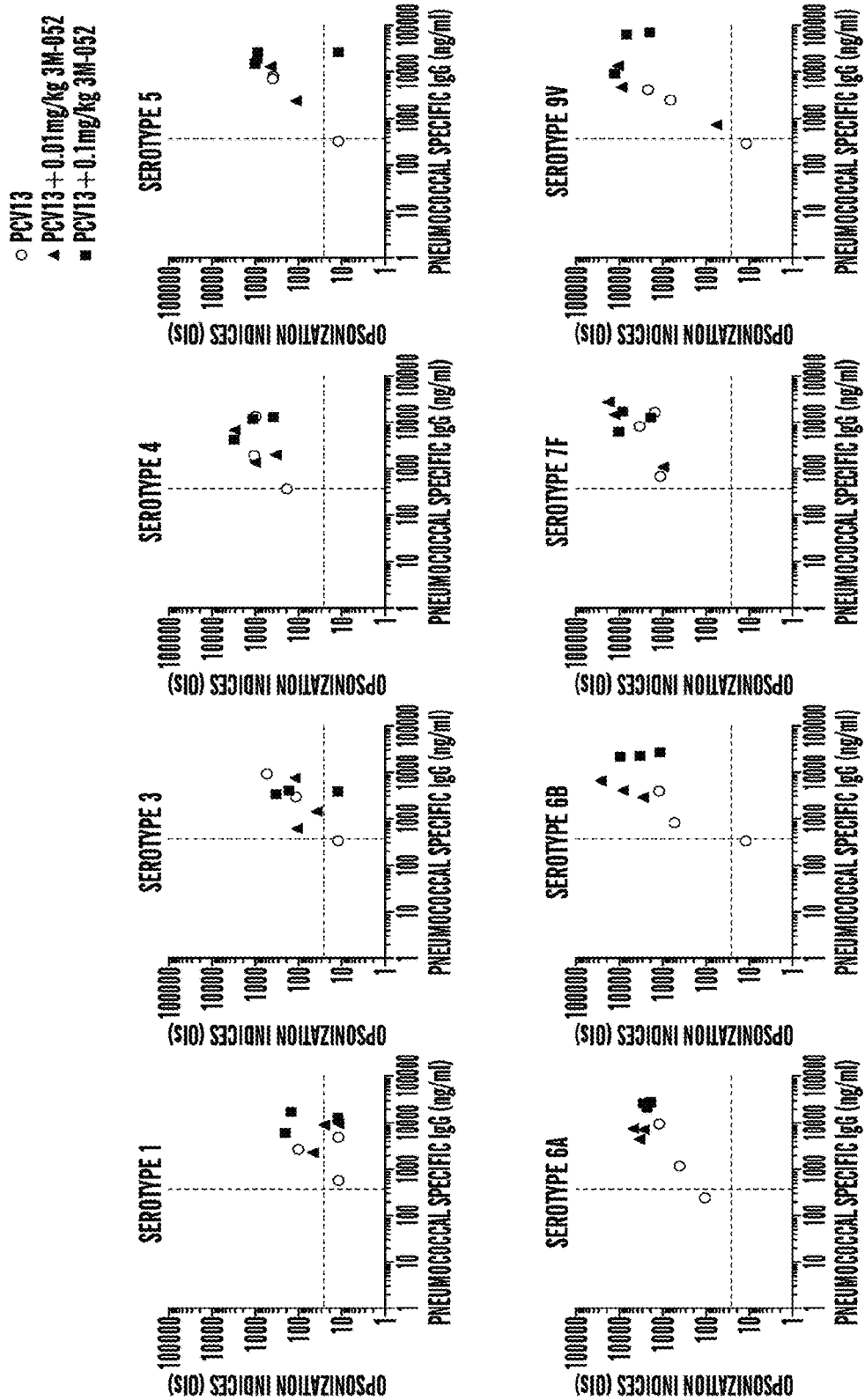
Figure 16:
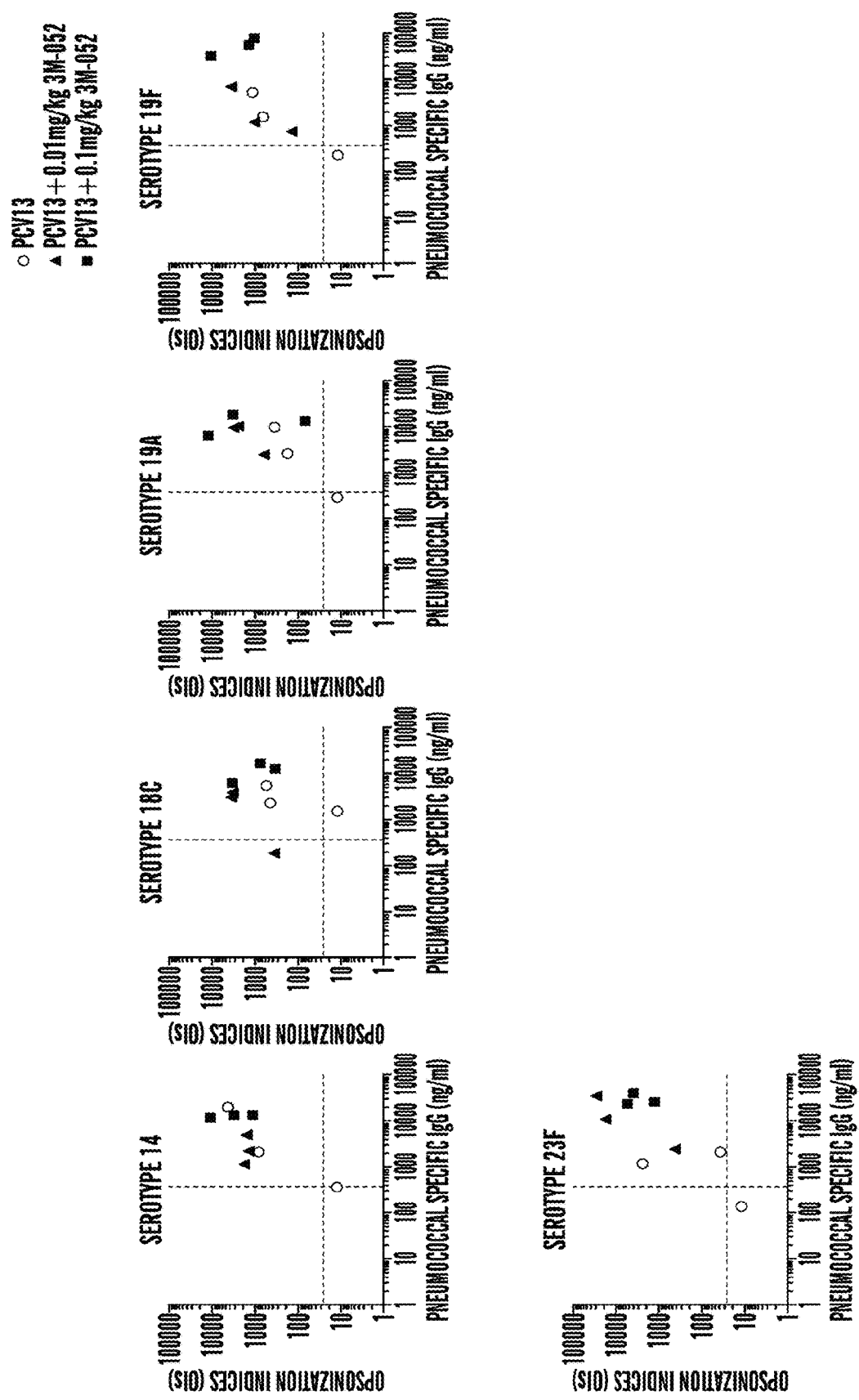

FIG. 16 demonstrates day 28 opsonophagocytic killing activity corresponds with accelerated serotype-specific antibody responses to TLR7/8 agonistadjuvanted pneumococcal conjugate vaccine. Neonatal and infant rhesus macaques were immunized at DOL0 with either PCV13 alone or (PCV13+3M-052). Peripheral blood was collected at the indicated time-points to obtain serum for measurement of IgG concentrations and opsonization indicies (OIs) as described in Example 1. Day 28 post-first immunization OIs (y-axis) are plotted as a function of IgG concentrations (x-axis) depicted as geometric mean titers (n=3 per treatment group). Samples with undetectable OIs were assigned an OI of 12. Results represent means±SEM.

Figure 17:
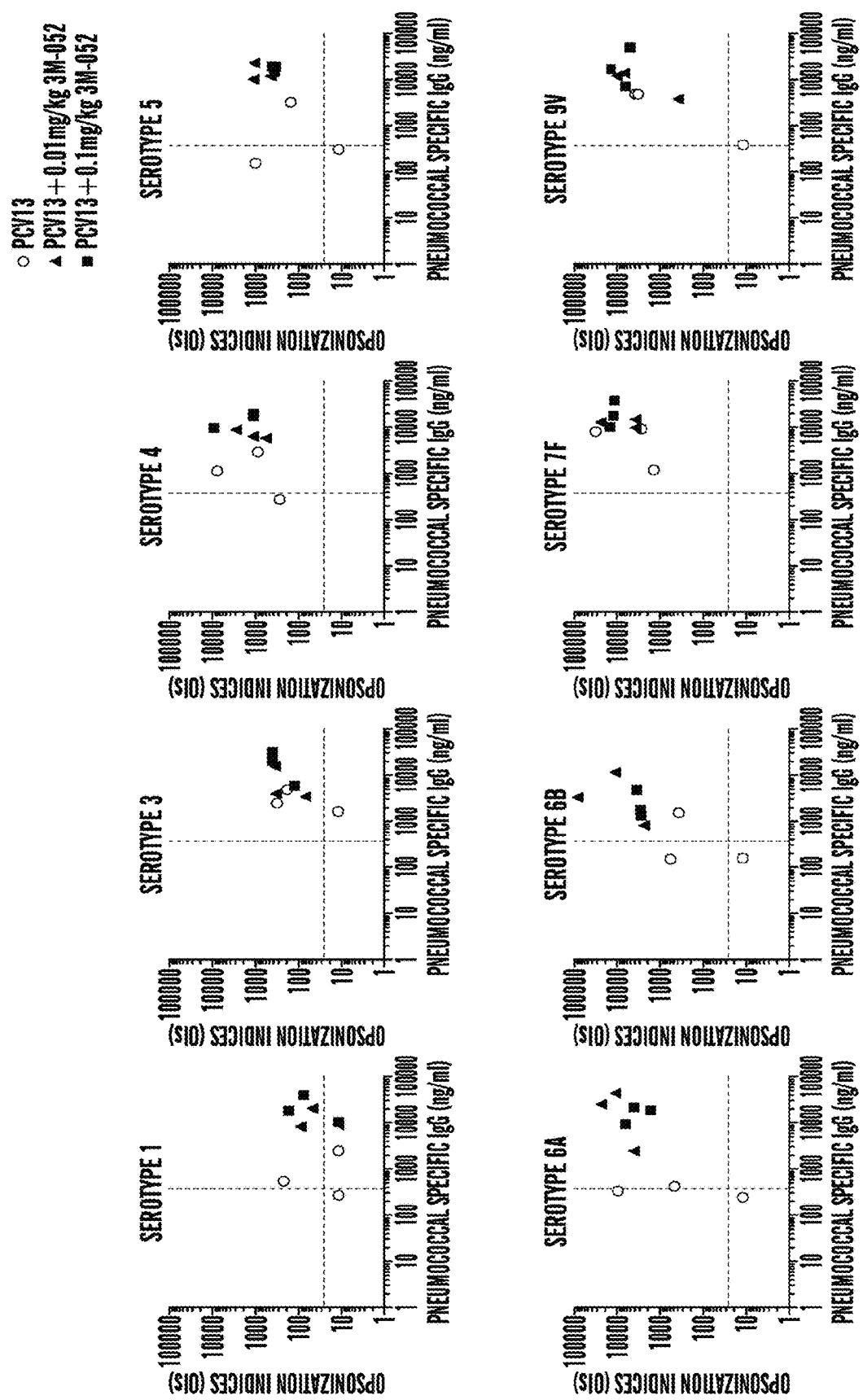
Figure 17:
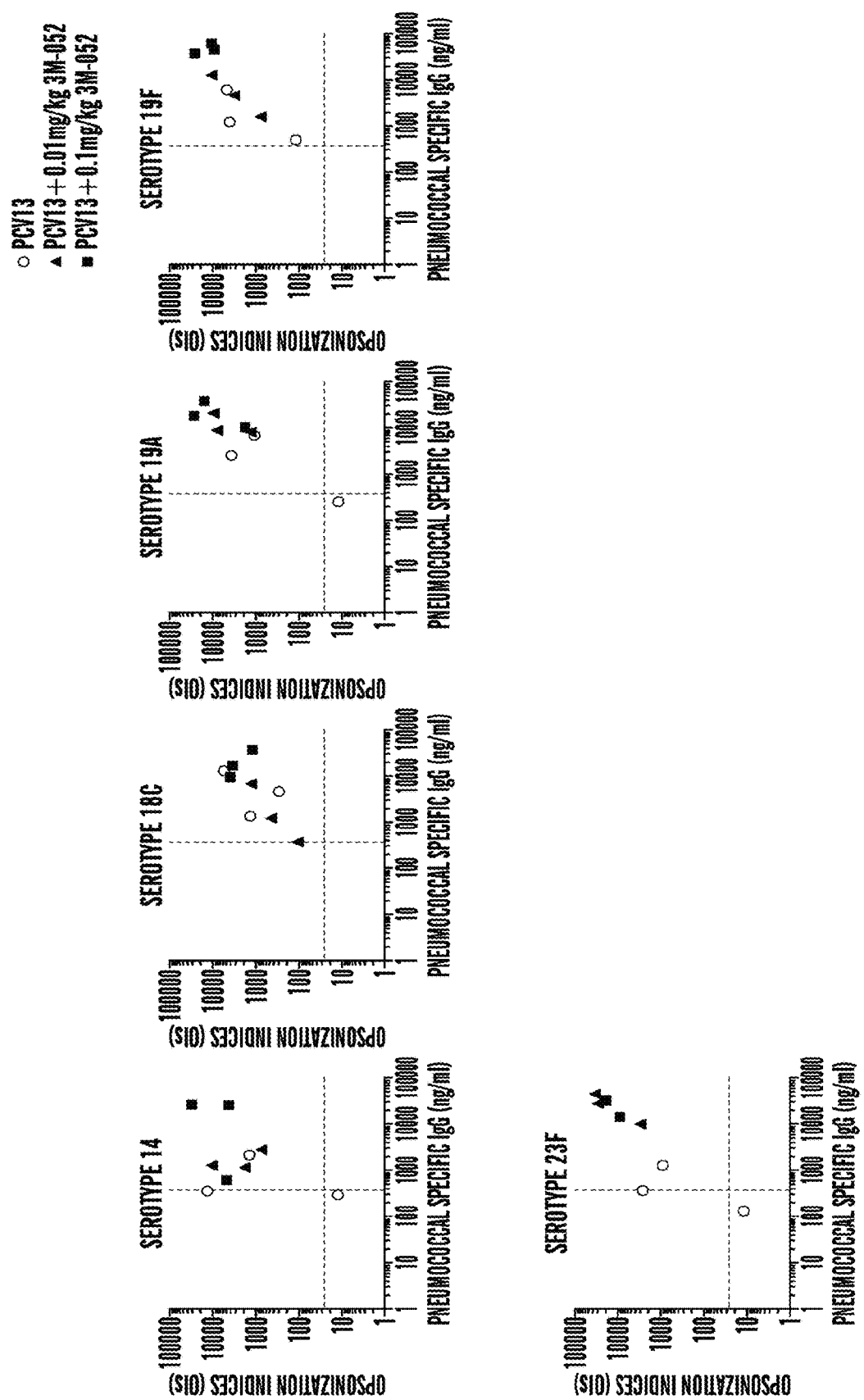

FIG. 17 demonstrates that TLR7/8 agonist-adjuvantation of PCV13 enhances Day 56 opsonophagocytic killing activity. Neonatal and infant rhesus macaques were immunized at DOL0 and 28 with either PCV13 alone or (PCV13+3M-052). Peripheral blood was collected at the indicated time-points to obtain serum for measurement of IgG concentrations and opsonization indicies (OIs) as described in Example 1. Day 56 post-first immunization OIs (y-axis) are plotted as a function of IgG concentrations (x-axis) depicted as geometric mean titers (n=3 per treatment group). Samples with undetectable OIs were assigned an OI of 12. Results represent means±SEM.

Figure 18:
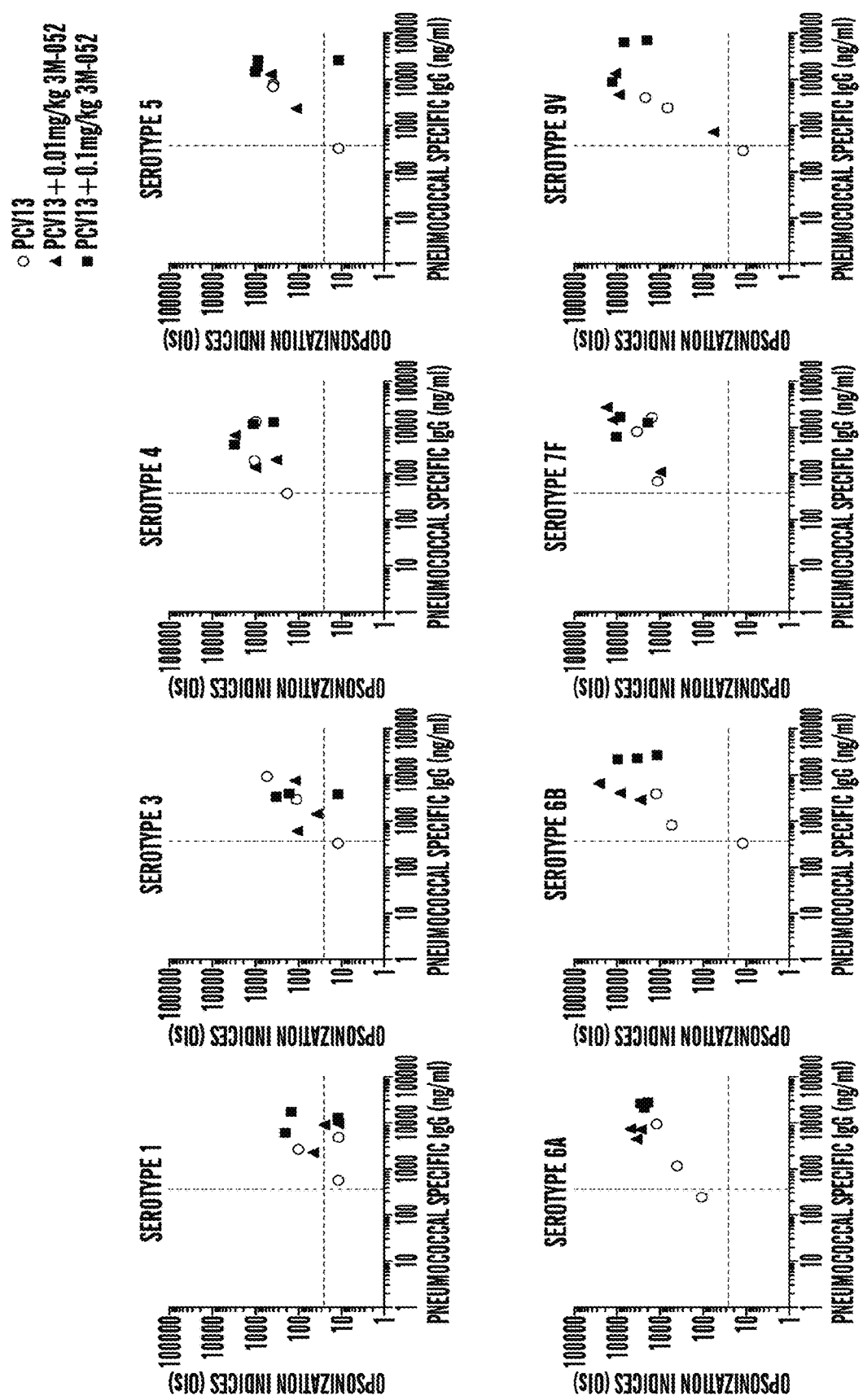
Figure 18:
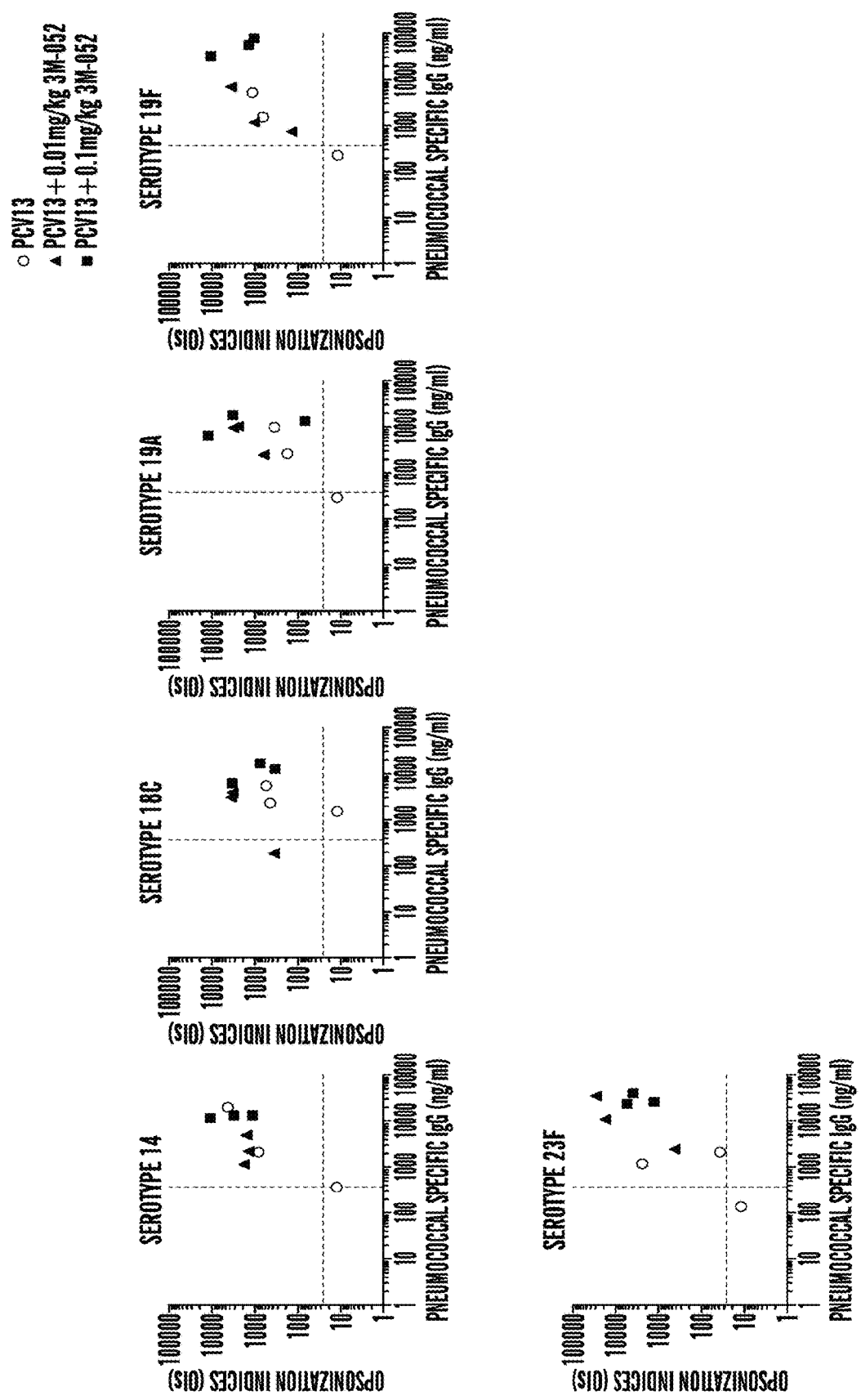

FIG. 18 demonstrates that TLR7/8 agonist-adjuvantation of PCV13 enhances Day 120 opsonophagocytic killing activity. Neonatal and infant rhesus macaques were immunized at DOL0, 28, and 56 with either PCV13 alone or (PCV13+3M-052). Peripheral blood was collected at the indicated time-points to obtain serum. Day 120 post-first immunization OIs (y-axis) are plotted as a function of IgG concentrations (x-axis) depicted as geometric mean titers (n=3 per treatment group). Samples with undetectable OIs were assigned an OI of 12. Results represent means±SEM.

Figure 19A:
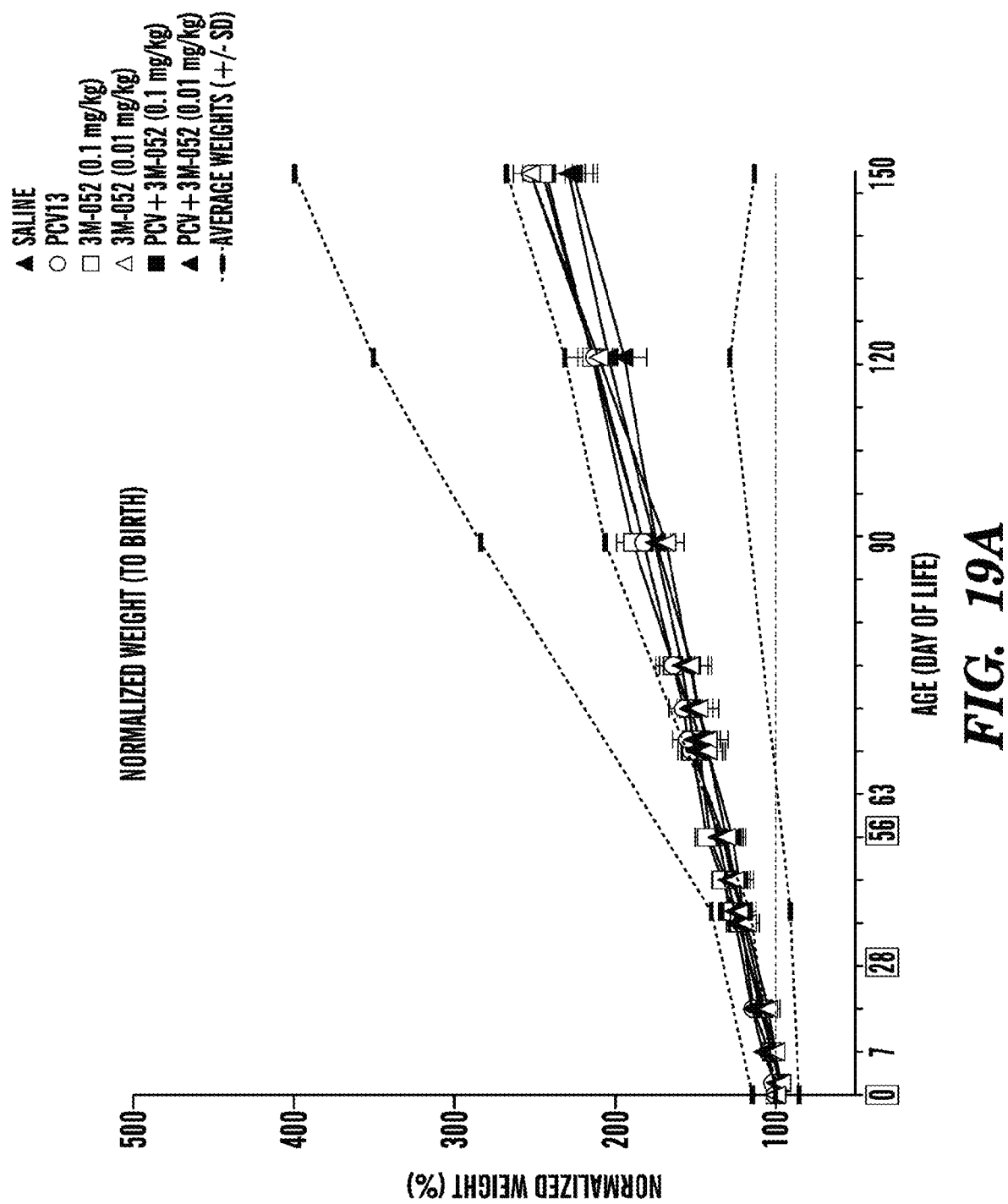
Figure 19B:
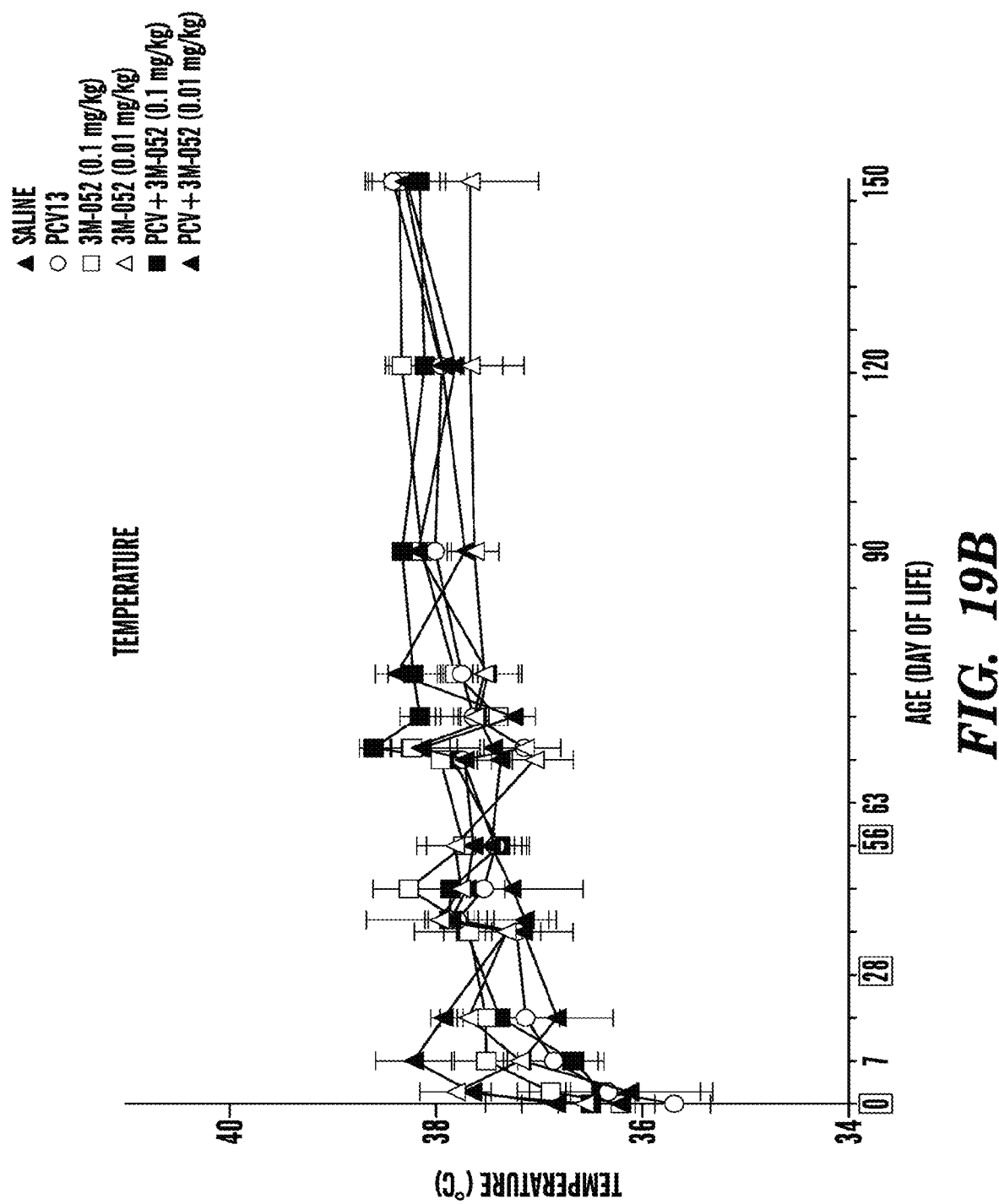
Figure 19C:
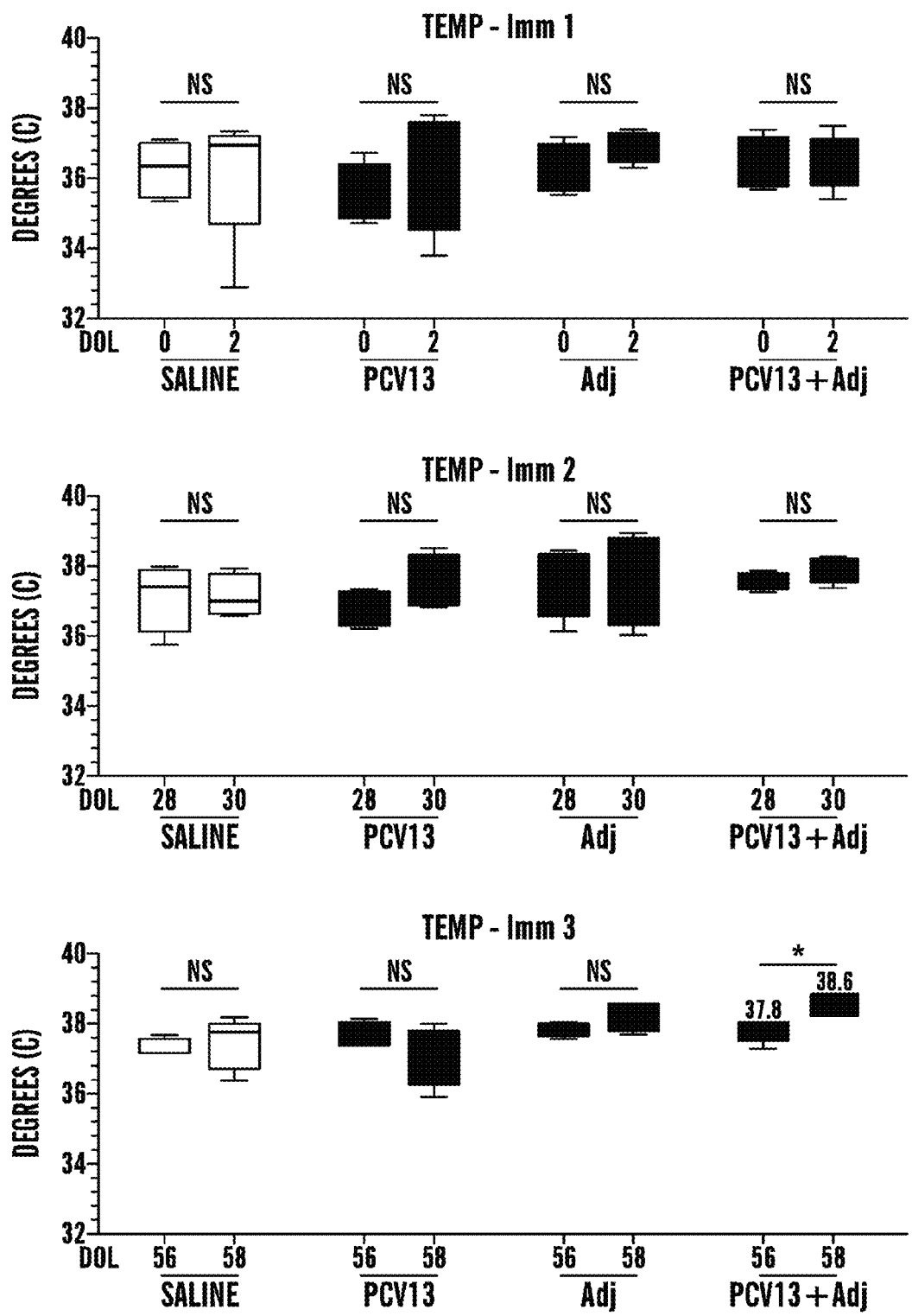

FIGS. 19A-19C demonstrate that weight and body temperature of immunized neonatal and infant rhesus macaques. FIG. 19A: Weight, a sensitive indicator of neonatal wellbeing, was measured regularly to DOL150 and are depicted as normalized values relative to birth weight (100%) for each treatment group. Dotted lines indicate normal age-matched norms with standard deviations. FIG. 19B: Body temperature was measured by rectal thermometer at regular intervals up to DOL150. FIG. 19C: Body temperatures pre- and post-each immunization at DOL0, 28, and 56. For comparison at individual time-points, the unpaired Mann-Whitney test was applied, with statistical significance denoted as $*p<0.05$. Results represent means±SEM of 3-5 animal's per group.

Figure 20A:
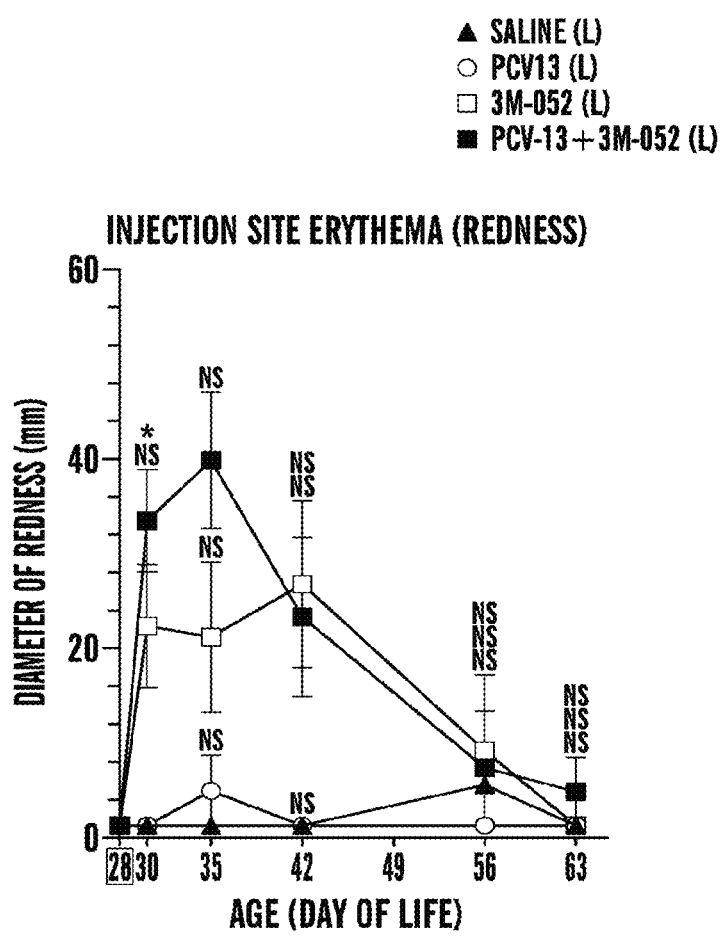
Figure 20B:
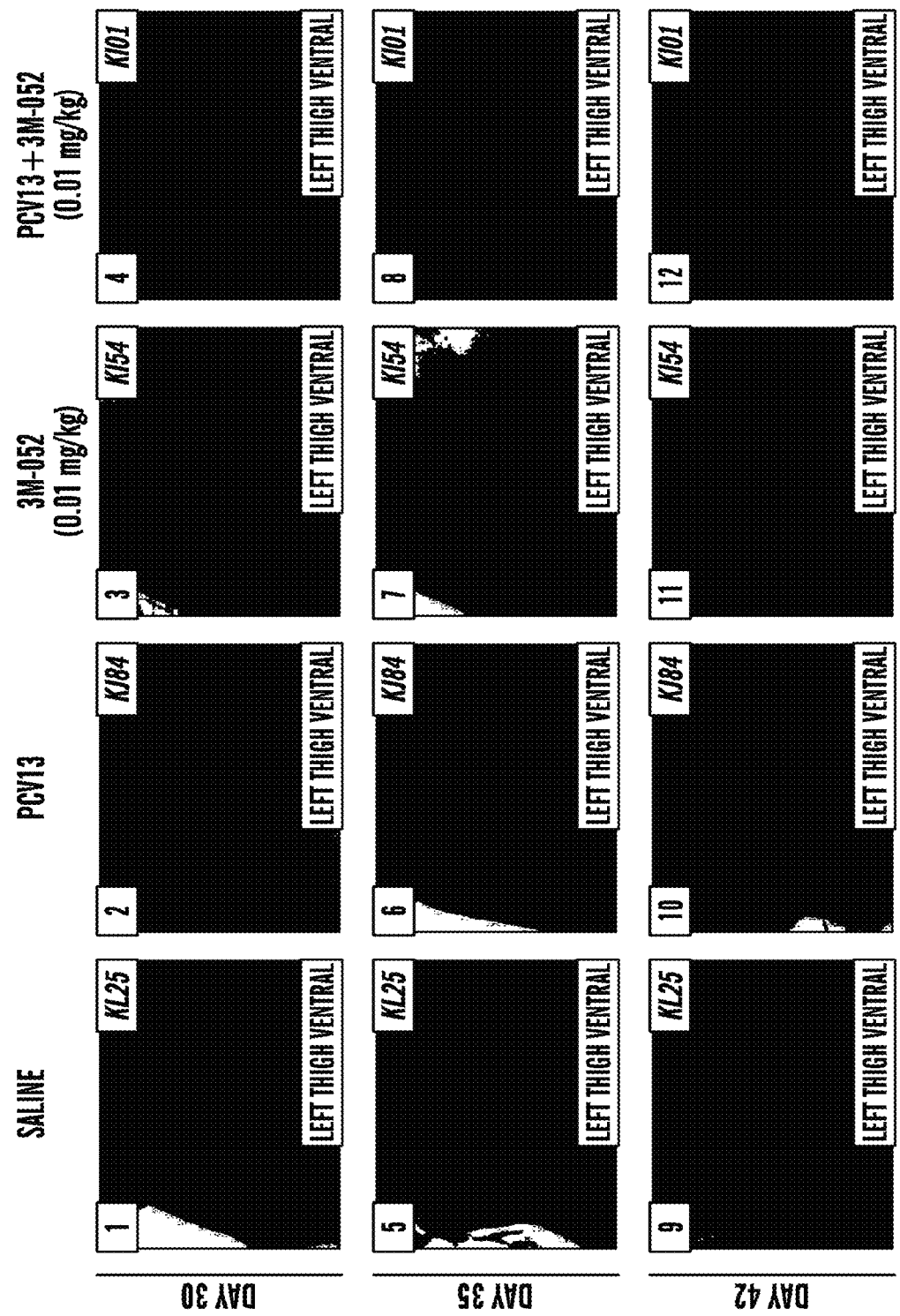

FIGS. 20A-20B demonstrate that Intramuscular injection of 3M-052 induces injection site erythema post-second immunization. Neonatal and infant rhesus macaques were immunized at DOL0, 28, and 56 with either PCV13 alone or (PCV13+3M-052). FIG. 20A: Significant injection site erythema (diameter of redness in mm as measured using calipers), as compared to saline (n=5), was only observed after the second of three immunizations with PCV13 co-administered with 3M-052 (n=8, combining both 0.01 and 0.1 mg/kg treatment groups). FIG. 20B: Photographs are labeled 1-12 in the top left corner and each individual animal study identification code is indicated in the top right corner of each image. Left thigh ventral photography of representative infant rhesus macaques on DOL30 (images 1-4), 35 (images 5-8), and 42 (images 9-12). While there was a trend towards increased erythema for some individual animals treated with 3M-052 or (PCV13+3M-052), no significant erythema at the site of injection was observed pre- or post-first or third immunization. As the maculopapular rash was only observed in a) the second of two birthing/enrollment seasons, b) co-housed animals and c) 3 of the total of 16 3M-052- (or (PCV13+3M-052))-treated infant animals, it was unclear whether it was adjuvant-related. For comparison at individual time-points, the unpaired Mann-Whitney test was applied, with with statistical significance denoted as $*p<0.05$ or NS (not significant) as compared to saline treatment group. Results represent means±SEM.

Figure 21A:
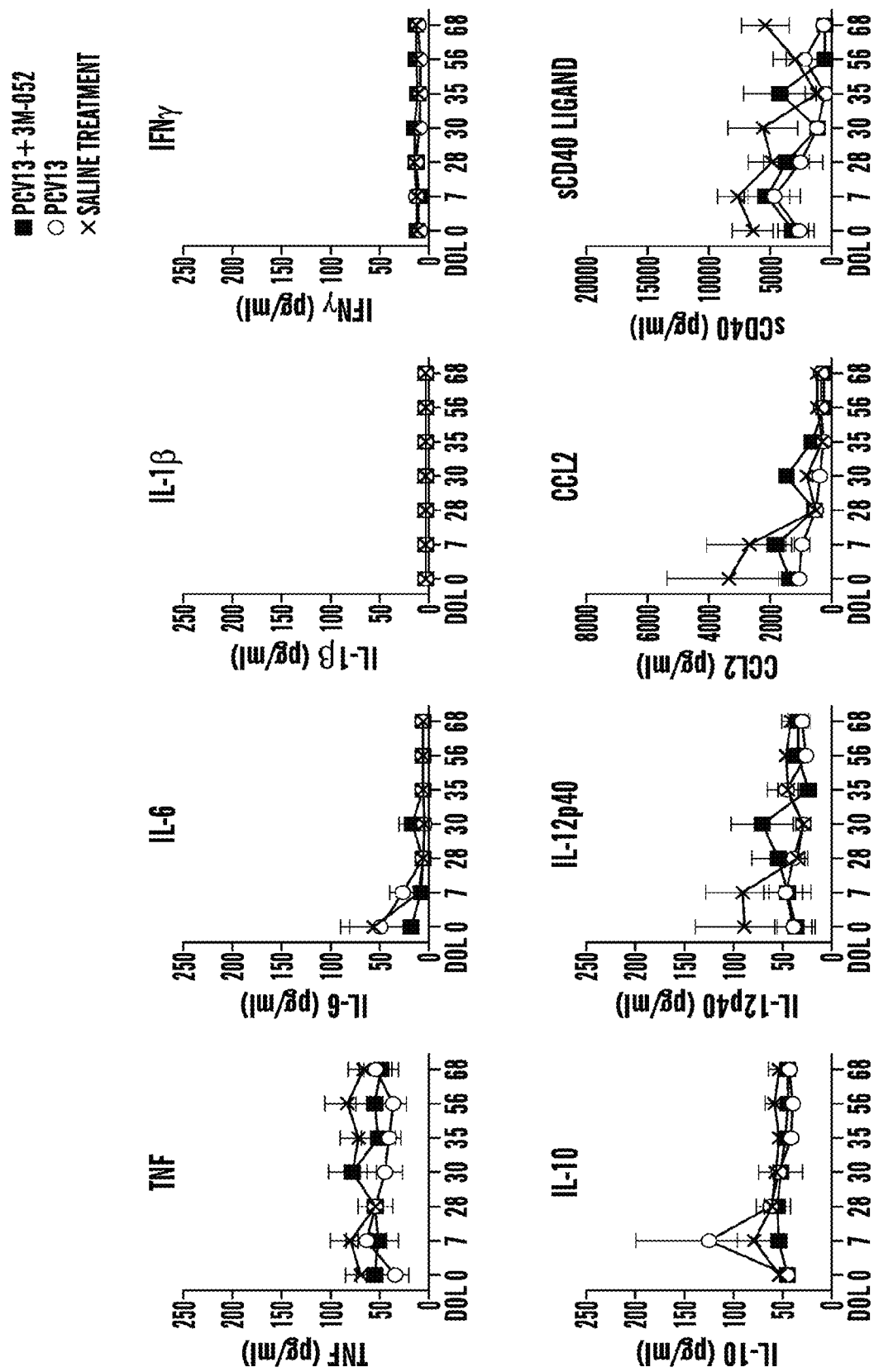
Figure 21D:
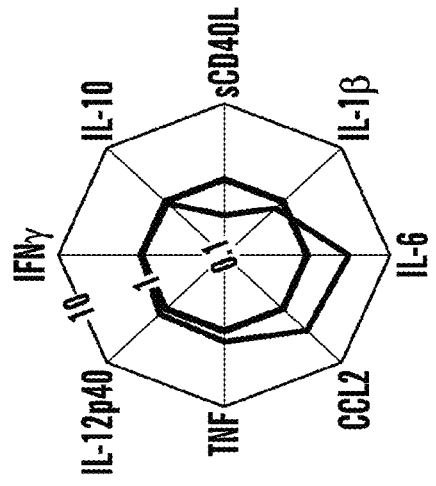
Figure 21C:
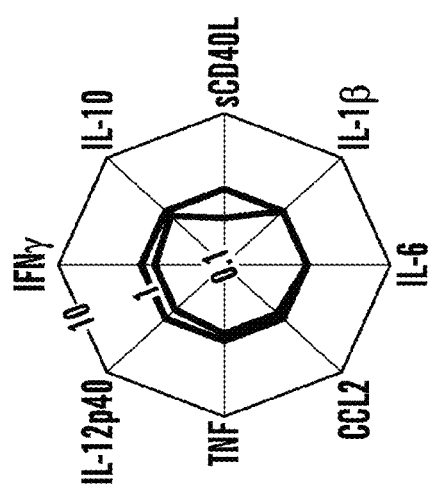
Figure 21B:
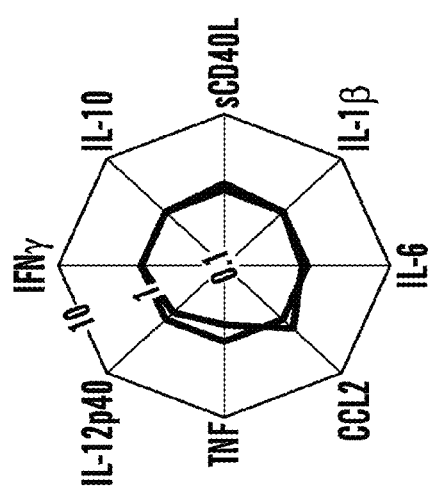

FIGS. 21A-21D demonstrate that 3M-052 administration with or without PCV13 does not induce systemic cytokines in neonatal/infant rhesus macaques. FIG. 21A: Evaluation of rhesus plasma cytokine kinetics post-each dose of IM PCV13 or (PCV13+0.1 mg/kg 3M-052) formulated in O/W emulsion (vehicle) or Saline (n=3-5). FIGS. 21B-21D: Evaluation of rhesus plasma cytokine pre- (DOL28) and post- (DOL30) single dose of (PCV13+0.1 mg/kg 3M-052) (n=3-4).

Figure 22A:
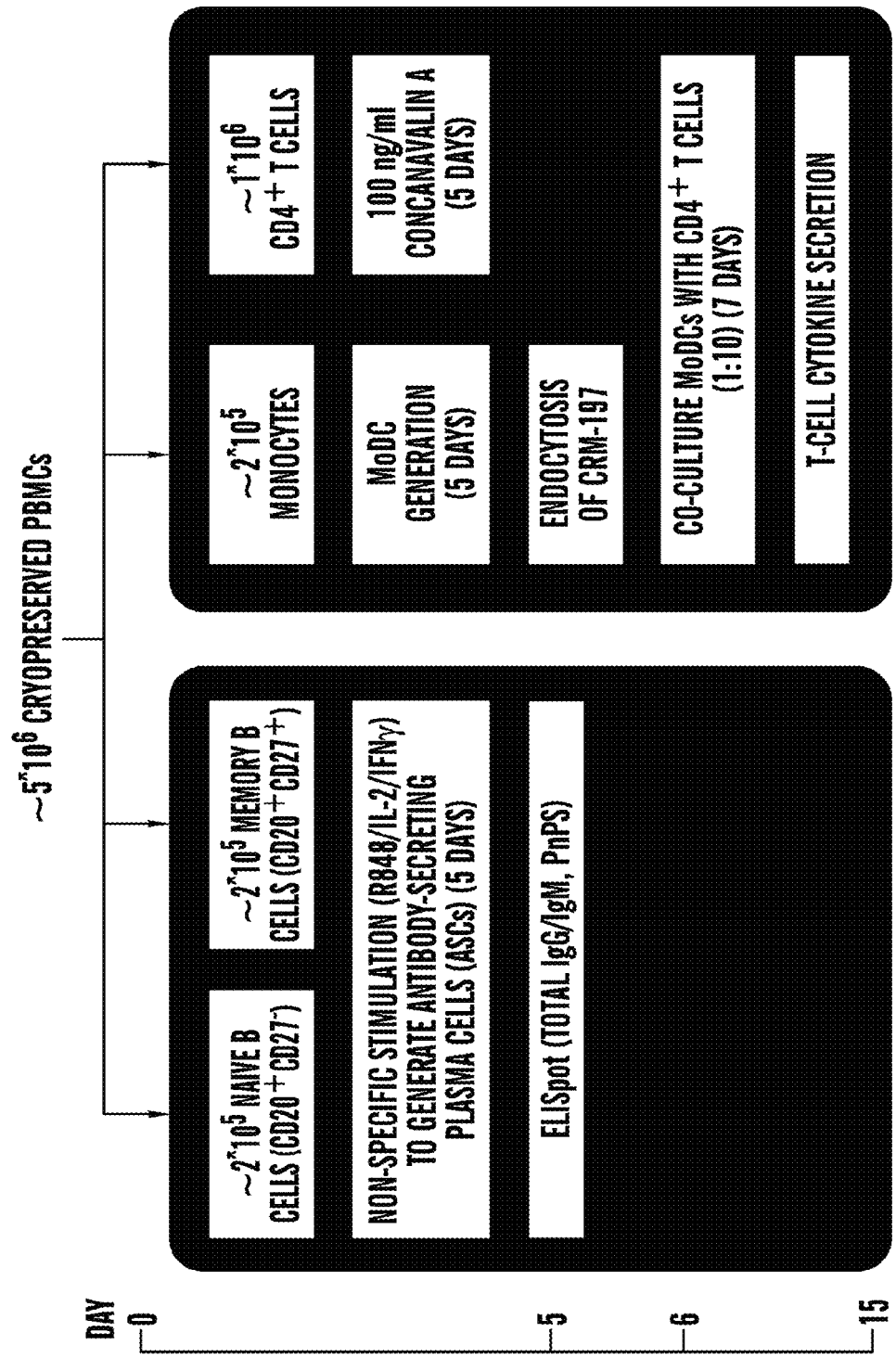
Figure 22B:
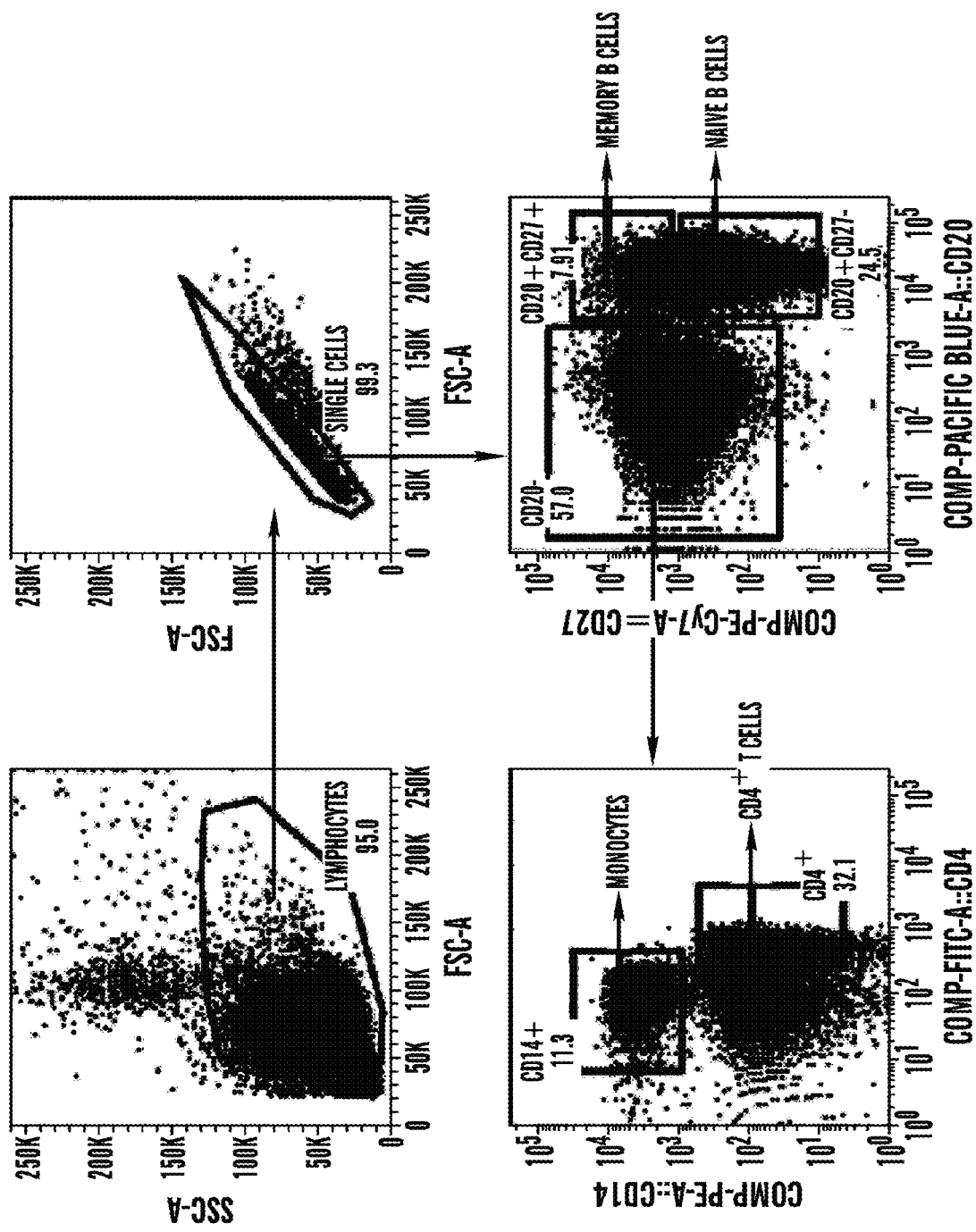

FIGS. 22A-22B demonstrate experimental approach used for mononuclear cell sorting and ex vivo assessment of vaccine-specific B and T cells in infant rhesus macaques. FIG. 22A: Sorted leukocytes were incubated as depicted. B cell subsets (left) were non-specifically stimulated with R848/IL-2/IFNγ to induce differentiation to Ab-secreting plasma cells. Plasma cells were subsequently plated on ELISpot plates for detection of pneumococcal polysaccharide (PnPS)-specific B cells. Monocytes were differentiated to monocyte-derived dendritic cells (MoDCs) by the addition of GM-CSF and IL-4. After treatment of MoDCs with CRM197 (the protein component of PCV13), cells were co-cultured with CD4+ and CD8+ T cells and activation of vaccine-specific T cells was measured. FIG. 22B: Frozen PBMCs were thawed and stained with CD20-Pacific Blue, CD27-PE.Cy7, CD14-PE, CD4-FITC, and CD8-APC.Cy7. Cells were subsequently sorted according to the gating strategy depicted on a FACSAria II cytometer.

FIGS. 23A-23D demonstrate that 3M-052 accelerated and enhanced the magnitude of neonatal and infant anti-PnPS antibody (IgG) responses and may enhance antibody avidity. Ab titer to pneumococcal conjugate vaccine serotypes 4, 6B, 14, and 23F were compared and confirmed using (FIG. 23A) WHO recommended ELISA total (n=3), (FIG. 23B) 96-well electrochemiluminescence (ECL) multiplex assay (n=5). Ab titer to all 13 pneumococcal conjugate vaccine serotypes were compared and confirmed using (FIG. 23C) ELISA and (FIG. 23D) avidity assay (n=3). For comparisons between overall groups (i.e., PCV13 vs. (PCV13+3M-052)), two-way repeated measures ANOVA for non-parametric sample populations were applied and statistical significance denoted as +p<0.05, or NS (not significant). For comparison at individual time-points (i.e. PCV13 vs. (PCV13+3M-052) at DOL56), unpaired Mann-Whitney test was applied at each time-point. Results represent means±SEM, with statistical significance denoted as *p<0.05.

Figure 24:
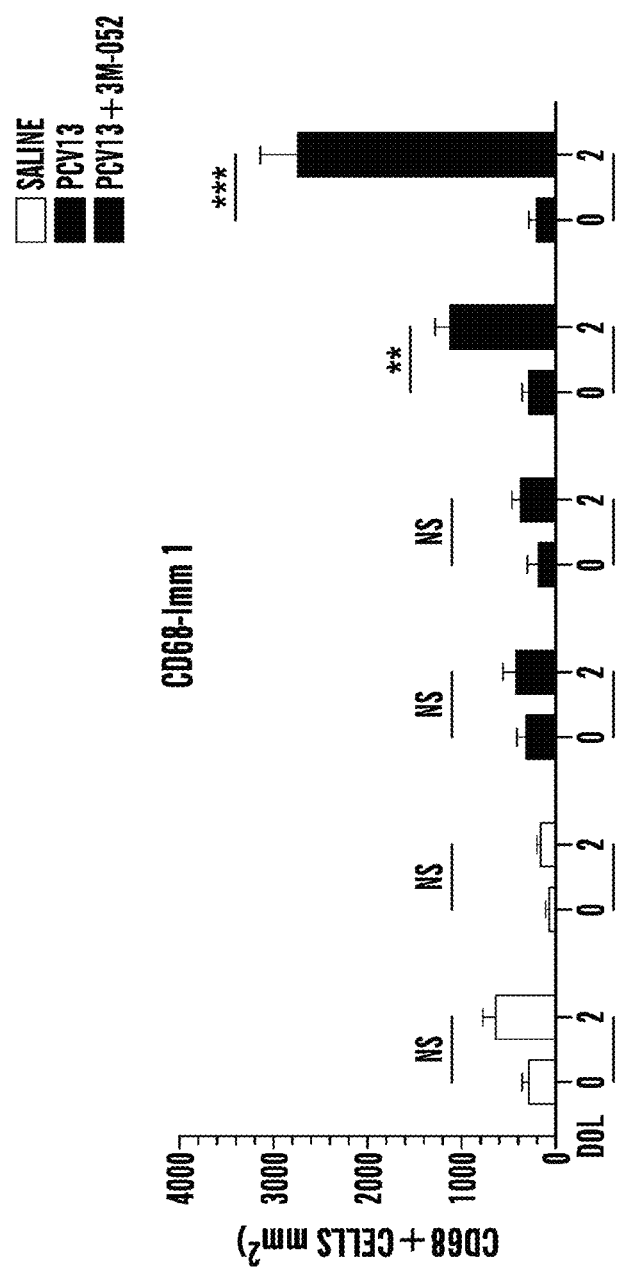

FIG. 24 demonstrates that co-administration of 3M-052 with PCV13 increased infiltration of CD68+ cells at the vaccine injection site. Immunization with (PCV13+3M-052) accelerates injection site infiltration by monocytes/macrophages. 2 mm cube muscle biopsies were obtained from the injection site (quadriceps muscle) prior to and 48 hours after each immunization (obtained in an alternating pattern (e.g. DOL0 left leg, DOL2 right leg)). Frequencies of CD68+ cells in muscle were determined by immunofluorescence. For comparison at individual time-points, the unpaired Mann-Whitney test was applied, with statistical significance denoted as *p<0.05, **p<0.01, or NS (not significant). Data are representative of two animals per treatment group.

FIGS. 25A-25C depict an overview of the core-aqueous imidazoquinoline and oxoadenine scaffolds. FIG. 25 depicts a table of naming convention, chemical class and TLR selectively of each core scaffolds; FIG. 25B depicts structures of core imidazoquinolines; and FIG. 25C depicts structures of core oxoadenines investigated in this study.

Figure 26A:
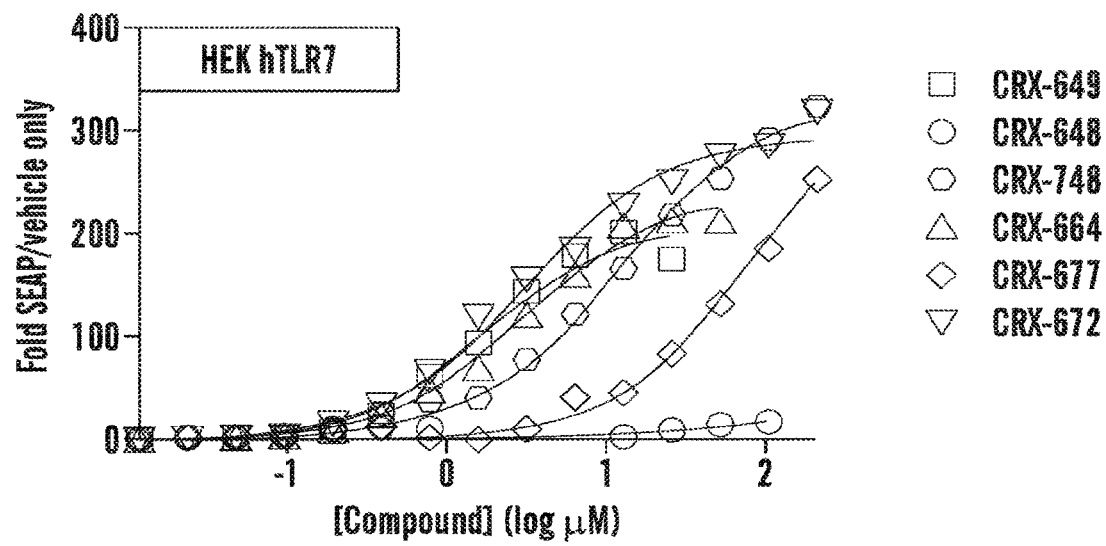
Figure 26B:
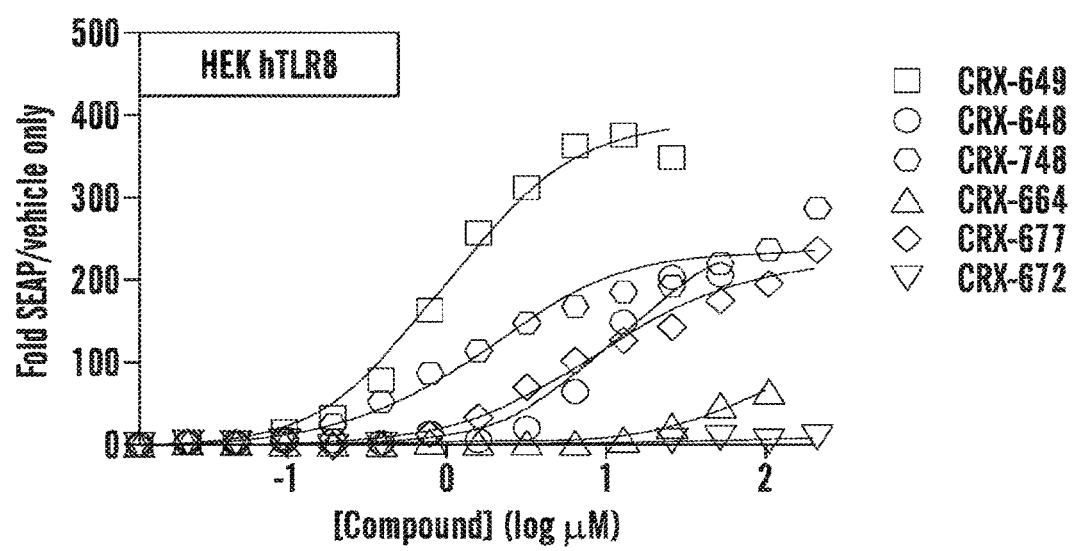

FIGS. 26A-26C demonstrate that CRX-649 has the greatest potency for both hTLR7 and hTLR8. Six TLR agonists were compared. HEK-293 cells transfected with human. FIG. 26C) TLR7 and (FIG. 26B) TLR8 and an NF-kB-driven reporter SEAP gene were stimulated for 18-24 h with TLR agonists. The y-axis shows the level of SEAP activity as a fold change over unstimulated cells. The x-axis shows the concentration of each compound in M. Each data point represents the mean of triplicate culture wells, and representative of three separate experiments. FIG. 26C demonstrates that amongst the IMQ and OA compounds evaluated in a HEK293 assay, CRX—is the most potent for both TLR7 and TLR8, with a preference for TLR8.

Figure 27A:
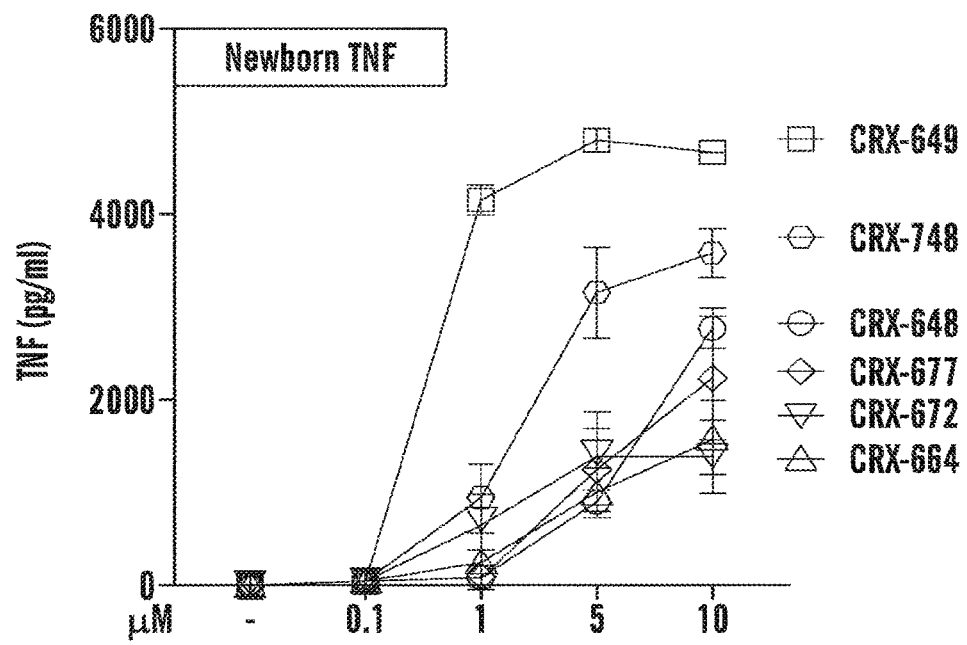
Figure 27B:
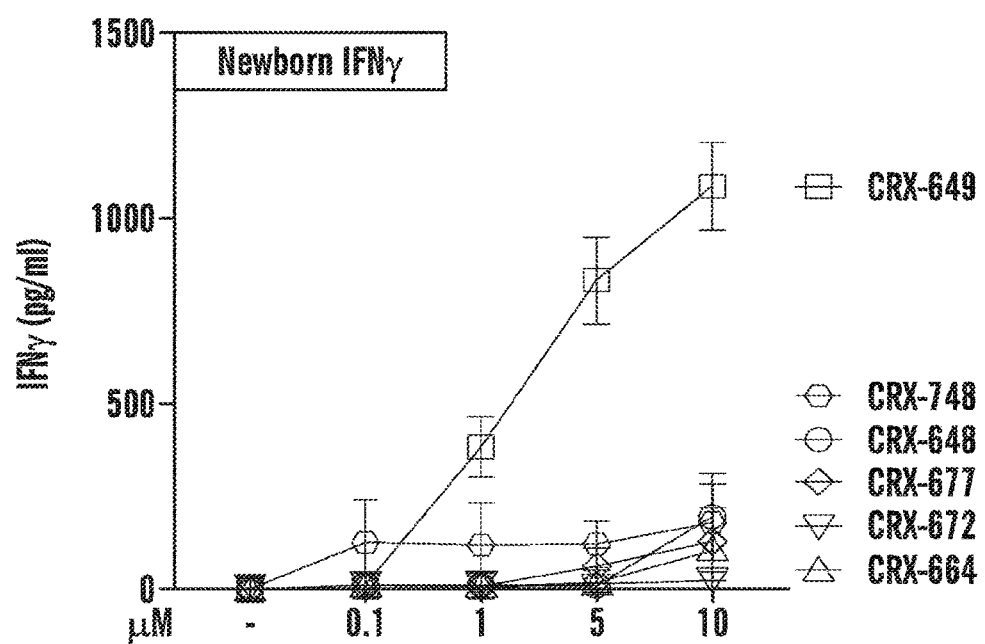
Figure 27C:
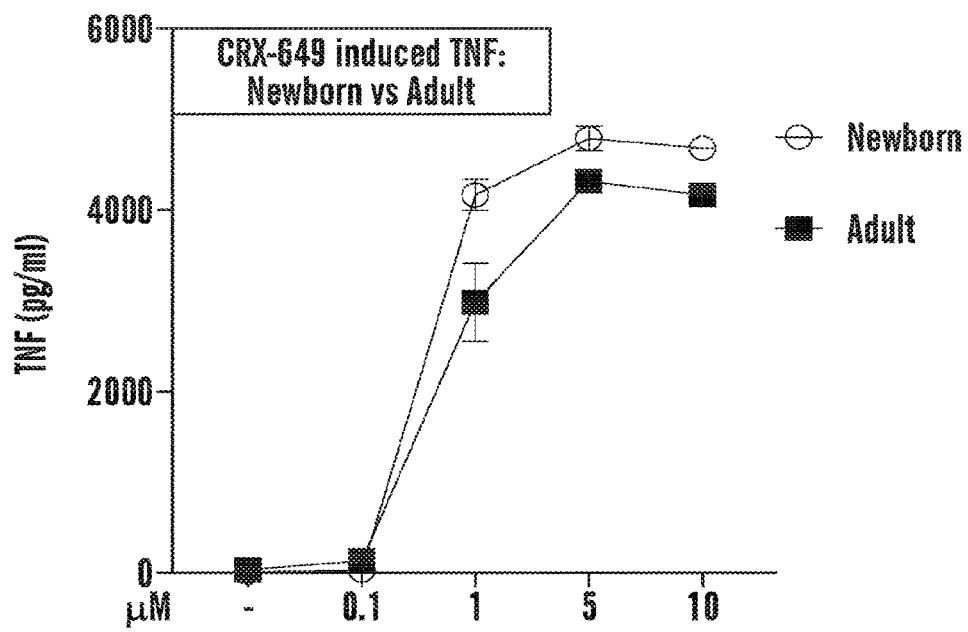
Figure 27D:
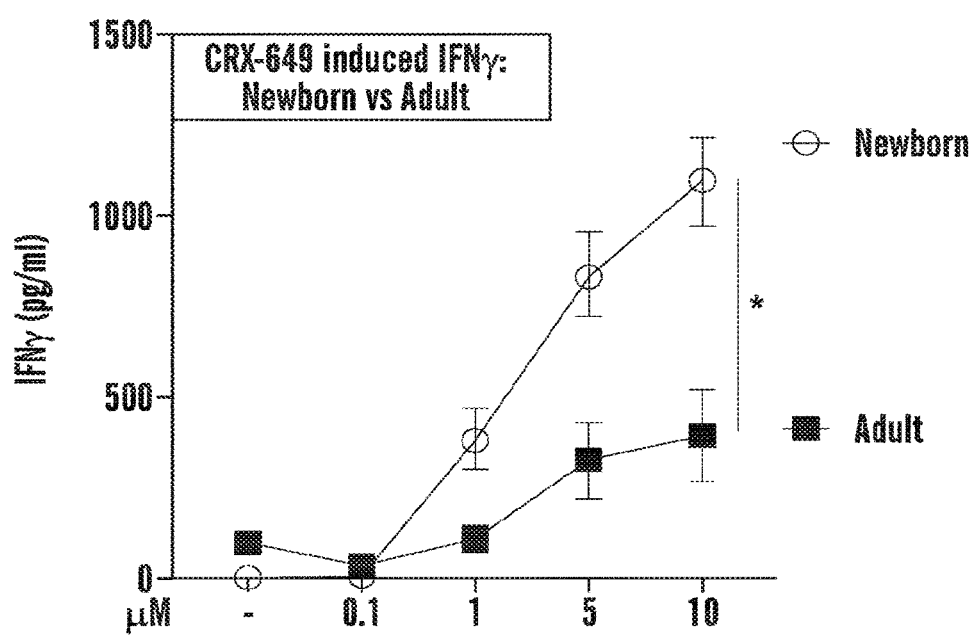

FIGS. 27A-27D demonstrate that imidazoquinoline CRX-649 demonstrates age-specific potency, effectiveness and IFNγ polarization in newborn cord blood. FIGS. 27A-27B depict experiments with human neonatal blood cultured in vitro for 6 hours with buffer control (RPMI) or with increasing concentrations of various CRX adjuvants. FIGS. 27C-27D depicts experiments with newborn versus adult blood cultured in vitro for 6 hours with CRX-649. Supernatants were collected for ELISA. Results represent means±SEM, FIGS. 27A-27B; N=3, FIGS. 27C-27D; N=3-4. For comparisons between overall groups (e.g., newborn vs. adult), non-parametric two-way repeated measures ANOVA was applied and statistical significance denoted as *p<0.05.

Figure 28B:
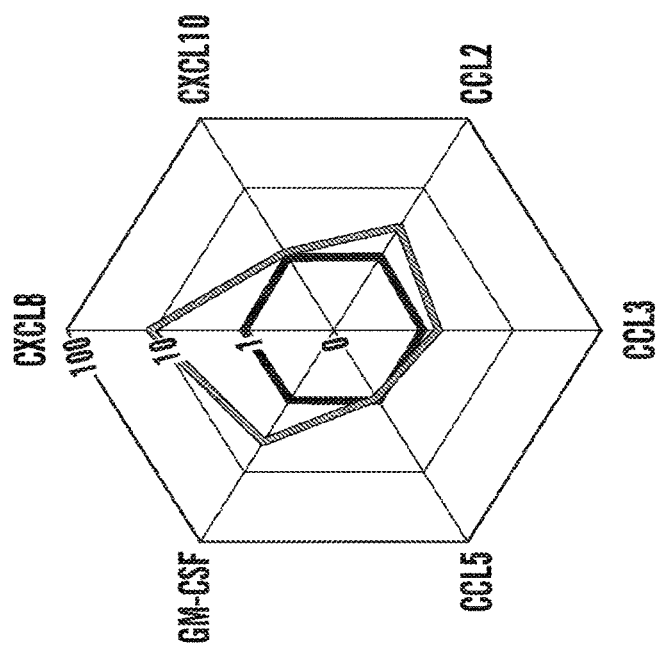
Figure 28A:
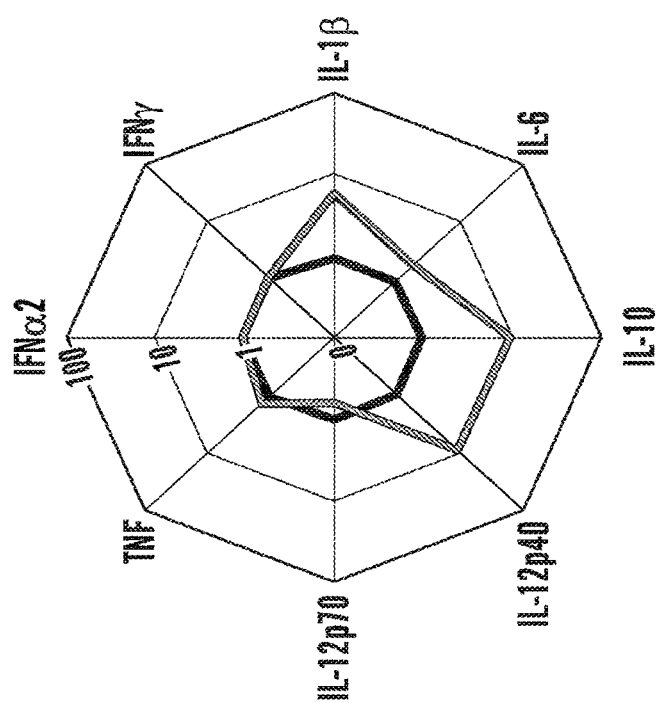
Figure 28D:
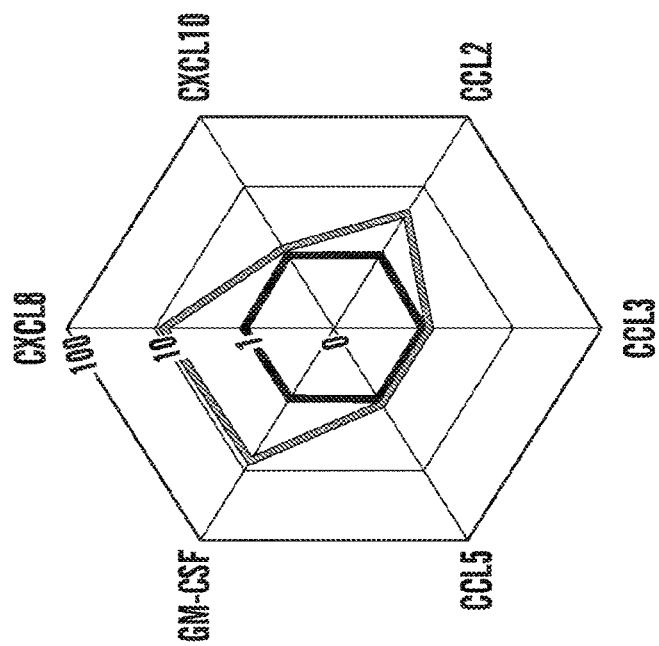
Figure 28C:
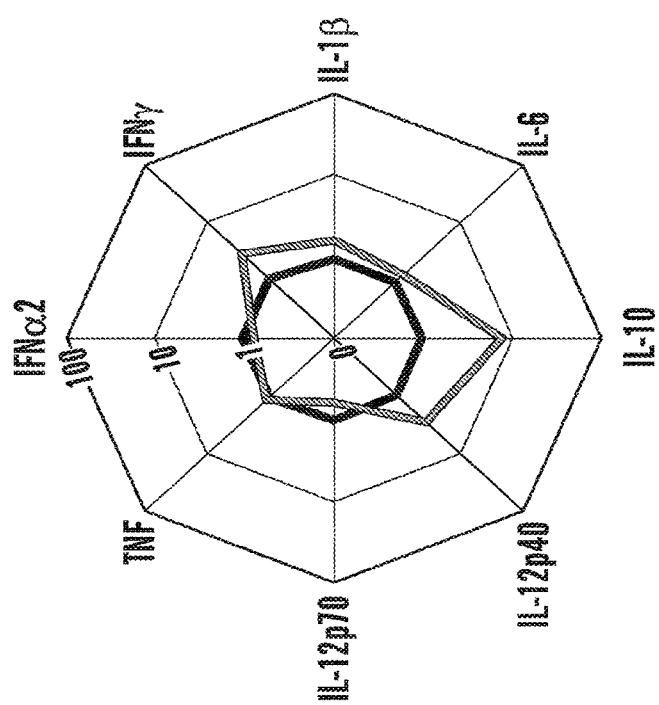
Figure 28E:
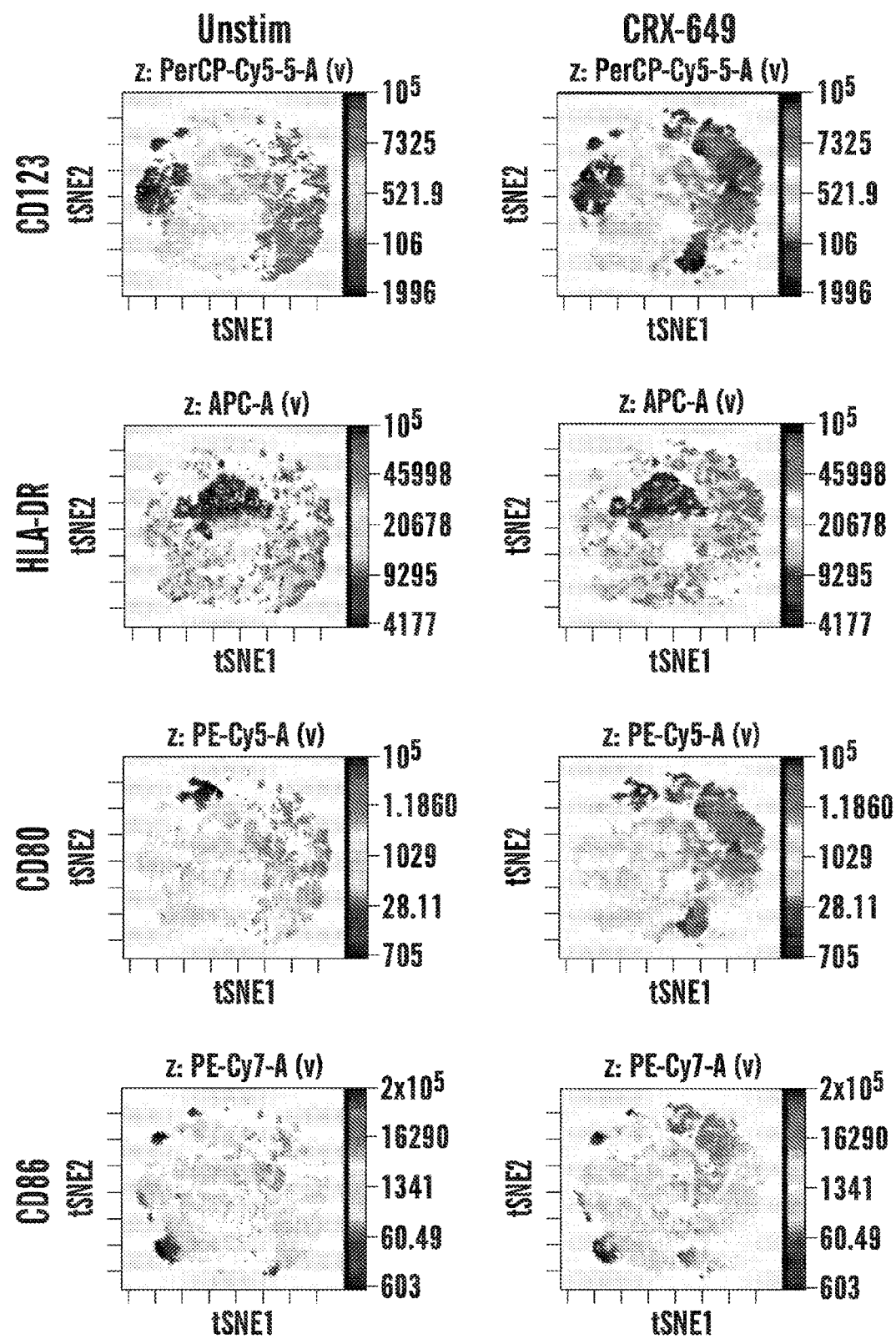
Figure 28F:
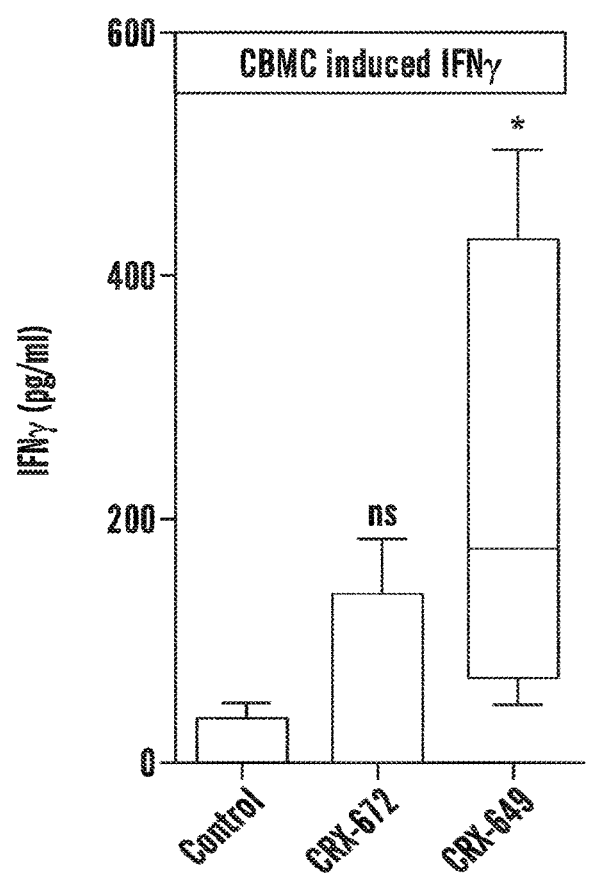

FIGS. 28A-28F demonstrate that imidazoquinoline CRX-649 demonstrates newborn-specific cytokine and chemokine potency and polarization. Cell supernatants were analyzed for cytokine expression by multiplex assay. Data are shown as fold change for newborn cold over adult stimulated whole blood for 1 μM (FIGS. 28A, 28B) and 10 μM (FIGS. 28C, 28D) CRX-649. (N=4 adults, N=2 newborn). (FIGS. 28A, 28C) cytokine and interferon production, (FIGS. 28B, 28D) chemokine and growth factor production. FIG. 28E depicts flow cytometry analysis of human adult PBMCs stimulated with CRX-649 for 24 h. CD123, HLA-D, CD80 and CD86 all show increases as compared to unstimulated cells. FIG. 28F depicts newborn CBMCs stimulated with CRX-649, in the presence of the polyclonal T cell activator αCD3 for 96 hours. IFNγ levels were measured in cell-free supernatants by ELISA. Results are shown as the median, the 25th and 75th percentiles (boxes) and the 5th and 95th percentiles (whiskers) of 5 independent experiments. N=4. For comparison at individual time points, the unpaired Mann-Whitney test was applied, *p<0.05.

Figure 29A:
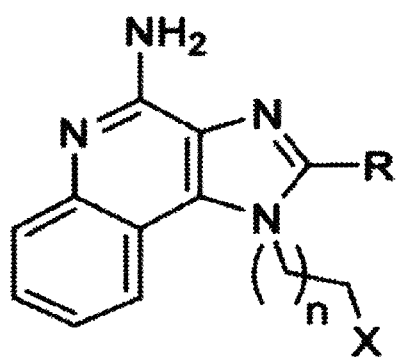
Figure 29B:
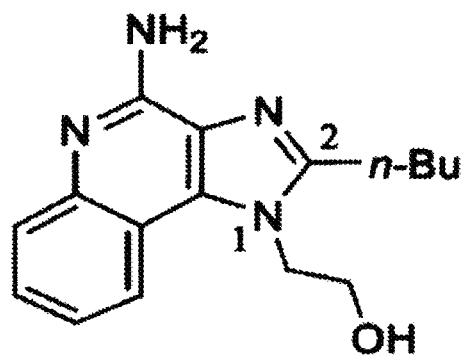
Figure 29C:
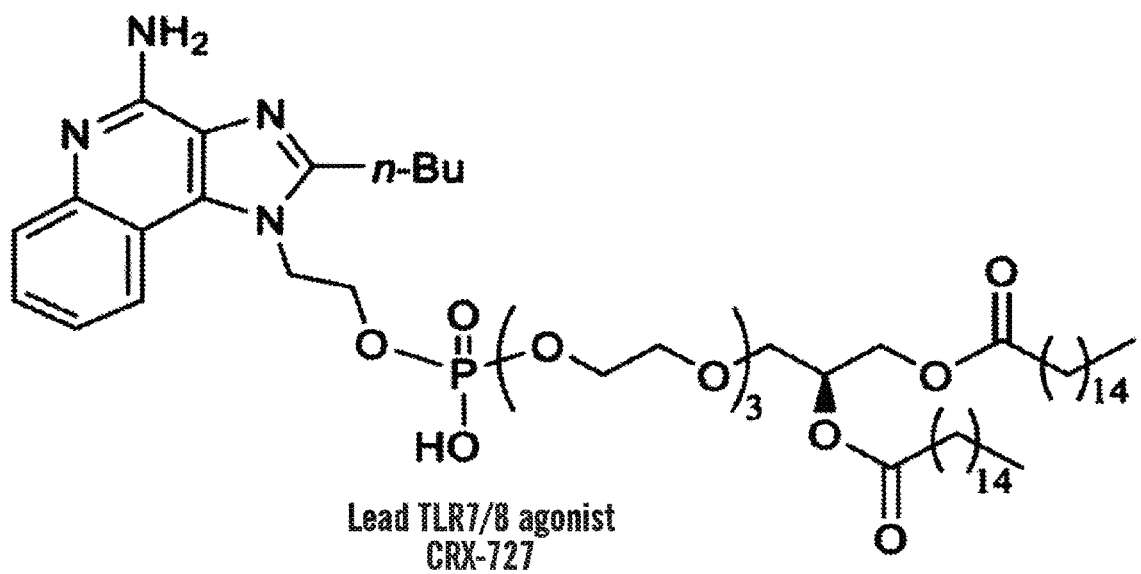
Figure 29D:
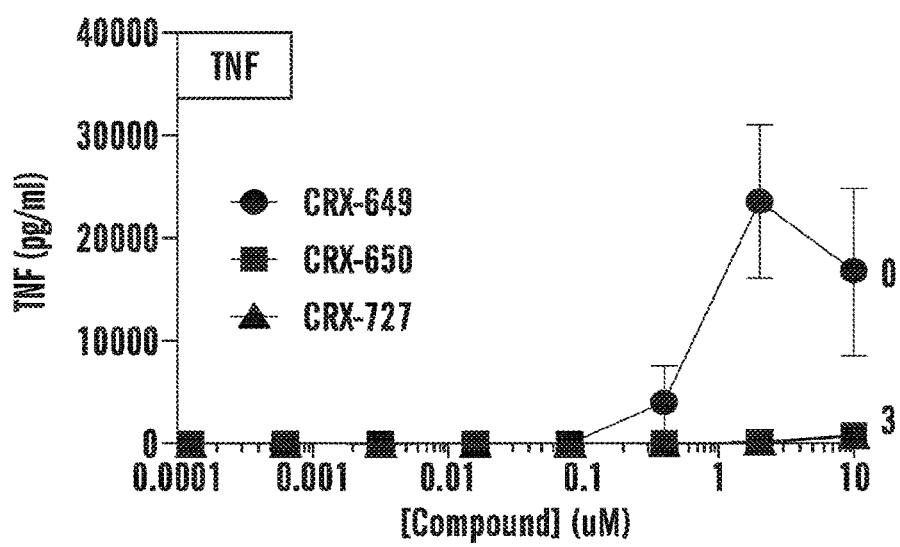

FIGS. 29A-29E demonstrate that lipidation of the basic IMQ scaffold changes the immunostimulatory properties in adult PBMCs. FIG. 29A depicts the basic imidazoquinoline (IMQ) pharmacophore of TLR7/8 agonist; FIG. 29B depicts optimized core CRX-649; and FIG. 29C depicts the lead TLR7/8 agonist CRX-727. The phosphorylated derivative of the IMQ CRX-649 (denoted as CRX-650, n=0) was modified through introduction of a Poly Ethylene Glycol (PEG) linker of 3 repeating units, termed CRX-727. These IMQs were evaluated for cytokine induction in adult human PBMCs. Addition of the phosphate to the core compound abolished it's TNFα induction ability, but slightly increased IFNα production. Further derivitization with the PEG3 moiety greatly enhanced this type I interferon activity (FIG. 29E) while maintaining low inflammatory cytokine production (FIG. 29D).

FIG. 30 depicts a table of lipidated TLR7/8 adjuvant CRX-727 rapidly and fully adsorbs to the alum/antigen while the core compound CRX-649 does not. Direct adsorption of CRX-727 (top panels) and CRX-649 (bottom panels) to aluminum hydroxide derived from DTaP vaccine, which has preexisting pertussis antigen adsorbed to its surface, was evaluated at 1, 2 and 24 hrs. CRX-727 fully adsorbed (~96-100%) to the alum/antigen within 1 hr, with or without excess alum (top panels). The core CRX-649 compound was only able to adsorb to the antigen ~4-7% within 1-2 hr (bottom panels), with peak area intensity levels similar to the unmixed controls, mAU: milli-absorbance units. The phosphorylated CRX-649 derivative, CRX-650, was also included as a control.

Figure 31A:
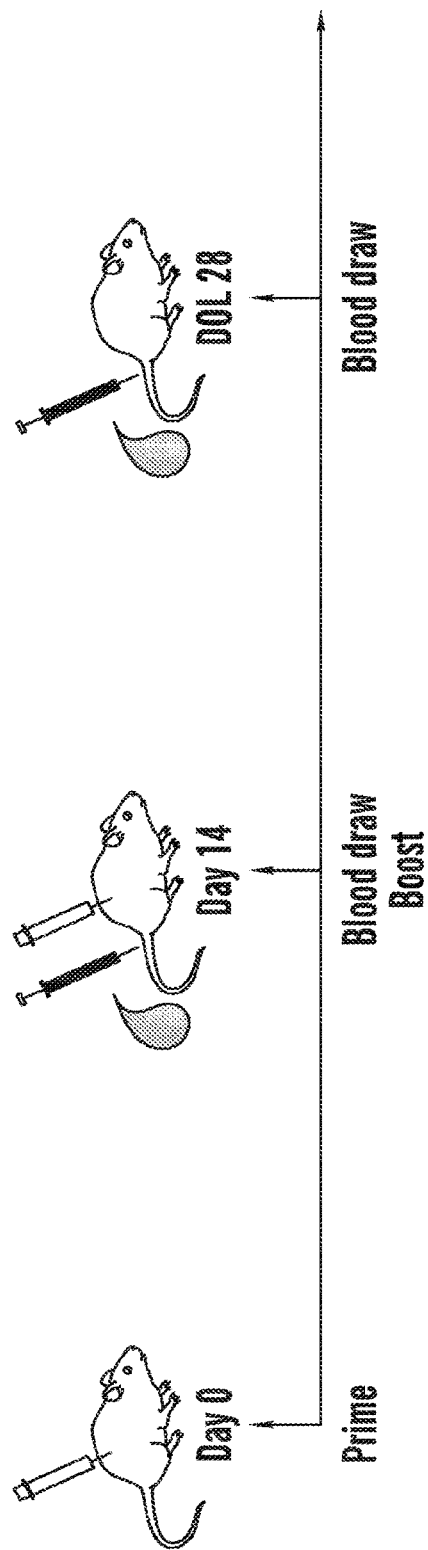
Figure 31B:
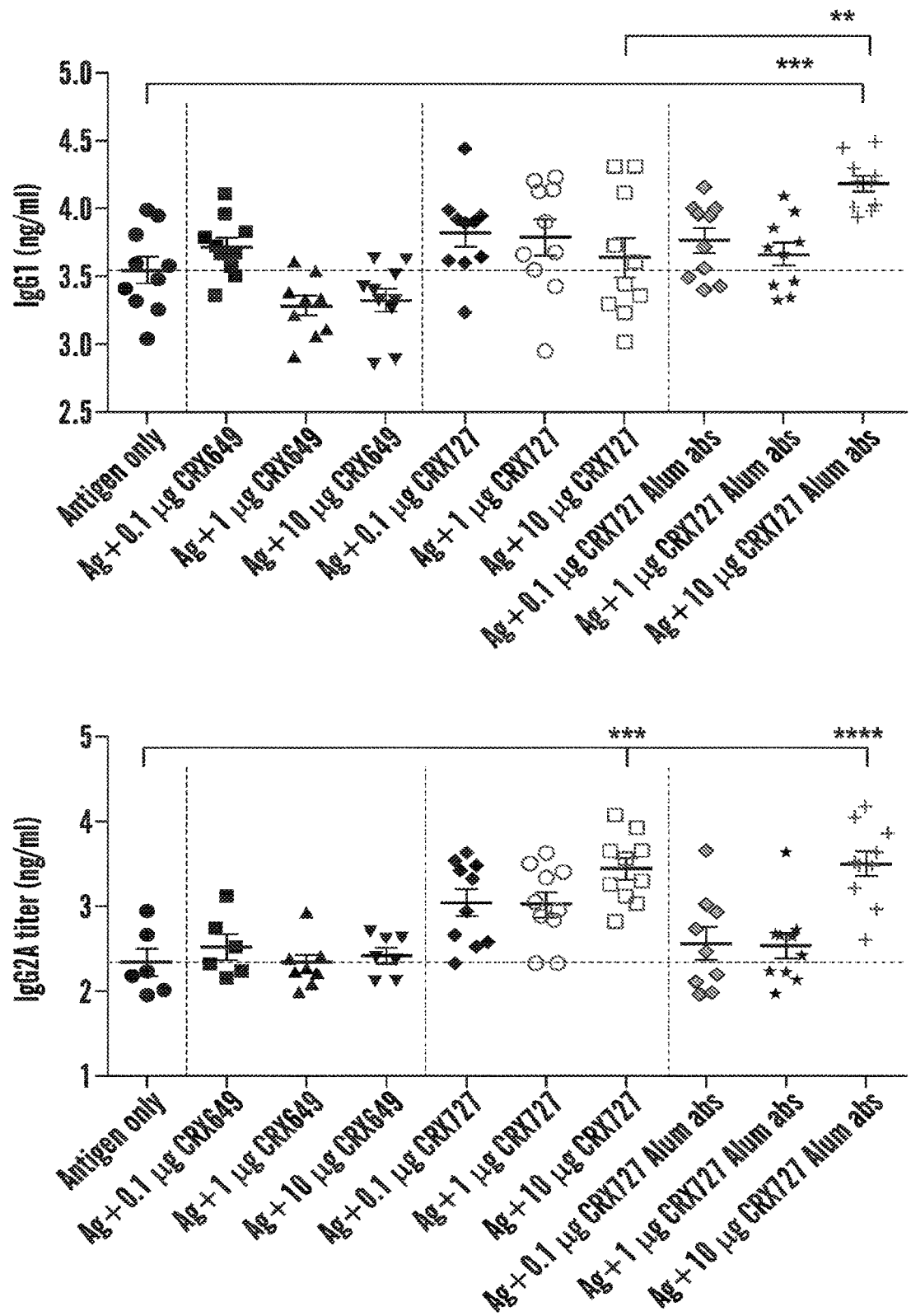
Figure 31C:
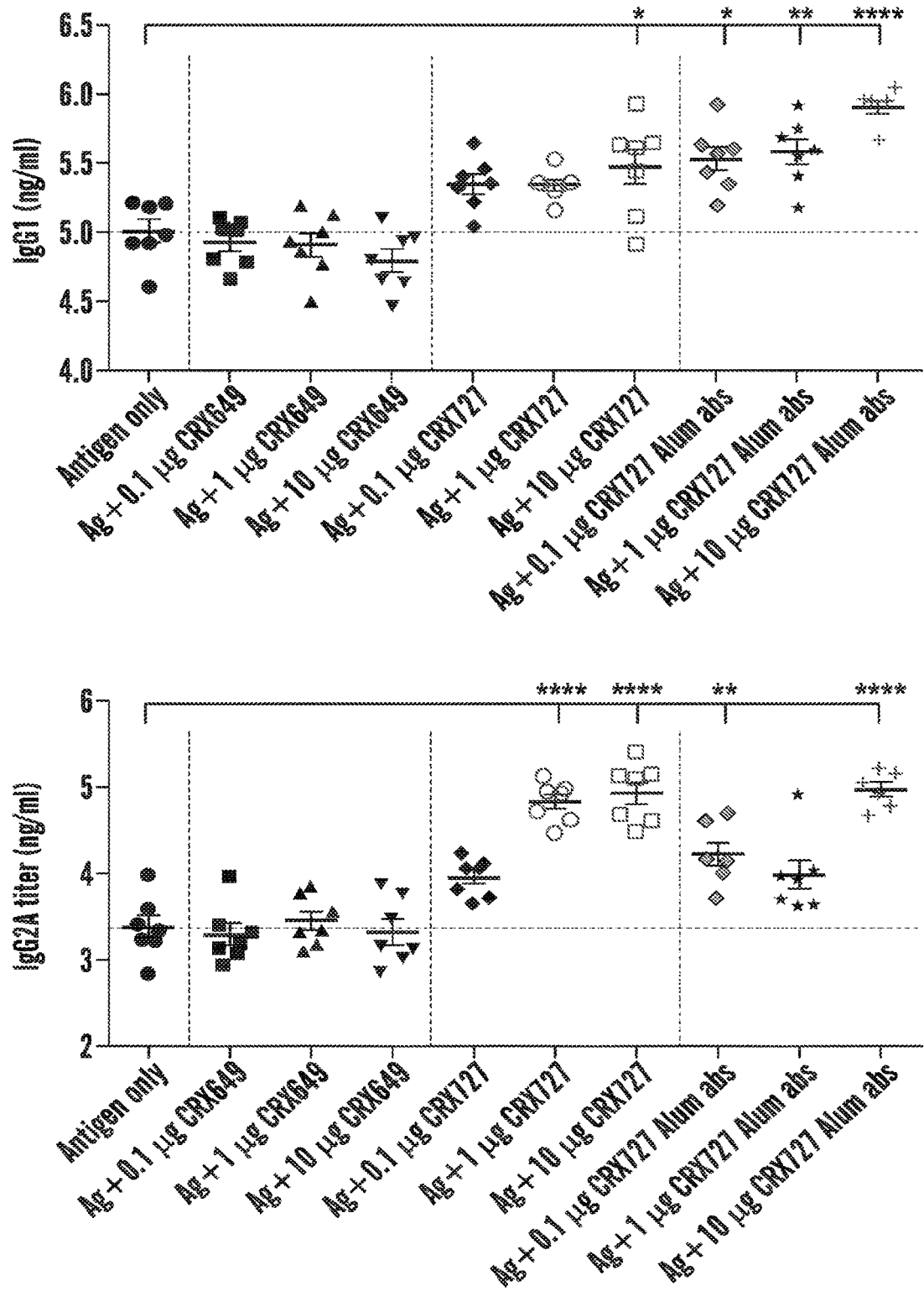

FIGS. 31A-31C demonstrate that antibody production in response to Infanrix with or without different formulations of CRX-727. Balb/c mice were immunized twice, 14 days apart (FIG. 31A) with Infanrix ($\frac{1}{100}^{th}$ of the human dose) ±CRX649 or CRX-727 at 0.1 µg, 1 µg or 10 µg per mouse in different formulations (aqueous or pre-adsorbed to alum). Serum was harvested 14 days following prime (FIG. 21B) or boost (FIG. 31C) and anti-FHA serum antibody IgG1 and IgG2a titers were measured by ELISA. Statistical comparison employed test one-way ANOVA; *<0.05, <0.01, **<0.0001 (n=10 or 7 per group), with comparison to Infanrix alone. Study is representative of two separate repeats.

Figure 32:
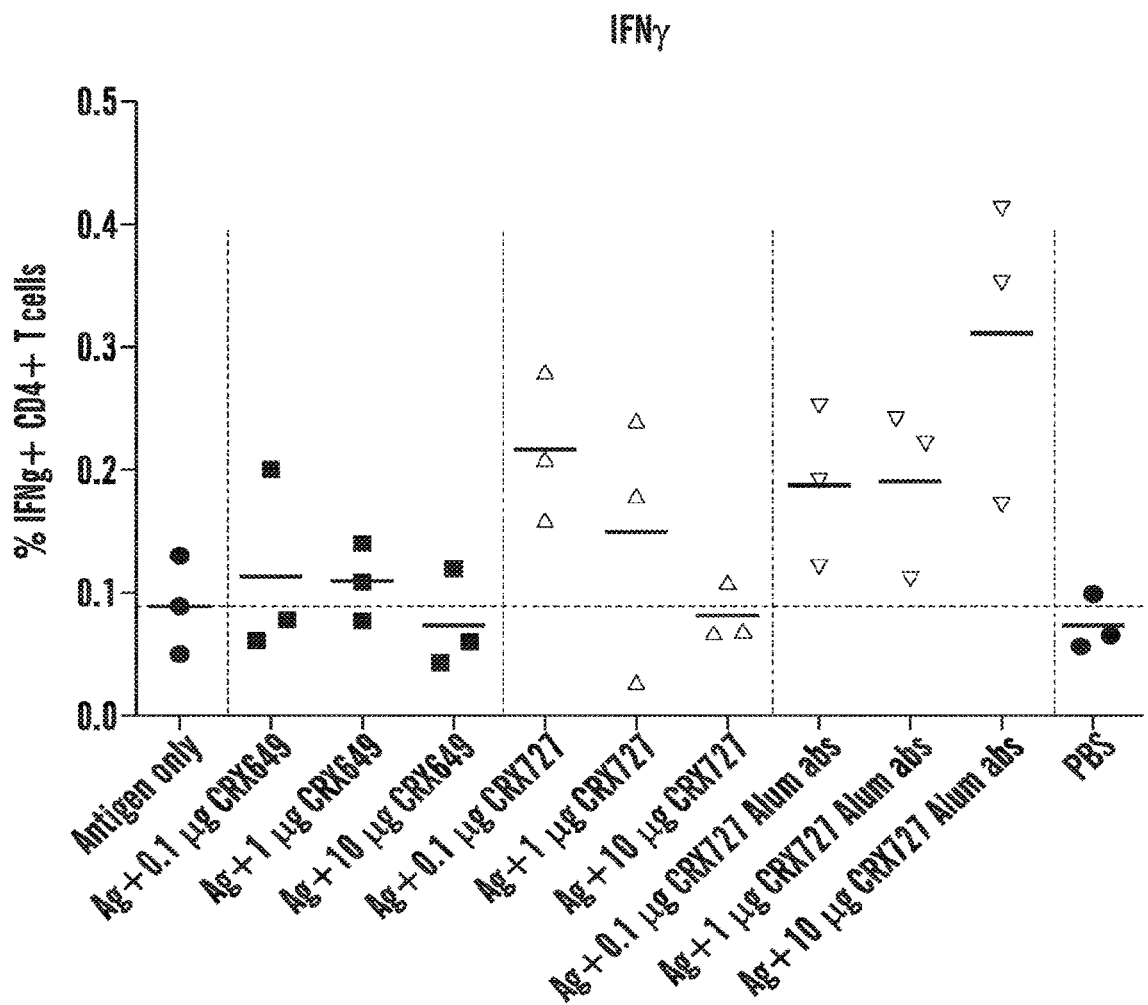

FIG. 32 demonstrates higher percentages of IFNγ-producing CD4$^+$ T cells after vaccination of DTaP with CRX-727 or alum adsorbed CRX-727. Balb/c mice were immunized twice, 14 days apart with Infanrix ($\frac{1}{100}^{th}$ of the human dose)±CRX649 or CRX-727 at 0.1 µg, 1 µg or 10 µg per mouse in different formulations. Cell-mediated immune response in spleens from 3 mice per group were harvested 5 days post-secondary immunization and restimulated with purified pertussis antigen followed by intracellular cytokine staining and analysis via flow cytometry. Data is represented as percentage IFNγ-positive CD4$^+$ T cells.

Figure 33A:
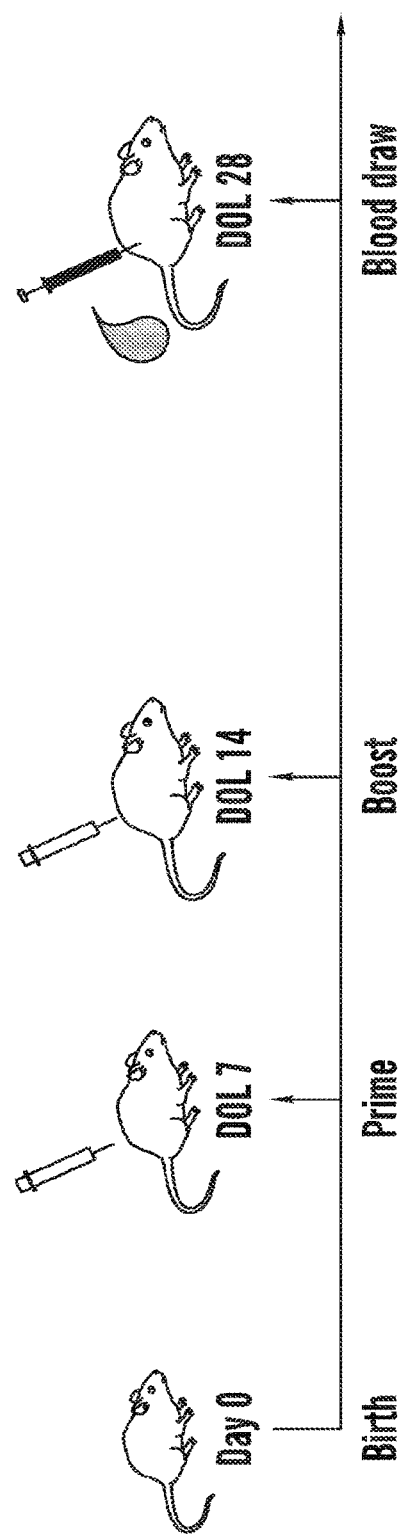
Figure 33B:
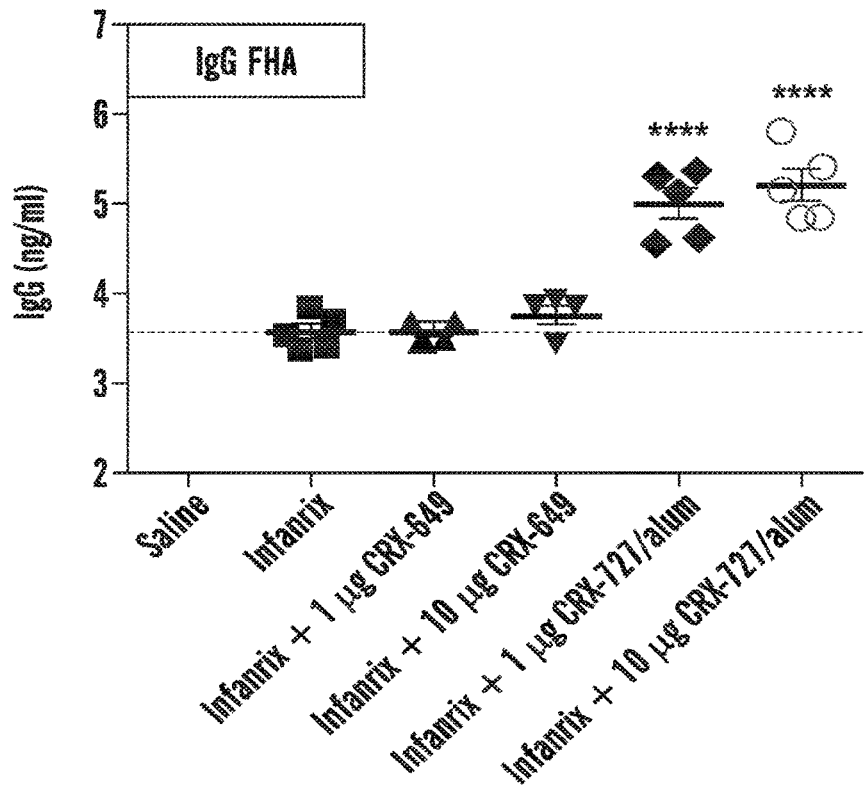
Figure 33C:
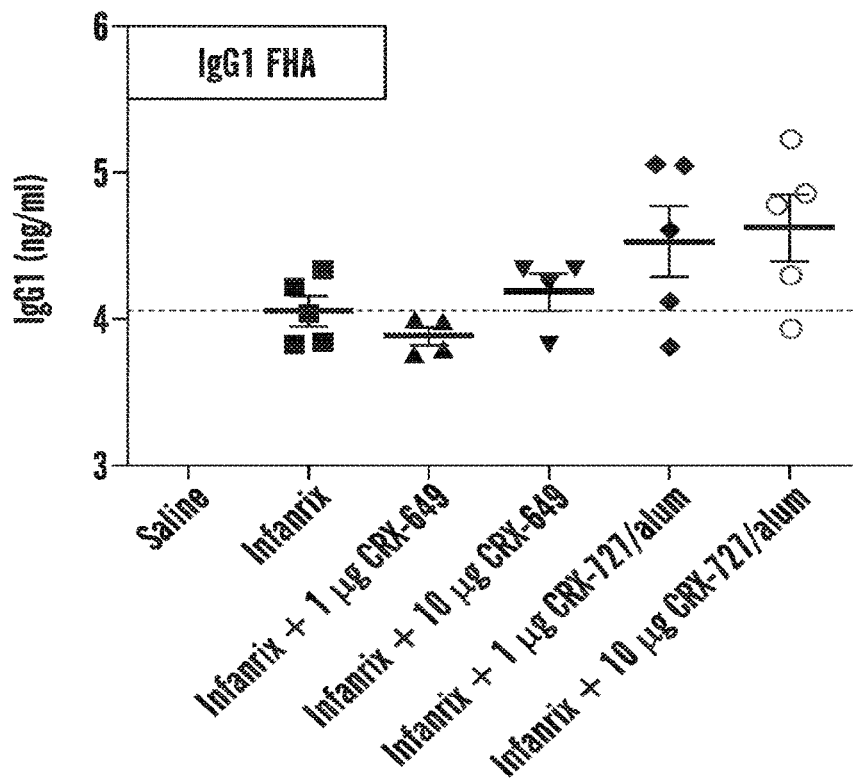
Figure 33E:
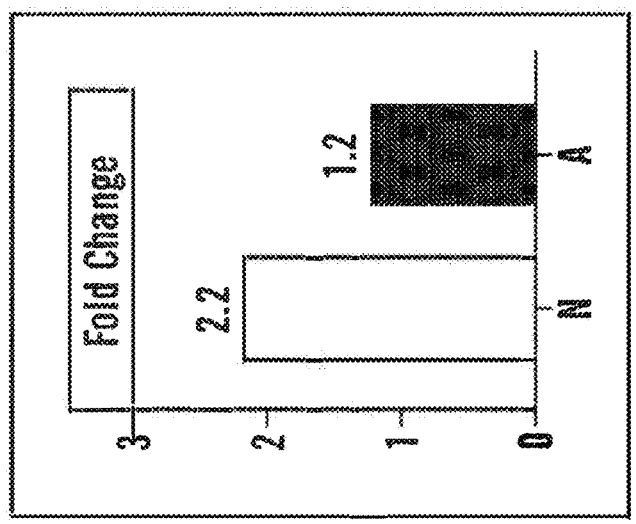
Figure 33D:
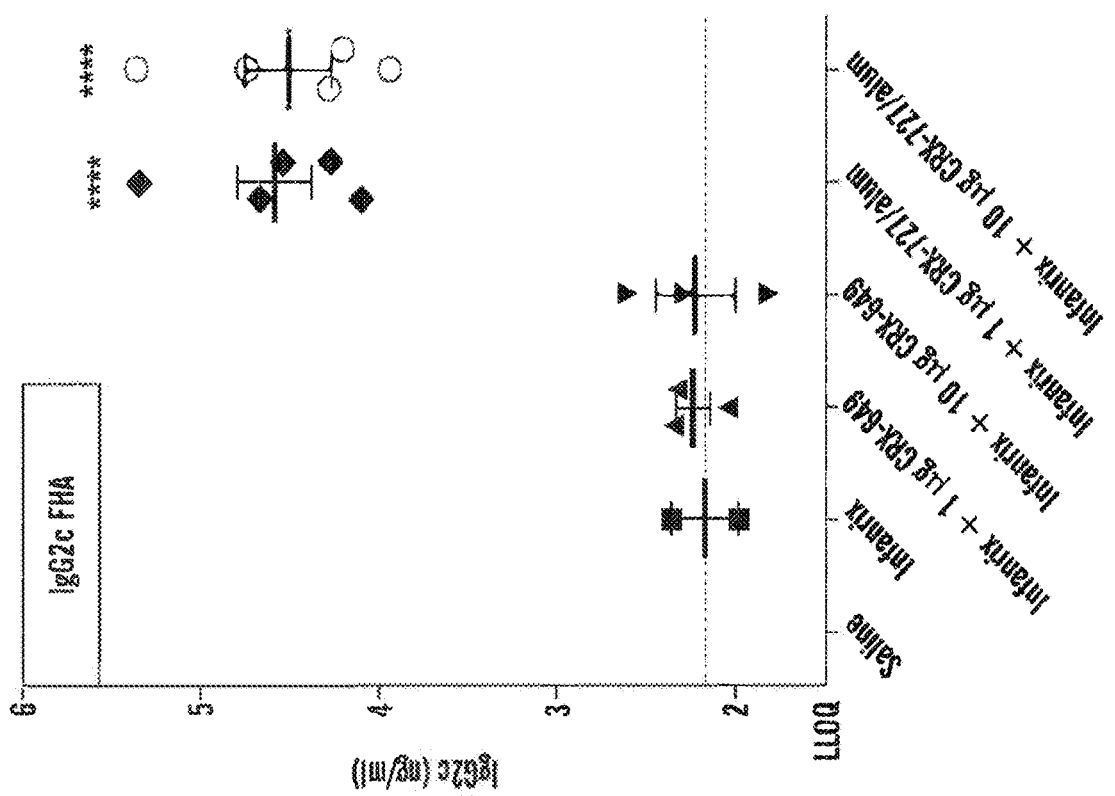

FIGS. 33A-33E demonstrate that antibody production in neonatal mice immunized with Infanrix combined with various formulations and doses of CRX-727. FIG. 33A depicts the results when 7 day old C57BL/6, 4-6 per group, were vaccinated (prime/boost) with Infanrix ($\frac{1}{100}^{th}$ of the human dose), ±CRX649 or CRX-727 at 0.1 rig, 1 µg or 10 µg per mouse in different formulations (aqueous, liposome or alum adsorbed "Alum Abs"). Serum was harvested 14 days following boost (14dp2) (DOL 28) and anti-FHA serum total IgG titers (FIG. 33B), IgG1 (FIG. 33C) and IgG2c (FIG. 33D) were measured by ELISA. FIG. 33E depicts the fold change analysis for antibody production with a 0.1 µM dose of CRX-727+DTaP, as compared DTaP alone (N; newborn, A; adult). Statistical comparison employed test by one way ANOVA; ****<0.0001, with comparison to Infanrix alone.

FIG. 34 depicts graphs demonstrating TNF and IFNα induced by PEGylated imidazoquinolines in human adult PBMCs. A phospholipidated IMQ (denoted as n=0) was modified through introduction of a Poly Ethylene Glycol (PEG) linker of 1, 3, 6 or 9 repeating units. These IMQs were evaluated for cytokine induction in human PBMCs (adult). A PEG3 unit (n=6) was required to increase TNFα induction, while a PEG3 unit (n=3) was sufficient to increase IFNα induction.

DETAILED DESCRIPTION

Infection is the most common cause of mortality in early life and immunization is the most promising biomedical intervention to reduce this burden. However, newborns fail to optimally respond to most vaccines. Patient responses to vaccines are routinely enhanced by administering an adjuvant as a component of the vaccine formulation, but currently utilized adjuvants do not provide sufficient responses in newborns. This improved vaccine response permits the use of fewer doses and/or lower doses of vaccine while also permitting effective vaccination at or immediately after birth, which is a critical concern in less-developed areas where regular post-delivery medical care is not common.

It is demonstrated that use of a TLR7/8 adjuvant provides the desired enhancements of the immune response, thereby providing methods and compositions that permit successful vaccination of newborns. As a further advantage, the adjuvants described herein are not complexed with the vaccine antigen itself, allowing the adjuvant to be administered separately or readily mixed with currently used vaccine formulations to enhance the immune response. This is a distinct advantage over many current adjuvants, which are bound to or complexed with the relevant antigen.

In one aspect, described herein is a method of method of immunizing a subject, the method comprising administering to the subject i) an adjuvant comprising an agonist of TLR7 and/or TLR8; and ii) at least one antigen; wherein the adjuvant and the at least one antigen are not conjugated to each other. In one aspect, described herein is a method of stimulating an immune response of a subject, the method comprising administering to the human an adjuvant comprising an agonist of TLR7 and/or TLR8. In some embodiments of any of the aspects, administration of an adjuvant comprising an agonist of TLR7 and/or TLR8, either with or without an antigen, can result in, e.g., a greater immune response, increased rate of an immune response and/or greater protection than in the absence of the adjuvant. In some embodiments of any of the aspects, administration of an adjuvant comprising an agonist of TLR7 and/or TLR8 and an antigen as described herein can provide protection at a lower dose or with fewer doses than the antigen administered without the adjuvant.

As used herein in the context of immunization, immune response and vaccination, the term "adjuvant" refers to any substance than when used in combination with a specific antigen that produces a more robust immune response than the antigen alone. When incorporated into a vaccine formulation, an adjuvant acts generally to accelerate, prolong, or enhance the quality of specific immune responses to the vaccine antigen(s).

As used herein, "TLR7" or "Toll-like receptor 7" refers to a transmembrane protein of the toll-like receptor family that recognizes ssRNA, particularly GU-rich ssRNA of viral origin. Sequences for TLR7 are known for a number of species, e.g., human TLR7 (NCBI Gene ID: 51284) mRNA sequences (NM_016562.3) and polypeptide sequences (NP_057646.1).

As used herein, "TLR8" or "Toll-like receptor 8" refers to a transmembrane protein of the toll-like receptor family that recognizes ssRNA, particularly GU-rich or G-rich ssRNA of viral origin. Sequences for TLR8 are known for a number of species, e.g., human TLR8 (NCBI Gene ID: 51311) mRNA sequences (NM_016610.3 and NM_138636.5) and polypeptide sequences (NP_057694.2 and NP_619542.1).

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, TLR7 and/or TLR8, e.g. its ability to increase the level and/or activity of TLR7 and/or TLR8 can be determined, e.g. by measuring the level of an expression product of TLR7 and/or TLR8 and/or the activity of TLR7 and/or TLR8. Methods for measuring the level of a given mRNA and/or polypeptide are known to one of skill in the art, e.g. RT-PCR with primers can be used to determine the level of RNA, and Western blotting with an antibody can be used to determine the level of a polypeptide. Non-limiting examples of suitable primers are provided in the Examples herein and antibodies to TLR7 and/or TLR8 are commercially available, e.g., Cat.

No. ab45371 and ab24185 from Abcam (Cambridge, Mass.). Assays for measuring the activity of TLR7 and/or TLR8, e.g. the increases in cytokine production, cell proliferation, and cell survival in response to ssRNA detection are known in the art.

In some embodiments of any of the aspects, an adjuvant described herein can comprise an agonist of TLR7 and/or TLR8. In some embodiments of any of the aspects, an adjuvant described herein can consist essentially of an agonist of TLR7 and/or TLR8. In some embodiments of any of the aspects, an adjuvant described herein can consist of an agonist of TLR7 and/or TLR8.

In some embodiments of any of the aspects, an agonist of TLR7 and/or TLR8 can be an agonist of TLR7 but not TLR8. In some embodiments of any of the aspects, an agonist of TLR7 and/or TLR8 can be a specific agonist of TLR7. In some embodiments of any of the aspects, an agonist of TLR7 and/or TLR8 can be an agonist of TLR8 but not TLR7. In some embodiments of any of the aspects, an agonist of TLR7 and/or TLR8 can be a specific agonist of TLR8. In some embodiments of any of the aspects, an agonist of TLR7 and/or TLR8 can be a specific agonist of TLR7 and TLR8. In some embodiments of any of the aspects, an agonist of TLR7 and/or TLR8 can be an agonist of TLR7 and TLR8.

Agonists of TLR7 and/or TLR8 are known in the art and can include, by way of non-limiting example, a single sstranded (ss) RNA; a ssRNA derived from a viral pathogen (e.g., HIV, HCV, influenza, Sendai, and Coxsackie viruses); an imidazoquinoline (e.g., R-848 (Formula III below), 3M-002 (CL075; Formula I below), 3M-013, 3M003 (4-amino-2-(ethoxymethyl)-α,α-dimethyl-6,7,8,9-tetrahydro-1H-imidazo[4,5-c]quinolines-1-ethanolhydrate), R837 (Imiquimiod, 4-amino-2ethoxymethyl-α,α-dimethyl-1H-imidazo[4,5-c]quinolines-1-ethanol, 1-(2-methylpropyl)-1H-imidazo[4,5-c]quinolin-4-arnme), 852 (Formula IIV below), S-34240 (Formula V below), 854A (Formula VI below), gardiquimod, CL097 (Formula II below)); a thiazoquinoline; an oxoadinine and a benzazepine (e.g. VTX-294). In addition, certain guanosine analogues, such as 7-deaza-G, 7-thia-8-oxo-G (TOG), and 7-allyl-8-oxo-G (Ioxoribine), have been shown to activate TLR7 at high concentrations (Lee, et al. (2003) Proc. Natl. Acad. Sci. USA 100:6646-51, which is incorporated by reference herein in its entirety). Agonists of TLR7 and/or TLR8 are further described, e.g, at Dowling et al. PLOS ONE 2013 8:e58164, Gorden et al., 2005 J. Immunol. 174:1259, Johansen 2005 Clin. Exp. Allerg. 35:1591, Heil et al. (2004) Science 303: 1526-29; WO 03/086280; WO 98/32462, and Philbin et al. Journal of Allergy and Clinical Immunology 2012 195-204; each of which is incorporated by reference herein in its entirety. Synthesis of imidaziquinoline (IMQ) and oxoadinine (OA)-based compounds are known in the art, e.g., in International Patent Publication WO2017102652A1 and Tetrahdron Lett., 2016, 57, 2063-2066; which are incorporated by reference herein in their entireties.

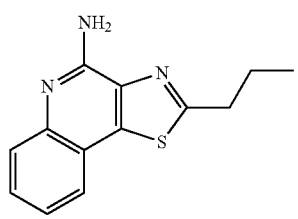

TLR7 agonists can also include (1) guanosine analogues, such as 7-deazaguanosine and related compounds, including those described in Townsend, (1976) Heterocyclic Chem, 13, 1363, and Seela, et al, (1981) Chem. Ber., 114(10), 3395-3402; 7-allyl, 8-oxo-guanosine (Ioxorabine) and related compounds, including those described in Reitz, et al., (1994) J. Med. Chem., 37, 3561-3578; 7-methyl, 9-deazaguanosine and related compounds including those described in Girgis et al., (1990) J. Med. Chem., 33, 2750-

2755; 8-bromoguanosine and other 8-halogen substituted purine compounds including those described in U.S. Pat. No. 4,643,992; 6-amino-9-benzyl-2-butoxy-9H-purin-8-ol, and other 2, 6, 8, 9-substituted purines including those described in Hirota et al., (2002) J. Med. Chem., 45, 5419-5422, Henry et al. (1990) J. Med. Chem. 33, 2127-2130, Michael et al., (1993) J. Med. Chem., 36, 3431-3436, Furneaux et al. (1999) J. Org. Chem., 64(22), 8411-8412; Barrio et al (1996) J. Org. Chem. 61, 6084-6085, U.S. Pat. Nos. 4,539,205, 5,011,828, 5,041,426, 4,880,784 and WO 94/07904; (2) imidazoquinolines, including 1-(4-amino-2-ethoxymethyl-imidazo[4,5-c]quinolin-1-yl)-2-methyl-propan-2-ol (imiquimod), as described in WO 94/17043; 1-isobutyl-1H-imidazo[4,5-c]quinolin-4-ylamine (resiquimod) as described in WO 94/17043 and US 2003/0195209, US 2003/0186949, US 2003/0176458, US 2003/0162806, 2003/0100764, US 2003/0065005 and US 2002/0173655); U.S. Pat. No. 5,395,937; WO 98/17279; and (3) pyrimidine derivatives, including 2-amino-6-bromo-5-phenyl-3H-pyrimidin-4-one (bropirimine), and similar substituted pyrimidines such as those described in Wierenga et al. (1980) J. Med. Chem., 23, 239-240; Fan et al., (1993) J. Heterocyclic Chem., 30, 1273; Skilnick et al. (1986) J. Med. Chem., 29, 1499-1504; Fried et al., (1980) J. Med. Chem., 23, 237-239, and Fujiwara et al. (2000) Bioorg. Med. Chem. Lett. 10(12): 1317-1320. Each of the foregoing references is incorporated by reference herein in its entirety.

US 2008/0171712 describes a novel class of stabilized immune modulatory RNA (SIMRA) compounds which bind to TLR7 and TLR8. SIMRA compounds that specifically activate TLR7, especially the compounds having a structure as set out in Formulas I-IV in Table 2, and specific compounds listed in Table 4, are described in US 2010/0215642 (Idera Pharmaceuticals, Inc). TLR7 agonists, including lipid-linked TLR7 agonists, are described in US 2010/0210598 (Regents of the University of California, San Diego). TLR7 agonists, including orally-available-linked TLR7 agonists and TLR7agonist prodrugs, are described in US 2010/0256169 (Anadys Pharmaceuticals). Non-selective TLR7 agonists are described in US 2009/0324551 (The Regents of The University of California). Immunostimulatory polymers that contain sequence-dependent immunostimulatory RNA motifs and methods for their use are described in US 2010/0272785. The sequence-dependent immunostimulatory RNA motifs and the polymers incorporating such motifs are selective inducers of TLR7 and the TLR7-associated cytokine IFN-α (Coley Pharmaceutical). US 2010/0029585 and WO 2010/014913 (VentiRx Pharmaceuticals) describe formulations of benzo[b]azepine compounds that are TLR7 and/or TLR8 agonists. TLR8 agonists that may be suitable in the context of the present invention include VTX-1463 and VTX-2337 (VentiRx Pharmaceuticals), both of which have successfully completed phase I clinical trials. A review article concerning TLR8 agonists is Philbin & Levy (2007) "Immunostimulatory activity of Toll-like receptor δ agonists towards human leucocytes: basic mechanisms and translational opportunities". *Biochemical Society Transactions* 35(6): 1485-90. Each of the foregoing references is incorporated by reference herein in its entirety.

In some embodiments of any of the aspects, the adjuvant comprising a TLR7 and/or TLR8 agonist can comprise a compound having the structure of Formula IX, wherein n is from 0 to 20, R is R is selected from H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino and C1-6alkoxyC1-6alkoxy; wherein the C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino or C1-6alkoxyC1-6alkoxy is branched or unbranched and optionally terminally substituted with a hydroxyl, amino, thio, hydrazino, hydrazido, azido, acetylenyl, carboxyl, or maleimido group and X is a phospholipid, lipid, lipidation, and/or PEG moiety.

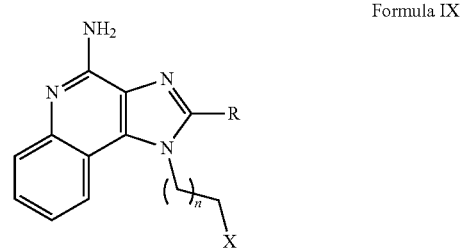

Formula IX

In some embodiments of any of the aspects, the adjuvant comprising a TLR7 and/or TLR8 agonist can comprise a compound having the structure of Formula X.

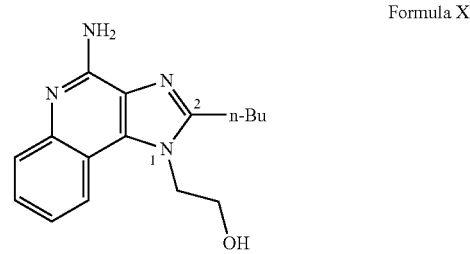

Formula X

In some embodiments of any of the aspects, the adjuvant comprising a TLR7 and/or TLR8 agonist can comprise a compound having the structure of Formula XI.

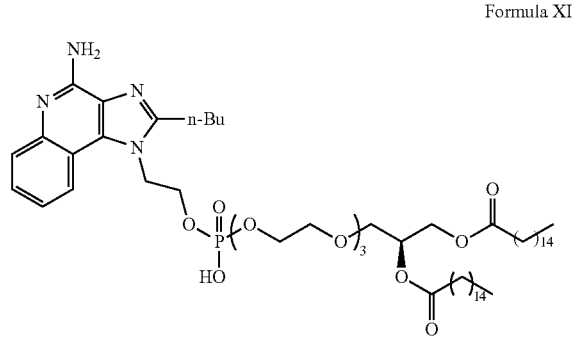

Formula XI

In some embodiments of any of the aspects, the adjuvant comprising a TLR7 and/or TLR8 agonist can comprise a compound having the structure of Formula XII, wherein n is from 1 to 15 and R2 is a lipid group.

Formula XII

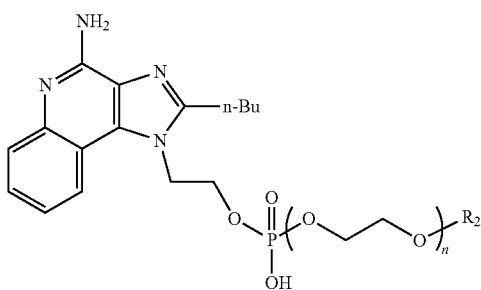

In some embodiments of any of the aspects, the $R_2$ group of Formula XII is:

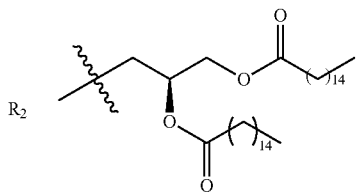

In some embodiments of any of the aspects, the adjuvant comprising an agonist of TLR7 and/or TLR8 comprises a compound selected from the group consisting of: 3M-052; CRX-648; CRX-649; CRX-664; CRX-672; CRX-677; and CRX-748. In some embodiments of any of the aspects, the adjuvant comprising an agonist of TLR7 and/or TLR8 consists essentially of a compound selected from the group consisting of: 3M-052; CRX-648; CRX-649; CRX-664; CRX-672; CRX-677; and CRX-748. In some embodiments of any of the aspects, the adjuvant comprising an agonist of TLR7 and/or TLR8 consists of a compound selected from the group consisting of: 3M-052; CRX-648; CRX-649; CRX-664; CRX-672; CRX-677; and CRX-748.

In some embodiments of any of the aspects, the adjuvant comprising an agonist of TLR7 and/or TLR8 comprises CRX-649 (Formula X). In some embodiments of any of the aspects, the adjuvant comprising an agonist of TLR7 and/or TLR8 consists essentially of CRX-649. In some embodiments of any of the aspects, the adjuvant comprising an agonist of TLR7 and/or TLR8 consists of CRX-649.

In some embodiments of any of the aspects, the adjuvant comprising an agonist of TLR7 and/or TLR8 comprises CRX-727 (Formula XI). In some embodiments of any of the aspects, the adjuvant comprising an agonist of TLR7 and/or TLR8 consists essentially of CRX-727. In some embodiments of any of the aspects, the adjuvant comprising an agonist of TLR7 and/or TLR8 consists of CRX-727.

In some embodiments of any of the aspects, the adjuvant can comprise one agonist of TLR7 and/or TLR8. In some embodiments of any of the aspects, the adjuvant can comprise two or more agonists of TLR7 and/or TLR8, e.g., two different agonists, three different agonists, or more agonists.

In some embodiments of any of the aspects, the adjuvant can comprise a phosphate group and/or a phospholipidation moiety, e.g., a phospholipid can be covalently bounded to the adjuvant (e.g., to the embodiments of adjuvants described above herein).

Lipidation can prevent or inhibit migration of the adjuvant, increasing local activity. In some embodiments of any of the aspects, the adjuvant can be lipidated and/or comprise a lipid moiety, e.g., a lipid can be covalently bonded to the adjuvant (e.g., to the embodiments of adjuvants described above herein). In some embodiments of any of the aspects, the adjuvant comprises a lipid covalently bound to the agonist of TLR7 and/or TLR8. Examples of lipids for used in the lipidated adjuvants described herein can include, but are not limited to C18 lipid moieties.

In some embodiments of any of the aspects, the lipid and/or phospholipid moiety (or phosphate group) can be located at (e.g., conjugated to) the ethanol group of 3M-052; CRX-648; CRX-649; CRX-664; CRX-672; CRX-677; or CRX-748 or an ethanol group corresponding to the ethanol group of 3M-052; CRX-648; CRX-649; CRX-664; CRX-672; CRX-677; or CRX-748. In some embodiments of any of the aspects, the lipid and/or phospholipid moiety (or phosphate group) can be located at (e.g., conjugated to) the N1 position of Formula X or an N corresponding to the N1 position of Formula X.

The adjuvant and the lipid can be covalently conjugated with each other using a reactive functional group present in their respective structures. The term "reactive functional group" refers to a functional group that is capable of reacting with another functional group. Exemplary reactive functional groups include, but are not limited to, hydroxyls, amines, thiols, thials, sulfinos, carboxylic acids, acyl chlorides, amides, and the like. The reactive functional group on the lipid and the adjuvant can be the same or different. In some embodiments of any of the aspects, the reactive group on the lipid is a carboxylic acid, a carboxylic acid derivative such as acid chloride or an ester, a hydroxyl, an amine or a thiol.

In some embodiments of any of the aspects, the reactive group on the adjuvant is an amine, a hydroxyl, a thiol, or a carboxylic acid. In some embodiments of any of the aspects, the amine can be acyclic, cyclic, aromatic amine, or heterocyclic amine. Some preferred amines in some aspects of the invention include, but are not limited to imidazole, aniline, indole, pyridine, piperidine, pyrimidine, pyrrole or pyrrolidine.

The term "lipid" as used herein means a substance that is soluble in organic solvents and includes, but is not limited to, oils, fats, sterols, triglycerides, fatty acids, phospholipids, and the like.

Without limitations the lipid can be selected from the group consisting of fatty acids, fatty acid derivatives such as chlorides or esters, fatty alcohols, sterol lipids, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments of any of the aspects, the lipid can be selected from the group consisting of cholesterol; 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/ Capric Triglyceride; Ceramide phosphorylcholine (Sphingomyelin, SPH); Ceramide phosphoryl ethanolamine (Sphingomyelin, Cer-PE); Ceramide phosphorylglycerol; Ceroplastic acid; Cerotic acid; ceryl alcohol; Cetearyl alcohol; Ceteth-10; cetyl alcohol; Cholanes; Cholestanes; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX®355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl 1,2-dipalmitate, glyceryl 1,3-dipalmitate, glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid. In some embodiments of any of the aspects, the lipid can be glyceryl 1,2-dipalmitate or glyceryl 1,3-dipalmitate.

In some embodiments of any of the aspects, the lipid is a fatty acid derivative of Palmitic acid, Stearic acid, Lauric acid, or Myristic acid. In some embodiments of any of the aspects, the fatty acid derivative is an acid chloride or an ester.

In some embodiments of any of the aspects, the adjuvant is a lipidated imidazoquinoline. In some embodiments of any of the aspects, the adjuvant is a lipidated oxoadinine.

In some embodiments of any of the aspects, the adjuvant is covalently linked to the lipid by a linker. In some embodiments of any of the aspects, the adjuvant is covalently bound to an $R_1$ group wherein $R_1$ has the formula alkylene-L-$R_{1-1}$, alkenylene-L-$R_{1-1}$ or alkynylene-L-$R_{1-1}$, wherein:

the alkylene, alkenylene and alkynylene groups are optionally interrupted with one or more —O— groups, and preferably interrupted with one —O-group;

L is a bond or a functional linking group selected from the group consisting of —NHS(O)$_2$—, —NHC(O)—, —NHC(S)—, —NHS(O)$_2$NR$_3$—, —NHC(O)NR$_3$—, —NHC(S)NR$_3$—, —NHC(O)O—, —O—, —S— and —S(O)$_2$—;

$R_3$ is selected from the group consisting of hydrogen and alkyl; and $R_{1-1}$ substituents are lipid moieties consisting of linear or branched aliphatic group having at least 11 carbon atoms, optionally including one or more unsaturated carbon-carbon bonds.

In some preferred embodiments, $R_{1-1}$ is —(CH$_2$)$_{10}$CH$_3$, —(CH$_2$)$_{12}$CH$_3$, —(CH$_2$)$_{14}$CH$_3$, —(CH$_2$)$_{16}$CH$_3$, —(CH$_2$)$_{18}$CH$_3$, —(CH$_2$)$_7$CH=CH(CH$_2$)$_5$CH$_3$, —(CH$_2$)$_7$CH=CH(CH$_2$)$_7$CH$_3$, (CH$_2$)$_6$(CH$_2$CH=CH)$_2$ (CH$_2$)$_4$CH$_3$, —(CH$_2$)$_6$(CH$_2$CH=CH)$_3$CH$_2$CH$_3$ or (CH$_2$)$_2$ (CH$_2$CH=CH)$_4$(CH$_2$)$_4$CH$_3$.

The term "aliphatic" group means a saturated or unsaturated linear or branched hydrocarbon group and includes alkyl, alkenyl and alkynyl groups. The term "alkyl" refers to saturated or non-saturated non-aromatic hydrocarbon chains that may be a straight chain, branched chain and cyclic groups. The term "alkenyl" refers to an alkyl that comprises at least one double bond. The term "alkynyl" refers to an alkyl that comprises at least one triple bond. Unless otherwise specified, these groups contain from 1 to 20 carbon atoms, with alkenyl groups containing from 2 to 20 carbon atoms and alkynyl groups containing from 2 to 20 carbon atoms. Unless otherwise specified, "alkylene," "alkenylene," "alkynylene" are divalent forms of the "alkyl," "alkenyl," "alkynyl" groups defined above.

In some embodiments of any of the aspects, the lipid (or lipid moiety) can be conjugated to adjuvant via a PEG linker. PEG linkers can comprise from 1 to 15 repeats, e.g., repeats of a single PEG molecule. In some embodiments, the PEG linker can comprise from 3 to 9 repeats. In some embodiments, the PEG linker can comprise from 3 to 6 repeats. In some embodiments, the PEG linker can comprise 3 repeats. In some embodiments, the PEG linker can consist essentially of 3 repeats. In some embodiments, the PEG linker can consist of 3 repeats.

As demonstrated in FIG. 34, the length of the PEG linker can influence the activity of the adjuvant. In some embodiments of any of the aspects, the PEG linker is 3 units or greater in length, e.g., 3 to 15, 3 to 9, 3 to 6, 3, 4, 5, 6, 7, 8, 9, 10, 11, 12, 13, 14, or 15 units in length. In some embodiments of any of the aspects, wherein the adjuvant is desired to increase IFNα production, the PEG linker is 3 units or greater in length, e.g., 3 to 15, 3 to 9, 3 to 6, 3, 4, 5, 6, 7, 8, 9, 10, 11, 12, 13, 14, or 15 units in length.

In some embodiments of any of the aspects, the PEG linker is 6 units or greater in length, e.g., 6 to 15, 6 to 9, 6, 7, 8, 9, 10, 11, 12, 13, 14, or 15 units in length. In some embodiments of any of the aspects, wherein the adjuvant is desired to increase TNFα production, the PEG linker is 6 units or greater in length, e.g., 6 to 15, 6 to 9, 6, 7, 8, 9, 10, 11, 12, 13, 14, or 15 units in length.

In some embodiments of any of the aspects, the PEG linker is 3, 4, or 5 units in length. In some embodiments of any of the aspects, wherein the adjuvant is desired to increase IFNα production but not TNFα, the PEG linker is 3, 4, or 5 units in length.

In some embodiments of any of the aspects, the adjuvant is 3M-052 (Formula VII below). 3M-052, related compounds, and methods of making the same are described, e.g., in U.S. Pat. No. 7,799,800; which is incorporated by reference herein in its entirety.

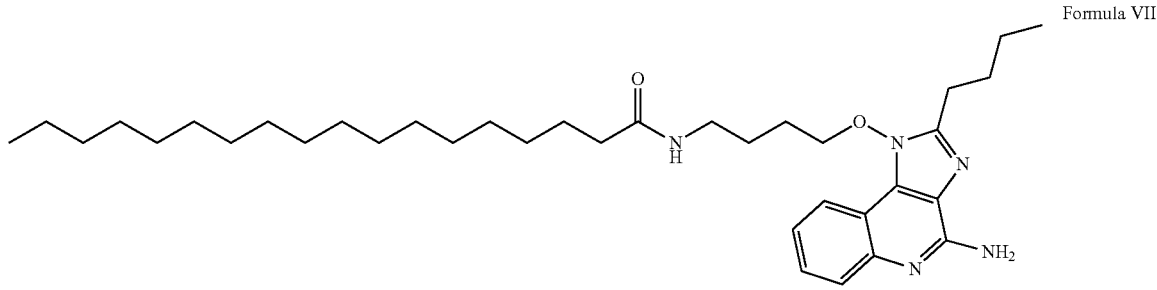 [SMILES: CCCCCCCCCCCCCCCCCC(=O)NCCCCOn1c(CCCC)nc2c(N)nc3ccccc3c21]

Formula VII

In some embodiments of any of the aspects, the adjuvant is a lipidated imidazoquinoline. In some embodiments of any of the aspects, the adjuvant is lipidated R-848, lipidated 3M-002, lipidated 3M-013, lipidated 3M003, lipidated R837, lipidated gardiquimod, or lipidated CL097. In some embodiments of any of the aspects, the adjuvant is a lipidated thiazoquinoline.

In some embodiments, the adjuvant can comprise both lipidated and unlipidated adjuvant molecules.

In some embodiments of any of the aspects, the adjuvant can be a Benzonaphthyridine.

In some embodiments of any of the aspects, the adjuvant comprising an agonist of TLR7 and/or TLR8 is not conjugated to an antigen. The term "conjugated" refers to the attachment of at least two entities to form one entity. The joining of the two entities can be direct (e.g., via covalent or non-covalent bonds) or indirect (e.g., via linkers etc.). Conjugation can be by means of linkers, chemical modification, peptide linkers, chemical linkers, covalent or non-covalent bonds, or protein fusion or by any means known to one skilled in the art. The joining can be permanent or reversible.

The term "linker" refers to any means, entity or moiety used to join two or more entities. Linker moieties include, but are not limited to, chemical linker moieties, or for example a peptide linker moiety.

As described herein, an "antigen" is a molecule that is specifically bound by a B cell receptor (BCR), T cell receptor (TCR), and/or antibody, thereby activating an immune response. An antigen can be pathogen-derived, or originate from a pathogen. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

In some embodiments of any of the aspects, the at least one antigen is comprised by a vaccine. In some embodiments of any of the aspects, the vaccine is an attenuated vaccine. Attenuated vaccines comprise weakened or compromised versions or variants of a disease-causing microbe. Attenuated vaccines can include mutated or engineered strains of a microbe and/or strains which have been passaged in culture, thereby resulting in a loss of pathogenicity.

In some embodiments of any of the aspects, the vaccine can be a subunit vaccine, including a recombinant subunit vaccine. A subunit vaccine does not comprise entire disease-causing microbes, but only a subset of antigens obtained from or derived from the disease-causing microbe. A subunit vaccine can comprise multiple different antigens. Subunit vaccines in which the antigens are produced via recombinant technologies are termed recombinant subunit vaccines.

In some embodiments of any of the aspects, the at least one antigen is comprised by a conjugate vaccine. In conjugate vaccines, polysaccharides from a disease-causing microbe (e.g., polysaccahrides found on the surface of the microbe) are administered in combination with (e.g., conjugated to) an antigen which the patient's immune system already recognizes or which the patient's immune system will readily respond to. This increases the patient's response to the polysaccharides and provides increased protection against live versions of the disease-causing microbe. In some embodiments of any of the aspects, the antigen is a polysaccharide.

Exemplary, non-limiting vaccines suitable for use in the methods and compositions described herein can include a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; a meningococcal (MV) vaccine; and/or pneumococcal conjugate vaccine (PCV)13.

In some embodiments of any of the aspects, multiple antigens are administered. In some embodiments of any of the aspects, multiple vaccines are administered.

In some embodiments of any of the aspects, the method described herein can further comprise administering a second adjuvant, e.g., sequentially or concurrently with the adjuvant comprising an agonist of TLR7 and/or TLR8. In some embodiments of any of the aspects, the second adjuvant can be alum. In some embodiments of any of the aspects, the antigen is bound to, adsorbed to, or conjugated to alum. In some embodiments of any of the aspects, the vaccine can comprise alum. In some embodiments of any of the aspects, the vaccine is alum-adjuvanted.

In some embodiments of any of the aspects, the adjuvant comprising an agonist of TLR7 and/or TLR8 can be absorbed onto alum. In some embodiments of any of the aspects, the adjuvant comprising an agonist of TLR7 and/or TLR8 can be alum-absorbed.

As described herein, an adjuvant comprising an agonist of TLR7 and/or TLR8 surprisingly induces superior immune responses in newborns. Accordingly the adjuvant comprising an agonst of TLR7 and/or TLR8 can be administered to newborns and young patients, e.g., those of an age in which traditional adjuvants fail to produce a sufficient immune response. In some embodiments of any of the aspects, the subject is a human subject. In some embodiments of any of the aspects, the subject is a human infant at the time of administration. In some embodiments of any of the aspects, the subject is a human of less than about 28 days of age at the time of administration. In some embodiments of any of the aspects, the subject is a human of less than 28 of age days at the time of administration. In some embodiments of any of the aspects, the subject is a human of less than about 4 days of age at the time of administration. In some embodiments of any of the aspects, the subject is a human of less than 4 days of age at the time of administration, e.g., less than 4 days, less than 3 days of age, less than 2 days of age, or less than 1 day of age. In some embodiments of any of the aspects, the administration occurs at the time of birth of the subject, e.g., during the perinatal period, during delivery, immediately following delivery, during transition, or during post-birth procedures. As used here, "perinatal period," when used in reference to human subjects, refers to a period beginning at 22 completed weeks (154 days) of gestation and ends seven completed days after birth.

In some embodiments of any of the aspects, the methods described herein can further comprise at least a second administration of the adjuvant comprising an agonst of TLR7 and/or TLR8, or the adjuvant comprising an agonst of TLR7 and/or TLR8 and the antigen. In some embodiments of any of the aspects, wherein the adjuvant comprising an agonst of TLR7 and/or TLR8 (or the adjuvant and the antigen) is administered multiple times, the first administration occurs when the subject is less than about 28 days of age. In some embodiments of any of the aspects, wherein the adjuvant comprising an agonst of TLR7 and/or TLR8 (or the adjuvant and the antigen) is administered multiple times, the first administration occurs when the subject is less than 28 days of age. In some embodiments of any of the aspects, wherein the adjuvant comprising an agonst of TLR7 and/or TLR8 (or the adjuvant and the antigen) is administered multiple times, the first administration occurs when the subject is less than about 1 day of age. In some embodiments of any of the aspects, wherein the adjuvant comprising an agonst of TLR7 and/or TLR8 (or the adjuvant and the antigen) is administered multiple times, the first administration occurs when the subject is less than 1 day of age. In some embodiments of any of the aspects, wherein the adjuvant comprising an agonst of TLR7 and/or TLR8 (or the adjuvant and the antigen) is administered multiple times, the first administration occurs at the birth of the subject.

In some embodiments of any of the aspects, the first and/or second administration occurs when the subject is less than about 6 months of age. In some embodiments of any of the aspects, the first and/or second administration occurs when the subject is less than 6 months of age. In some embodiments of any of the aspects, the first and/or second administration occurs when the subject is less than about 28 days of age. In some embodiments of any of the aspects, the first and/or second administration occurs when the subject is less than 28 days of age. In some embodiments of any of the aspects, the first and/or second administration occurs when the subject is from about 28 days to about 6 months of age. In some embodiments of any of the aspects, the first and/or second administration occurs when the subject is from 28 days to 6 months of age.

In some embodiments of any of the aspects, the first and second administrations occur when the subject is less than about 6 months of age. In some embodiments of any of the aspects, the first and second administrations occur hen the subject is less than 6 months of age. In some embodiments of any of the aspects, the first and second administrations occur when the subject is less than about 28 days of age. In some embodiments of any of the aspects, the first and second administrations occur when the subject is less than 28 days of age. In some embodiments of any of the aspects, the first and second administrations occur when the subject is from about 28 days to about 6 months of age. In some embodiments of any of the aspects, the first and second administrations occur when the subject is from 28 days to 6 months of age.

In some embodiments of any of the aspects, the second administration occurs within about 28 days of the first administration. In some embodiments of any of the aspects, the second administration occurs within 28 days of the first administration.

In some embodiments of any of the aspects, the adjuvant comprising an agonist of TLR7 and/or TLR8 is administered to a human infant. In some embodiments of any of the aspects, the adjuvant comprising an agonist of TLR7 and/or TLR8 is administered to a human newborn.

In some embodiments of any of the aspects, the adjuvant comprising an agonist of TLR7 and/or TLR8 and the antigen (and optionally a second adjuvant) are administered in the same formulation. In some embodiments of any of the aspects, the adjuvant comprising an agonist of TLR7 and/or TLR8 and the antigen (and optionally a second adjuvant) are administered in an admixture.

In some embodiments of any of the aspects, the adjuvant comprising an agonist of TLR7 and/or TLR8 and the antigen (and optionally a second adjuvant) are administered in different fomulations. In some embodiments of any of the aspects, the adjuvant comprising an agonist of TLR7 and/or TLR8 and the antigen (and optionally a second adjuvant) are administered in different fomulations at the same time (e.g. simultaneously or immediately concurrently). In some embodiments of any of the aspects, the adjuvant comprising an agonist of TLR7 and/or TLR8 and the antigen (and optionally a second adjuvant) are administered in different fomulations at the same time and in substantially the same location. In some embodiments of any of the aspects, the adjuvant comprising an agonist of TLR7 and/or TLR8 and the antigen (and optionally a second adjuvant) are administered in different fomulations at different times. In some embodiments of any of the aspects, the adjuvant comprising an agonist of TLR7 and/or TLR8 and the antigen (and optionally a second adjuvant) are administered in different fomulations and substantially at the same location.

The compositions and methods described herein can be administered to a subject in need of vaccination, immunization, and/or stimulation of an immune response. In some embodiments of any of the aspects, the methods described herein comprise administering an effective amount of compositions described herein, e.g. to a subject in order to stimulate an immune response or provide protection against the relevant pathogen the antigen was derived from. Providing protection against the relevant pathogen is stimulating the immune system such that later exposure to the antigen (e.g., on or in a live pathogen) triggers a more effective immune response than if the subject was naïve to the antigen. Protection can include faster clearance of the pathogen, reduced severity and/or time of symptoms, and/or lack of development of disease or symptoms. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical, administration. Administration can be local or systemic. In some embodiments of any of the aspects, the administration can be intramuscular or subcutaneous.

The term "effective amount" as used herein refers to the amount of adjuvant needed to stimulate the immune system, or in combination with an antigen, to provide a protective effect against subsequent infections, and relates to a sufficient amount of pharmacological composition to provide the desired effect. The term "therapeutically effective amount" therefore refers to an amount of the adjuvant (and optionally, the antigen) that is sufficient to provide a particular immune stimulatory effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or prevent a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition which achieves a half-maximal inhibition of symptoms or induction of desired responses) as determined in cell culture, or in an appropriate animal model. Levels in plasma can be measured, for example, by high performance liquid chromatography. The effects of any particular dosage can be monitored by a suitable bioassay, e.g., assay for antibody titers, among others. The dosage can be determined by a physician and adjusted, as necessary, to suit observed effects of the treatment.

In some embodiments of any of the aspects, the technology described herein relates to a pharmaceutical composition comprising an adjuvant comprising an agonist of TLR7 and/or TLR8 as described herein, and optionally a pharmaceutically acceptable carrier. In some embodiments of any of the aspects, the active ingredients of the pharmaceutical composition comprises an adjuvant comprising an agonist of TLR7 and/or TLR8 as described herein. In some embodiments of any of the aspects, the active ingredients of the pharmaceutical composition consist essentially of an adjuvant comprising agonist of TLR7 and/or TLR8 as described herein. In some embodiments of any of the aspects, the active ingredients of the pharmaceutical composition consist of an adjuvant comprising an agonist of TLR7 and/or TLR8 as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. an adjuvant comprising an agonist of TLR7 and/or TLR8 as described herein.

In some embodiments of any of the aspects, the pharmaceutical composition comprising an adjuvant comprising an agonist of TLR7 and/or TLR8 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an adjuvant as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an adjuvant comprising an agonist of TLR7 and/or TLR8 as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the adjuvant can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the methods described herein can further comprise administering a second agent and/or treatment to the subject, e.g. as part of a combinatorial therapy.

In some embodiments of any of the aspects, an effective dose of a composition comprising an adjuvant comprising an agonist of TLR7 and/or TLR8 as described herein can be administered to a patient once. In some embodiments of any of the aspects, an effective dose of a composition comprising an adjuvant comprising an agonist of TLR7 and/or TLR8 can be administered to a patient repeatedly. For systemic administration, subjects can be administered a therapeutic amount of a composition comprising an adjuvant comprising an agonist of TLR7 and/or TLR8, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, the adjuvant comprising an agonist of TLR7 and/or TLR8 is administered at a dose of from about 0.001 mg per kilogram of a subject's body mass to about 10.0 mg per kilogram of the subject's body mass. In some embodiments of any of the aspects, the adjuvant comprising an agonist of TLR7 and/or TLR8 is administered at a dose of from 0.001 mg per kilogram of a subject's body mass to 10.0 mg per kilogram of the subject's body mass.

In some embodiments of any of the aspects, the adjuvant comprising an agonist of TLR7 and/or TLR8 is administered at a dose of from about 0.01 mg per kilogram of a subject's body mass to about 10.0 mg per kilogram of the subject's body mass. In some embodiments of any of the aspects, the adjuvant comprising an agonist of TLR7 and/or TLR8 is administered at a dose of from 0.01 mg per kilogram of a subject's body mass to 10.0 mg per kilogram of the subject's body mass.

In some embodiments of any of the aspects, the adjuvant comprising an agonist of TLR7 and/or TLR8 is administered at a dose of from about 0.01 mg per kilogram of a subject's body mass to about 5.0 mg per kilogram of the subject's body mass. In some embodiments of any of the aspects, the adjuvant comprising an agonist of TLR7 and/or TLR8 is administered at a dose of from 0.01 mg per kilogram of a subject's body mass to 5.0 mg per kilogram of the subject's body mass.

In some embodiments of any of the aspects, the adjuvant comprising an agonist of TLR7 and/or TLR8 is administered at a dose of from about 0.05 mg per kilogram of a subject's body mass to about 5.0 mg per kilogram of the subject's body mass. In some embodiments of any of the aspects, the adjuvant comprising an agonist of TLR7 and/or TLR8 is administered at a dose of from 0.05 mg per kilogram of a subject's body mass to 5.0 mg per kilogram of the subject's body mass.

In some embodiments of any of the aspects, the adjuvant comprising an agonist of TLR7 and/or TLR8 is administered at a dose of from about 0.01 mg per kilogram of a subject's body mass to about 1.0 mg per kilogram of the subject's body mass. In some embodiments of any of the aspects, the adjuvant comprising an agonist of TLR7 and/or TLR8 is administered at a dose of from 0.01 mg per kilogram of a subject's body mass to 1.0 mg per kilogram of the subject's body mass.

In some embodiments of any of the aspects, the adjuvant comprising an agonist of TLR7 and/or TLR8 is administered at a dose of from about 0.05 mg per kilogram of a subject's body mass to about 0.5 mg per kilogram of the subject's body mass. In some embodiments of any of the aspects, the adjuvant comprising an agonist of TLR7 and/or TLR8 is administered at a dose of from 0.05 mg per kilogram of a subject's body mass to 0.5 mg per kilogram of the subject's body mass.

In some embodiments of any of the aspects, the adjuvant comprising an agonist of TLR7 and/or TLR8 is administered at a dose of about 0.1 mg per kilogram of a subject's body mass. In some embodiments of any of the aspects, the adjuvant comprising an agonist of TLR7 and/or TLR8 is administered at a dose of 0.1 mg per kilogram of a subject's body mass.

In some embodiments of any of the aspects, the adjuvant comprising an agonist of TLR7 and/or TLR8 is alum-absorbed and administered at a dose of from about 0.01 mg per kilogram of a subject's body mass to about 10.0 mg per kilogram of the subject's body mass. In some embodiments of any of the aspects, the adjuvant comprising an agonist of TLR7 and/or TLR8 is alum-absorbed and administered at a dose of from 0.01 mg per kilogram of a subject's body mass to 10.0 mg per kilogram of the subject's body mass. In some embodiments of any of the aspects, the adjuvant comprising an agonist of TLR7 and/or TLR8 is alum-absorbed and administered at a dose of about 0.01 mg per kilogram of a subject's body mass. In some embodiments of any of the aspects, the adjuvant comprising an agonist of TLR7 and/or TLR8 is alum-absorbed and administered at a dose of 0.01 mg per kilogram of a subject's body mass. In some embodiments of any of the aspects, the adjuvant comprising an agonist of TLR7 and/or TLR8 is alum-absorbed and administered at a dose of about 10.0 mg per kilogram of a subject's body mass. In some embodiments of any of the aspects, the adjuvant comprising an agonist of TLR7 and/or TLR8 is alum-absorbed and administered at a dose of 10.0 mg per kilogram of a subject's body mass.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the adjuvant and/or the antigen. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses over a period of weeks or months.

The dosage ranges for the administration of an adjuvant comprising an agonist of TLR7 and/or TLR8 according to the methods described herein depend upon, for example, the form of the adjuvant, its potency, and the extent to which symptoms, markers, or indicators of a response described herein are desired to be induced, for example the percentage inducation desired for an immune response. The dosage should not be so large as to cause adverse side effects, such as inflammatory responses. Generally, the dosage will vary with the age, condition, and sex of the patient and can be determined by one of skill in the art. The dosage can also be adjusted by the individual physician in the event of any complication.

The efficacy of the adjuvant comprising an agonist of TLR7 and/or TLR8 in, e.g. to induce a response as described herein (e.g. an immune response or immunization) can be determined by the skilled clinician. However, a treatment is considered "effective treatment," as the term is used herein, if one or more of the signs or symptoms of a condition described herein are altered in a beneficial manner, other clinically accepted signs or symptoms are improved, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Immune responses can be detected by a variety of methods known to those skilled in the art, including but not limited to, antibody production, cytotoxicity assay, proliferation assay and cytokine release assays. For example, samples of blood can be drawn from the immunized mammal and analyzed for the presence of antibodies against the antigen administered in the respective vaccine and the titer of these antibodies can be determined by methods known in the art.

Efficacy of an agent can be determined by assessing physical indicators of a desired response, (e.g. immune response, cytokine production, antibody titers, etc). It is well within the ability of one skilled in the art to monitor efficacy of administration and/or treatment by measuring any one of such parameters, or any combination of parameters. Efficacy can be assessed in animal models of a condition described herein, for example immunization of monkeys. When using an experimental animal model, efficacy of treatment is evidenced when a statistically significant change in a marker is observed.

In vitro and animal model assays are provided herein which allow the assessment of a given dose of an adjuvant and/or antigen. By way of non-limiting example, the effects of a dose of adjuvant can be assessed by measuring the antibody titers or cytokine production.

The efficacy of a given dosage combination can also be assessed in an animal model, e.g. immunization of infant or newborn monkeys as described in the Examples herein.

In one aspect of any of the embodiments, described herein is a kit comprising an adjuvant comprising an agonist of TLR7 and/or TLR8 and optionally at least one antigen. In some embodiments of any of the aspects, the adjuvant and antigen are not conjugated to each other. The adjuvant and antigen can be present in the same formulation of the kit or in separate formulations of the kit, e.g., for separate administration or for mixing prior to administration.

A kit is any manufacture (e.g., a package or container) comprising at least one reagent, e.g., an adjuvant comprising an agonist of TLR7 and/or TLR8, the manufacture being promoted, distributed, or sold as a unit for performing the methods described herein. The kits described herein can optionally comprise additional components useful for performing the methods described herein. By way of example, the kit can comprise fluids and compositions (e.g., buffers, needles, syringes etc.) suitable for performing one or more of the administrations according to the methods described herein, an instructional material which describes performance of a method as described herein, and the like. Additionally, the kit may comprise an instruction leaflet.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an adjuvant). In some embodiments of the aspects described herein, the response is specific for a particular antigen (an "antigen-specific response"), and refers to a response by a CD4 T cell, CD8 T cell, or B cell via their antigen-specific receptor. In some embodiments of the aspects described herein, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. Stimulation of an immune response refers to an induction or increase of the immune response.

In some embodiments of any of the aspects, an immune response can be cytokine production by Th1 cells. In some embodiments of any of the aspects, an immune response can be an increase in the level of Th1 antigen-specific neonatal CD4+ cells. In some embodiments of any of the aspects, an immune response can be an increase in the level of Th1 neonatal CD4+ cells. In some embodiments of any of the aspects, an immune response can be an increase in the level of Th1 neonatal cells. In some embodiments of any of the aspects, an immune response can be an increase in the level of neonatal CD4+ cells. In some embodiments of any of the aspects, an immune response can be an increase in the level of Th1 CRM-197-specific neonatal CD4+ cells.

In some embodiments of any of the aspects, the immune response is an increase in the IgG2a/c subclass. In some embodiments of any of the aspects, the immune response is an increase in the IgG2a/c subclass and the adjuvant comprising an agonist of TLR7 and/or TLR8 is absorbed to alum.

An immune response to an antigen can be the development in a subject of a humoral and/or a cell-mediated immune response to molecules present in the antigen or vaccine composition of interest. For purposes of the present invention, a "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

The term "treatment" (including variations thereof, e.g., "treat" or "treated") as used herein means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided that treat, including prophylactically and/or therapeutically immunize, a host animal against a microbial infection (e.g., a bacterium or virus). The methods of the present invention are useful for conferring prophylactic and/or therapeutic immunity to a subject. The methods of the present invention can also be practiced on subjects for biomedical research applications.

In some embodiments of any of the aspects, an immunogenic amount or immunologically effective amount of the adjuvant comprising an agonist of TLR7 and/or TLR8 (an optionally the antigen) is administered. The term an "immunogenic amount," and "immunologically effective amount," both of which are used interchangeably herein, refers to the amount of the antigen or immunogenic composition sufficient to elicit an immune response, either a cellular (T-cell) or humoral (B-cell or antibody) response, or both, as measured by standard assays known to one skilled in the art.

The term "vaccine composition" used herein is defined as composition used to elicit an immune response against an antigen within the composition in order to protect or treat an organism against disease. In some embodiments of any of the aspects, the vaccine composition is a suspension of attenuated or killed microorganisms (e.g., viruses, bacteria, or rickettsiae), or of antigenic proteins derived from them, administered for prevention, amelioration, or treatment of infectious diseases. The terms "vaccine composition" and "vaccine" are used interchangeably.

As used herein, the term "newborn" refers to an infant from the time of birth through the 28th day of life. In some embodiments of any of the aspects, the newborn is a human infant. In the embodiment that the newborn is a premature birth, the $28^{th}$ day is extended to include the number of days of premature birth.

As used herein, the term "infant" refers to a young from the time of birth to one year of age.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of immunization and immune response. A subject can be male or female.

A subject can be one who has been previously diagnosed with or identified as suffering from or having a condition in need of treatment (e.g. susceptibility to infection) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an atom or group at the specified or enumerated position in a molecule, or an atom or group that is equivalent to a specified or enumerated atom or group in a second molecule. Equivalent specified or enumerated atoms/groups can be determined by one of skill in the art, e.g., by identifying shared core structures or formulas.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of immunizing a subject, the method comprising administering to the subject
    i) an adjuvant comprising an agonist of TLR7 and/or TLR8; and
    ii) at least one antigen;
    wherein the adjuvant and the at least one antigen are not conjugated to each other.
2. The method of paragraph 1, wherein the adjuvant is selected from the group consisting of:
    a single sstranded (ss) RNA; an imidazoquinoline; a thiazoquinoline and a benzazepine.
3. The method of any of paragraphs 1-2, wherein the adjuvant is lipidated.
4. The method of any of paragraphs 1-3, wherein the adjuvant is 3M-052.
5. The method of any of paragraphs 1-4, wherein the administration of the adjuvant and antigen causes a greater immune response, increased rate of an immune response and/or greater protection than the same dose of the antigen administered without the adjuvant.
6. The method of any of paragraphs 1-5, wherein the administration of the adjuvant and antigen provides protection at a lower dose or with fewer doses than the antigen administered without the adjuvant.
7. The method of any of paragraphs 1-6, wherein the at least one antigen is comprised by an attenuated vaccine.
8. The method of any of paragraphs 1-6, wherein the antigen is comprised by a subunit vaccine or recombinant subunit vaccine.
9. The method of any of paragraphs 1-6, wherein the antigen is comprised by a conjugate vaccine.
10. The method of paragraph 9, wherein the antigen is a polysaccharide.
11. The method of any of paragraphs 1-10, wherein the antigen is bound to or adsorbed to alum.
12. The method of any of paragraphs 1-11, wherein the antigen is comprised by a vaccine selected from the group consisting of:
    a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine.
13. The method of paragraph 12, wherein the vaccine is pneumococcal conjugate vaccine (PCV)13.
14. The method of any of paragraphs 1-13, wherein the vaccine is alum-adjuvanted.
15. The method of any of paragraphs 1-14, further comprising administering a second adjuvant.
16. The method of paragraph 15, wherein the second adjuvant is alum.
17. The method of any of paragraphs 1-16, wherein the subject is a human infant at the time of administration.
18. The method of any of paragraphs 1-17, wherein the subject is a human of less than 28 days of age at the time of administration.
19. The method of any of paragraphs 1-18, wherein the subject is a human of less than 4 days of age at the time of administration.
20. The method of any of paragraphs 1-19, wherein the subject is a human of less than 2 days of age at the time of administration.
21. The method of any of paragraphs 1-20, wherein the subject is a human of less than 24 hours of age at the time of administration.
22. The method of any of paragraphs 1-21, wherein the administration occurs at birth.
23. The method of any of paragraphs 1-22, wherein the adjuvant is administered at a dose of from about 0.01 mg per kilogram of a subject's body mass to about 1.0 mg per kilogram of the subject's body mass.
24. The method of any of paragraphs 1-22, wherein the adjuvant is administered at a dose of about 0.1 mg per kilogram of the subject's body mass.
25. The method of any of paragraphs 1-24, wherein the adjuvant is administered intramuscularly or subcutaneously.
26. The method of any of paragraphs 1-25, further comprising at least a second administration of the adjuvant and antigen.
27. The method of paragraph 26, wherein the first administration occurs when the subject is less than 1 day of age.
28. The method of paragraph 26, wherein the first administration occurs at the birth of the subject.
29. The method of paragraph 26, wherein the first administration occurs when the subject is less than 28 days of age.
30. The method of any of paragraphs 1-29, wherein the first and/or second administration occur when the subject is less than 6 months of age.
31. The method of any of paragraphs 1-29, wherein the first and/or second administration occur when the subject is less than 28 days of age.
32. The method of any of paragraphs 1-29, wherein the first and/or second administration occur when the subject is from 28 days to 6 months of age.
33. The method of any of paragraphs 26-32, wherein the second administration occurs within 28 days of the first administration.
34. The method of any of paragraphs 1-33, wherein the adjuvant and the antigen are administered in the same formulation.
35. The method of any of paragraphs 1-34, wherein the adjuvant and the antigen are administered in different formulations and/or at different times.
36. A method of stimulating an immune response of a subject, the method comprising administering to the human an adjuvant comprising an agonist of TLR7 and/or TLR8.
37. The method of paragraph 36, wherein the immune response is T helper 1-cytokine production.
38. The method of paragraph 36, wherein the immune response is an increase in the level of Th1 CRM-197-specific neonatal CD4+ cells.
39. The method of any of paragraphs 36-38, wherein the adjuvant is selected from the group consisting of:
    a single sstranded (ss) RNA; an imidazoquinoline; a thiazoquinoline; and a benzazepine.

40. The method of any of paragraphs 36-39, wherein the adjuvant is lipidated.
41. The method of any of paragraphs 36-40, wherein the adjuvant is 3M-052.
42. The method of any of paragraphs 36-41, further comprising administering a second adjuvant.
43. The method of paragraph 42, wherein the second adjuvant is alum.
44. The method of any of paragraphs 36-43, wherein the subject is a human infant at the time of administration.
45. The method of any of paragraphs 36-43, wherein the subject is a human of less than 28 days of age at the time of administration.
46. The method of any of paragraphs 36-43, wherein the subject is a human of less than 4 days of age at the time of administration.
47. The method of any of paragraphs 36-43, wherein the subject is a human of less than 2 days of age at the time of administration.
48. The method of any of paragraphs 36-43, wherein the subject is a human of less than 24 hours of age at the time of administration.
49. The method of any of paragraphs 36-43, wherein the administration occurs at birth.
50. The method of any of paragraphs 36-49, wherein the adjuvant is administered at a dose of from about 0.01 mg per kilogram of a subject's body mass to about 1.0 mg per kilogram of the subject's body mass.
51. The method of any of paragraphs 36-50, wherein the adjuvant is administered at a dose of about 0.1 mg per kilogram of the subject's body mass.
52. The method of any of paragraphs 36-51, wherein the adjuvant is administered intramuscularly or subcutaneously.
53. The method of any of paragraphs 36-52, further comprising at least a second administration of the adjuvant and antigen.
54. The method of paragraph 53, wherein the first administration occurs when the subject is less than 1 day of age.
55. The method of paragraph 53, wherein the first administration occurs at the birth of the subject.
56. The method of paragraph 53, wherein the first administration occurs when the subject is less than 28 days of age.
57. The method of any of paragraphs 53-56, wherein the first and/or second administration occur when the subject is less than 6 months of age.
58. The method of any of paragraphs 53-56, wherein the first and/or second administration occur when the subject is less than 28 days of age.
59. The method of any of paragraphs 53-56, wherein the first and/or second administration occur when the subject is from 28 days to 6 months of age.
60. The method of any of paragraphs 53-56, wherein the second administration occurs within 28 days of the first administration.
61. A composition for use in immunizing a subject or stimulating an immune response in a subject, the composition comprising an adjuvant comprising an agonist of TLR7 and/or TLR8.
62. The composition of paragraph 61, wherein the composition further comprises at least one antigen, wherein the adjuvant and the at least one antigen are not conjugated to each other.
63. A composition or kit comprising a first formulation comprising an adjuvant comprising an agonist of TLR7 and/or TLR8 and a second formulation comprising at least one antigen, wherein the formulations are for use in immunizing a subject or stimulating an immune response in a subject.
64. A kit comprising an adjuvant comprising an agonist of TLR7 and/or TLR8.
65. The kit of paragraph 64, further comprising at least one antigen.
66. The composition or kit of any of paragraphs 61-65, wherein the adjuvant is selected from the group consisting of:
a single sstranded (ss) RNA; an imidazoquinoline; a thiazoquinoline and a benzazepine.
67. The composition or kit of any of paragraphs 61-66, wherein the adjuvant is lipidated.
68. The composition or kit of any of paragraphs 61-67, wherein the adjuvant is 3M-052.
69. The composition or kit of any of paragraphs 61-68, wherein the administration of the adjuvant and antigen causes a greater immune response, increased rate of an immune response and/or greater protection than the same dose of the antigen administered without the adjuvant.
70. The composition or kit of any of paragraphs 61-69, wherein the administration of the adjuvant and antigen provides protection at a lower dose or with fewer doses than the antigen administered without the adjuvant.
71. The composition or kit of any of paragraphs 61-70, wherein the at least one antigen is comprised by an attenuated vaccine.
72. The composition or kit of any of paragraphs 61-71, wherein the antigen is comprised by a subunit vaccine or recombinant subunit vaccine.
73. The composition or kit of any of paragraphs 61-72, wherein the antigen is comprised by a conjugate vaccine.
74. The composition or kit of paragraph 73, wherein the antigen is a polysaccharide.
75. The composition or kit of any of paragraphs 61-74, wherein the antigen is bound to or adsorbed to alum.
76. The composition or kit of any of paragraphs 61-75, wherein the antigen is comprised by a vaccine selected from the group consisting of:
a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine.
77. The composition or kit of paragraph 76, wherein the vaccine is pneumococcal conjugate vaccine (PCV)13.
78. The composition or kit of any of paragraphs 61-77, wherein the vaccine is alum-adjuvanted.
79. The composition or kit of any of paragraphs 61-78, further comprising a second adjuvant.
80. The composition or kit of paragraph 79, wherein the second adjuvant is alum.
81. The composition or kit of any of paragraphs 61-80, wherein the subject is a human infant at the time of administration.
82. The composition or kit of any of paragraphs 61-80, wherein the subject is a human of less than 28 days of age at the time of administration.
83. The composition or kit of any of paragraphs 61-80, wherein the subject is a human of less than 4 days of age at the time of administration.
84. The composition or kit of any of paragraphs 61-80, wherein the subject is a human of less than 2 days of age at the time of administration.

85. The composition or kit of any of paragraphs 61-80, wherein the subject is a human of less than 24 hours of age at the time of administration.
86. The composition or kit of any of paragraphs 61-80, wherein the administration occurs at birth.
87. The composition or kit of any of paragraphs 61-86, wherein the adjuvant is formulated at a dose of from about 0.01 mg per kilogram of a subject's body mass to about 1.0 mg per kilogram of the subject's body mass.
88. The composition or kit of any of paragraphs 61-87, wherein the adjuvant is formulated at a dose of about 0.1 mg per kilogram of the subject's body mass.
89. The composition or kit of any of paragraphs 61-88, wherein the adjuvant is administered intramuscularly or subcutaneously.
90. The composition or kit of any of paragraphs 61-89, wherein the subject is further administered at least a second administration of the adjuvant and antigen.
91. The composition or kit of paragraph 90, wherein the first administration occurs when the subject is less than 1 day of age.
92. The composition or kit of paragraph 90, wherein the first administration occurs at the birth of the subject.
93. The composition or kit of paragraph 90, wherein the first administration occurs when the subject is less than 28 days of age.
94. The composition or kit of any of paragraphs 61-93, wherein the first and/or second administration occur when the subject is less than 6 months of age.
95. The composition or kit of any of paragraphs 61-93, wherein the first and/or second administration occur when the subject is less than 28 days of age.
96. The composition or kit of any of paragraphs 61-93, wherein the first and/or second administration occur when the subject is from 28 days to 6 months of age.
97. The composition or kit of any of paragraphs 61-96, wherein the second administration occurs within 28 days of the first administration.

Some embodiments of the technology described herein can be defined according to any of the following numbered paragraphs:

1. A method of immunizing a subject, the method comprising administering to the subject
   i) an adjuvant comprising an agonist of TLR7 and/or TLR8; and
   ii) at least one antigen;
   wherein the adjuvant and the at least one antigen are not conjugated to each other.
2. The method of paragraph 1, wherein the adjuvant is selected from the group consisting of:
   a single sstranded (ss) RNA; an imidazoquinoline; a thiazoquinoline; an oxoadinine; and a benzazepine.
3. The method of any of paragraphs 1-2, wherein the adjuvant comprising an agonist of TLR7 and/or TLR8 comprises a compound having the structure of Formula IX:

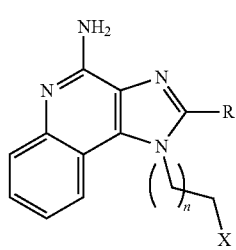

Formula IX wherein n is from 0 to 20,
R is R is selected from H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino and C1-6alkoxyC1-6alkoxy; wherein the C1-6alkyl, C1-6alkylamino, C1-6alkoxy, C3-6cycloalkylC1-6alkyl, C3-6cycloalkylC1-6alkylamino, 20 C3-6cycloalkylC1-6alkoxy, C1-6alkoxyC1-6alkyl, C1-6alkoxyC1-6alkylamino or C1-6alkoxyC1-6alkoxy is branched or unbranched and optionally terminally substituted with a hydroxyl, amino, thio, hydrazino, hydrazido, azido, acetylenyl, carboxyl, or maleimido group and
X is a phospholipid, lipid, lipidation, and/or PEG moiety.

4. The method of any of paragraphs 1-4, wherein the adjuvant comprising an agonist of TLR7 and/or TLR8 comprises a compound having the structure of Formula X:

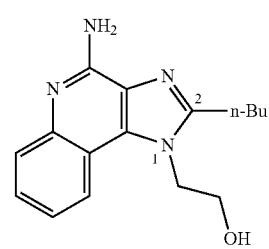

Formula X

5. The method of any of paragraphs 1-4, wherein the adjuvant comprising an agonist of TLR7 and/or TLR8 comprises a compound having the structure of Formula XI:

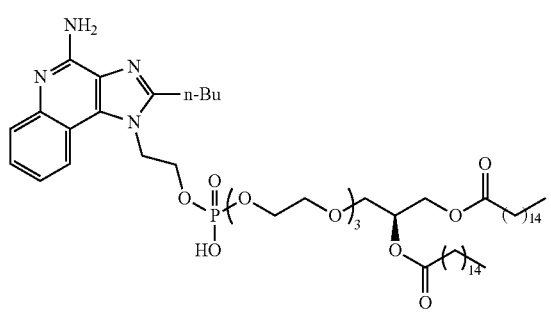

Formula XI

6. The method of any of paragraphs 1-5, wherein the adjuvant comprising an agonist of TLR7 and/or TLR8 comprises a compound selected from the group consisting of: 3M-052; CRX-648; CRX-649; CRX-664; CRX-672; CRX-677; and CRX-748.
7. The method of any of paragraphs 1-6, wherein the adjuvant comprising an agonist of TLR7 and/or TLR8 comprises CRX-649.
8. The method of any of paragraphs 1-7, wherein the adjuvant comprising an agonist of TLR7 and/or TLR8 further comprises a lipid moiety
9. The method of any of paragraphs 1-8, wherein the adjuvant further comprises a phosphorylation or phospholipid moiety.

10. The method of any of paragraphs 1-9, wherein the moiety is located at the ethanol group of 3M-052; CRX-648; CRX-649; CRX-664; CRX-672; CRX-677; or CRX-748.
11. The method of any of paragraphs 1-10, wherein the moiety is located at an N position corresponding to the N1 of Formula X.
12. The method of any of paragraphs 1-11, wherein the moiety is conjugated to the adjuvant via a PEG linker.
13. The method of any of paragraphs 1-12 wherein the PEG linker comprises from 3 to 9 repeats of PEG.
14. The method of any of paragraphs 1-13, wherein the PEG linker comprises 3 repeats of PEG.
15. The method of any of paragraphs 1-14, wherein the administration of the adjuvant and antigen causes a greater immune response, increased rate of an immune response and/or greater protection than the same dose of the antigen administered without the adjuvant.
16. The method of any of paragraphs 1-15, wherein the administration of the adjuvant and antigen provides protection at a lower dose or with fewer doses than the antigen administered without the adjuvant.
17. The method of any of paragraphs 1-16, wherein the at least one antigen is comprised by an attenuated vaccine.
18. The method of any of paragraphs 1-17, wherein the antigen is comprised by a subunit vaccine or recombinant subunit vaccine.
19. The method of any of paragraphs 1-18, wherein the antigen is comprised by a conjugate vaccine.
20. The method of paragraph 19, wherein the antigen is a polysaccharide.
21. The method of any of paragraphs 1-20, wherein the antigen is bound to or adsorbed to alum.
22. The method of any of paragraphs 1-21, wherein the antigen is comprised by a vaccine selected from the group consisting of:
   a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine.
23. The method of paragraph 22, wherein the vaccine is pneumococcal conjugate vaccine (PCV)13.
24. The method of any of paragraphs 1-23, wherein the vaccine is alum-adjuvanted.
25. The method of any of paragraphs 1-24, further comprising administering a second adjuvant.
26. The method of paragraph 25, wherein the second adjuvant is alum.
27. The method of paragraph 26, wherein the adjuvant comprising the agonist of TLR7 and/or TLR8 is absorbed onto the alum.
28. The method of any of paragraphs 1-27, wherein the subject is a human infant at the time of administration.
29. The method of any of paragraphs 1-28, wherein the subject is a human of less than 28 days of age at the time of administration.
30. The method of any of paragraphs 1-29, wherein the subject is a human of less than 4 days of age at the time of administration.
31. The method of any of paragraphs 1-30, wherein the subject is a human of less than 2 days of age at the time of administration.
32. The method of any of paragraphs 1-31, wherein the subject is a human of less than 24 hours of age at the time of administration.
33. The method of any of paragraphs 1-32, wherein the administration occurs at birth.
34. The method of any of paragraphs 1-33, wherein the adjuvant is administered at a dose of from about 0.01 mg per kilogram of a subject's body mass to about 10.0 mg per kilogram of the subject's body mass.
35. The method of any of paragraphs 1-33, wherein the adjuvant is administered at a dose of from about 0.05 mg per kilogram of a subject's body mass to about 5.0 mg per kilogram of the subject's body mass.
36. The method of any of paragraphs 1-33, wherein the adjuvant is administered at a dose of from about 0.01 mg per kilogram of a subject's body mass to about 5.0 mg per kilogram of the subject's body mass.
37. The method of any of paragraphs 1-33, wherein the adjuvant is administered at a dose of from about 0.01 mg per kilogram of a subject's body mass to about 1.0 mg per kilogram of the subject's body mass.
38. The method of any of paragraphs 1-33, wherein the adjuvant is administered at a dose of about 0.1 mg per kilogram of the subject's body mass.
39. The method of any of paragraphs 1-38, wherein the adjuvant is administered intramuscularly or subcutaneously.
40. The method of any of paragraphs 1-39, further comprising at least a second administration of the adjuvant and antigen.
41. The method of paragraph 40, wherein the first administration occurs when the subject is less than 1 day of age.
42. The method of paragraph 40, wherein the first administration occurs at the birth of the subject.
43. The method of paragraph 40, wherein the first administration occurs when the subject is less than 28 days of age.
44. The method of any of paragraphs 1-43, wherein the first and/or second administration occur when the subject is less than 6 months of age.
45. The method of any of paragraphs 1-44, wherein the first and/or second administration occur when the subject is less than 28 days of age.
46. The method of any of paragraphs 1-44, wherein the first and/or second administration occur when the subject is from 28 days to 6 months of age.
47. The method of any of paragraphs 40-46, wherein the second administration occurs within 28 days of the first administration.
48. The method of any of paragraphs 1-47, wherein the adjuvant and the antigen are administered in the same formulation.
49. The method of any of paragraphs 1-48, wherein the adjuvant and the antigen are administered in different formulations and/or at different times.
50. A method of stimulating an immune response of a subject, the method comprising administering to the human an adjuvant comprising an agonist of TLR7 and/or TLR8.
51. The method of paragraph 50, wherein the immune response is T helper 1-cytokine production.
52. The method of paragraph 50, wherein the immune response is an increase in the level of Th1 CRM-197-specific neonatal CD4+ cells.
53. The method of paragraph 50, wherein the immune response is an increase in the IgG2a/c subclass and the adjuvant is absorbed to alum.

54. The method of any of paragraphs 50-53, wherein the adjuvant comprising an agonsit of TLR7 and/or TLR8 is selected from the group consisting of:
a single sstranded (ss) RNA; an imidazoquinoline; a thiazoquinoline; an oxoadinine; and a benzazepine.

55. The method of any of paragraphs 50-54, wherein the adjuvant comprising an agonist of TLR7 and/or TLR8 comprises a compound having the structure of Formula IX:

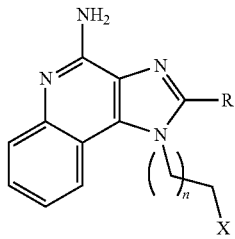

Formula IX wherein n is from 0 to 20,

R is R is selected from H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino and C1-6alkoxyC1-6alkoxy; wherein the C1-6alkyl, C1-6alkylamino, C1-6alkoxy, C3-6cycloalkylC1-6alkyl, C3-6cycloalkylC1-6alkylamino, 20 C3-6cycloalkylC1-6alkoxy, C1-6alkoxyC1-6alkyl, C1-6alkoxyC1-6alkylamino or C1-6alkoxyC1-6alkoxy is branched or unbranched and optionally terminally substituted with a hydroxyl, amino, thio, hydrazino, hydrazido, azido, acetylenyl, carboxyl, or maleimido group and X is a phospholipid, lipid, lipidation, and/or PEG moiety.

56. The method of any of paragraphs 50-55, wherein the adjuvant comprising an agonist of TLR7 and/or TLR8 comprises a compound having the structure of Formula X:

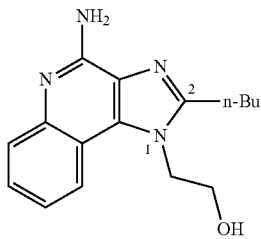

Formula X

57. The method of any of paragraphs 50-56, wherein the adjuvant comprising an agonist of TLR7 and/or TLR8 comprises a compound having the structure of Formula XI:

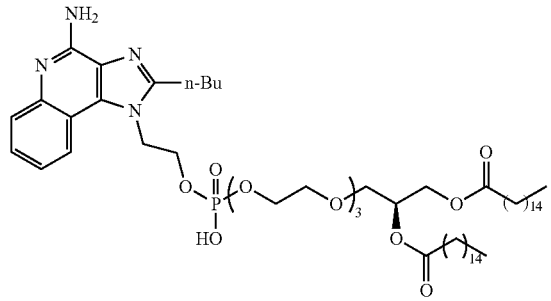

Formula XI

58. The method of any of paragraphs 50-56, wherein the adjuvant comprising an agonist of TLR7 and/or TLR8 comprises a compound selected from the group consisting of: 3M-052; CRX-648; CRX-649; CRX-664; CRX-672; CRX-677; and CRX-748.

59. The method of any of paragraphs 50-56, wherein the adjuvant comprising an agonist of TLR7 and/or TLR8 comprises CRX-649.

60. The method of any of paragraphs 50-59, wherein the adjuvant comprising an agonist of TLR7 and/or TLR8 further comprises a lipid moiety.

61. The method of any of paragraphs 50-60, wherein the adjuvant further comprises a phosphorylation or phospholipid moiety.

62. The method of any of paragraphs 60-61, wherein the moiety is located at the ethanol group of 3M-052; CRX-648; CRX-649; CRX-664; CRX-672; CRX-677; or CRX-748.

63. The method of any of paragraphs 60-62, wherein the moiety is located at an N position corresponding to the N1 of Formula X.

64. The method of any of paragraphs 60-63, wherein the moiety is conjugated to the adjuvant via a PEG linker.

65. The method of paragraph 64, wherein the PEG linker comprises from 3 to 9 repeats of PEG.

66. The method of any of paragraphs 64-65, wherein the PEG linker comprises 3 repeats of PEG.

67. The method of any of paragraphs 50-66, further comprising administering a second adjuvant.

68. The method of paragraph 67, wherein the second adjuvant is alum.

69. The method of paragraph 68, wherein the adjuvant comprising the agonist of TLR7 and/or TLR8 is absorbed onto the alum.

70. The method of any of paragraphs 50-69, wherein the subject is a human infant at the time of administration.

71. The method of any of paragraphs 50-70, wherein the subject is a human of less than 28 days of age at the time of administration.

72. The method of any of paragraphs 50-71, wherein the subject is a human of less than 4 days of age at the time of administration.

73. The method of any of paragraphs 50-72, wherein the subject is a human of less than 2 days of age at the time of administration.

74. The method of any of paragraphs 50-73, wherein the subject is a human of less than 24 hours of age at the time of administration.

75. The method of any of paragraphs 50-74, wherein the administration occurs at birth.

76. The method of any of paragraphs 50-75, wherein the adjuvant is administered at a dose of from about 0.01 mg per kilogram of a subject's body mass to about 10.0 mg per kilogram of the subject's body mass.

77. The method of any of paragraphs 50-75, wherein the adjuvant is administered at a dose of from about 0.05 mg per kilogram of a subject's body mass to about 5.0 mg per kilogram of the subject's body mass.

78. The method of any of paragraphs 50-75, wherein the adjuvant is administered at a dose of from about 0.01 mg per kilogram of a subject's body mass to about 5.0 mg per kilogram of the subject's body mass.

79. The method of any of paragraphs 50-75, wherein the adjuvant is administered at a dose of from about 0.01 mg per kilogram of a subject's body mass to about 1.0 mg per kilogram of the subject's body mass.

80. The method of any of paragraphs 50-75, wherein the adjuvant is administered at a dose of about 0.1 mg per kilogram of the subject's body mass.

81. The method of any of paragraphs 50-80, wherein the adjuvant is administered intramuscularly or subcutaneously.

82. The method of any of paragraphs 50-81, further comprising at least a second administration of the adjuvant.

83. The method of paragraph 82, wherein the first administration occurs when the subject is less than 1 day of age.

84. The method of paragraph 82, wherein the first administration occurs at the birth of the subject.

85. The method of paragraph 82, wherein the first administration occurs when the subject is less than 28 days of age.

86. The method of any of paragraphs 50-85, wherein the first and/or second administration occur when the subject is less than 6 months of age.

87. The method of any of paragraphs 50-86, wherein the first and/or second administration occur when the subject is less than 28 days of age.

88. The method of any of paragraphs 50-87, wherein the first and/or second administration occur when the subject is from 28 days to 6 months of age.

89. The method of any of paragraphs 50-88, wherein the second administration occurs within 28 days of the first administration.

90. A composition for use in immunizing a subject or stimulating an immune response in a subject, the composition comprising an adjuvant comprising an agonist of TLR7 and/or TLR8.

91. The composition of paragraph 90, wherein the composition further comprises at least one antigen, wherein the adjuvant and the at least one antigen are not conjugated to each other.

92. A composition or kit comprising a first formulation comprising an adjuvant comprising an agonist of TLR7 and/or TLR8 and a second formulation comprising at least one antigen, wherein the formulations are for use in immunizing a subject or stimulating an immune response in a subject.

93. A kit comprising an adjuvant comprising an agonist of TLR7 and/or TLR8.

94. The kit of paragraph 93, further comprising at least one antigen.

95. The composition or kit of any of paragraphs 90-94, wherein the adjuvant comprising an agonist of TLR7 and/or TLR8 is selected from the group consisting of:
    a single sstranded (ss) RNA; an imidazoquinoline; a thiazoquinoline; an oxoadinine; and a benzazepine.

96. The composition or kit of any of paragraphs 90-95, wherein the adjuvant comprising an agonist of TLR7 and/or TLR8 comprises a compound having the structure of Formula IX:

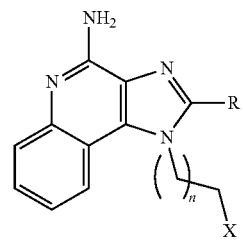

Formula IX wherein n is from 0 to 20,

R is R is selected from H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino and C1-6alkoxyC1-6alkoxy; wherein the C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino or C1-6alkoxyC1-6alkoxy is branched or unbranched and optionally terminally substituted with a hydroxyl, amino, thio, hydrazino, hydrazido, azido, acetyletnyl, carboxyl, or maleimido group and X is a phospholipid, lipid, lipidation, and/or PEG moiety.

97. The composition or kit of any of paragraphs 90-96, wherein the adjuvant comprising an agonist of TLR7 and/or TLR8 comprises a compound having the structure of Formula X:

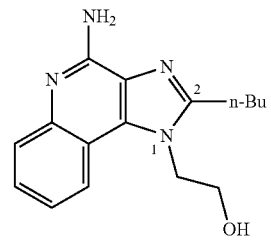

Formula X

98. The composition or kit of any of paragraphs 90-97, wherein the adjuvant comprising an agonist of TLR7 and/or TLR8 comprises a compound having the structure of Formula XI:

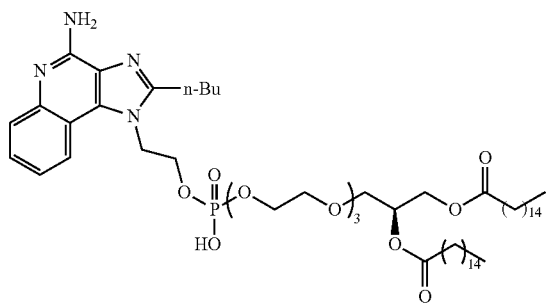

Formula XI

99. The composition or kit of any of paragraphs 90-97, wherein the adjuvant comprising an agonist of TLR7 and/or TLR8 comprises a compound selected from the group consisting of: 3M-052; CRX-648; CRX-649; CRX-664; CRX-672; CRX-677; and CRX-748.
100. The composition or kit of any of paragraphs 90-99, wherein the adjuvant comprising an agonist of TLR7 and/or TLR8 comprises CRX-649.
101. The composition or kit of any of paragraphs 90-100, wherein the adjuvant comprising an agonist of TLR7 and/or TLR8 further comprises a lipid moiety
102. The composition or kit of any of paragraphs 90-101, wherein the adjuvant further comprises a phosphorylation or phospholipid moiety.
103. The composition or kit of any of paragraphs 101-102, wherein the moiety is located at the ethanol group of 3M-052; CRX-648; CRX-649; CRX-664; CRX-672; CRX-677; or CRX-748.
104. The composition or kit of any of paragraphs 101-102, wherein the moiety is located at an N position corresponding to the N1 of Formula X.
105. The composition or kit of any of paragraphs 101-104, wherein the moiety is conjugated to the adjuvant via a PEG linker.
106. The composition or kit of paragraph 105, wherein the PEG linker comprises from 3 to 9 repeats of PEG.
107. The composition or kit of paragraph 105, wherein the PEG linker comprises 3 repeats of PEG.
108. The composition or kit of any of paragraphs 90-107, wherein the administration of the adjuvant and antigen causes a greater immune response, increased rate of an immune response and/or greater protection than the same dose of the antigen administered without the adjuvant.
109. The composition or kit of any of paragraphs 90-108, wherein the administration of the adjuvant and antigen provides protection at a lower dose or with fewer doses than the antigen administered without the adjuvant.
110. The composition or kit of any of paragraphs 90-109, wherein the at least one antigen is comprised by an attenuated vaccine.
111. The composition or kit of any of paragraphs 90-109, wherein the antigen is comprised by a subunit vaccine or recombinant subunit vaccine.
112. The composition or kit of any of paragraphs 90-109, wherein the antigen is comprised by a conjugate vaccine.
113. The composition or kit of paragraph 112, wherein the antigen is a polysaccharide.
114. The composition or kit of any of paragraphs 90-113, wherein the antigen is bound to or adsorbed to alum.
115. The composition or kit of any of paragraphs 90-114, wherein the antigen is comprised by a vaccine selected from the group consisting of:
a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine.
116. The composition or kit of paragraph 115, wherein the vaccine is pneumococcal conjugate vaccine (PCV)13.
117. The composition or kit of any of paragraphs 90-116, wherein the vaccine is alum-adjuvanted.
118. The composition or kit of any of paragraphs 90-117, further comprising administering a second adjuvant.
119. The composition or kit of paragraph 118, wherein the second adjuvant is alum.
120. The composition or kit of paragraph 119, wherein the adjuvant comprising the agonist of TLR7 and/or TLR8 is absorbed onto the alum.
121. The composition or kit of any of paragraphs 90-120, formulated for administration to a human infant at the time of administration.
122. The composition or kit of any of paragraphs 90-121, formulated for administration to a human of less than 28 days of age at the time of administration.
123. The composition or kit of any of paragraphs 90-122, formulated for administration to a human of less than 4 days of age at the time of administration.
124. The composition or kit of any of paragraphs 90-123, formulated for administration to a human of less than 2 days of age at the time of administration.
125. The composition or kit of any of paragraphs 90-124, formulated for administration to a human of less than 24 hours of age at the time of administration.
126. The composition or kit of any of paragraphs 90-125, formulated for administration to a human subject at birth.
127. The composition or kit of any of paragraphs 90-126, wherein the adjuvant is formulated at a dose of from about 0.01 mg per kilogram of a subject's body mass to about 10.0 mg per kilogram of the subject's body mass.
128. The composition or kit of any of paragraphs 90-126, wherein the adjuvant is formulated at a dose of from about 0.05 mg per kilogram of a subject's body mass to about 5.0 mg per kilogram of the subject's body mass.
129. The composition or kit of any of paragraphs 90-126, wherein the adjuvant is formulated at a dose of from about 0.01 mg per kilogram of a subject's body mass to about 5.0 mg per kilogram of the subject's body mass.
130. The composition or kit of any of paragraphs 90-126, wherein the adjuvant is formulated at a dose of from about 0.01 mg per kilogram of a subject's body mass to about 1.0 mg per kilogram of the subject's body mass.
131. The composition or kit of any of paragraphs 90-130, wherein the adjuvant is formulated at a dose of about 0.1 mg per kilogram of the subject's body mass.
132. The composition or kit of any of paragraphs 90-131, wherein the adjuvant is formulation for administration intramuscularly or subcutaneously.
133. The composition or kit of any of paragraphs 90-132, further comprising at least a second administration of the adjuvant and antigen.

134. The composition or kit of paragraph 133, formulated for the first administration to occur when the subject is less than 1 day of age.
135. The composition or kit of paragraph 133, formulated for the first administration to occur at the birth of the subject.
136. The composition or kit of paragraph 133, formulated for the first administration to occur when the subject is less than 28 days of age.
137. The composition or kit of any of paragraphs 133-136, formulated for the first and/or second administration to occur when the subject is less than 6 months of age.
138. The composition or kit of any of paragraphs 133-137, formulated for the first and/or second administration to occur when the subject is less than 28 days of age.
139. The composition or kit of any of paragraphs 133-138, formulated for the first and/or second administration to occur when the subject is from 28 days to 6 months of age.
140. The composition or kit of any of paragraphs 133-139, formulated for the second administration to occur within 28 days of the first administration.
141. The composition or kit of any of paragraphs 90-140, wherein the adjuvant and the antigen are present in the same formulation.
142. The composition or kit of any of paragraphs 90-140, wherein the adjuvant and the antigen are present in different formulations.

EXAMPLES

Example 1: TLR7/8 Adjuvant Overcomes Newborn Hyporesponsiveness to Pneumococcal Conjugate Vaccine at Birth Infection is the most common cause of mortality in early life and immunization is the most promising biomedical intervention to reduce this burden. However, newborns fail to optimally respond to most vaccines. Adjuvantation is a key approach to enhancing vaccine immunogenicity, but responses of human newborn leukocytes to most candidate adjuvants, including most Toll-like receptor (TLR) agonists, are functionally distinct. Herein, we demonstrate that 3M-052 is a locally-acting lipidated imidazoquinoline TLR7/8 agonist adjuvant in mice, that when properly formulated, can induce robust T helper 1-cytokine production by human newborn leukocytes in vitro, both alone and in synergy with the Alum-adjuvanted pneumococcal conjugate vaccine (PCV)13. When admixed with PCV13 and administered intramuscularly on the first day of life to rhesus macaques, 3M-052 dramatically enhanced generation of Th1 CRM-197-specific neonatal CD4+ cells, activation of newborn and infant Streptococcus pneumoniae polysaccharide (PnPS)-specific B cells as well as serotype-specific antibody titers and opsonophagocytic killing. Remarkably, a single birth dose of (PCV13+0.1 mg/kg 3M-052) induced PnPS-specific IgG responses that were ~10-100 times greater than a single birth dose of PCV13 alone, rapidly exceeding the serologic correlate of protection, as early as 28 days of life. Overall, we demonstrate that neonatal non-human primates can respond robustly to a single dose of a sustained-release TLR7/8 adjuvant-containing vaccine formulation at birth to overcome newborn hyporesponsiveness to PCV and confer protective immunity, thereby furthering efforts to improve adjuvantation strategies for early life vaccines. This potent immunization strategy, potentially effective with one birth dose, represents a new paradigm in early life vaccine development.

Early life immunization is desirable, but vaccine-induced responses of newborns and young infants demonstrate slow initiation, low immunogenicity and reduced persistence of functional antibodies (Abs) and cell-mediated responses (1). Although the majority of global immunization schedules are focused on the pediatric age group, development of early life vaccines has been hampered by this distinct immunity and an ad hoc approach in developing vaccines for adults prior to infant trials (2). By comparison to initiation of immunization in infancy, accelerated neonatal immunization strategies may be highly advantageous (3, 4) because: a) newborn vaccines achieve relatively high population penetration as birth is the most reliable point of health care contact worldwide (5), b) there is high risk of severe infection after very early life colonization, and c) reduced vaccine responses can occur after bacterial colonization (6, 7). Adjuvantation is a key tool to enhance vaccine-induced immunity. Adjuvants can enhance, prolong, and modulate immune responses to vaccinal antigens to maximize protective immunity (8), and may potentially enable effective immunization in the very young (1). However, responses of human newborn leukocytes to most adjuvants, including most Toll-like receptor (TLR) agonists (TLRAs) are functionally distinct (2).

Considerations in selecting a clinically relevant adjuvanted vaccine formulation include (a) minimizing systemic inflammation (9), that can occur with TLRAs included in soluble or, to a lesser extent, with TLRA adjuvant-conjugated nanoparticle-based formulations (10), and (b) ensuring activity towards the target population—not a forgone conclusion in newborns, given age-specific soluble and cellular factors (1) that shape distinct T helper (Th)-mediated immunity (11), potentially limiting immune responses to vaccines and pathogens (12, 13). Among the TLRAs, those that most effectively activate human newborn leukocytes are agonists of TLR7 and 8, a sub-family of endosomal leukocyte pattern recognition receptors (PRRs) that recognize uridine-rich single stranded ribonucleic acid (RNA) molecules, as are found in viral RNA, and synthetic imidazoquinolines (IMQs) (14-16). It was contemplated herein that the activity of TLR7/8As towards neonatal leukocytes suggests possible utility as neonatal vaccine adjuvants. To our knowledge, no studies have addressed whether TLRA adjuvantation of common Alum-adjuvanted conjugate vaccines—key to the pediatric immunization schedule—is feasible and effective at birth (i.e., the first 24 hours of life), a key point of global healthcare contact during which the immune system is most distinct. To test the hypothesis that agents activating human neonatal leukocytes in vitro would also be active in newborns at birth in vivo, a rational vaccine design approach was undertaken, employing a TLR7/8A adjuvant. 3M-052, a locally-acting lipidated IMQ TLR7/8A which can induce tumor-specific immunity by forming agonist depots for a gradual sustained release (17) was utilized.

Immunization approaches that lead to more rapid and early protection against pneumococcus would be highly advantageous (18). Pneumococcus is an important pediatric pathogen comprised of ≥92 different capsular polysaccharide serotypes that causes serious invasive disease, including meningitis, sepsis, otitis media, and pneumonia, and is responsible for ~10% of worldwide deaths in children less than 5 years of age (19). The poor efficacy of plain polysaccharide vaccines in young children prompted the development of PCVs that induce T cell-dependent mechanisms (20), with a recommended 3 to 4-dose schedule starting at 2 months of age (21). However, PCV-induced protection may not be fully achieved until 6-12 months of life (18), and the inclusion of Alum, though safe and effective, appears to be Th2-polarizing (22) and results in a formulation that requires multiple doses prior to achieving protective Ab titers. In this context, we have selected pneumococcal conjugate vaccine (PCV), which protects against *S. pneumoniae*, as a model vaccine to adjuvant because: 1) PCV is a well studied vaccine with known correlates of protection, therefore allowing clear and unambiguous evaluation of our adjuvantation strategy, 2) current PCVs can prevent severe disease in older children, and offer newborns some indirect herd protection, but newborns are not directly protected, 3) pneumococcal diseases strikes in early life, particularly in resource poor countries such as Papua New Guinea, making a vaccine that provides rapid protection in early life desirable (3, 4), and 4) although studies of PCV7 immunization, with a 3-dose schedule starting at birth, induced protective serum Ab concentrations in human infants as early as 18 weeks (4.5 months), neonatal hypo-responsiveness was noted for several vaccine serotypes as compared to infants starting a 3-dose schedule of PCV7 at 2 months of life (22, 23).

As described herein, 3M-052 induced robust Th1-cytokine production by human newborn and adult leukocytes in vitro, both alone and in synergy with Alum-adjuvanted PCV13. Using a clinically relevant neonatal rhesus macaque model, it is demonstrated that, when admixed with PCV13 and administered intramuscularly, 3M-052 dramatically accelerated and enhanced neonatal B and T cell immune responses rapidly amplifying functional serotype-specific Ab titers to concentrations that correlate with protection after the first dose of a 3-dose series (Day of Life (DOL) 0, 28, and 56), without serious adverse effects. This novel rational design approach to identify adjuvants active towards distinct populations is broadly applicable, potentially closing the window of vulnerability to infections in early life.

Results 3M-052 is a Locally Acting TLR7/8 Agonist

Figure 1A:
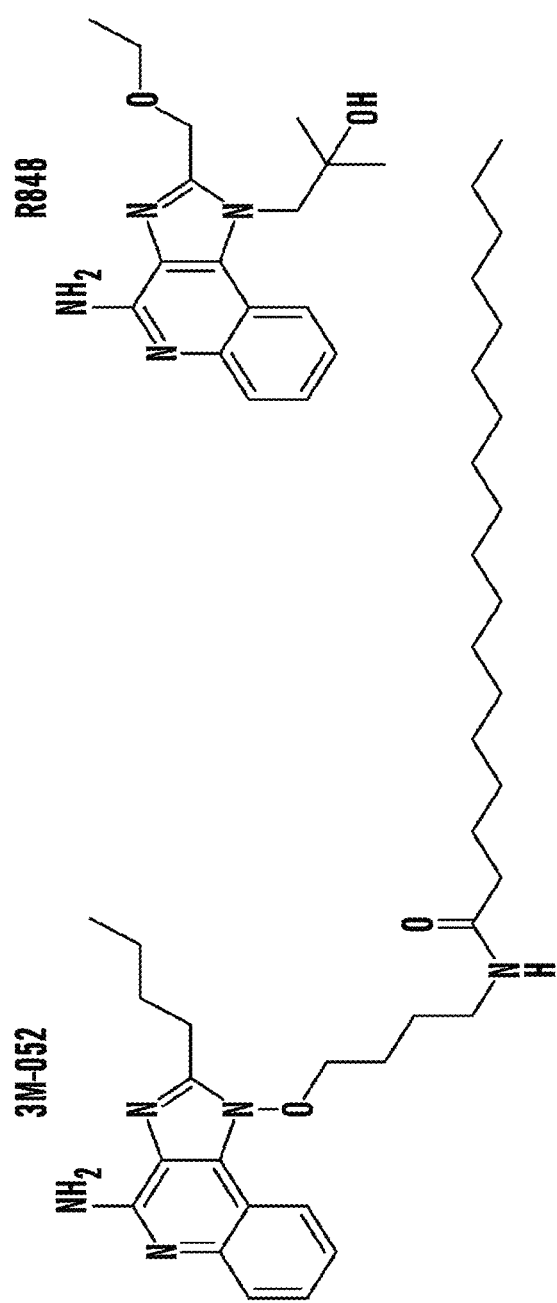
FIGS. 1A-1D demonstrate that 3M-052 is a lipidated, locally-acting TLR7/8 Agonist that, unlike R848, does not result in robust systemic levels and systemic cytokine production.
Figure 1B:
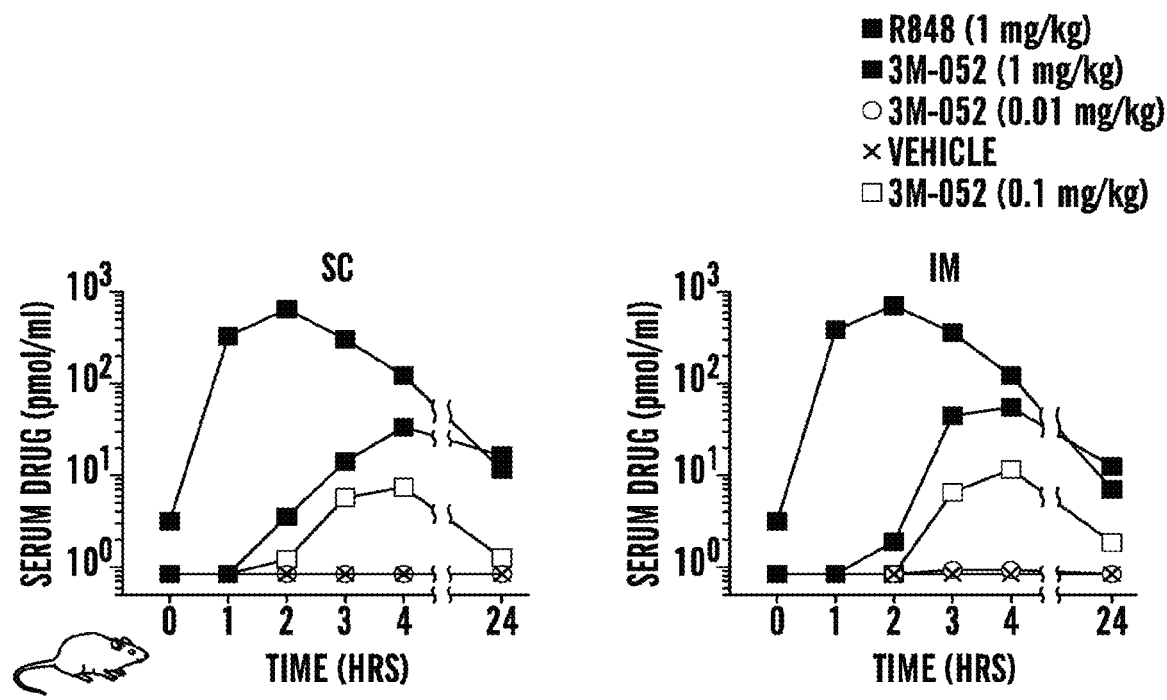
Figure 1C:
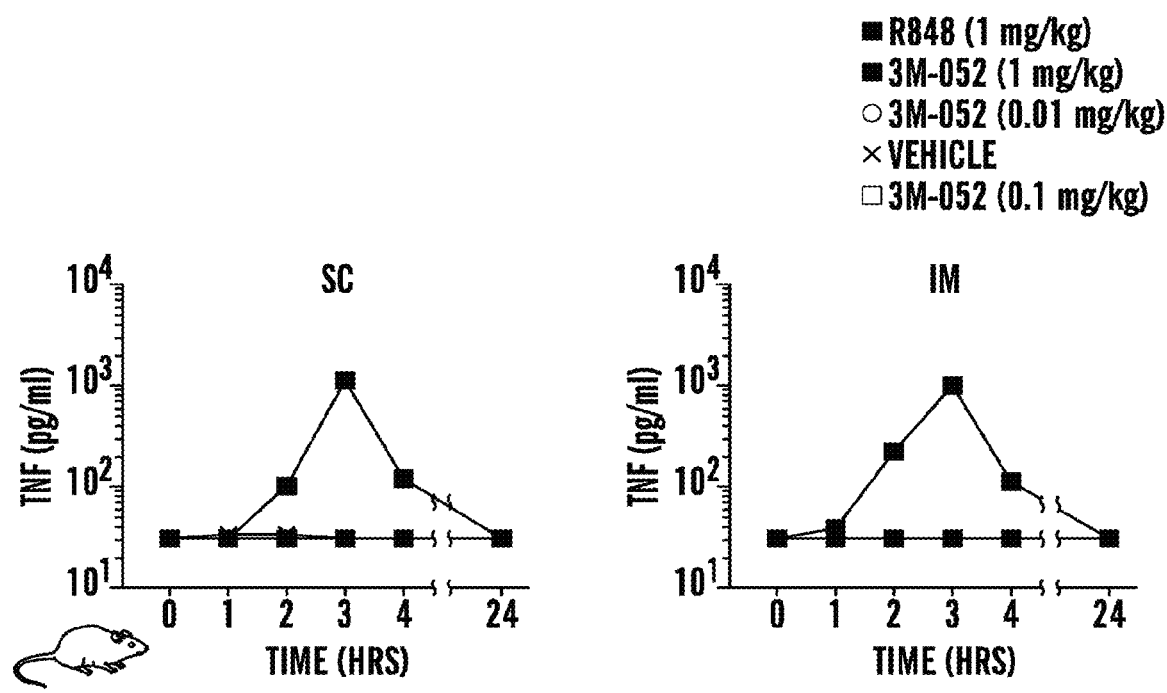
Figure 1D:
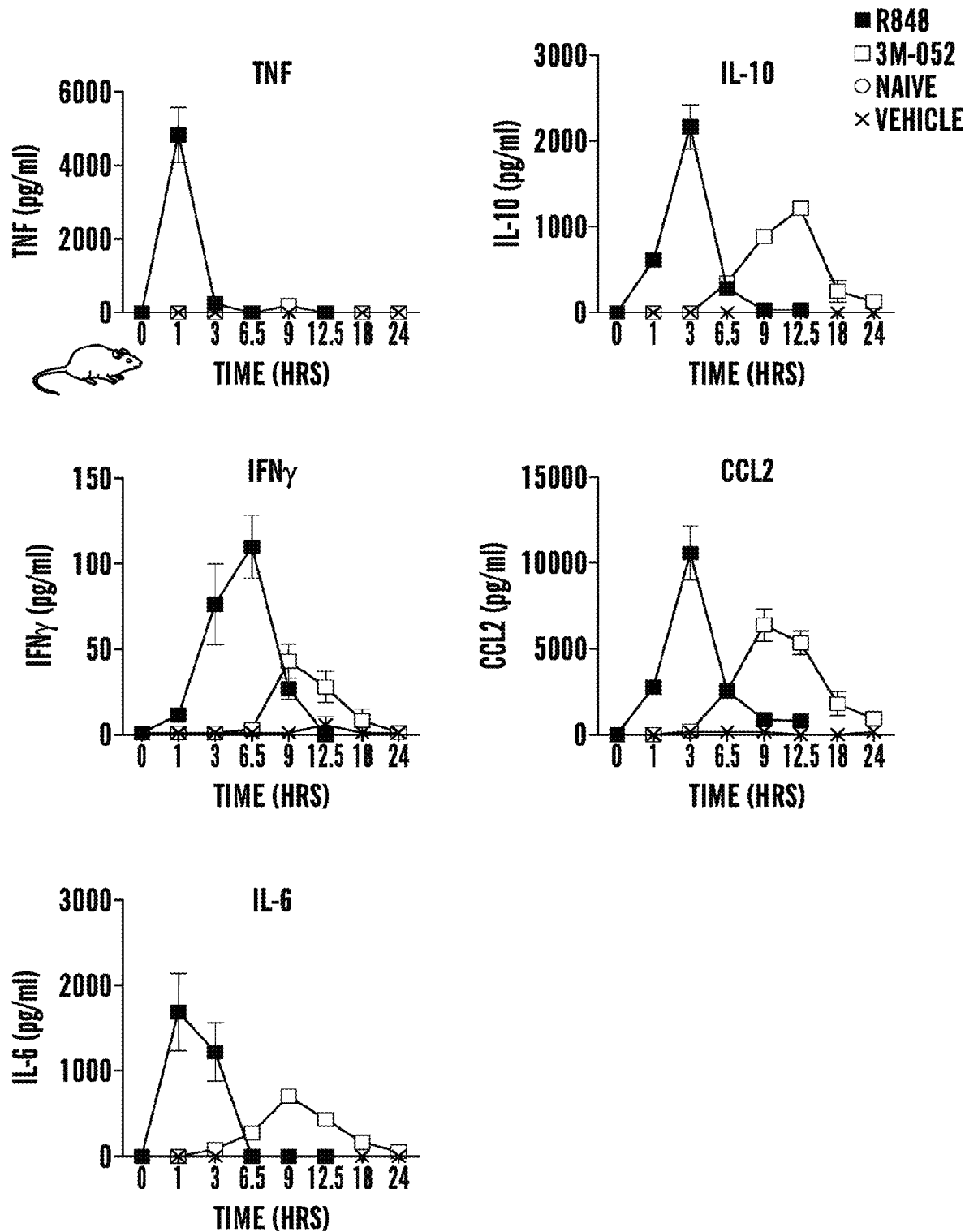
Figure 2A:
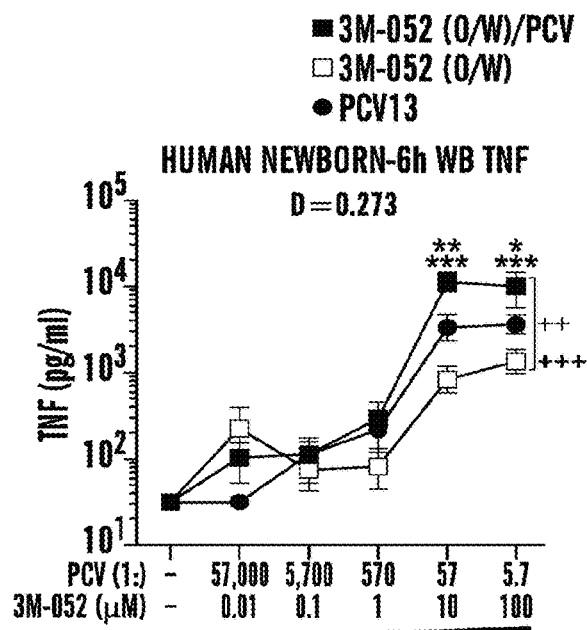
FIGS. 2A-2D demonstrate that 3M-052 synergistically enhances Type 1 immunity from newborn leukocytes when combined with pneumococcal conjugate vaccine in vitro. Human neonatal and adult blood cultured in vitro for 6 hours with buffer control (RPMI), O/W vehicle, PCV13 alone (1:5.7-57,000 v/v), 3M-052 alone (0.01, 0.1, 1, 10, 100 µM), or combinations of each. Supernatants were collected for ELISA and multiplex assay, TNF (FIG. 2A, 2B, n=12), IFNγ (FIG. 2C, 2D, n=10). For comparisons between overall groups (e.g., (PCV13+3M-052) vs. PCV13), statistical significance denoted as ++$p<0.01$, +++$p<0.001$. For comparison at individual concentrations, statistical significance denoted as *$p<0.05$, $p<0.01$, *$p<0.001$. Results represent means±SEM. Level of synergy was calculated using an adapted Loewe definition of additivity, (D>1: antagonism, D=1: additivity, D<1: synergy).
Figure 2B:
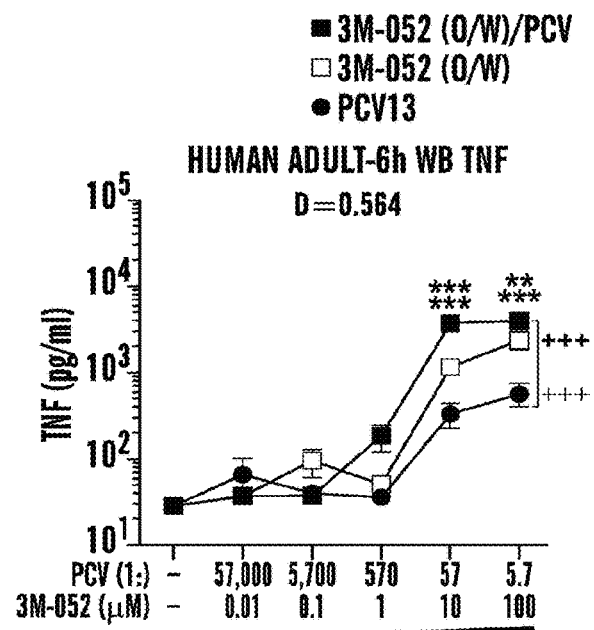
Figure 2C:
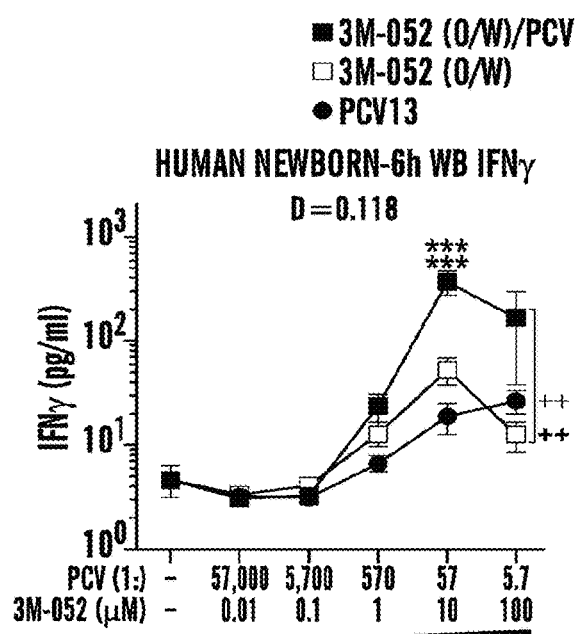
Figure 2D:
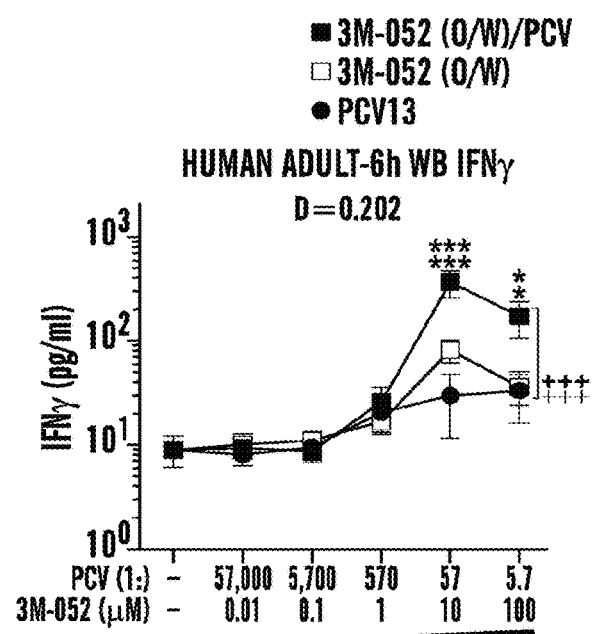

Key to preventing excessive adjuvant reactogenicity, including fever and malaise, is avoiding systemic adjuvant distribution and consequent peripheral cytokine induction (9). Therefore 3M-052, a TLR7/8A that bears a C18 lipid moiety (24) that serves to localize its action, was selected. Rodent pharmacokinetic (PK) and pharmacodynamic (PD) studies were conducted to compare the IMQ TLR7/8A R848 (Resiquimod) and its lipidated congener 3M-052 (FIG. 1A), that can be formulated in an oil-in-water (O/W) emulsion vehicle (Table 3). Distinct PK differences were observable by measurement of R848 or 3M-052 serum drug levels determined by liquid chromatography-mass spectrometry (LC-MS/MS) pre- and post- a single intramuscular (IM, to quadriceps) or subcutaneous (SC, to scruff of neck) administration (FIG. 1B). One hour post-IM or SC injection in rats (both 1 mg/kg), serum R848 concentrations were >1,000 pmol/ml, while only a 4 hour peak of ~50 pmol/ml of 3M-052 was detected at equal treatment dosages. A 10-fold lower dose of 3M-052 (0.1 mg/kg) was not detectable in serum up to 24 hours post-dose. Blood tumor necrosis factor (TNF) concentrations mirrored drug PK patterns with a peak of ~1,000 pg/ml detectable in the R848 treated group, and no induced systemic TNF detectable in any of the 3M-052 treated groups (FIG. 1C). The relative PKs of R848 and 3M-052 were further characterized in mice that received a single SC dose of R848 or 3M-052 (each ~0.1 mg/kg) (FIG. 1D). These studies confirmed the serum TNF PK observations in rats, and demonstrated distinct serum and inducible mRNA expression kinetics between R848 and 3M-052 for interleukin (IL)-6, IL-10, interferon (IFN)γ, and CCL2 (FIG. 1D) in lymph node tissue (FIG. 7A) and splenocytes (FIG. 7B). In all cases, cytokine mRNA expression peaked at 1-3 hours after R848 and at 6 hours after 3M-052 administration. SC administration of 3M-052 induced little if any cytokine mRNA expression, but robust IFN-related and TLR7 gene expression in the spleens of treated mice (FIG. 7A-7B). Compared to R848, 3M-052 thus demonstrated reduced systemic distribution to the blood/serum with induction of responses in the spleen suggesting confinement of this adjuvant to local and lymphatic leukocytes. Overall, although focused on adult and not newborn rodents, these data support the concept that 3M-052 has distinct advantages over R848 by being a locally acting adjuvant in vivo that avoids extensive systemic distribution and consequent induction of systemic inflammation.

3M-052 Enhances Type 1 Immunity In Vitro

To confirm activity of our adjuvanted vaccine formulation towards neonatal leukocytes the cytokine-inducing activity of 3M-052 was characterized alone or in combination with the Food and Drug Administration (FDA)-approved Alum-containing 13-valent PCV (PCV13; Prevnar 13, Pfizer-subsidiary Wyeth Pharmaceuticals) in vitro. The ability of the Alum-containing PCV13, 3M-052, and the admixed formulation (3M-052+PCV) to induce concentration-dependent cytokine production in human neonatal and adult blood was tested (FIGS. 2A-2D). As combining adjuvants such as Alum (in the PCV13 formulation) and 3M-052 may have antagonistic, additive, or synergistic effects, combinations of PCV13+O/W (no 3M-052) or PCV13+O/W formulated with 3M-052—i.e., (PCV+3M-052) were tested at multiple concentrations. Both PCV13 and O/W-formulated 3M-052 alone activated neonatal and adult blood in a concentration-dependent manner, significantly inducing production of TNF over baseline (n=12, p>0.001). The vehicle control did not induce TNF or IFNγ production at any concentration tested (not shown). Of note, (3M-052+PCV13) synergistically induced TNF (n=12) and IFNγ (n=10) in both newborn cord and adult peripheral blood (FIGS. 1A-1D, and FIGS. 8A-8B). Synergy between 3M-052 and the Alum-adjuvanted PCV was of greatest magnitude in neonatal blood (TNF, with a synergy measure D=0.273; IFNγ D=0.118). The synergistic effects of (3M-052+PCV13) were mainly restricted to Th1-polarizing cytokines of TNF and IFNγ, with some evidence of enhanced neonatal IL-12p70 and IL-6 as well (FIGS. 9 and 10). This human in vitro whole blood data was consistent with the ability of 3M-052 to act in combination with Alum to induce a mixed Th1/Th2-response and enhance antigen-specific immunoglobulin G (IgG)2a production when administered to mice in vivo (FIGS. 11A-11B, 12A-12C).

Addition of a TLR7/8A Accelerates Neonatal Serotype-Specific Antibody Responses to PCV13

Figure 3A:
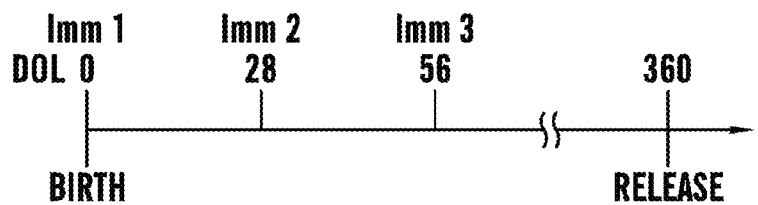
FIGS. 3A-3B demonstrate that addition of a TLR7/8A accelerates neonatal serotype-specific antibody responses to PCV13.
Figure 3B:
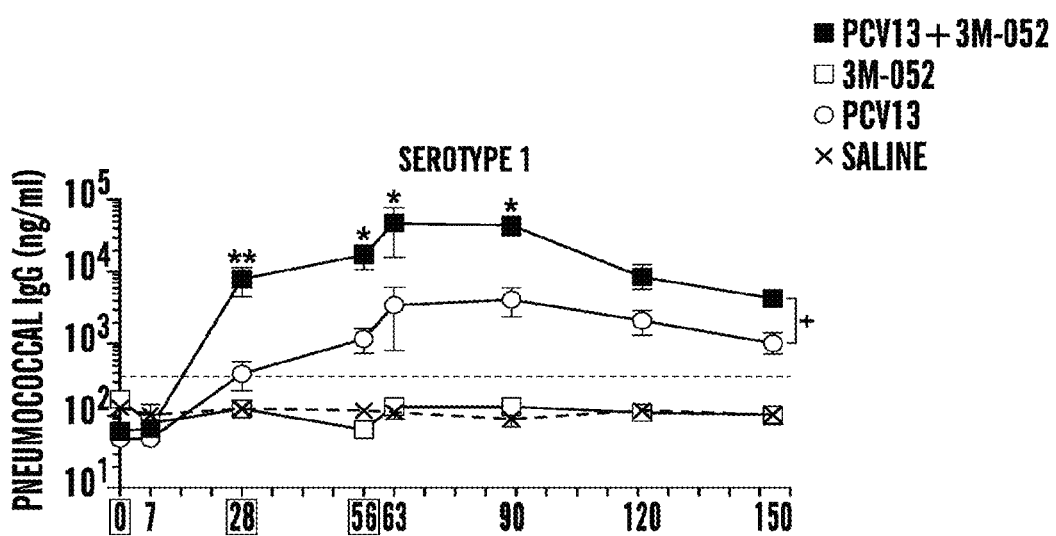
Figure 3B:
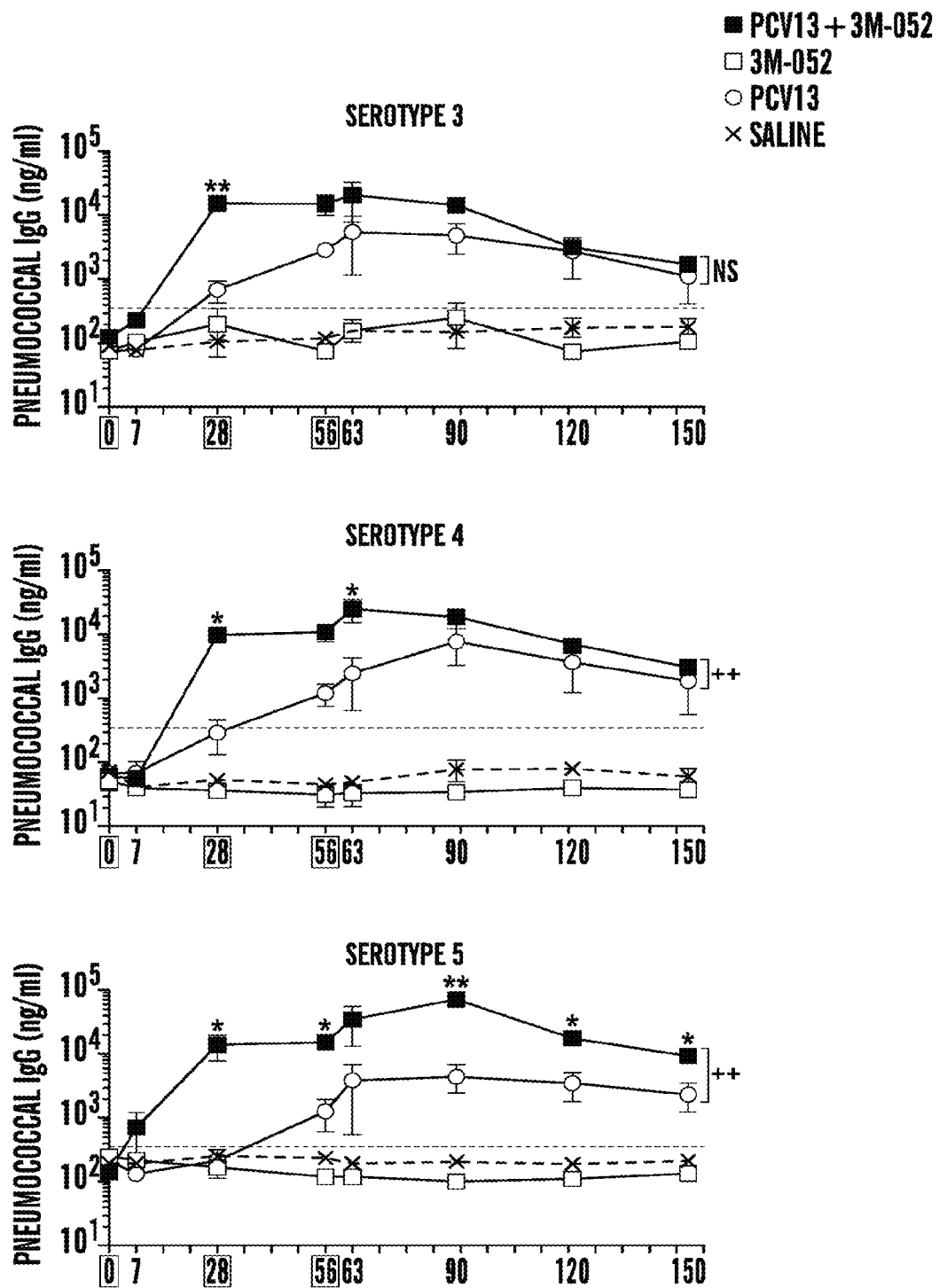
Figure 3B:
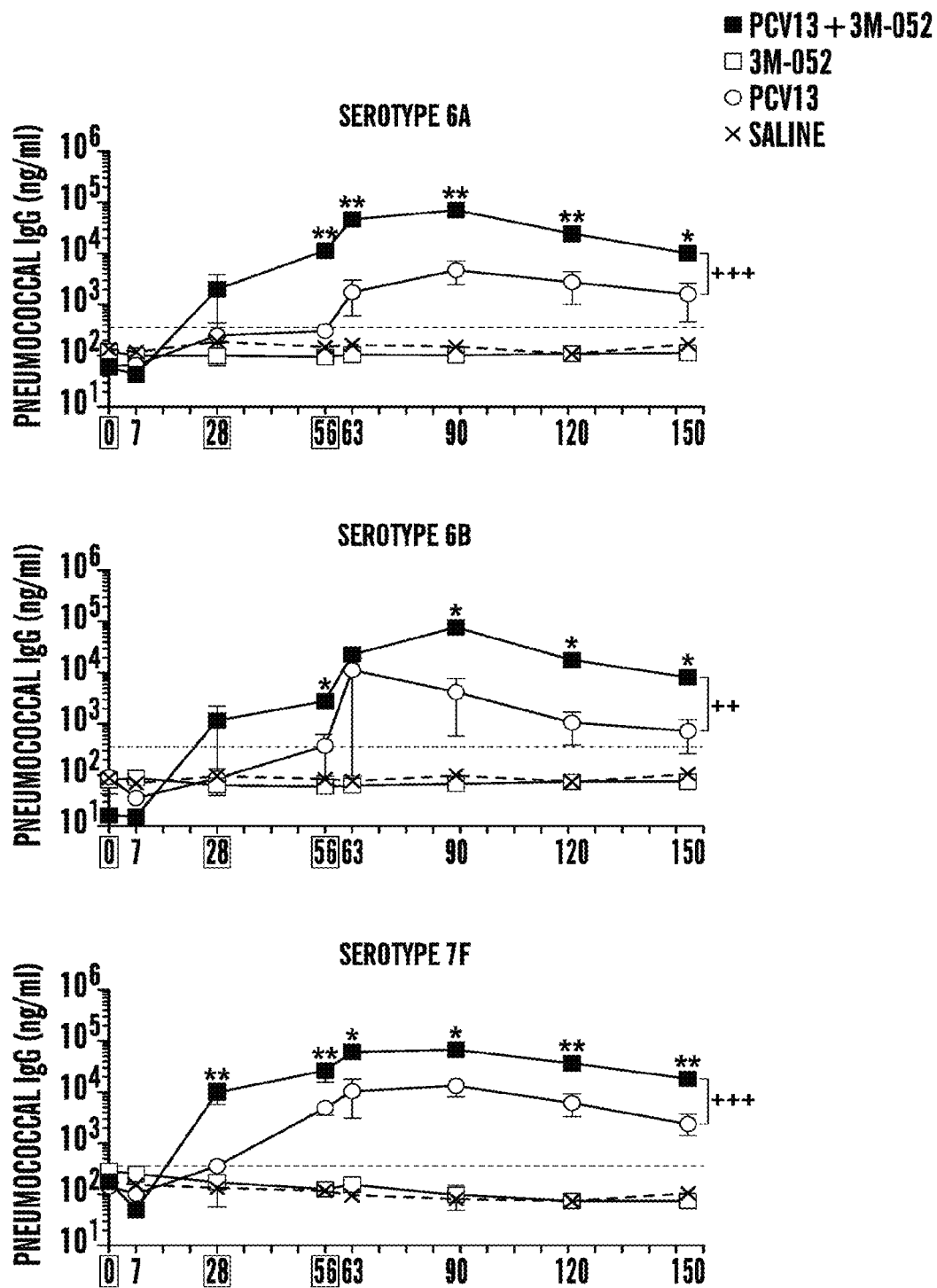
Figure 3B:
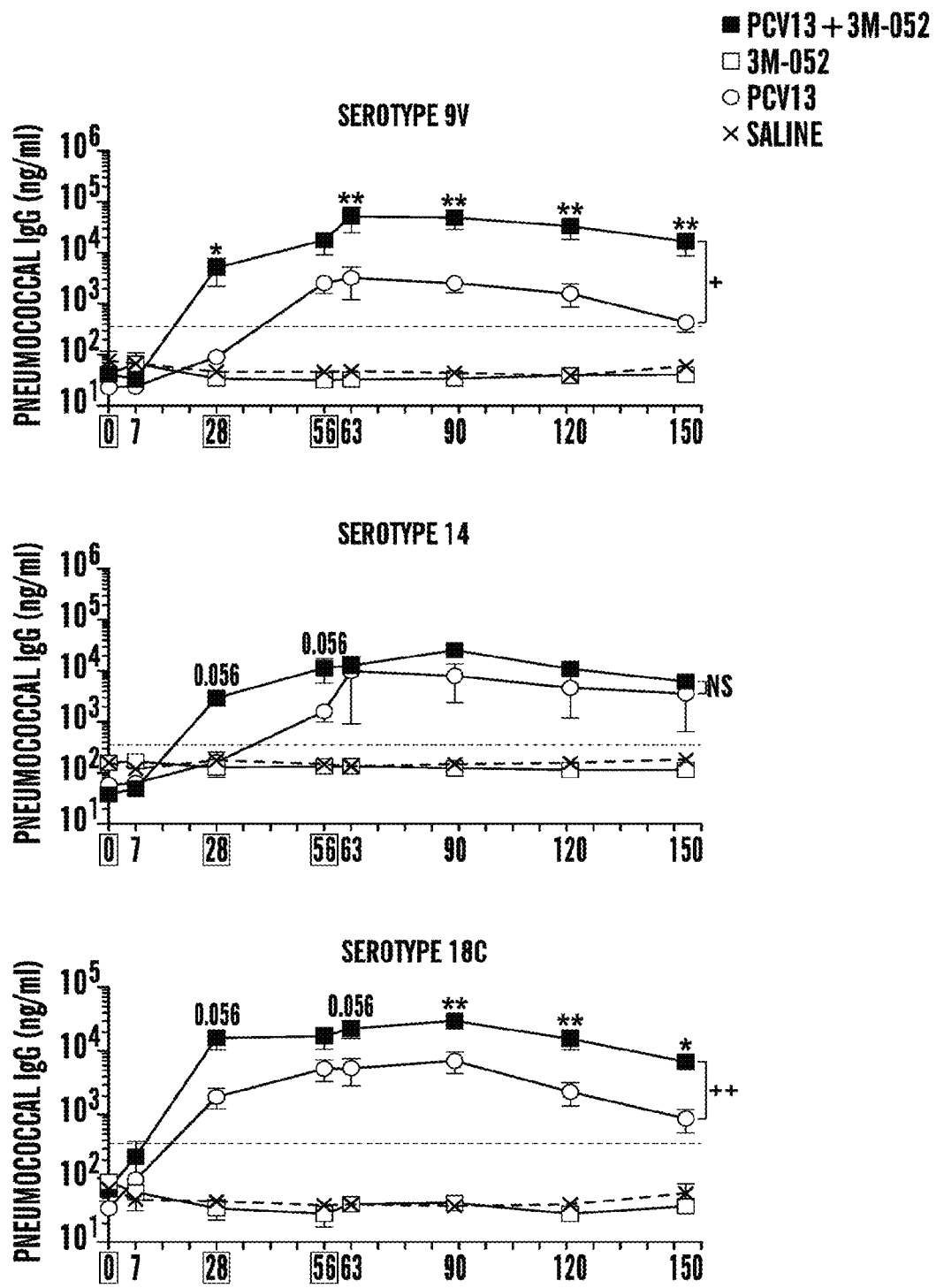
Figure 3B:
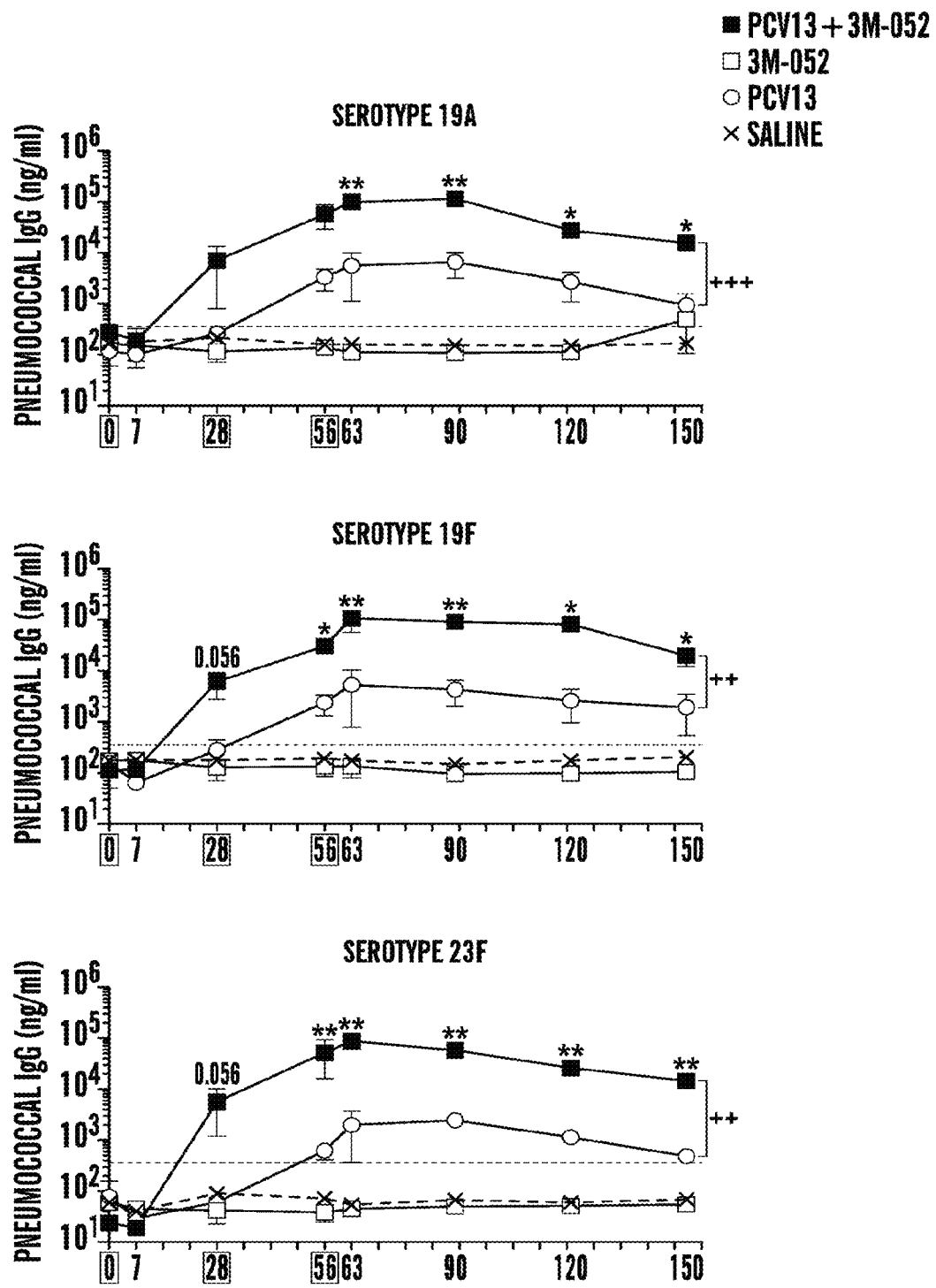

Having demonstrated a low reactogenicity potential of 3M-052 in vivo as well as a high Th1/Th2-polarizing activity towards human neonatal leukocytes in vitro and mice in vivo, the impact of 3M-052 on PCV13 immunogenicity was next assessed in neonatal animals. As human TLR8 is structurally and functionally divergent from murine TLR8, but is closely similar to monkey TLR8 (25), the study was conducted in non-human primates (NHPs); Indian origin rhesus macaques (*Macaca mulatta*). Most studies to date investigating immunogenicity of PCVs in human or NHP neonates have employed half of the recommended human infant dose (22, 23, 26). Therefore, four cohorts of five rhesus macaques per cohort (FIG. 3A) were immunized IM with saline (control), 3M-052 adjuvant alone (0.1 mg/kg 3M-052, or 40 µg per animal), a half dose of PCV13 alone, or PCV13 admixed with 3M-052 (PCV13+0.1 mg/kg 3M-052). All treatments began with a birth dose (DOL0), followed by booster doses at one (DOL28) and two months (DOL56) of life (FIG. 3B). Peripheral blood was collected at the indicated time-points to obtain plasma for an assay of anti-pneumococcal serotype Ab titers by polysaccharide-IgG binding microarray (Table 4).

After a single immunization, PCV13 alone failed to induce anti-pneumococcal serotype Ab responses above 0.35 µg/ml (FIG. 3C), the World Health Organization's (WHOs) reference IgG Ab concentration that is a correlate of protection in humans (27). In marked contrast, PCV13 adjuvanted with 3M-052 dramatically induced robust Ab responses, as early as DOL28 (FIG. 3C). Remarkably, a single birth dose of (PCV13+0.1 mg/kg 3M-052) induced pneumococcal polysaccharide (PnPS)-specific IgG responses that were ~10-100 times greater than a single birth dose of PCV13 alone (FIG. 3C, FIG. 4). These Ab responses significantly surpassed the WHO recommended minimal protective Ab concentrations (0.35 µg/ml) for 7 serotypes (FIG. 4A) and 6 serotypes as compared to PCV13 alone (FIG. 4B).

In Vivo Adjuvanticity of 3M-052 is Dose Dependent

The PD immunogenicity range of 3M-052 was evaluated by repeating the above immunization schedule, but with a 10-fold reduced dose. Two additional cohorts of three rhesus macaques per cohort were immunized IM with the lower dose of 3M-052 adjuvant alone (0.01 mg/kg 3M-052, or 4 µg per animal), or PCV13 admixed with the lower dose of 3M-052 (PCV13+0.01 mg/kg 3M-052). As before, all treatments began with a birth dose (DOL0), followed by booster doses at one (DOL28) and two months (DOL56) of life and peripheral blood collection for down stream analysis (Table 4). DOL28 Ab responses to PCV13 adjuvanted with the lower dose of 3M-052 only significantly surpassed the WHO recommended minimal protective Ab concentrations (0.35 µg/ml) for serotypes 3 (FIG. 4A), and serotypes 3,7F and 9V as compared to PCV13 alone (FIG. 4B). Subsequent boosting immunizations on the second and third months enhanced the Ab responses in all groups receiving PCV13. However, while the (PCV13+0.01 mg/kg 3M-052) showed significantly enhanced responses to serotypes 6A, 6B and 19A, only the (PCV13+0.1 mg/kg 3M-052) group demonstrated significantly elevated anti-PnPs Ab responses to all 13 serotypes by DOL120 (FIG. 4A and FIG. 13), demonstrating that TLR7/8A adjuvant dosage can be used to determine a therapeutic window of enhanced immunogenicity.

TLR7/8A Adjuvantation Dramatically Accelerates and Enhances Serotype-Specific Pneumococcal Opsonophagocytic Killing To further characterize humoral immunity to the novel vaccine formulation, DOL0, 28, 56 and 120 sera from neonatal and infant rhesus macaques immunized with either PCV13 alone, (PCV13+0.01 mg/kg 3M-052) and (PCV13+0.1 mg/kg 3M-052) were examined in a pneumococcal opsonophagocytosis assay (OPA). As expected, all rhesus macaque serum samples had limited or no opsonic ability to all 13 serotypes evaluated at birth (Table 1 and FIG. 14). All (PCV13+0.1 mg/kg 3M-052)-immunized rhesus macaques demonstrated functional Ab responses to all 13 PS serotypes contained in PCV13. Consistent with the striking observations seen for PnPS-specific IgG titers, functional Ab-mediated responses were dramatically accelerated in animals receiving a single dose of (PCV13+3M-052)—i.e., PCV adjuvanted with either dose of adjuvant. All animals receiving (PCV13+0.1 mg/kg 3M-052) demonstrated a robust functional Ab activity to 11 of the 13 serotypes tested by DOL28, with opsonization indices (OIs) ~10-100 greater than PCV13 alone (Table 1). In addition, for animals receiving (PCV13+0.1 mg/kg 3M-052) serum opsonophagocytic activity at DOL120 (post-immunization 3) was 2-(for serotypes 4, 14, 1, 5, 7F), 4-(18C, 6A) or 10-fold (6B, 9V, 19F, 23F, 19A) greater than that of animals receiving PCV alone (FIGS. 14 and 15A-15B). Opsonophagocytic killing activity correlated with accelerated serotype-specific Ab responses to (PCV13+3M-052) (FIGS. 16-18).

3M-052 has Limited Systemic Activity in Neonatal and Infant Primates

This study included assessments of the general health of enrolled animals as well as detailed monitoring for potential local and systemic reactogenicity. During the entire study period through DOL360, no serious adverse effects (28) were observed in any of the enrolled animals. Weight curves were documented throughout the course of the study, as weight is a sensitive indicator of infant well-being. Weight gains were similar in all treatment groups (FIG. 19A). Similarly, fever was not reported up to DOL150 in all treatment groups, with the only significantly minor change in body temperature (a 0.8° C. increase (n=5, p=0.05)) observed in the (PCV13+0.1 mg/kg 3M-052) treatment group 48 hours after the third immunization (FIGS. 19B and 19C). During the second of two birthing/enrollment seasons, three-cohoused 3M-052-(or (PCV13+3M-052))-treated infant animals presented with a transient and mild macu-lopapular rash. Complete blood counts (CBCs) are shown in Table 5. When present, erythema (redness) at the site of injection was localized and mild to moderate. For the second immunization, the diameter of injection site erythema at 48 hours post-IM injection was significantly greater in the (PCV13+3M-052) treatment groups (p=0.05; FIG. 20A-20B) but not significant for any of the other treatment conditions or time points evaluated to DOL63. In all animals with localized erythema, this erythema resolved fully with no visible sequelae. In line with the murine studies, and in accordance with its chemical design as a hydrophobic/locally-acting adjuvant, 3M-052 administration with or without PCV13 did not induce systemic cytokine induction in neonatal/infant rhesus macaques over the first 63 days of life (FIG. 21A) or 48 hours post-(DOL30) a single dose of (PCV13+0.01 mg/kg 3M-052) (FIGS. 21B, 21C, and 21D).

Unlike PCV13, (PCV13+3M-052) Significantly Enhanced Th1 CRM-197-Specific Neonatal CD4+ Cells A novel methodology for the evaluation of vaccine-specific B- and T lymphocytes from peripheral blood was developed for this study, driven by the fact that only limited volumes of blood can be obtained from infant macaques. Briefly, peripheral blood mononuclear cells were sorted to obtain highly pure populations of B cells, T cells and monocytes that were used for the evaluation of antigen specific vaccine-induced B- and T-cells in infant rhesus macaques by means of enzyme-linked immunospot (ELIS-POT) and intracellular cytokine staining assays, respectively. Cryopreserved peripheral-blood mononuclear cells (PBMCs) obtained at DOL28, 56, and 90, were used for re-stimulation in vitro as outlined in FIGS. 22A-22B. Autologous monocytes were differentiated to monocyte-derived dendritic cells (MoDCs), and after treatment of MoDCs with CRM197 (the protein component of PCV13), cells were co-cultured with neonatal and infant CD4+ T cells for 10 days (FIG. 22A). CRM197-specific CD4+ T cells were quantified to determine the proportion of memory cells producing IL-4, IL-17, or IFNγ (FIGS. 5A, 5B and 5C).

Similar numbers of CRM197-specific IL-17 memory CD4+ T cells, associated with reduced pneumococcal carriage, were observed in response to PCV13 and (PCV13+0.1 mg/kg 3M-052) (FIGS. 5B and 5D). Remarkably, by DOL28 animals that received (PCV13+0.1 mg/kg 3M-052) at birth had significantly higher proportions of CRM197-specific memory CD4+ T cells producing IFNγ than those who received PCV13 alone (~0.61% vs. ~0.08%, p=0.04) (FIG. 5C). Indeed, the IL-17+:IL-4+:IFNγ+ ratio in the (PCV13+ 3M-052) group was ~1:0.82:1.49 vs. ~1:0.65:0.27 for PCV13 (FIG. 4A-4B). A significant response was observed for DOL56 (~1.01% vs. ~0.01%, ratio ~1:0.40:2.33 vs. ~1:0.14:0.02, p=0.018), and a trend for DOL90 (~0.33% vs. ~0.11%, ratio ~1:0.25:0.50 vs. ~1:0.9:7.81, p=0.08) (FIGS. 5C and 5D).

3M-052 Enhances and Accelerates Activation of Early Life PnPS-Specific B Cells

Figure 23A:
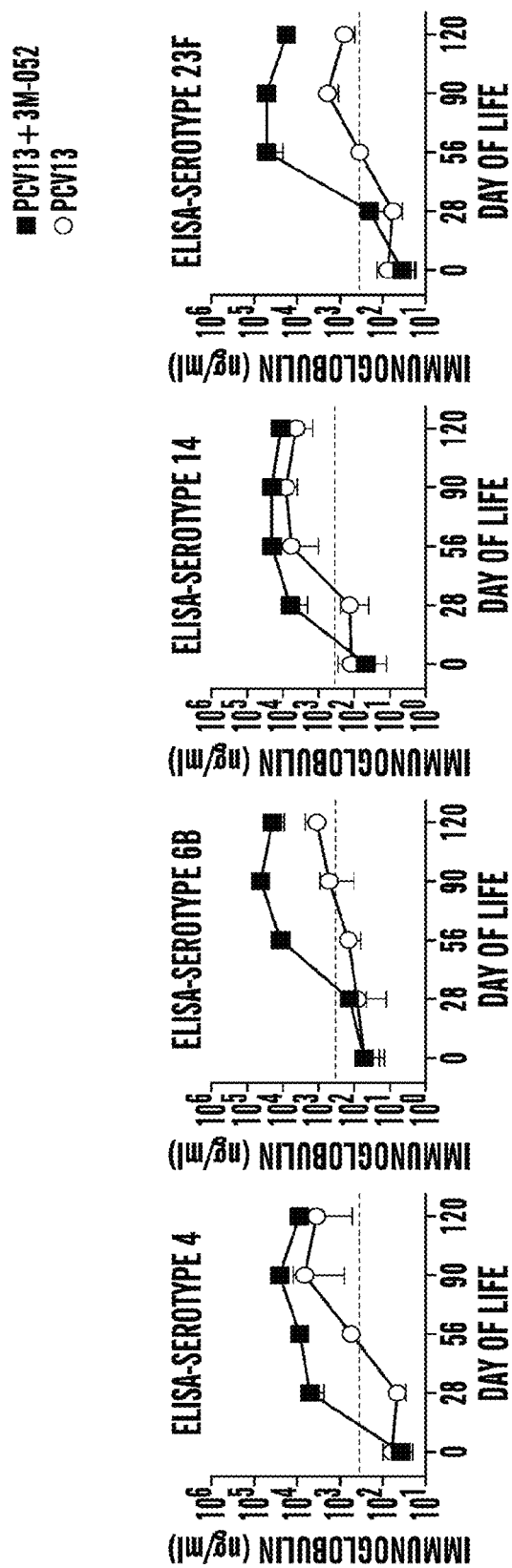

Mirroring its enhancement of PCV-specific Ab and T cell responses, when compared to PCV13 alone, inclusion of 3M-052 also significantly enhanced frequencies of PnPs-specific CD20+CD27− naïve B cells (FIGS. 6A and 22B) and CD20+CD27+ memory B cells (FIG. 6B) on DOL56 and DOL90. Of note, the switch from naïve to a memory phenotype occurred much earlier in life for the (PCV13+ 3M-052) immunized animals (DOL28) than for the PCV13 alone group (DOL56). In fact, DOL28 PnPs-specific memory cells were significantly elevated in the (PCV13+ 3M-052) treatment group while significantly lower for PCV13 alone (FIG. 6C). Both the quantity and quality (avidity) of 4-, 6B-, 14-, and 23F-serotype-specific (FIGS. 23A and 23B) and total (FIG. 23C) anti-S. pneumoniae capsular polysaccharides Abs by ELISA and ECL support these observations. These data not only confirm the earlier increase in PnPS-specific Ab titer in the (PCV13+3M-052) treatment groups, but also demonstrates a trend of increased Ab avidity, which, together with an earlier switch in B cell memory phenotype observed by ELISPOT, indicates that 3M-052 accelerated and enhanced B cell activation (FIG. 23D). Indeed, addition of 3M-052 to PCV13 was associated with increased infiltration of CD68+ cells (i.e., monocytes/macrophages) into the injection site muscle (FIG. 24).

Discussion

Until the end of the 20th century, vaccine adjuvantation was largely limited to the use of aluminum salts (Alum) (29). Over the past 20 years there has been explosive growth of information regarding PRRs that can activate leukocytes and thereby enhance immune responses. In parallel, a growing menu of adjuvants is now becoming available to immunologists and vaccinologists (30). Newborns and young infants demonstrate distinct immune responses, are at the greatest risk of infection of any age group and receive most vaccines, yet to date; adjuvanted vaccine development programs have usually not systematically selected or optimized adjuvants for use in early life. Therefore, many vaccine formulations produce distinct and potentially suboptimal responses in the very young. A number of adjuvanted, including live (self)-adjuvanted vaccines, induce relatively robust immunogenicity in early life: (a) in mice, measles vaccines employing DNA (31) and a live-replicating attenuated strain of Listeria monocytogenes (32) induced early protection; (b) in infant Rhesus macaques, liposome adjuvant/replicon particles induce anti-measles immunity (33); and (c) in human newborns, Bacille Calmette Guérin (BCG), a live attenuated Mycobacterium bovis vaccine that activates multiple PRRs, induces robust Th1 responses at birth (34). However, to our knowledge, a pure adjuvant that can help induce adult-level immunogenicity/protection in newborn primates had yet to be described.

An increased appreciation of immune ontogeny may inform future research and design of age-specific vaccine formulations. Accordingly, and as neither rodent models nor adult human leukocytes accurately model human newborn and infant responses (1), a candidate early life TLR7/8 adjuvantation system was explored herein that was active towards human newborn leukocytes in vitro coupled with in vivo evaluation in an animal species (Macaca mulatta) that expresses TLR8 that is structurally and functionally similar to its human counterpart (14). In vitro modeling identified 3M-052 as a lipidated TLR7/8A adjuvant that both alone and in synergy with Alum induced Th1-cytokine responses at birth, and that when administered with Alum-adjuvanted PCV13 in vivo dramatically accelerated and enhanced neonatal antigen-specific immunogenicity after a single immunization. Moreover, 3M-052 synergistically enhanced type II interferon and Th1-polarizing human cord blood cytokine production to PCV13 in vitro, and dramatically accelerated S. pneumoniae antigen-specific neonatal rhesus macaque B- and Th1-cell responses ex vivo. The ability of 3M-052 to enhance and accelerate activation of anti-PnPs-IgG, PnPS-specific B cells, Th1-polarized CRM197-specific CD4+ T cells and synergistically activated type II IFN responses in vitro shares similarity with the immune polarizing effects of systemic viral infection (35) and signatures of bacterial viability (36), highlighting the potential of TLR7/8-triggered pathways to fundamentally shape immune responses (37), especially vaccinal antigen-specific-IFNγ-producing T cells in early life (10). In light of the ability of 3M-052 to prime at a high dose (0.1 mg/kg) and boost at a lower dose (0.1 mg/kg), it is possible that (PCV13+3M-052) may enhance induction of extra-follicular B cell responses (38). Indeed, it is contemplated that vaccine adjuvantation with agonists of TLR7/8, PRRs key to detecting microbial RNAs, can induce a response that more closely resembles natural infection with live pneumococci inducing Th1/Th17-polarized cell-mediated immunity (39) and supporting Tfh cell differentiation circumventing the neonatal inhibitory milieu and T cell-intrinsic factors and thereby enabling early life germinal center B cell responses (40). Without wishing to be limited by theory, it is hypothesized herein that the trend towards reduced numbers of blood circulating CRM197-specific IL-17 memory CD4+ T cells at Day 90 in the (PCV13+3M-052) immunized animals may reflect migration of pneumococcal-specific IL-17 cells to mucosal sites where they may play roles in reducing pneumococcal carriage (41).

A key concern regarding adjuvanted vaccine development is reactogenicity, the propensity of a formulation to cause acute inflammatory events either locally—e.g., erythema, tenderness—or systemically as fever. Of note, vaccine adjuvants are not licensed separately; rather, the adjuvant is a constituent of the licensed vaccine formulation. Therefore, as demonstrated in the assays described herein, adjuvants must be evaluated both alone and as a component of a vaccine formulation. To the extent that they reflect activity in vivo, development of reliable platforms for in vitro modeling may help exclude adjuvants with high potential to induce unacceptable reactogenicity in the very young (1, 4). Through the present adjuvantation approach, not only was the systemic inflammation associated with TLR7/8 stimulation reduced, but also adjuvant efficacy was maintained in newborns. Thus, it is demonstrated herein that a rationallydesigned adjuvanted vaccine approach taking both age- and species-specificity into account permits effective early life immunization.

The persistently high global burden of infections in the very young (43) provides a compelling rationale for developing additional safe and effective early life vaccines. Overall, four key aspects of our findings deserve particular emphasis: (a) human in vitro systems can be able to predict age-specific adjuvanticity, (b) chemical modification of adjuvants can help limit systemic reactogenicity, (c) newborn primates are not inherently incapable of robust immune responses at birth, but can mount robust Th1- and Th2-cell and humoral responses when stimulated with an appropriately adjuvanted vaccine formulation, and (d) TLR7/8As, such as 3M-052, offer substantial advantages for adjuvantation of PCV and other vaccines. To our knowledge, ours is the first report of employing medicinal chemistry and human in vitro modeling for development of a locally-targeted, age-specific adjuvanted neonatal vaccine formulation with robust in vivo activity at birth, a key point of healthcare contact. Another practical feature of our approach is that it builds upon a traditional Alum-adjuvanted vaccine formulation, providing a potentially practical path to modify common pediatric conjugate vaccines for greater efficacy. Overall, study of individual and combined adjuvantation systems with activity towards specific age groups can open new paths to develop adjuvanted vaccines for distinct vulnerable populations such as the young and elderly.

Materials and Methods

Ethics statement. All experiments were conducted in accordance with relevant institutional and national guidelines, regulations and approvals. All rodents were obtained from Charles River Laboratories (Wilmington, Mass.), and studies were approved by the 3M Drug Delivery Systems Institutional Animal Care and Use Committee (IACUC). Non-identifiable human cord blood samples were collected with approval from the Ethics Committee of The Brigham & Women's Hospital, Boston, Mass. (protocol number 2000-P-000117) and Beth Israel Deaconess Medical Center Boston, Mass. (protocol number 2011P-000118). Blood samples from adult volunteers were collected after written informed consent with approval from the Ethics Committee of Boston Children's Hospital, Boston, Mass. (protocol number X07-05-0223). The longitudinal rhesus monkey experimental protocol (number P0184) was approved by the IACUC at Tulane University and performed at Tulane National Primate Research Center (TNPRC; Covington, La.). Additionally, peripheral blood samples from rhesus macaques were derived from New England Primate Research Center (NEPRC) (Southborough, Mass.) and used under Harvard University IACUC approval (protocol number 04936).

In vivo rodent vaccination studies. To evaluate drug pharmacokinetics (PK) (serum drug levels) and pharmacodynamics (PD) (serum TNF), female crl:CD(SD) rats (~350-400 g) (Charles River Laboratories; Wilmington, Mass.) received a single subcutaneous (SC, scruff of neck) or two intramuscular (IM, quadriceps) administrations of 3M-052 or R848 (Resiquimod) formulated in oil-in-water (O/W) emulsion (vehicle). Rat serum was collected 5 min, 30 min, 2, 4, and 24 hours post-dose. 3M-052 and R848 serum drug levels were determined by LC-MS/MS pre- or post-dose with a lower limit of quantification (LLQ) of 0.84 and 3.2 pmol/ml, respectively. Similarly, serum TNF concentrations were measured by ELISA at the indicated times pre- or post-dose, with a LLQ of 31 pg/ml. To determine systemic cytokine response and IFN-inducible gene expression following free or lipidated TLR7/8 imidazoquinoline administration, 6-8 week old female C57BL/6J mice (The Jackson Laboratory; Bar Harbor, Me.) weighing ~18 g each were administered a single SC dose of 3M-052 or R848 formulated (both 1 mg/kg, (20 μg/mouse)) in oil-in-water (O/W) emulsion (vehicle). After administration, whole blood was collected 1, 3, 6, 9, 18, and 24 hours post-dose, while draining lymph nodes (brachial and axillary) and spleen were collected 1, 3, 6 and 18 hours post-dose. TNF, IL-6, IL-10, IFNγ, CCL2 serum cytokine kinetics were evaluated by flow cytometry cytometric bead array (BD Biosciences). mRNA expression in draining lymph nodes and spleen post-administration were determined by quantitative RT-PCR (Applied Biosystems; Carlsbad, Calif.) as described previously (24) and represented as relative fold-change expression (i.e., treatment relative expression/naïve relative expression). For rodent studies, 6-8 week old male Balb/c mice were immunized by subcutaneous injection (scruff of neck) with recombinant influenza A hemagglutinin (HA, 10 μg) alone or in combination with 0.01, 0.03, 0.1, 0.3, or 1 mg/kg 3M-052, or in combination with Alum, three times (prime, boost, boost) 14 days apart. HA-specific serum Ig levels measured by ELISA on day 77, 21 days post-final immunization as described previously (24).

Human blood sample processing and in vitro stimulation. Peripheral blood was collected from healthy adult volunteers, while human newborn cord blood was collected immediately after Cesarean section delivery of the placenta. Births to known HIV-positive mothers were excluded. Human experimentation guidelines of the U.S. Department of Health and Human Services, The Brigham & Women's Hospital, Beth Israel Deaconess Medical Center Boston, and Boston Children's Hospital were observed, following protocols approved by the local institutional review boards. Human blood was anti-coagulated with 20 units/ml pyrogen-free sodium heparin (American Pharmaceutical Partners, Inc.; Schaumberg, Ill.). All blood products were kept at room temperature and processed within 4 hours from collection. Human whole blood assays were completed as previously described (44). Briefly, neonatal cord blood or adult whole blood (WB) was mixed 1:1 with sterile pre-warmed (37° C.) RPMI 1640 medium (Invitrogen; Carlsbad, Calif.) and 180-225 μl of the 1:1 suspension was added to each well of a 96 well U-bottom plate (Becton Dickinson; Franklin Lakes, N.J., USA) containing 20-25 μl freshly prepared specific TLRAs at 10× the final concentration. Suspensions containing 200-250 μl/well were gently mixed by pipetting and incubated for 6 hours at 37° C. in a humidified incubator at 5%, CO2. After culture, plates were centrifuged at 500×g and ~100-150 μl of supernatant was carefully removed by pipetting without disturbing the cell pellet. Supernatants derived from human leukocyte stimulations were assayed by ELISA for TNF (BD Biosciences; San Jose, Calif., USA) and IL-1β (eBiosciences; San Diego, Calif.). Additionally, whole blood assay supernatants were analyzed by multiplex cytokine assays (Millipore; Billerica, Mass., USA). The minimum threshold for each analyte was set at the minimum detectable concentration for a given assay, defined as three standard deviations above the mean background.

TLR agonists and multi-analyte assays. Commercially available TLRAs were used at the concentrations noted in the figure legends. R848 (TLR7/8) was purchased from InvivoGen (San Diego, Calif.). All TLR7/8As and emulsions used in both in vitro and in vivo studies were verified to be free of endotoxin (<1 EU/ml) by the Limulus amoebocyte lysate (LAL) assay per the manufacturer's instructions (Charles River; Wilmington, Mass.). Cytokine and chemokine expression profiles in cell culture supernatants and peripheral blood plasma were measured using customized Milliplex human and non-human primate cytokine/chemokine magnetic bead panels (Millipore), respectively. Assays were analyzed on the Luminex® 100/200™ System employing xPOTENT® software (Luminex; Austin, Tex.) and Millipore Milliplex Analyst (version 3.5.5.0).

Vaccine formulation. The point-of-use mixed vaccine formulation consisted of 2 components. Firstly, an oil-in-water emulsion (O/W) consisting of a pH 6 citrate buffer, soybean oil, and surfactants that contains 0.04-0.4 mg/ml of N-[4-[(4-amino-2-butyl-1H-imidazo[4,5-c]quinolin-1-yl)oxy]butyl]octadecanamide (3M-052) (24) (3M Drug Delivery Systems Division, 3M Center; St. Paul, Minn.). Concentrations of 3M-052 O/W emulsion preparations were confirmed by high-performance liquid chromatography (HPLC). The 3M-052 O/W emulsion formulations were sterile filtered, aliquoted into sterile 2 ml serum vials sealed with rubber septa, and stored at 2-8° C. until use. Dual agonist activity of 3M-052 was confirmed using HEK293 cells stably expressing either human TLR7 or TLR8 (24). The dosing range of 3M-052 was approximately 4-40 μg (0.01-0.1 mg/kg; 400 g birth weight) (Table 3). Secondly, one-half of the recommended human infant dose of the Pneumococcal 13-valent Conjugate Vaccine [Diphtheria CRM197 Protein] (Pfizer, New York City, N.Y., USA), that included the 13 pneumococcal conjugates (serotypes 1, 3, 4, 5, 6A, 6B, 7F, 9V, 14, 18C, 19A, 19F, 23F). Each PCV13 containing administration totaled 1.1 μg per dose of saccharide per serotype, except for serotype 6B, which totaled 2.2 μg per dose. Each of the polysaccharides is conjugated separately to CRM197, and adsorbed on aluminum phosphate (0.0625 mg Aluminum). Sodium chloride, succinic acid, Polysorbate 80, and water for injection are also included in PCV13. Were possible, components were verified to be free of endotoxin (<1 EU/ml) as measured by the Limulus amebocyte lysate (LAL) assay per the manufacturer's instructions (Charles River, Wilmington, Mass.).

For the injection of animals, all preparations were made within 1 hour of planned injection using sterile techniques. Briefly, a premade PCV13 vial was gently mixed by hand several times. The total volume (500 μl) of the PCV13 vial was sterilely injected into the pre-aliquoted adjuvant vials containing 3M-052 adjuvant O/W emulsion (making a combined total volume of 700 μl). The combined (PCV13+3M-052) vial was then vortexed for 20-30 seconds. Using a 1 ml pyrogen-free syringe 22-25 G needle, 350 μl of the formulation was removed and injected intramuscularly (IM) to the quadriceps muscle. The vial containing the remaining 350 μl of the formulation was discarded. Both the adjuvant alone and half recommended human infant dose of PCV13 alone were treated similarly, replacing equal volumes of saline for O/W emulsion. 0.35 ml clinical grade saline (sterile/pyrogen-free 0.9% NaCl solution for injection) was used as a placebo control. Oil droplet particle size was determined by dynamic light scattering (DLS) using a ZETASIZER™ nanoseries instrument (Malvern Nano-ZS, 1 1/4 532 nm; Westborough, Mass.) as previously described (45). The particle size data refer to scattering intensity distributions (z-average) with accompanying polydispersity/heterogeneity index (PDI), with a PDI<0.2 considered mono-disperse.

Selection of rhesus macaque model. Murine TLR8 is divergent from human and monkey TLR8, and mice mount distinct immune responses to TLR7/8As and TLR8As (46). Rhesus macaques are likely a relevant animal model for predicting TLR8 adjuvant responses in human infants (26, 47). To date, ten TLR/TIR orthologues have been identified within the Rhesus macaque (M. mulata) genome, with an overall mean amino acid identity of 96.7% to their corresponding human TLR/TIR sequences, compared with 87.4% to mouse TLR/TIR sequences (25). The most highly conserved TLR/TIR is TLR8, which demonstrates 98.6% amino acid identity to human TLR8. Moreover, TLR8 in Rhesus macaques and humans is highly conserved in terms of its predicted distribution pattern of extracellular LRRs. Rhesus macaques are also well suited for our study because: (a) adult rhesus macaques have demonstrated human-like responses to TLR7/8As in vivo (48-50), (b) both infant and adult rhesus macaques demonstrate human-like TLR7/8A-induced cytokine responses in vitro (14), and (c) like humans, infant rhesus macaques respond immunologically to conjugated, but not to unconjugated polysaccharides in vivo.

In vivo neonatal and infant rhesus macaque vaccination studies. Rhesus macaques (Indian origin *Macaca mulatta*) were obtained from the TNPRC specific pathogen-free breeding colony. Upon identification, pregnant dams were transferred to an indoor social group to allow for monitoring and delivery of infants. At birth, neonatal rhesus macaques (<24 hours of age) were enrolled into the longitudinal immunization study. Exclusion criteria were, a) maternal fever (≥40° C.) during infant exam on DOL0, b) birth weight<400 g, c) clinical signs of neonatal infection (e.g. infant temperature ≥36.5° C.; nasal, ocular discharge; respiratory distress, cardiovascular instability), d) congenital defects (e.g. abnormal digits, omphalocele) and/or e) abnormal cling. Animals were group-housed in dam/infant pairs with a maximum of 4 pairs (8 animals) together. All animals received standard environmental enrichment, including manipulanda in the cage, perches/swings, various food supplements, foraging or task-oriented feeding methods, and regular human interaction with caretakers. Animals were assigned to either the phlebotomy group or the biopsy/phlebotomy group in a pre-designed random sequential order (Table 4). As a per-protocol analysis method was employed, one enrolled animal that died of natural causes unrelated to the study treatments within 24 hours of birth was not included in the final analysis. A standardized procedure for tattooing, physical exam, assessment of local reactogenicity, including photographic documentation, and immunization of neonatal and infant rhesus macaques was employed. Briefly, on the day of immunization (DOL0, DOL28, and DOL56), the leg designated to receive treatment was clipped to remove hair, and a tattoo applied (at birth only) on the thorax. Standard physiological safety parameters, extrapolated from human infant clinical trials of PCV (28), included temperature and weight (normalized to Tulane National Primate Research Center reference standard for rhesus macaques), which were recorded at multiple time-points at observation/sample-acquisition, as well as local signs of reactogenicity such as leg circumference pre/post-immunization and photographic documentation of erythema (Table 4). A standardized physical exam and assessment of local reactogenicity, including photographic documentation, were repeated 48 hours after immunization through DOL70 according to the schedule in Table 4. For photography, animals were positioned in a standardized way and 9 sequential photographs obtained. These included Photograph 1: the tattoo number (to avoid false attribution of pictures to animals); Photograph 2: both ventral thighs; Photographs 3 and 4: each ventral thigh individually; and Photographs 5-8: each thigh individually from medial and lateral aspects. If local erythema (redness) or swelling were noted, a higher magnification photograph was taken of the area. Finally, the newborn underwent IM vaccination as outlined above. After DOL70, physical exam alone (i.e., without photography) was conducted according to the same schedule, up to 1 year of life. For biopsy samples, animals were anesthetized via IM ketamine hydrochloride (10 mg/kg) and dexmedetomidine (7.5-15 µg/kg IM) or IM tiletimine/zolazepam (8 mg/kg). IM buprenorphine (0.01 mg/kg) was also administered for analgesia when indicated, and atipamezole was administered IM as a reversal agent when dexmedetomidine was used. The cranial aspect of the rear limb distal to the coxo-femoral joint and proximal to the stifle were surgically prepped, a sterile fenestrated drape placed on the cranial aspect of the rear limb, and #15 scalpel blade used to make a 3 mm incision through the skin. Skin adjacent to the incision was undermined, and muscle tissue was exteriorized using sterile rat tooth forceps. Curved scissors were used to excise a 2 mm length of superficial musculature. Once completed, sterile gauze was placed over the skin incision if hemorrhage occurred. Finally, the skin incision was closed with a single interrupted suture or skin glue. The 2 mm cube muscle biopsies were obtained from the injection site (quadriceps muscle) prior to and 48 hours after each immunization (one in each thigh), and obtained in an alternating pattern (e.g. DOL0 left leg, DOL2 right leg, DOL30 left leg, DOL58 right leg). Lymph node biopsies were obtained on DOL7 and 63, and followed a similar pattern of alternation. Peripheral blood samples were drawn from each group at multiple time-points per Supplemental Table 2, including at DOL0 (pre-immunization), DOL7, 28, 30, 35, 56, 63, 90, 150, 180, 240, and 360. Serum and plasma samples were stored at −80° C. for subsequent immunogenicity assays. Peripheral blood mononuclear cells (PBMCs) were isolated and stored in liquid Nitrogen. For select peripheral blood samples, standard hematology, serum chemistry and urinalysis assays were conducted at the Clinical Laboratory Improvement Amendments (CLIA)-certified Department of Laboratory Medicine, Boston Children's Hospital (Boston, Mass., USA). Biomarkers evaluated included: serum chemistry (electrolytes, creatinine, ALT, AST; to monitor for renal or hepatic damage). Macroscopic and microscopic urinalysis was employed to assess possible renal damage and/or inflammation. Complete blood counts (to detect dyscrasias) were measured at TNPRC within 2 hours of phlebotomy.

Multiplexing electrochemiluminescence and opsonophagocytosis assays. Ab response in infant monkey sera was measured in a 96-well electrochemiluminescence (ECL) multiplex assay employing Meso Scale Discovery (MSD; Gaithersburg, Md.) technology, as previously described (51, 52). Two ten-spot (per single microtiter well) 96-well plates were used to monitor responses Ab responses to all 13 pneumococcal serotypes. Pneumococcal polysaccharides were obtained from the American Type Culture Collection (ATCC; Manassas, Va., USA) or Statens Serum Institut (SSI; Copenhagen, Denmark) for Danish serotype designations 3, 4, 6B, 9V, 14, 18C, 19F, and 23F. These were individually spotted in each well (100 µg/ml coating concentration, 5 ng/spot for all types) on one plate, while polysaccharides 1, 5, 6A, 7F, 19A, 22F, and 33F were individually spotted in each well on the second plate. Before addition to the plate, primate serum samples were combined with an absorbent containing C-polysaccharide (C-PS), 25A, and 45 capsular PS (from SSI) to neutralize Ab binding to C-PS and other common contaminants present in the PnPS coating antigens. A Sulfo-tag labeled goat anti-human IgG that emits light upon electrochemical stimulation was used as a secondary Ab. The total IgG concentration in rhesus serum was calculated with MSD Workbench™ v. 3 software using the human anti-pneumococcal reference serum, lot 89SF-2 (Lederle-Praxis Biologicals) (52) and 007SP (53), as controls. Pneumococcal opsonophagocytosis assays were conducted at the Laboratory of Dr. Moon Nahm (University of Alabama; Birmingham, Ala.). The multiplexed opsonophagocytic killing assay, MOPA4, was used to test the infant rhesus macaque sera, as previously described (54, 55) and as outlined on the world wide web at vaccine.uab.edu. Serum was heat inactivated at 56° C. for 30 min prior to incubation with target pneumococcal bacterial strains (BEI Resources; VA, USA) for an additional 30 min. The opsonophagocytic incubation reaction occurred at 56° C. for 30 min with baby rabbit serum (Pel-freez Biologicals, Rogers; AR, USA) as the complement source and human pro-myelocytic cell line HL-60 cells (ATCC) as the phagocytic cells. At the end of opsonophagocytic incubation reaction, mixtures were transferred to agar media to allow bacterial growth, digital images obtained, and surviving colonies enumerated using automated software (US National Institute of Standards and Technology (NIST) Integrated Colony Enumerator). Opsonization titers (OT) were defined as the serum dilution that kills 50% of bacteria. The lowest detectable titer in the MOPA was 24, and therefore, samples identified as negative in the assay (i.e., samples having no functional activity detected) were assigned a titer of 12 (i.e., half the lowest limit of detection).

Characterization of pneumococcal polysaccharide-specific B cells. Rhesus macaque peripheral blood mononuclear cells (PBMCs) were labeled with anti-CD14-PE (clone M5E2), CD20-V450 (clone L27), CD27-PE.Cy7 (clone M-T271), CD4-FITC (clone SK3) Ab's (BD Biosciences). Sorting of CD14+ monocytes, CD20+CD27− naïve B cells, CD20+CD27+ memory B cells, and CD4+Th cells employed a FACSAria™ II cell sorter. Anti-pneumococcal B cells in peripheral blood were enumerated in sorted B cell populations. Sorted B cell populations were cultured at a concentration of 5×106/ml for 5 days at 37° C., 5% CO2 in RPMI media supplemented with Penicillin/Streptomycin, 10% fetal bovine serum (FBS, Invitrogen, Carlsbad, Calif., USA), 1 µg/ml R848 (Invivogen; San Diego, Calif., USA), 10 IU/ml IL-2 (R&D Systems; Minneapolis, Minn., USA), and 8000 U/ml IFNγ (Abcam; Cambridge, Mass., USA). ELISpot plates (Millipore) were coated either with a combination of 10 µg/ml anti-rhesus IgG-Fc and anti-rhesus IgM-Fc (Nordic Immunological Laboratories; Eindhoven, The Netherlands) in phosphate-buffered saline (PBS), or with a 10 µg/ml pool of the following pneumococcal polysaccharides: Danish designations 1, 3, 4, 5, 6A, 6B, 9V, 14, 18C, 19A, 23F (ATCC), 7F, and 19F (SSI) in PBS. Plates were coated overnight at 4° C. and blocked with RPMI 1640/10% FBS for 1 hour prior to plating of cells. After 5 days of culture, B cells were incubated for 16 hours on the coated and blocked ELISpot™ plate in RPMI supplemented with Penicillin/Streptomycin and 10% FBS. Unless indicated otherwise, 10% of each culture (~50,000 cells) was plated in anti-rhesus IgG/IgM-coated wells and 90% of each culture (~450,000 cells) was plated in wells coated with polysaccharides. Secreted immunoglobulins were detected using horseradish peroxidase-conjugated goat-anti-rhesus immunoglobulin (Nordic Immunological Laboratories; Eindhoven, The Netherlands). Spots were developed using 3,3',5,5'-Tetramethylbenzidine (TMB) (Mabtech, Mariemont; OH, USA) and visualized and counted using a series 5 ELISpot™ analyzer (Cellular Technology Limited, Shaker Heights; OH, USA). The fraction of pneumococcal polysaccharide-specific B cells was quantified as the ratio of the spots detected in polysaccharide-coated wells to spots detected in immunoglobulin-coated wells, after correction for dilution.

Characterization of CRM197-specific CD4+ T cells. Monocytes and T cells were sorted as described above. Sorted CD4+ T cells were non-specifically maintained by culturing in RPMI 1640 media supplemented with penicillin/streptomycin, 10% fetal bovine albumin and 100 ng/ml Concanavalin A (Sigma-Aldrich; Saint Louis, Mo., USA) during the generation of MoDCs from sorted monocytes. Monocytes were cultured at a concentration of 0.75-1×10^6/ml for 5 days in RPMI supplemented with penicillin/streptomycin, 10% FBS, 100 ng/ml Granulocyte-macrophage colony-stimulating factor (GM-CSF) and 50 ng IL-4 (R&D Systems, Minneapolis, Minn., USA). On day 5, MoDCs were harvested and incubated in the absence or presence of 5 µg/ml CRM197 (Sigma-Aldrich, Saint Louis, Mo., USA) for 5 hours in RPMI without FBS. After 5 hours, FBS was added to 10% (v/v) and 100 ng/ml lipopolysaccharide (ultra-pure from List Biological Laboratories; Campbell, Calif., USA) was added for an additional 18 hours. MoDCs were subsequently harvested, washed and co-cultured at 5,000 cells per well with 50,000 T cells for 7 days. On day 7, cells producing IFNγ, IL-4 or IL-17 were analyzed by intracellular cytokine staining after the addition of BD Golgi-plug (BD Biosciences) during the final 6 hours of culture. T cells were made permeable with Cytofix/Cytoperm reagents (BD Biosciences). Cells were stained with anti-IFNγ-PE.Cy7 (clone B27, BD Biosciences), anti-IL-17-APC (clone 41802, R&D Systems), and anti-IL-4-V450 (clone 8D4-8, BD Biosciences). Cells were analyzed for production of these three cytokines by flow cytometry (LSRFortessa flow cytometer, Beckton Dickinson; San Jose, Calif., USA) and analyzed with Flowjo software version 10 (Tree Star, Inc., Ashland, Oreg., USA).

ELISAs. Quantitation of total *S. pneumoniae* and capsular polysaccharides serotype 4-, 6B-, 14-, and 23F-specific IgG were determined by use of an adapted WHO recommended ELISA protocol, as outlined by the Bacterial Respiratory Pathogen Reference Laboratory at the University of Alabama at Birmingham (on the wold wide web at vaccine.uab.edu/ELISA%20Protocol.pdf). Briefly, primate sera were combined with an absorbent containing C—PS and 22F capsular PS to neutralize Ab binding to C-PS, and other common contaminants present in the PnPS-coating antigens. ELISA plates were coated with total PCV13 PnPS serotype antigens and selected dilutions of absorbed primate sera were added to the ELISA plates. Serotype-specific Ab bound was detected with an HRP-conjugated goat-anti-rhesus immunoglobulin, polyclonal (Accurate Chemical & Scientific Corp.; Westbury, N.Y., U.S.A.). Serum Ab concentrations were calculated by comparing the optical density of each unknown well at 405 nm and 690 nm (reference), and to the optical density of the standard (human anti-pneumococcal reference serum, lot 89-SF). For avidity determination, assessment of the overall strength of binding between Ab and antigen, a 0-4 M NaSCN gradient was used to determine the NaSCN concentration that competes off approximately 50% of the bound rhesus immunoglobulins (56).

Statistical analyses and graphics. Statistical significance and graphs were generated using Prism™ v. 5.0b (GraphPad Software, La Jolla, Calif., USA) and Microsoft Excel (Microsoft Corporation, Redmond, Wash.). For data analysis by normalization to control values (vehicle), column statistics were conducted using the two-tailed Wilcoxon Signed Rank Test or unpaired Mann-Whitney test as appropriate. Gaussian sample distributions were assessed by Shapiro-Wilk normality test. Group comparisons employed one-way ANOVA with Dunnett's Multiple Comparison Post-test or two-way repeated measures ANOVA comparing column and row effects. Results were considered significant at $p<0.05$, and indicated as follows: $+p<0.05$, $++p<0.01$, $+++p<0.001$, $*p<0.05$, $p<0.01$, $*p<0.001$. Level of synergy was calculated using the Loewe definition of additivity (57), with $D>1$ indicating antagonism, $D=1$ additivity, and $D<1$ synergy.

REFERENCES

1. Dowling D J, and Levy O. Ontogeny of early life immunity. Trends Immunol. 2014; 35(7):299-310.
2. Dowling D J, and Levy O. Pediatric vaccine adjuvants: Components of the modern vaccinologist's toolbox. The Pediatric infectious disease journal. 2015.
3. van den Biggelaar A H, and Pomat W S. Immunization of newborns with bacterial conjugate vaccines. Vaccine. 2013; 31(21):2525-30.
4. Sanchez-Schmitz G, and Levy O. Development of newborn and infant vaccines. Sci Transl Med. 2011; 3(90):90ps27.
5. Rainey J J, Watkins M, Ryman T K, Sandhu P, Bo A, and Banerjee K. Reasons related to non-vaccination and under-vaccination of children in low and middle income countries: findings from a systematic review of the published literature, 1999-2009. Vaccine. 2011; 29(46):8215-21.
6. Dagan R, Givon-Lavi N, Greenberg D, Fritzell B, and Siegrist C A. Nasopharyngeal carriage of *Streptococcus pneumoniae* shortly before vaccination with a pneumococcal conjugate vaccine causes serotype-specific hypo-responsiveness in early infancy. J Infect Dis. 2010; 201(10):1570-9.
7. van den Biggelaar A H, Pomat W S, Phuanukoonnon S, Michael A, Aho C, Nadal-Sims M A, Devitt C J, Jacoby P A, Hales B J, Smith W A, et al. Effect of early carriage of *Streptococcus pneumoniae* on the development of pneumococcal protein-specific cellular immune responses in infancy. Pediatr Infect Dis J. 2012; 31(3):243-8.
8. Reed S G, Orr M T, and Fox C B. Key roles of adjuvants in modern vaccines. Nat Med. 2013; 19(12):1597-608.
9. Mastelic B, Garcon N, Del Giudice G, Golding H, Gruber M, Neels P, and Fritzell B. Predictive markers of safety and immunogenicity of adjuvanted vaccines. Biologicals: journal of the International Association of Biological Standardization. 2013; 41(6):458-68.
10. Holbrook B C, Kim J R, Blevins L K, Jorgensen M J, Kock N D, D'Agostino R B, Jr., Aycock S T, Hadimani M B, King S B, Parks G D, et al. A Novel R848-Conjugated Inactivated Influenza Virus Vaccine Is Efficacious and Safe in a Neonate Nonhuman Primate Model. J Immunol. 2016; 197(2):555-64.
11. Corbett N P, Blimkie D, Ho K C, Cai B, Sutherland D P, Kallos A, Crabtree J, Rein-Weston A, Lavoie P M, Turvey S E, et al. Ontogeny of Toll-like receptor mediated cytokine responses of human blood mononuclear cells. PLoS One. 2010; 5(11):e15041.
12. Levy O. Innate immunity of the newborn: basic mechanisms and clinical correlates. Nat Rev Immunol. 2007; 7(5):379-90.
13. Adkins B, Leclerc C, and Marshall-Clarke S. Neonatal adaptive immunity comes of age. Nat Rev Immunol. 2004; 4(7):553-64.

14. Philbin V J, Dowling D J, Gallington L C, Cortes G, Tan Z, Suter E E, Chi K W, Shuckett A, Stoler-Barak L, Tomai M, et al. Imidazoquinoline Toll-like receptor 8 agonists activate human newborn monocytes and dendritic cells through adenosine-refractory and caspase-1-dependent pathways. J Allergy Clin Immunol. 2012; 130(1):195-204 e9.

15. Levy O, Zarember K A, Roy R M, Cywes C, Godowski P J, and Wessels M R. Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol. 2004; 173(7):4627-34.

16. Levy O, Suter E E, Miller R L, and Wessels M R. Unique efficacy of Toll-like receptor 8 agonists in activating human neonatal antigen-presenting cells. Blood. 2006; 108(4):1284-90.

17. Singh M, Khong H, Dai Z, Huang X F, Wargo J A, Cooper Z A, Vasilakos J P, Hwu P, and Overwijk W W. Effective Innate and Adaptive Antimelanoma Immunity through Localized TLR7/8 Activation. J Immunol. 2014; 193(9):4722-31.

18. Pollard A J, Perrett K P, and Beverley P C. Maintaining protection against invasive bacteria with protein-polysaccharide conjugate vaccines. Nat Rev Immunol. 2009; 9(3):213-20.

19. O'Brien K L, Wolfson L J, Watt J P, Henkle E, Deloria-Knoll M, McCall N, Lee E, Mulholland K, Levine O S, and Cherian T. Burden of disease caused by *Streptococcus pneumoniae* in children younger than 5 years: global estimates. Lancet. 2009; 374(9693):893-902.

20. Avci F Y, Li X, Tsuji M, and Kasper D L. A mechanism for glycoconjugate vaccine activation of the adaptive immune system and its implications for vaccine design. Nat Med. 2011; 17(12):1602-9.

21. Gadzinowski J, Albrecht P, Hasiec B, Konior R, Dziduch J, Witor A, Mellelieu T, Tansey S P, Jones T, Sarkozy D, et al. Phase 3 trial evaluating the immunogenicity, safety, and tolerability of manufacturing scale 13-valent pneumococcal conjugate vaccine. Vaccine. 2011; 29(16):2947-55.

22. van den Biggelaar A H, Richmond P C, Pomat W S, Phuanukoonnon S, Nadal-Sims M A, Devitt C J, Siba P M, Lehmann D, and Holt P G. Neonatal pneumococcal conjugate vaccine immunization primes T cells for preferential Th2 cytokine expression: a randomized controlled trial in Papua New Guinea. Vaccine. 2009; 27(9): 1340-7.

23. Scott J A, Ojal J, Ashton L, Muhoro A, Burbidge P, and Goldblatt D. Pneumococcal conjugate vaccine given shortly after birth stimulates effective antibody concentrations and primes immunological memory for sustained infant protection. Clin Infect Dis. 2011; 53(7):663-70.

24. Smirnov D, Schmidt J J, Capecchi J T, and Wightman P D. Vaccine adjuvant activity of 3M-052: An imidazoquinoline designed for local activity without systemic cytokine induction. Vaccine. 2011; 29(33):5434-42.

25. Sanghavi S K, Shankarappa R, and Reinhart T A. Genetic analysis of Toll/Interleukin-1 Receptor (TIR) domain sequences from rhesus macaque Toll-like receptors (TLRs) 1-10 reveals high homology to human TLR/TIR sequences. Immunogenetics. 2004; 56(9):667-74.

26. Skinner J M, Indrawati L, Cannon J, Blue J, Winters M, Macnair J, Pujar N, Manger W, Zhang Y, Antonello J, et al. Pre-clinical evaluation of a 15-valent pneumococcal conjugate vaccine (PCV15-CRM197) in an infant-rhesus monkey immunogenicity model. Vaccine. 2011; 29(48): 8870-6.

27. Standardization WECoB. Recommendations to assure the quality, safety and efficacy of pneumococcal conjugate vaccines-proposed replacement of TRS 927. 2009; Annex 2

28. Yeh S H, Gurtman A, Hurley D C, Block S L, Schwartz R H, Patterson S, Jansen K U, Love J, Gruber W C, Emini E A, et al. Immunogenicity and safety of 13-valent pneumococcal conjugate vaccine in infants and toddlers. Pediatrics. 2010; 126(3):e493-505.

29. Rappuoli R, Mandl C W, Black S, and De Gregorio E. Vaccines for the twenty-first century society. Nat Rev Immunol. 2011; 11(12):865-72.

30. Coffman R L, Sher A, and Seder R A. Vaccine adjuvants: putting innate immunity to work. Immunity. 2010; 33(4): 492-503.

31. Capozzo A V, Ramirez K, Polo J M, Ulmer J, Barry E M, Levine M M, and Pasetti M F. Neonatal immunization with a Sindbis virus-DNA measles vaccine induces adult-like neutralizing antibodies and cell-mediated immunity in the presence of maternal antibodies. J Immunol. 2006; 176(9):5671-81.

32. Reikie B A, Smolen K K, Fortuno E S, 3rd, Loeffler D I, Cai B, Blimkie D, and Kollmann T R. A single immunization near birth elicits immediate and lifelong protective immunity. Vaccine. 2010; 29(1):83-90.

33. Pan C H, Greer C E, Hauer D, Legg H S, Lee E Y, Bergen M J, Lau B, Adams R J, Polo J M, and Griffin D E. A chimeric alphavirus replicon particle vaccine expressing the hemagglutinin and fusion proteins protects juvenile and infant rhesus macaques from measles. J Virol. 2010; 84(8):3798-807.

34. Smith K C, Ormem I. M., and J. R. S. Tuberculosis vaccines. Philadelphia, Pa.: Saunders. 2013; Plotkin, S. A., Orenstein, W. A., Offit, P. A. (Eds.), Vaccines (6th ed)(789-811.

35. Longhi M P, Trumpfheller C, Idoyaga J, Caskey M, Matos I, Kluger C, Salazar A M, Colonna M, and Steinman R M. Dendritic cells require a systemic type I interferon response to mature and induce CD4+Th1 immunity with poly IC as adjuvant. J Exp Med. 2009; 206(7):1589-602.

36. Sander L E, Davis M J, Boekschoten M V, Amsen D, Dascher C C, Ryffel B, Swanson J A, Muller M, and Blander J M. Detection of prokaryotic mRNA signifies microbial viability and promotes immunity. Nature. 2011; 474(7351):385-9.

37. Kasturi S P, Skountzou I, Albrecht R A, Koutsonanos D, Hua T, Nakaya H I, Ravindran R, Stewart S, Alam M, Kwissa M, et al. Programming the magnitude and persistence of antibody responses with innate immunity. Nature. 2011; 470(7335):543-7.

38. MacLennan I C, Toellner K M, Cunningham A F, Serre K, Sze D M, Zuniga E, Cook M C, and Vinuesa C G. Extrafollicular antibody responses. Immunol Rev. 2003; 194(8-18.

39. Olliver M, Hiew J, Mellroth P, Henriques-Normark B, and Bergman P. Human monocytes promote Th1 and Th17 responses to *Streptococcus pneumoniae*. Infect Immun. 2011; 79(10):4210-7.

40. Mastelic B, Kamath A T, Fontannaz P, Tougne C, Rochat A F, Belnoue E, Combescure C, Auderset F, Lambert P H, Tacchini-Cottier F, et al. Environmental and T cell-intrinsic factors limit the expansion of neonatal follicular T 40. helper cells but may be circumvented by specific adjuvants. J Immunol. 2012; 189(12):5764-72.
41. Lu Y J, Gross J, Bogaert D, Finn A, Bagrade L, Zhang Q, Kolls J K, Srivastava A, Lundgren A, Forte S, et al. Interleukin-17A mediates acquired immunity to pneumococcal colonization. PLoS pathogens. 2008; 4(9): e1000159.
42. Polack F P, Lydy S L, Lee S H, Rota P A, Bellini W J, Adams R J, Robinson H L, and Griffin D E. Poor immune responses of newborn rhesus macaques to measles virus DNA vaccines expressing the hemagglutinin and fusion glycoproteins. Clin Vaccine Immunol. 2013; 20(2):205-10.
43. Liu L, Johnson H L, Cousens S, Perin J, Scott S, Lawn J E, Rudan I, Campbell H, Cibulskis R, Li M, et al. Global, regional, and national causes of child mortality: an updated systematic analysis for 2010 with time trends since 2000. Lancet. 2012; 379(9832):2151-61.
44. Dowling D J, Tan Z, Prokopowicz Z M, Palmer C D, Matthews M A, Dietsch G N, Hershberg R M, and Levy O. The ultra-potent and selective TLR8 agonist VTX-294 activates human newborn and adult leukocytes. PLoS One. 2013; 8(3):e58164.
45. Palmer C D, Ninkovic J, Prokopowicz Z M, Mancuso C J, Marin A, Andrianov A K, Dowling D J, and Levy O. The effect of stable macromolecular complexes of ionic polyphosphazene on HIV Gag antigen and on activation of human dendritic cells and presentation to T-cells. Biomaterials. 2014; 35(31):8876-86.
46. Heil F, Hemmi H, Hochrein H, Ampenberger F, Kirschning C, Akira S, Lipford G, Wagner H, and Bauer S. Species-specific recognition of single-stranded RNA via toll-like receptor 7 and 8. Science. 2004; 303(5663):1526-9.
47. Shen C, Xu H, Liu D, Veazey R S, and Wang X. Development of serum antibodies during early infancy in rhesus macaques: implications for humoral immune responses to vaccination at birth. Vaccine. 2014; 32(41): 5337-42.
48. Wille-Reece U, Flynn B J, Lore K, Koup R A, Kedl R M, Mattapallil J J, Weiss W R, Roederer M, and Seder R A. HIV Gag protein conjugated to a Toll-like receptor 7/8 agonist improves the magnitude and quality of Th1 and CD8+ T cell responses in nonhuman primates. Proc Natl Acad Sci USA. 2005; 102(42):15190-4.
49. Wille-Reece U, Flynn B J, Lore K, Koup R A, Miles A P, Saul A, Kedl R M, Mattapallil J J, Weiss W R, Roederer M, et al. Toll-like receptor agonists influence the magnitude and quality of memory T cell responses after prime-boost immunization in nonhuman primates. J Exp Med. 2006; 203(5):1249-58.
50. Wille-Reece U, Wu C Y, Flynn B J, Kedl R M, and Seder R A. Immunization with HIV-1 Gag protein conjugated to a TLR7/8 agonist results in the generation of HIV-1 Gag-specific Th1 and CD8+ T cell responses. J Immunol. 2005; 174(12):7676-83.
51. Marchese R D, Puchalski D, Miller P, Antonello J, Hammond O, Green T, Rubinstein L J, Caulfield M J, and Sikkema D. Optimization and validation of a multiplex, electrochemiluminescence-based detection assay for the quantitation of immunoglobulin G serotype-specific anti-pneumococcal antibodies in human serum. Clin Vaccine Immunol. 2009; 16(3):387-96.
52. Goldblatt D, Ashton L, Zhang Y, Antonello J, and Marchese R D. Comparison of a new multiplex binding assay versus the enzyme-linked immunosorbent assay for measurement of serotype-specific pneumococcal capsular polysaccharide IgG. Clin Vaccine Immunol. 2011; 18(10): 1744-51.
53. Goldblatt D, Plikaytis B D, Akkoyunlu M, Antonello J, Ashton L, Blake M, Burton R, Care R, Durant N, Feavers I, et al. Establishment of a new human pneumococcal standard reference serum, 007sp. Clin Vaccine Immunol. 2011; 18(10):1728-36.
54. Burton R L, and Nahm M H. Development and validation of a fourfold multiplexed opsonization assay (MOPA4) for pneumococcal antibodies. Clin Vaccine Immunol. 2006; 13(9):1004-9.
55. Burton R L, and Nahm M H. Development of a fourfold multiplexed opsonophagocytosis assay for pneumococcal antibodies against additional serotypes and discovery of serological subtypes in *Streptococcus pneumoniae* serotype 20. Clin Vaccine Immunol. 2012; 19(6):835-41.
56. Pullen G R, Fitzgerald M G, and Hosking C S. Antibody avidity determination by ELISA using thiocyanate elution. J Immunol Methods. 1986; 86(1):83-7.
57. Berenbaum M C. Correlations between methods for measurement of synergy. J Infect Dis. 1980; 142(3):476-80.

Example 2

Animals were injected intramuscularly in the quadriceps muscle with one of the following preparations:
1. 350 µL saline
2. 350 µL of a 2:5 mixture of 0.4 mg/mL 3M-052: saline
3. 350 µL of a 2:5 mixture of saline/PCV13
4. 350 µL of a 2:5 mixture of 0.4 mg/mL 3M-052: PCV13
Solutions are Vortexed for 20-30 Seconds to Emulsify the Foregoing Mixtures.

Example 3: Age-Specific TLR7/8 Adjuvant Formulation Overcomes Hyporesponsiveness to Neonatal Acellular Pertussis Vaccination in a Mouse Model Infection is the most common cause of mortality early in life, in large measure due to suboptimal early life vaccination strategies as compared to older age groups. New adjuvants are absolutely cardinal to further optimize current immunization approaches. However, only a few classes of adjuvants are presently incorporated in vaccines approved for human use.

The development of an effective infant *Bordetella pertussis* vaccine is now urgent because of the resurgence of pertussis in many countries, contemporaneous to the switch from whole cell to acellular vaccines. In this context, TLR7/8 adjuvant strategies described herein may be key to enhance early life immunogenicity by creating a vaccine formulation that induces both robust and persistent immunity (i.e., overcome waning immunity) to *B. pertussis*. Described herein is the optimization of a) the formulation delivery system, b) stability, and c) immunologic activity of novel small molecule imidazoquinoline TLR7/8 adjuvants towards human infant leukocytes. Next, in both adult and neonatal mouse models, it is demonstrated that this TLR7/8 adjuvant can overcome neonatal hyporesponsiveness to acellular pertussis vaccination by driving Th1 favoring responses to a licensed acellular vaccine (DTaP). This potent immunization strategy is of fundamental importance in vaccine development and represents a new paradigm for effective pertussis immunization in early life.

Infection is the most common cause of mortality early in life, substantively due to suboptimal vaccination strategies for newborns and infants as compared to older age groups. The development of an effective infant pertussis vaccine has become urgent because of the resurgence of pertussis in many countries. Current alum adjuvanted acellular pertussis (aP) vaccines have various shortcomings, which may contribute to their suboptimal infant responses.

New adjuvants may allow for the development of new vaccines and/or further optimizing current immunization approaches. In this context, age-focused adjuvant strategies may be the most singular solution to enhance early life immunogenicity by creating a vaccine formulation that induces both robust and persistent immunity to Bordetella pertussis. Described herein is the selection of a core TLR7/8 compound structure based on it's strong in vitro activity towards human newborn leukocytes, modification of it by lipidation and absorption onto alum. In a neonatal mouse immunization model, the alum adsorbed TLR7/8 adjuvant enhanced antibody responses to a licensed acellular vaccine, by polarizing towards Th1 favoring responses. This strategy represents a new example of how a combined alum+TLR7/8 adjuvant approach could reshape our current immunization schedules with significant potential to impact *B. pertussis* infectious rates in the pediatric population.

Whooping cough is a very severe respiratory infection caused by the Gram-negative encapsulated bacterium *Bordetella pertussis*, which can lead to severe complications and death, especially in newborns and young infants [1]. Vaccination remains the most effective strategy to prevent whooping cough. According to the World Health Organization, worldwide vaccination programs starting in the mid 20th century reduced the incidence of *B. pertussis* infection and associated mortality by 90% [2]. During the latter $20^{th}$ century, effective but reactogenic whole-cell pertussis (wP) vaccines were replaced by acellular pertussis (aP) vaccines formulated with purified bacterial antigens adsorbed onto alum. Currently employed aP vaccines significantly enhances protection against the respiratory disease caused by *B. pertussis*, but often require 5 doses starting from 2 months through 4-6 years of age and can wane over time [3]. Notably, since 2010, upwards of 50,000 cases of whooping cough are reported each year in the United States, interspersed with prominent epidemics [4].

As such, an improved infant *B. pertussis* vaccine is now urgently needed [5]. Although the majority of global immunization schedules are focused on the pediatric age group, development of new *B. pertussis* vaccines has been hampered by distinct early life immunity and an ad hoc approach in developing vaccines for adults prior to infant trials [6]. Decreased magnitude of immunogenicity and reduced persistence of functional antibodies are major challenges to early life immunization strategies [7]. Historically, solutions to these challenges included use of multi-dose pediatric immunization schedules, expanding the length of time between vaccine doses and/or administration of doses later in infancy, all of which increase immunogenicity [8]. However, innovative adjuvant strategies tailored to enhance early life responses may be the single most effective immunization approach [9]. Alum based subunit vaccines consisting of purified microbial products often lack the necessary adjuvant activity to induce and optimally shape an immune response [10]. Accordingly, development of rationally designed vaccine formulations, which include adjuvants that more effectively enhance immune responses in childhood, are warranted [11, 12]. In this context, TLR7/8 agonists are demonstrated herein to have unique age-specific utility.

Formulation science has traditionally been underappreciated in adjuvant discovery and development. However, over the past decade, the development of more fully characterized vaccine formulations has become a major goal for many vaccinologists and pharmaceutical companies [20]. The same holds true for the discovery and delivery of TLR7/8 agonists as vaccine adjuvants.

Typically the unformulated synthetic small molecule IMQs TLR7/8 ligands do not work well in comparison to their larger molecular weight counterparts' such as alum, since they are prone to diffuse away from the injection site, which can also result in systemic toxicity [21]. Most notably, R848 has a poor tolerability profile when tested systemically in humans. Common systemic side effects of this aqueous formulation include injection site reactogenicity and flu-like symptoms (fever, headache and malaise) correlating to systemic immune activation, seen with high concentrations of numerous inflammatory cytokines in the blood [22, 23].

As described herein, TLR7/8 adjuvantation can overcome newborn hyporesponsiveness to pneumococcal conjugate vaccination at birth [24]. 3M-052, a locally-acting lipidated IMQ TLR7/8 agonist adjuvant bearing a fatty acid tail (C18 lipid moiety), was shown to drive robust T helper 1-cytokine production by human newborn leukocytes in vitro, both alone and in synergy with the alum-adjuvanted pneumococcal conjugate vaccine (PCV)13 [24]. Moreover, a single administration of 3M-052 in combination with PCV13 on the first day of life, accelerated and enhanced anti-*S. pneumoniae* polysaccharide-specific B cells, serotype-specific antibody titers, and antibody-mediated phagocytic killing, to levels ~10-100 times greater than a single birth dose of PCV13 alone. These data indicate that appropriately formulated TLR7/8 agonist adjuvants, especially in the context of co-administration with alum, can enhance responses to vaccines administered even very shortly after birth [24].

This Example highlights a novel formulation approach to use alum to safely deliver a potent TLR7/8 adjuvant. It is demonstrated that immunization of newborn mice with alum adsorbed TLR7/8 adjuvanted DTaP vaccine drives IFNγ-driven type 1 immunity and switching toward the highly functional IgG2a/c subclass. This novel rational design approach to identify adjuvants active towards distinct populations is broadly applicable, closing the window of vulnerability to infections in early life.

Results

TLR7/8 Agonist CRX-649 Demonstrates Robust Newborn Th1 Polarizing Immune Activity.

To determine if TLR7/TLR8 agonists are able to adjuvant the immune response to the aP vaccine, six novel imidaziquinoline (IMQ) and oxoadinine (OA) scaffold-based compounds were synthesized as described previously (patent WO2017102652A1 and Tetrahdron Lett., 2016, 57, 2063-2066; which are incorporated by reference herein in their entireties) and evaluated. Three IMQ compounds, CRX-648, CRX-649 and CRX-664 (FIG. 25A, 25B) and three OA compounds, CRX-672, CRX-677 and CRX-748 (FIG. FIG. 25A, 25C), were found to have variable TLR7 and TLR8 selectivity and potency in HEK293 assay (FIG. 25A, and FIGS. 26A-26C). Though their TLR7 vs. TLR8 potency or selectivity did not correlate to their structure or side chain modifications, CRX-649 had the greatest potency for both hTLR7 and hTLR8 (FIGS. 26A-26C).

Next, the ability of the core IMQs and OAs to induce concentration-dependent leukocyte cytokine production in age-specific in vitro human neonatal and adult blood models was tested (FIGS. 27A-27D). All six of the TLR agonists tested demonstrated titration-dependent induction of TNF (FIG. 27A) and IFNγ (FIG. 27B) from the neonatal cells. The vehicle control did not induce TNF or IFNγ production. Interestingly, CRX-649 demonstrated a more than adult-like age-specific potency and effectiveness for TNF production in newborn cord blood (FIG. 27C). Of note, CRX-649 demonstrated the greatest potency, effectiveness and IFNγ polarization in newborn cord blood. CRX-649 mediated IFNγ production in newborn blood was most evident at 10 μM, reaching ~1200 pg/ml, twice the produced in similarly treated adult blood, (FIG. 27D, p<0.01).

CRX-649 also demonstrated a broader ability to induce a newborn-specific cytokine and chemokine potency and polarization. When whole blood treated supernatants were analyzed for cytokine/chemokine/interferon expression by multiplex assay, and the results graphed as fold change for newborn cold over adult, at both a low (1 μM, FIGS. 28A, 28B) and high (10 μM, FIGS. 28C, 28D) concentration of CRX-649, induced concentration-dependent production of IL-1β, L-6, IL-10, and IL-12p40 (FIGS. 28A, 28C). CXCL8, CXCL10, CCL2 and GM-CSF also demonstrated greater CRX-649 induced production in newborn blood (FIGS. 28B, 28D).

Human adult PBMCs stimulated with CRX-649 for 24 h demonstrated increased expression of CD123, HLA-D, CD80 and CD86 as compared to unstimulated cells. The ip regulation of co-stimulatory molecule expression pattern in PBMCs was greater than those observed in similarly MPLA or CpG treated groups (data not shown). Next, a human newborn Th1 polarization assay was employed, which leverages the intrinsic characteristics of the newborn T cell compartment (composed mainly of naïve T cells) to evaluate how CRX-649 modulated T cell polarization in a mixed mononuclear cell culture in the presence of a TCR-mediated stimulus. Additionally, the CBMCs were cultured in the presence of autologous plasma, a rich source of age-specific soluble immunomodulatory factors [25]. CBMCs stimulated with αCD3 (polyclonal T cell activator) with 10 μM of CRX-649 for 96 hrs demonstrated an significantly enhanced ability to induce IFNγ production by newborn T cells (FIG. 28F, p<0.01).

Figure 29E:
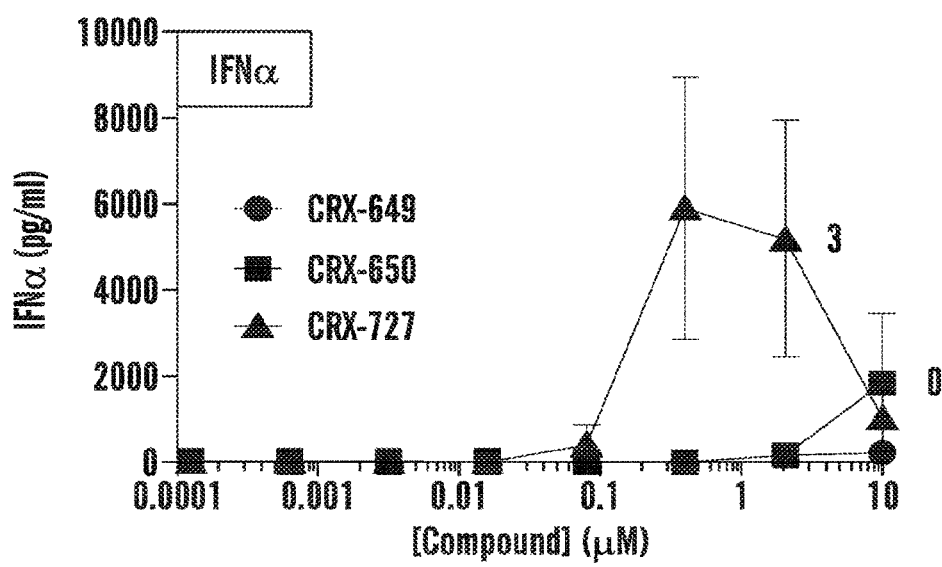

Precise lipidation of the basic IMQ scaffold changes the immunostimulatory properties. Upon determining that these agonists, and CRX-649 in particular, have the ability to significantly enhance newborn Th1 (IFN) responses, their utility as adjuvants upon derivatization using lipid conjugation was further explored. Locally acting adjuvants may have distinct advantages in vivo by avoiding extensive systemic distribution and consequent induction of systemic inflammation [26-28]. In addition, cellular uptake is a prerequisite for cellular activation in response to TLR7/8 ligands since these receptors are localized in the endosomal/lysosomal compartments [29]. Thus, there is considerable interest in strategies that will increase the penetration of the TLR7/8 ligand into the endosome of DCs and other immune cells as well as ameliorate toxic effects. Lipid conjugation of nucleoside drugs including TLR7/8 agonists [30] is one strategy known to facilitate endocytosis, enhance oral bioavailability, and decrease toxic side effects by creating a depot effect. The basic imidaziquinoline pharmacophore (FIG. 29A) was optimized to contain a 2 n-butyl and 1 ethanol creating CRX-649 (FIG. 29B). For nucleolipidation studies this core was further derivitized by addition of a phosphate off the ethanol at the 1 position, followed by addition of an optimally determined 3 PEG linker (FIG. 29C). The core compound CRX-649 was compared for cytokine induction from adult PBMCs in relation to the phosphorylated derivative, CRX-650, or the phospholipidated derivative, CRX-727. While the core compound does not contain a phosphate moiety and thus cannot adsorb to alum, present in many vaccines as adjuvants and antigen stabilizers, the addition of the phosphate on the core can facilitate this. Addition of the PEG linker, though not the phosphate alone, to CRX-649 vastly changed the cytokine skewing from pro-inflammatory biased, TNF production, to type I interferon biased (FIGS. 29D-29E). As well, it was determined that TNF induction strength and potency was directly correlated with linker length, For IFNα a less clear structure activity relationship (SAR) trend was seen, although the >3 PEG linker compound displayed greater strength and potency for induction of this cytokine. This change in phenotype allowed for selection of a compound, n=3 (hereby CRX-727), that displayed a skewed type I interferon response with very minimal inflammatory cytokine production suggesting it would have reduced reactogenicity while maintaining immunogenicity.

Lipid conjugation to Alum unlocks TLR7/8 adjuvanticity. Collectively, this data supports the potential of both the core and lipidated molecules to serve as immunomodulatory vaccine adjuvants. To investigate their ability to augment response to aP vaccine, a commercially utilized, Food and Drug Administration (FDA) approved, pediatric DTaP vaccine (Trade name: Infanrix) was investigated. The acellular vaccine contains three recombinant B. pertussis proteins, the inactivated pertussis toxoid (PT), the adhesin filamentous hemagglutinin (FHA), and outer membrane protein, pertacin. All three proteins are unstable unless adsorbed to aluminum hydroxide (alum). The nucleolipid derivative compound(s) contain phosphate groups which are theoretically also able to adsorb to alum in the vaccine. Thus an adsorption study was undertaken to determine how the different IMQ adjuvant compounds would interact with the final vaccine antigen formulation (i.e., DTaP). Aqueous suspensions of the lipidated compound CRX-727 and its parent pharmacophore CRX-649 were incubated with DTaP vaccine and aliquots were assayed at various time points (1, 2, 24 hrs) post admixture to assess amounts of unbound compounds in the supernatant via reversed-phase high-performance liquid chromatography (RP-HPLC). As suspected, the lipidated compound fully adsorbed (~96-100%) to the alum/antigen within 1 hr (FIG. 30, top). The addition of excess alum, through pre-adsorption of the compound on the alum, had little effect on CRX-727 adsorption (~99% after 1 hr) (FIG. 30, second from top panel). However, in all circumstances tested, the core CRX-649 compound was only able to adsorb to the antigen ~4-7% within 1-2 hr (FIG. 30, bottom panels), with peak area intensity levels similar to the unmixed controls.

These formulations of DTaP:TLR7/8 adjuvant were then tested for immunogenicity in adult mice. Mice were immunized twice, 14 days apart with Infanrix (1/100th of the human dose)±CRX-649 or CRX-727 at 0.1, 1 or 10 μg per mouse in different formulations. Serum was harvested 14 days following prime and boost (FIG. 31A). At two weeks post primary vaccination, anti-FHA IgG2a serum antibody titers were significantly elevated over antigen alone vaccinated mice when 10 μg of CRX-727, with (p<0.0001) or without alum (p<0.001) pre-adsorption of the adjuvant, was included in the vaccine (FIG. 31A, right). IgG1 anti-FHA titers were only significantly boosted vs. antigen alone with CRX-727 pre-adsorbed on alum (p<0.001) (FIG. 31A, left) demonstrating a potential difference in effect for alum adsorption in driving a Th1 vs. Th2 skewed immune response. CRX-727+ alum also induced significantly enhanced IgG2a as compared to CRX-727 post primary vaccination (FIG. 31A).

By 14 days post-secondary immunization serum anti-FHA titers were much higher and nearing a plateau for many groups (FIG. 31B). Again, it was seen that addition of CRX-727 both with and without pre-alum adsorption facilitated significantly higher IgG1 and IgG2a antibody titers. For both 14 days post primary and secondary addition of the core imidaziquinoline CRX-649 was not able to enhance either IgG1 or IgG2a antibody titers in the adult mice. Of note, potency increases were observed when boosting with a 1 µg dose CRX-727 alone (p<0.0001) and a 0.1 µg dose CRX-727+alum (FIG. 33C, p<0.01). Overall, these data indicate that it is either the adsorption of the adjuvant to the alum or type I interferon skewing that is necessary for enhancement of immune response to this vaccine. This is further supported from data examining the cell-mediated immune response of vaccinated animals. Spleens from 3 mice per group were harvested 5 days post-secondary immunization and restimulated with purified pertussis antigen followed by intracellular cytokine staining and analysis via flow cytometry. Though no differences were statistical, likely because of small group sizes and variability, there was a clear trend of higher percentages of IFNγ-producing $CD4^+$ T cells from animals vaccinated with antigen plus CRX-727, specifically when alum adsorbed (FIG. 32).

TLR7/8 adjuvant formulated with alum overcomes neonatal hyporesponsisves to DTaP. Having demonstrated the potential of alum adsorbed lipidated TLR7/8 adjuvanting to enhance both the correlates of immunogenicity and antibody subclass induction in adult mice, it was assessed if the same phenotype is achievable in a neonatal setting. Of note, vaccine driven antibody isotype switching toward IgG2c, with alum as the sole adjuvant, is diminished or not achievable in early life [31]. 7 day old C57BL/6 were vaccinated with a prime-boost schedule (two injections one week apart, at DOL 7 and 14) with DTaP (1/100th of the human dose), ±CRX649 or CRX-727 at 0.1 µg, 1 µg or 10 µg per mouse in different formulations. Serum was harvested 14 days following boost (day of life 28) and assessed for antibody production (FIG. 33A). Firstly, it was found that only DTaP alum adsorbed CRX-727 (both 1 and 10 µg doses) significantly enhanced anti-FHA serum total IgG (FIG. 33B, p<0.0001). Unlike vaccinated adult mice, which demonstrated significantly enhanced anti-FHA serum total IgG1 titers with the 10 g dose of CRX-727 alone, newborn mice were not able to induce significantly increased levels of IgG1 (FIG. 33C). Most encouragingly, significantly elevated FHA-specific IgG2c titers were observed in newborn mice vaccinated with DTaP and either a 1 µg or 10 µg dose of CRX-727 in an alum-adsorbed formulation (FIG. 33D, p<0.0001) as compared to DTaP alone. Intriguingly, newborn mice receiving the lowest adjuvant dose of CRX-727 demonstrated a ~2.2-fold change in FHA-specific IgG2c compared DTaP alone (FIG. 33E). In adult mice this change was only ~1.2-fold, leading to a higher IgG2c/IgG1 ratio in the neonatal mice. These results clearly highlight the age specific nature of the TLR7/8:DTaP formulation and is supportive of the predictive nature of the in vitro Th1 polarizing studies employing human leukocytes for in vivo activity.

Discussion

Even in the era of vaccination, infection is still the most common cause of mortality early in life, often due to poor early life immunization as compared to adults. Small molecule TLR7/8 agonists have demonstrated great potential as vaccine adjuvants, since they directly activate APCs and can enhance both humoral and cellular immune responses, especially Th1 responses. Along with effective adjuvantation, vaccine delivery systems, improvement in antigen design and increased knowledge about human immune responses, are key technological advances fueling the current revolution in vaccine discovery and development [32]. Rational vaccine design approaches, employing immunoengineering and novel delivery systems may allow for the controlled preparation of vaccine complexes of the desired immunostimulatory properties, particulate size, and antigen load, all of which also improve safety by potentially limiting systemic toxicities by their targeted nature [33]. The persistently high global burden of infections in the very young [34] provides a compelling rationale for developing additional safe and effective early life vaccines.

The present project synergistically combined three innovative approaches to provide unique insight into and overcome early life aP vaccine hyporesponsiveness: 1) the use of age specific human in vitro and murine in vivo models, 2) the employment of cutting edge medicinal chemistry and 3) formulation science techniques to optimize small molecule adjuvanticity and delivery. Next generation pertussis vaccines might require increased amounts of appropriate antigens and potentially novel adjuvantation systems as well. In addition to enhanced immunogenicity, relatively low reactogenicity will be an important feature of successful next generation pertussis vaccines.

In summary, it is demonstrated herein that immunization of newborn mice with TLR7/8 adjuvanted DTaP vaccine drives IFNγ-driven type 1 immunity, enhance robust early life immunogenicity and switching toward the highly functional IgG2a/c subclass. By combining transformative delivery technologies, relevant early life in vitro and in vivo models translational models, benchmarking to licensed vaccines coupled with innovative serological insights, our study provides a fresh paradigm for rational vaccine design to inform development of novel age-targeted development of neonatal and pediatric vaccines. The results from this immunization strategy are of fundamental importance in vaccine development and represent a new paradigm for effective pertussis immunization in early life.

Materials and Methods

Ethics Statements.

All experiments were conducted in accordance with relevant institutional and national guidelines, regulations and approvals. All experiments involving animals were approved by the Institutional Animal Care and Use Committees (IACUC) of Boston Children's Hospital and Harvard Medical School (protocol numbers 15-11-3011 and 16-02-3130) and the University of Montana (protocol number 037-16ASDBS-061416). C57BL/6 and BALB/c mice were obtained from Taconic Biosciences, Charles River Laboratories or Envigo and housed in specific pathogen-free conditions in the animal research facilities at Boston Children's Hospital and the University of Montana. For breeding purposes, mice were housed in couples, and cages checked daily to assess pregnancy status of dams and/or the presence of pups. When a new litter was discovered, that day was recorded as day of life (DOL) 0. Both male and female pups were used for neonatal experiments. Non-identifiable human cord blood samples were collected with approval from the Ethics Committee of The Brigham & Women's Hospital, Boston, Mass. (protocol number 2000-P-000117) and Beth Israel Deaconess Medical Center Boston, Mass. (protocol number 2011P-000118). Blood samples from adult volunteers were collected after written informed consent with approval from the Ethics Committee of Boston Children's Hospital, Boston, Mass. (protocol number X07-05-0223) or the University of Montana Institutional Review Board (protocol number 43-16).

Human Blood Sample Processing and In Vitro Stimulation.

Peripheral blood was collected from healthy adult volunteers, while human newborn cord blood was collected immediately after Cesarean section delivery of the placenta. Births to known HIV-positive mothers were excluded. Human experimentation guidelines of the U.S. Department of Health and Human Services, The Brigham & Women's Hospital, Beth Israel Deaconess Medical Center Boston, Boston Children's Hospital and the University of Montana were observed, following protocols approved by the local institutional review boards.

Human blood was anti-coagulated with 20 units/ml pyrogen-free sodium heparin (American Pharmaceutical Partners, Inc.; Schaumberg, Ill.). All blood products were kept at room temperature and processed within 4 hours from collection. Human whole blood assays were completed as previously described [14, 17]. Briefly, neonatal cord blood or adult whole blood (WB) was mixed 1:1 with sterile pre-warmed (37° C.) RPMI 1640 medium (Invitrogen; Carlsbad, Calif.) and 180-225 µl of the 1:1 suspension was added to each well of a 96 well U-bottom plate (Becton Dickinson; Franklin Lakes, N.J., USA) containing 20-25 µl freshly prepared specific TLRAs at 10× the final concentration. Suspensions containing 200-250 µl/well were gently mixed by pipetting and incubated for 6 hours at 37° C. in a humidified incubator at 5%, $CO_2$. After culture, plates were centrifuged at 500×g and ~100-150 µl of supernatant was carefully removed by pipetting without disturbing the cell pellet. Supernatants derived from human leukocyte stimulations were assayed by ELISA for TNF and IFNγ (BD Biosciences; San Jose, Calif., USA).

For adult PBMC stimulation only, primary human PBMCs were isolated from fresh blood from healthy donors via Ficoll gradient separation. PBMCs were resuspended and maintained in RPMI-1640 culture media (Invitrogen, Grand Island, N.Y.), antibiotics (Pen/Step/Glut, Invitrogen) and 10% FBS (Sigma). Cells were plated at $0.5 \times 10^6$ cells/well in 96-well tissue culture plates and stimulated for 24 h with aqueous formulations of indicated compounds. Culture supernatants were harvested and analyzed for IFNα and TNF induction using human TNF DuoSet™® ELISA kit human IFNα VeriKine ELISA kit (Pestka Biomedical Laboratories, Inc., Piscataway, N.J.).

Additionally, for both newborn and adult readouts, cytokine and chemokine expression profiles in cell culture supernatants and peripheral blood plasma were measured using customized Milliplex™ human cytokine/chemokine magnetic bead panels (Millipore; Billerica, Mass., USA). Assays were analyzed on the Luminex® 100/200™ System employing xPOTENT® software (Luminex; Austin, Tex.) and Millipore Milliplex Analyst™ (version 3.5.5.0). The minimum threshold for each analyte was set at the minimum detectable concentration for a given assay, defined as three standard deviations above the mean background. CL075 (TLR8/7) was purchased from InvivoGen (San Diego, Calif.) and used at the concentrations noted in the figure legends.

Quantification of CRX-727 Adsorption onto Alum Derived from DTaP Vaccine.

To quantify the extent of CRX-727 adsorption to aluminum hydroxide (Alhydrogel™) 100 µl of CRX-727 was mixed with 100 µl of Infanrix™ (combination vaccine for diphtheria, tetanus, and acellular pertussis (DTaP)) (a 1:10 CRX-727:alum mass ratio) plus 300 µl of 0.9% saline. After vortexing for 10 seconds the sample was placed in a 37° C. incubator. Every 15 minutes the sample was vortexed for an additional 5 seconds and placed back into the incubator. Aliquots (0.75 ml) were taken at t=0.25, 0.5, 1, 2, 4 and 24 hours and centrifuged at 3000 RPM (rcf=664 g) to separate the alum from the supernatant. Supernatant was immediately removed and placed into an autosampler vial undiluted for analysis by reverse-phase high performance liquid chromatography (RP-HPLC) to determine adsorption as a function of time. RP-HPLC samples were run on a Waters 2695 HPLC equipped with a 2996 photodiode array detector at a wavelength of 254 nm. A gradient was performed using a two mobile phase system of 0.1% trifluoroacetic acid in water and 0.1% trifluoroacetic acid in acetonitrile, on an Agilent Zorbax Eclipse Plus C18, 4.6×150 mm, 5 micron column at 25° C. The response (peak area) of the samples were compared against a 50 µl CRX-727 plus 200 µl 0.9% saline control and a separate 100 µl alum plus 400 µl saline control.

Human Newborn Th1 Polarization Assay.

Newborn cord blood mononuclear cells (CBMCs), a mixed mononuclear cell culture which is a largely naïve newborn T cell population, were stimulated with the TLR7/8 agonists in the presence of the polyclonal T cell activator αCD3 for 96 hours. T cell polarization was evaluated by IFNγ levels measured in cell-free supernatants by ELISA.

In Vivo Rodent Immunization, Antigens, and Antibody Quantification.

For immunization experiments, both neonate and adult mice were immunized intramuscularly (i.m.) in the posterior thigh with 50 µl of total vaccine dose. For adult mouse studies, Balb/c mice (6-8 weeks of age) were immunized with Infanrix (GSK, 1/100th of the human dose)±CRX649 or CRX-727 at 0.1 µg, 1 µg or 10 µg per mouse in different formulations (aqueous choline salt, liposome or alum pre-adsorbed). Serum was harvested 14 days following prime (14dp1) or boost (14dp2) and anti-FHA serum antibody IgG1 and IgG2a titers were measured by ELISA, as described below. For neonatal mouse studies, 7 day old Balb/c and C57BL/6 mice were immunized with a prime-boost schedule (two injections one week apart, for newborn mice at DOL 7 and 14). Serum was harvested 14 days following boost (14dp2) (day of life 28) and anti-FHA serum total IgG titers, IgG1 and IgG2a/IgG2c were measured by ELISA.

For anti-filamentous hemagglutinin (FHA) ELISAs, Nunc MaxiSorp™ flat bottom 96-well plates (ThermoFisher Scientific) were coated with 5 µg/ml FHA (B. pertussis Filamentous Hemagglutinin, Strain: NCTC 10739, The Native Antigen Company/Cedarlane, Burlington, N.C.) in carbonate buffer pH 9.6, incubated overnight at 4° C., washed 3× with wash buffer (KPL 10× Phosphate Buffered Saline with Tween 20 (Fisher Scientific)) and blocked with Super-block™ (ScyTek) for 1 h at room temperature (RT). Then, sera from vaccinated mice were added with an initial dilution of 1:100 and 1:2 serial dilutions in EIA buffer (PBS+BSA 1%+Tween 20 0.1%+Heat inactivated FBS 5%) and incubated for 2 h at RT. Plates were then washed 3× and incubated for 1 h at RT with HRP-conjugated anti-mouse IgG, IgG1, IgG2c or IgG2a (Southern Biotech). At the end of the incubation plates were washed again and developed with KPL Sure Blue TMB™ Microwell Peroxidase Substrate (Fisher Scientific) for 15 minutes, then stopped with 1 N $H_2SO_4$. The optical density was read at 450 nm Versamax™ microplate reader with SoftMax Pro Version 5™

(both from Molecular Devices) and endpoint titers were calculated using as cutoff three times the optical density of the background.

For cell mediated immunity analysis, 3 mice per group were sacrificed 5 days post-secondary injection and spleens were harvested, homogenized through a 100 m filter and washed. Red blood cells were lysed (RBC lysis buffer, BioLegend) followed by washing and plating into 96-well culture plate at $50 \times 10^6$ cells/ml, 100 µl/well. Cells were restimulated with a final concentration of 5 µg/ml pertussis toxin and FHA for 13 hours followed by addition of GolgiPlug™ (BD Biosciences) for an additional 5 hours. Cells were then washed, stained for viability (Tonbo Biosciences Ghost 510) and then surface stained for 30 min with anti-CD3, CD8 and CD4 antibodies (clones 145-2C11, 25-0042, 60-0081 (all Tonbo), respectively). Cells were then washed, fixed/permeabilized (BD fix/per buffer, BD Biosciences) and intracellularly stained for 30 min with and IFNγ (XMG1.2 (BD) antibody. Cells were then washed and analyzed on an LSR II flow cytometer (BD) using FACSDiva™ software and FlowJo™ v10 software for post-acquisition analysis.

HEK293 Assay for Human TLR7 and TLR8 Selectivity.

Human embryonic kidney (HEK)293 cells expressing human TLR7 or TLR8 with an NF-κB-responsive secreted embryonic alkaline phosphatase (SEAP) reporter gene were obtained from Novus Biologicals (Littleton, Colo.) and Invivogen (San Diego, Calif.), respectively. Cells were maintained in DMEM with 10% HI-FBS and selection antibiotics per the manufacturer's instructions. Cells were plated at $5 \times 10^5$ cells/96-well and stimulated with indicated agonist(s) for 24 h. Supernatants were harvested and analyzed for NF-κB/SEAP activation using the QuantiBlue™ kit (Invivogen). Values are expressed as fold change in $OD_{650}$ over vehicle-only treated samples.

Statistical Analyses and Graphics.

Statistical significance and graphic output were generated using Prism™ v. 5.0a and 7.0a (GraphPad™ Software) and Microsoft Excel™ (Microsoft Corporation, Redmond, Wash.). For experiments where values were normalized to control, column statistics were conducted using two-tailed Wilcoxon Signed Rank Test or one-sample T test comparing to control. Group comparisons were performed by One-way ANOVA with Dunnett's multiple comparison post test or Two-way ANOVA comparing column and row effects. Results were considered significant at $p<0.05$, and indicated as follows: $*p<0.05$, $p<0.01$, $*p<0.001$.

REFERENCES

1. Mattoo S, Cherry J D. Molecular pathogenesis, epidemiology, and clinical manifestations of respiratory infections due to *Bordetella pertussis* and other *Bordetella* subspecies. Clin Microbiol Rev. 2005; 18(2):326-82. Epub Apr. 16, 2005. doi: 10.1128/cmr. 18.2.326-382.2005. PubMed PMID: 15831828; PubMed Central PMCID: PMCPMC1082800.
2. Tan T, Trindade E, Skowronski D. Epidemiology of pertussis. The Pediatric infectious disease journal. 2005; 24(5 Suppl): S10-8. Epub May 7, 2005. PubMed PMID: 15876918.
3. Burdin N, Handy L K, Plotkin S A. What Is Wrong with Pertussis Vaccine Immunity? The Problem of Waning Effectiveness of Pertussis Vaccines. Cold Spring Harbor perspectives in biology. 2017; 9(12). Epub Mar. 16, 2017. doi: 10.1101/cshperspect.a029454. PubMed PMID: 28289064.
4. Skoff T H, Baumbach J, Cieslak P R. Tracking Pertussis and Evaluating Control Measures through Enhanced Pertussis Surveillance, Emerging Infections Program, United States. Emerg Infect Dis. 2015; 21(9):1568-73. Epub Aug. 21, 2015. doi: 10.3201/eid2109.150023. PubMed PMID: 26291475; PubMed Central PMCID: PMCPMC4550149.
5. Poolman J T. Shortcomings of pertussis vaccines: why we need a third generation vaccine. Expert Rev Vaccines. 2014; 13(10):1159-62. Epub Aug. 5, 2014. doi: 10.1586/14760584.2014.944902. PubMed PMID: 25089373.
6. Dowling D J, Levy O. Pediatric vaccine adjuvants: Components of the modern vaccinologist's toolbox. The Pediatric infectious disease journal. 2015. Epub Sep. 10, 2015. doi: 10.1097/inf.0000000000000893. PubMed PMID: 26353029.
7. Dowling D J, Levy O. Ontogeny of early life immunity. Trends Immunol. 2014; 35(7):299-310. Epub Jun. 2, 2014. doi: 10.1016/j.it.2014.04.007. PubMed PMID: 24880460; PubMed Central PMCID: PMC4109609.
8. Pollard A J, Perrett K P, Beverley P C. Maintaining protection against invasive bacteria with protein-polysaccharide conjugate vaccines. Nat Rev Immunol. 2009; 9(3):213-20. Epub Feb. 14, 2009. doi: nri2494 [pii] 10.1038/nri2494 [doi]. PubMed PMID: 19214194.
9. Allen A C, Mills K H. Improved pertussis vaccines based on adjuvants that induce cell-mediated immunity. Expert Rev Vaccines. 2014; 13(10):1253-64. Epub Jul. 16, 2014. doi: 10.1586/14760584.2014.936391. PubMed PMID: 25017925.
10. van Haren S D, Ganapathi L, Bergelson I, Dowling D J, Banks M, Samuels R C, et al. In vitro cytokine induction by TLR-activating vaccine adjuvants in human blood varies by age and adjuvant. Cytokine. 2016; 83:99-109. Epub Apr. 16, 2016. doi: 10.1016/j.cyto.2016.04.001. PubMed PMID: 27081760; PubMed Central PMCID: PMCPmc4906944.
11. Dowling D J, Levy O. Pediatric Vaccine Adjuvants: Components of the Modern Vaccinologist's Toolbox. The Pediatric infectious disease journal. 2015; 34(12): 1395-8. Epub Sep. 10, 2015. doi: 10.1097/inf.0000000000000893. PubMed PMID: 26353029.
12. Reed S G, Orr M T, Fox C B. Key roles of adjuvants in modern vaccines. Nat Med. 2013; 19(12):1597-608. Epub Dec. 7, 2013. doi: nm.3409 [pii]10.1038/nm.3409 [doi]. PubMed PMID: 24309663.
13. Philbin V J, Dowling D J, Gallington L C, Cortes G, Tan Z, Suter E E, et al. Imidazoquinoline Toll-like receptor 8 agonists activate human newborn monocytes and dendritic cells through adenosine-refractory and caspase-1-dependent pathways. J Allergy Clin Immunol. 2012; 130(1):195-204 e9. Epub Apr. 24, 2012. doi: 10.1016/j.jaci.2012.02.042. PubMed PMID: 22521247; PubMed Central PMCID: PMC3387351.
14. Dowling D J, Tan Z, Prokopowicz Z M, Palmer C D, Matthews M A, Dietsch G N, et al. The ultra-potent and selective TLR8 agonist VTX-294 activates human newborn and adult leukocytes. PLoS One. 2013; 8(3):e58164. Epub Mar. 14, 2013. doi: 10.1371/journal.pone.0058164. PubMed PMID: 23483986; PubMed Central PMCID: PMC3587566.
15. Dowling D J, Scott E A, Scheid A, Bergelson I, Joshi S, Pietrasanta C, et al. Toll-like receptor 8 agonist nanoparticles mimic immunomodulating effects of the live BCG vaccine and enhance neonatal innate and adaptive immune responses. J Allergy Clin Immunol. 2017; 140 (5):1339-50. Epub Mar. 28, 2017. doi: 10.1016/j.jaci.2016.12.985. PubMed PMID: 28343701.

16. Holbrook B C, Aycock S T, Machiele E, Clemens E, Gries D, Jorgensen M J, et al. An R848 adjuvanted influenza vaccine promotes early activation of B cells in the draining lymph nodes of non-human primate neonates. Immunology. 2017; ([Epub ahead of print]). Epub Sep. 25, 2017. doi: 10.1111/imm.12845. PubMed PMID: 28940186.

17. Dowling D J, van Haren S D, Scheid A, Bergelson I, Kim D, Mancuso C J, et al. TLR7/8 adjuvant overcomes newborn hyporesponsiveness to pneumococcal conjugate vaccine at birth. 2017; 2(6):e91020. doi: 10.1172/jci.insight.91020. PubMed PMID: 28352660.

18. Pettengill M A, van Haren S D, Li N, Dowling D J, Bergelson I, Jans J, et al. Distinct TLR-mediated cytokine production and immunoglobulin secretion in human newborn naïve B cells. Innate Immun. 2016. Epub Jun. 3, 2016. doi: 10.1177/1753425916651985. PubMed PMID: 27252169.

19. Misiak A, Leuzzi R, Allen A C, Galletti B, Baudner B C, D'Oro U, et al. Addition of a TLR7 agonist to an acellular pertussis vaccine enhances Th1 and Th17 responses and protective immunity in a mouse model. Vaccine. 2017; 35(39):5256-63. Epub Aug. 22, 2017. doi: 10.1016/j.vaccine.2017.08.009. PubMed PMID: 28823618.

20. Brito L A, Malyala P, O'Hagan D T. Vaccine adjuvant formulations: A pharmaceutical perspective. Semin Immunol. 2013; 25(2):130-45. Epub Jul. 16, 2013. doi: S1044-5323(13)00037-7 [pii]10.1016/j.smim.2013.05.007 [doi]. PubMed PMID: 23850011.

21. Vasilakos J P, Tomai M A. The use of Toll-like receptor 7/8 agonists as vaccine adjuvants. Expert Rev Vaccines. 2013; 12(7):809-19. Epub Jul. 28, 2013. doi: 10.1586/14760584.2013.811208. PubMed PMID: 23885825.

22. Sauder D N, Smith M H, Senta-McMillian T, Soria I, Meng T C. Randomized, single-blind, placebo-controlled study of topical application of the immune response modulator resiquimod in healthy adults. Antimicrobial agents and chemotherapy. 2003; 47(12):3846-52. Epub Nov. 26, 2003. PubMed PMID: 14638493; PubMed Central PMCID: PMCPMC296201.

23. Szeimies R M, Bichel J, Ortonne J P, Stockfleth E, Lee J, Meng T C. A phase II dose-ranging study of topical resiquimod to treat actinic keratosis. The British journal of dermatology. 2008; 159(1):205-10. Epub May 15, 2008. doi: 10.1111/j.1365-2133.2008.08615.x. PubMed PMID: 18476957.

24. Dowling D J, van Haren S D, Scheid A, Bergelson I, Kim D, Mancuso C J, et al. TLR7/8 adjuvant overcomes newborn hyporesponsiveness to pneumococcal conjugate vaccine at birth. JCI insight. 2017; 2(6):e91020. Epub Mar. 30, 2017. doi: 10.1172/jci.insight.91020. PubMed PMID: 28352660; PubMed Central PMCID: PMCPMC5360187 from VentiRx Pharmaceuticals, 3M Drug Delivery Systems, MedImmune, Crucell (Johnson & Johnson), and Shire.

25. Pettengill M A, van Haren S D, Levy O. Soluble mediators regulating immunity in early life. Frontiers in immunology. 2014; 5:457. Epub Oct. 14, 2014. doi: 10.3389/fimmu.2014.00457. PubMed PMID: 25309541; PubMed Central PMCID: PMCPmc4173950.

26. Mastelic B, Garcon N, Del Giudice G, Golding H, Gruber M, Neels P, et al. Predictive markers of safety and immunogenicity of adjuvanted vaccines. Biologicals: journal of the International Association of Biological Standardization. 2013; 41(6):458-68. Epub Sep. 28, 2013. doi: 10.1016/j.biologicals.2013.08.006. PubMed PMID: 24071553.

27. Horscroft N J, Pryde D C, Bright H. Antiviral applications of Toll-like receptor agonists. The Journal of antimicrobial chemotherapy. 2012; 67(4):789-801. Epub Jan. 20, 2012. doi: 10. 1093/jac/dkr588. PubMed PMID: 22258929.

28. Strominger N L, Brady R, Gullikson G, Carpenter D O. Imiquimod-elicited emesis is mediated by the area postrema, but not by direct neuronal activation. Brain Research Bulletin. 2001; 55(3):445-51.

29. Lee J, Chuang T H, Redecke V, She L, Pitha P M, Carson D A, et al. Molecular basis for the immunostimulatory activity of guanine nucleoside analogs: activation of Toll-like receptor 7. Proceedings of the National Academy of Sciences of the United States of America. 2003; 100(11): 6646-51. Epub May 10, 2003. doi: 10.1073/pnas.0631696100. PubMed PMID: 12738885; PubMed Central PMCID: PMCPMC164501.

30. Chan M, Hayashi T, Kuy C S, Gray C S, Wu C C N, Corr M, et al. Synthesis and Immunological Characterization of Toll-Like Receptor 7 Agonistic Conjugates. Bioconjugate chemistry. 2009; 20(6): 1194-200. doi: 10.1021/bc900054q.

31. Borriello F, Pietrasanta C, Lai J C Y, Walsh L M, Sharma P, O'Driscoll D N, et al. Identification and Characterization of Stimulator of Interferon Genes As a Robust Adjuvant Target for Early Life Immunization. Frontiers in immunology. 2017; 8:1772. Epub Jan. 10, 2018. doi: 10.3389/fimmu.2017.01772. PubMed PMID: 29312305; PubMed Central PMCID: PMCPMC5732947.

32. Koff W C, Burton D R, Johnson P R, Walker B D, King C R, Nabel G J, et al. Accelerating next-generation vaccine development for global disease prevention. Science. 2013; 340(6136):1232910. Epub Jun. 1, 2013. doi: 10.1126/science.1232910. PubMed PMID: 23723240; PubMed Central PMCID: PMCPmc4026248.

33. Delany I, Rappuoli R, De Gregorio E. Vaccines for the 21st century. EMBO molecular medicine. 2014; 6(6):708-20. Epub May 8, 2014. doi: 10.1002/emmm.201403876. PubMed PMID: 24803000; PubMed Central PMCID: PMCPmc4203350.

34. Liu L, Johnson H L, Cousens S, Perin J, Scott S, Lawn J E, et al. Global, regional, and national causes of child mortality: an updated systematic analysis for 2010 with time trends since 2000. Lancet. 2012; 379(9832):2151-61. Epub May 15, 2012. doi: S0140-6736(12)60560-1 [pii] 10.1016/S0140-6736(12)60560-1 [doi]. PubMed PMID: 22579125.

35. Wu T Y, Singh M, Miller A T, De Gregorio E, Doro F, D'Oro U, et al. Rational design of small molecules as vaccine adjuvants. Sci Transl Med. 2014; 6(263): 263ra160. Epub Nov. 21, 2014. doi: 10.1126/scitranslmed.3009980. PubMed PMID: 25411473.

36. Cortez A, Li Y, Miller A T, Zhang X, Yue K, Maginnis J, et al. Incorporation of Phosphonate into Benzonaphthyridine Toll-like Receptor 7 Agonists for Adsorption to Aluminum Hydroxide. J Med Chem. 2016; 59(12):5868-78. Epub Jun. 9, 2016. doi: 10.1021/acs.jmedchem.6b00489. PubMed PMID: 27270029.

37. Buonsanti C, Balocchi C, Harfouche C, Corrente F, Galli Stampino L, Mancini F, et al. Novel adjuvant Alum-TLR7 significantly potentiates immune response to glycoconjugate vaccines. Sci Rep. 2016; 6:29063. Epub Jul. 22, 2016. doi: 10.1038/srep29063. PubMed PMID: 27439378; PubMed Central PMCID: PMCPMC4954951.

38. Smith A J, Li Y, Bazin H G, St-Jean J R, Larocque D, Evans J T, et al. Evaluation of novel synthetic TLR7/8 agonists as vaccine adjuvants. Vaccine. 2016; 34(36): 4304-12.
39. Bazin H G, Li Y, Khalaf J K, Mwakwari S, Livesay M T, Evans J T, et al. Structural requirements for TLR7-selective signaling by 9-(4-piperidinylalkyl)-8-oxoadenine derivatives. Bioorganic & medicinal chemistry letters. 2015; 25(6):1318-23.

What is claimed herein is:

1. A method of immunizing a subject, the method comprising administering to the subject
   i) an adjuvant comprising an agonist of TLR7 and/or TLR8; and
   ii) at least one antigen;
wherein the adjuvant and the at least one antigen are not conjugated to each other; and
wherein the adjuvant comprises an agonist of TLR7 and/or TLR8, and the agonist of TLR7 and/or TLR8 comprises a compound selected from the group consisting of Formula IX; Formula XII; 3M-052; CRX-672; CRX-677; and CRX-748:

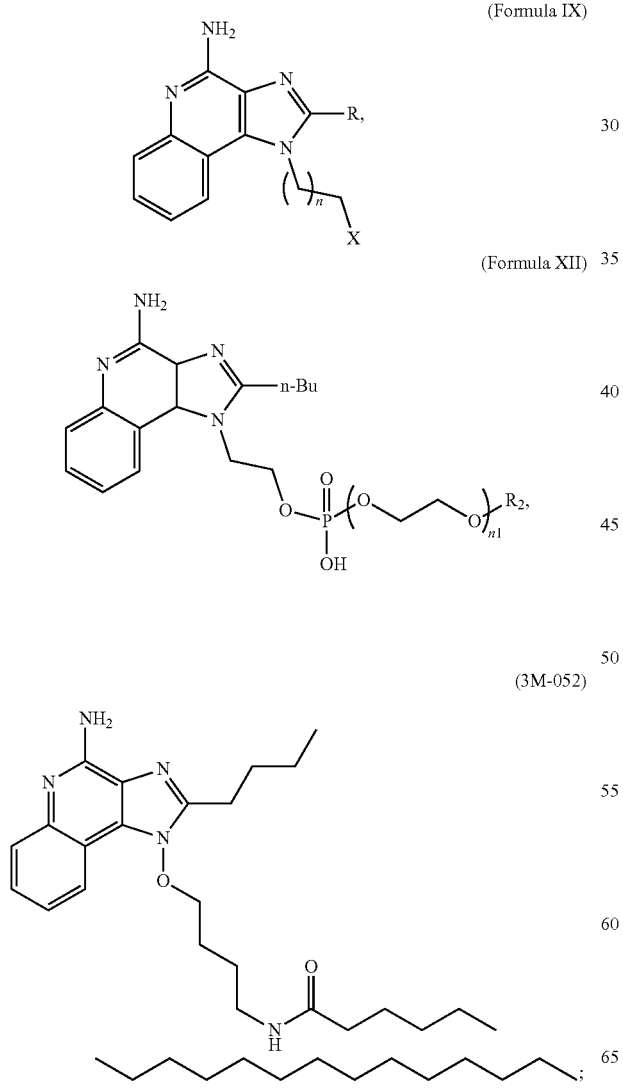

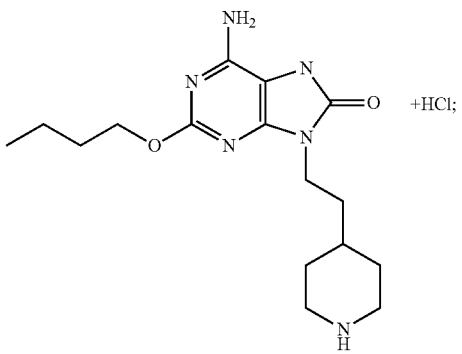

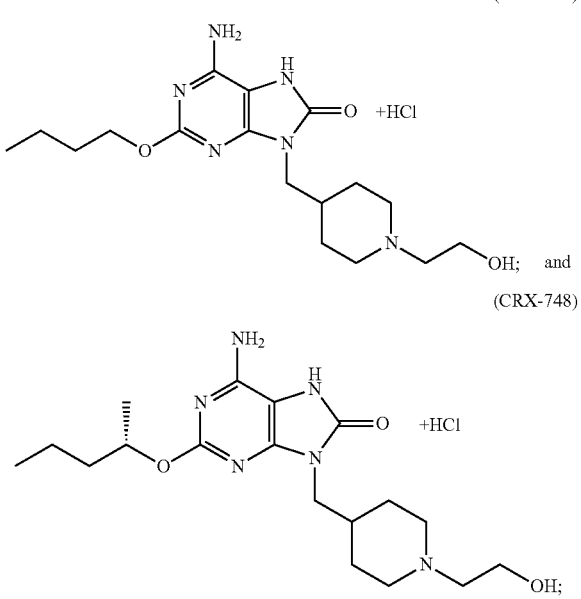

wherein n is a number between 0 and 20,
n1 is between 1 and 15;
R is H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino, or C1-6alkoxyC1-6alkoxy;
wherein each of C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino or C1-6alkoxyC1-6alkoxy is branched or unbranched, and optionally terminally substituted with a hydroxyl, amino, thio, hydrazino, hydrazido, azido, acetylenyl, carboxyl, or maleimido group;
$R_2$ is a lipid group; and
X is —CH$_2$OH; —CH$_2$CH$_2$OH; polyunsaturated fatty acid with two or more carbon-carbon double bonds in its hydrocarbon chain; polyunsaturated fatty alcohol with two or more carbon-carbon double bonds in its hydrocarbon chain; a sterol lipid; or glycerolipid.

2. The method of claim 1, wherein X is —CH$_2$OH.

3. The method of claim 1, wherein the agonist of TLR7 and/or TLR8 comprises a compound having the structure of CRX-649 (Formula X):

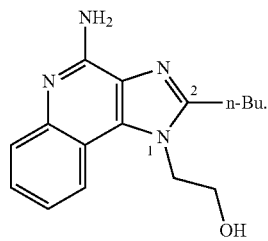

CRX-649

Formula X

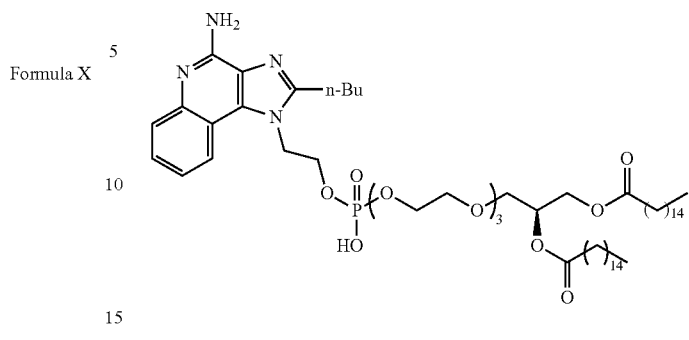

Formula XI

4. The method of claim 1, wherein the agonist of TLR7 and/or TLR8 comprises a compound having the structure of Formula XI:

5. The method of claim 1, wherein the agonist of TLR7 and/or TLR8 comprises a compound selected from the group consisting of:

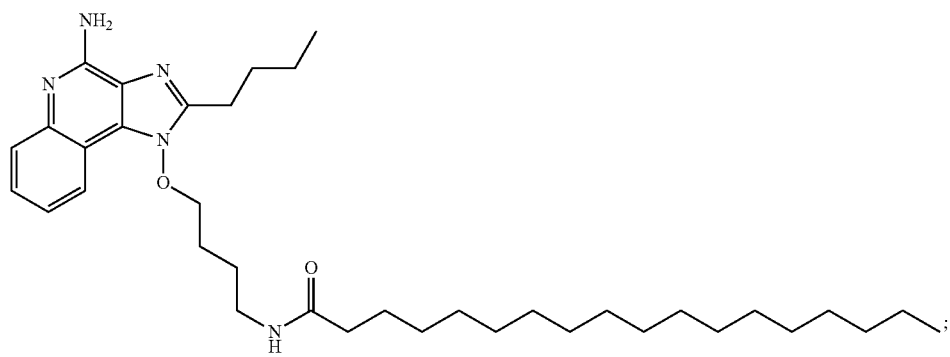

(3M-052)

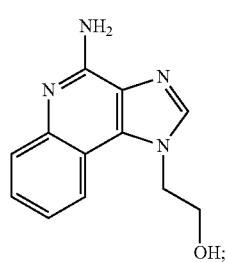

(CRX-648)

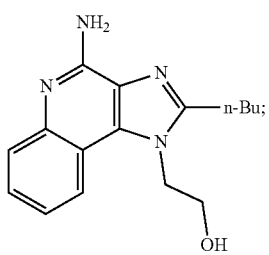

(CRX-649; Formula X)

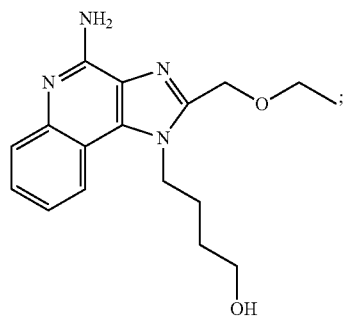

(CRX-664)

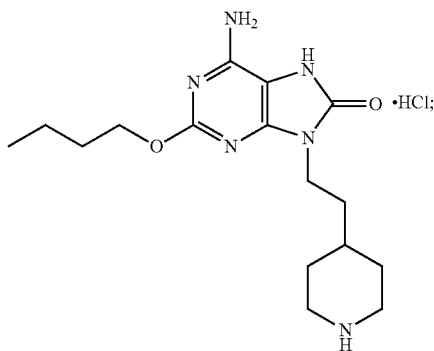

(CRX-672)

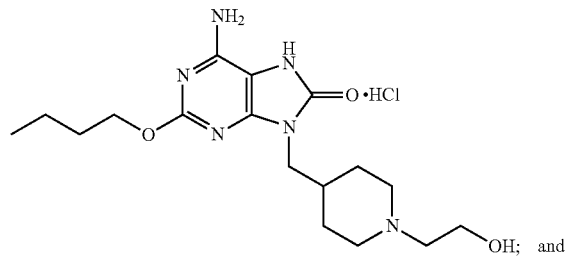 (CRX-677)

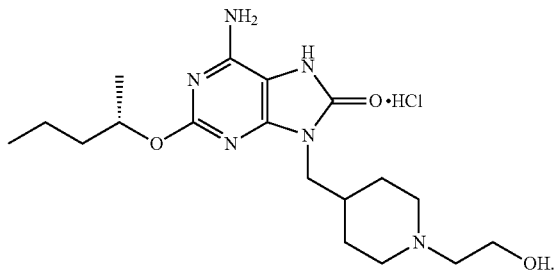 (CRX-748)

6. The method of claim 1, wherein the agonist of TLR7 and/or TLR8 comprises a hydroxyl group, and the agonist of TLR7 and/or TLR8 further comprises a lipid moiety, phosphorylation, or phospholipid moiety conjugated to the hydroxyl group.

7. The method of claim 6, wherein the lipid moiety or phospholipid moiety is conjugated to the hydroxyl group of

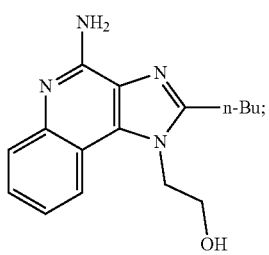 (CRX-649; Formula X)

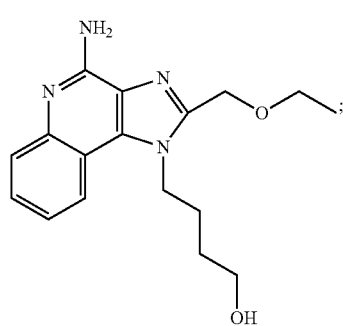 (CRX-664)

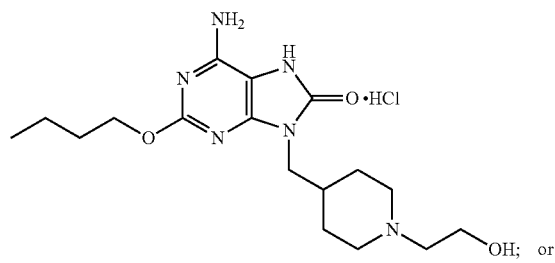 (CRX-677)

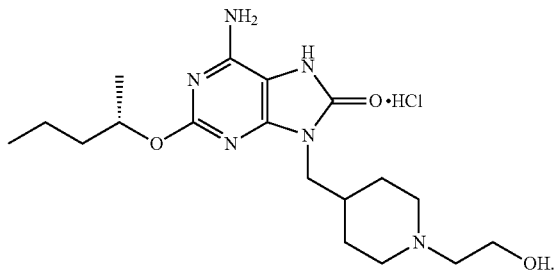 (CRX-748)

8. The method of claim 1, wherein the administration of the adjuvant and antigen provides protection at a lower dose or with fewer doses than the antigen administered without the adjuvant.

9. The method of claim 1, wherein the antigen is comprised by a vaccine selected from the group consisting of:
a pneumococcal vaccine; a hepatitis B (HBV) vaccine; an acellular pertussis (aP) vaccine; a diphtheria tetanus acellular pertussis (DTaP) vaccine; a hepatitis A (HAV) vaccine; and a meningococcal (MV) vaccine.

10. The method of claim 9, wherein the vaccine is pneumococcal conjugate vaccine (PCV)13.

11. The method of claim 1, wherein the subject is a human infant at the time of administration.

12. A method of stimulating an immune response of a subject, the method comprising administering to the human an adjuvant comprising an agonist of TLR7 and/or TLR8; and wherein the adjuvant comprises an agonist of TLR7 and/or TLR8, and the agonist of TLR7 and/or TLR8 comprises a compound selected from the group consisting of Formula IX; Formula XII; 3M-052; CRX-672; CRX-677; and CRX-748:
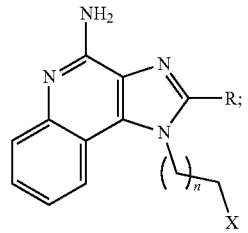
(Formula IX)
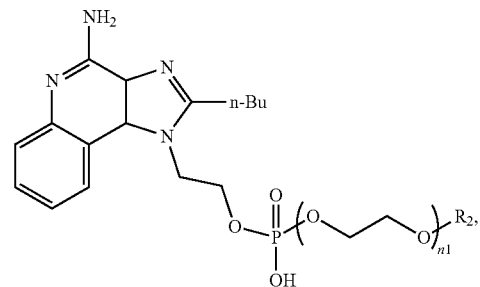
(Formula XII)
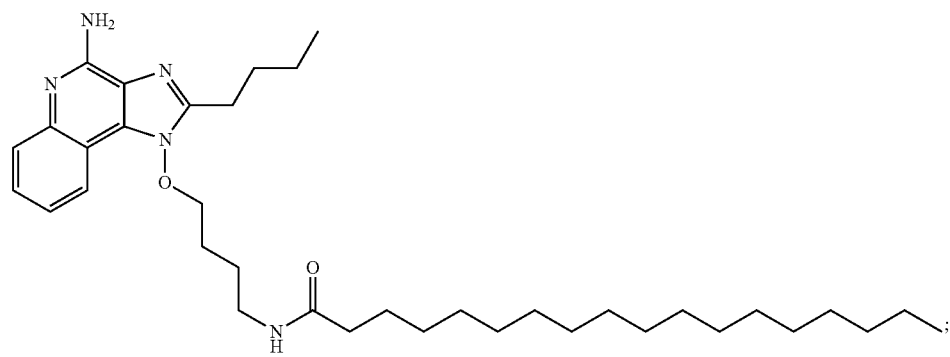
(3M-052)
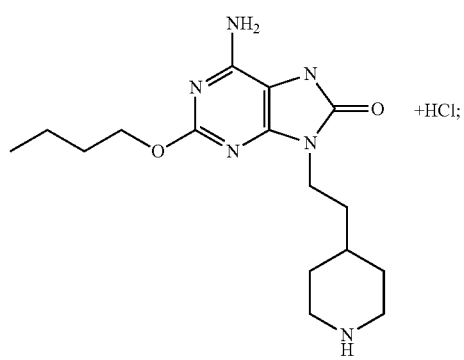
(CRX-672)
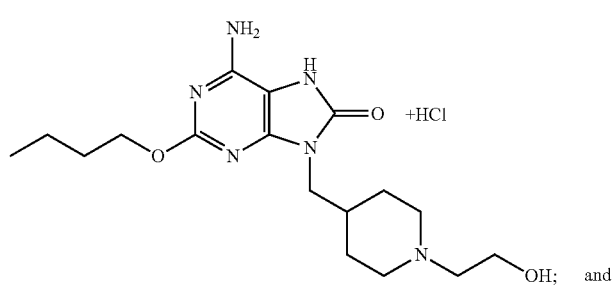
(CRX-677)
and (CRX-748)

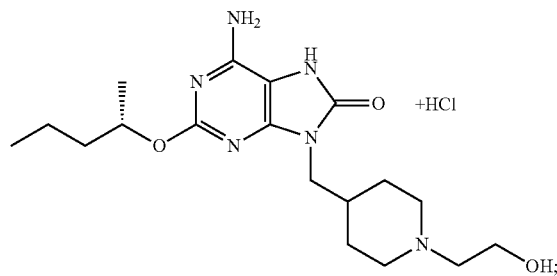

wherein n is a number between 0 and 20, n1 is a number between 1 and 15;

R is H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino, or C1-6alkoxyC1-6alkoxy;

wherein each of the C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino or C1-6alkoxyC1-6alkoxy is branched or unbranched, and optionally terminally substituted with a hydroxyl, amino, thio, hydrazino, hydrazido, azido, acetylenyl, carboxyl, or maleimido group;

R$_2$ is a lipid group; and

X is —CH$_2$OH; —CH$_2$CH$_2$OH; polyunsaturated fatty acid with two or more carbon-carbon double bonds in its hydrocarbon chain; polyunsaturated fatty alcohol with two or more carbon-carbon double bonds in its hydrocarbon chain; a sterol lipid; or glycerolipid.

13. A kit comprising an adjuvant comprising an agonist of TLR7 and/or TLR8; and wherein the adjuvant comprises an agonist of TLR7 and/or TLR8, and the agonist of TLR7 and/or TLR8 comprises a compound selected from the group consisting of Formula IX; Formula XII; 3M-052; CRX-672; CRX-677; and CRX-748:

Formula IX

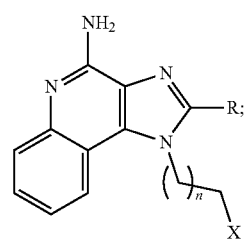

(Formula XII)

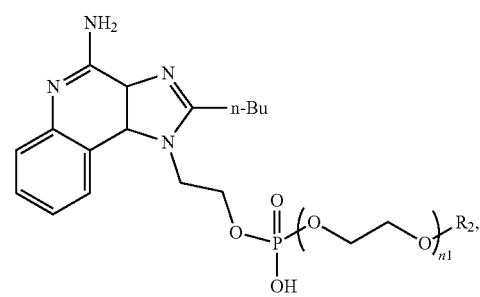

(3M-052)

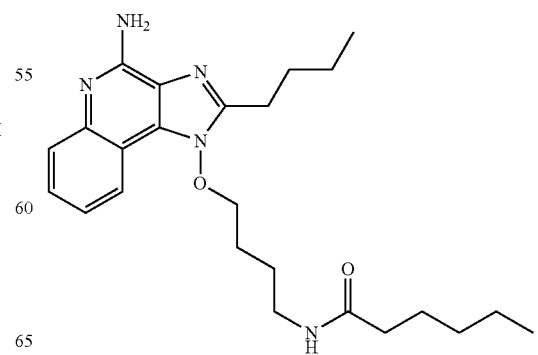

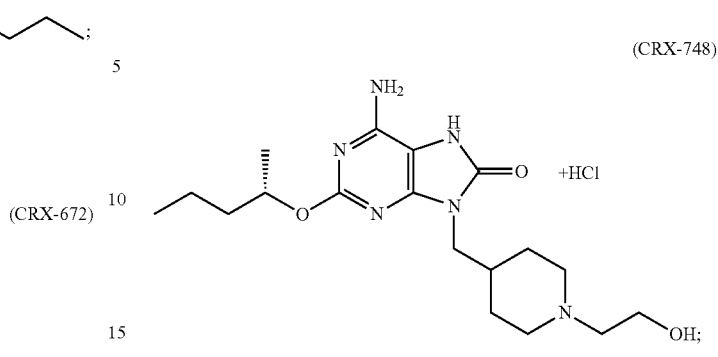
(CRX-748)

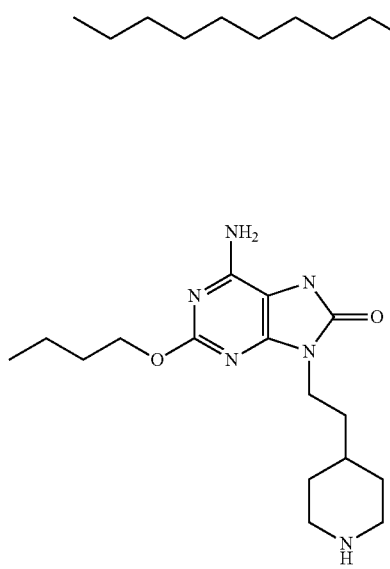
(CRX-672)

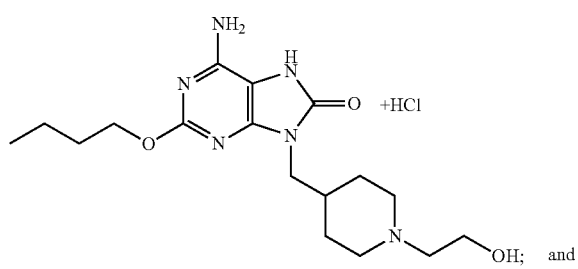
(CRX-677)
and wherein n is a number between 0 and 20,
n1 is a number between 1 and 15;
R is H, C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino, or C1-6alkoxyC1-6alkoxy;
wherein each of the C1-6alkyl, C1-6alkylamino, C1-6alkoxy, C3-6cycloalkylC1-6alkyl, C3-6cycloalkylC1-6alkylamino, C3-6cycloalkylC1-6alkoxy, C1-6alkoxyC1-6alkyl, C1-6alkoxyC1-6alkylamino or C1-6alkoxyC1-6alkoxy is branched or unbranched, and optionally terminally substituted with a hydroxyl, amino, thio, hydrazino, hydrazido, azido, acetylenyl, carboxyl, or maleimido group;
$R_2$ is a lipid group; and
X is —$CH_2OH$; —$CH_2CH_2OH$; polyunsaturated fatty acid with two or more carbon-carbon double bonds in its hydrocarbon chain; polyunsaturated fatty alcohol with two or more carbon-carbon double bonds in its hydrocarbon chain; a sterol lipid; or glycerolipid.

14. The kit of claim 13, further comprising at least one antigen.

15. The method of claim 1, wherein the agonist of TLR7 and/or TLR8 is a compound of formula:

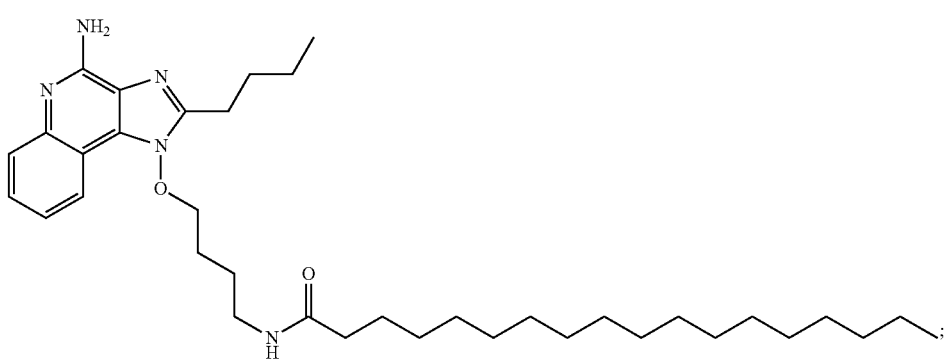
(3M-052)

16. The method of claim 1, wherein R is C1-6alkyl.
17. The method of claim 1, wherein R is C1-6alkoxyC1-6alkyl.
18. The method of claim 1, wherein R₂ is
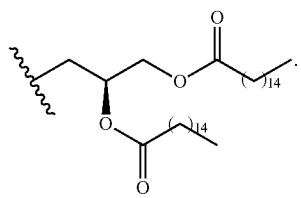
19. The method of claim 1, wherein the agonist of TLR7 and/or TLR8 is a compound of formula:
(Formula XI)
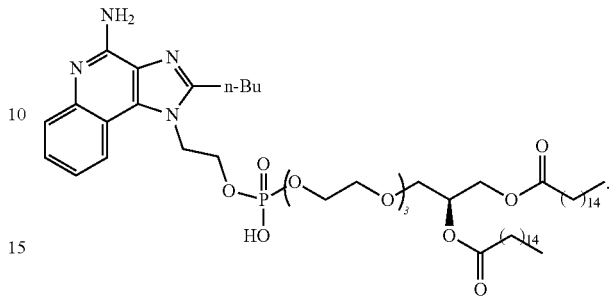
* * * * *

UNITED STATES PATENT AND TRADEMARK OFFICE
CERTIFICATE OF CORRECTION

| | |
|---|---|
| PATENT NO. | : 11,464,854 B2 |
| APPLICATION NO. | : 16/495901 |
| DATED | : October 11, 2022 |
| INVENTOR(S) | : Ofer Levy et al. |

It is certified that error appears in the above-identified patent and that said Letters Patent is hereby corrected as shown below:

In the Specification

At Column 1, Line 13, please replace the paragraph titled "GOVERNMENT SUPPORT" with the following paragraph:
FEDERALLY SPONSORED RESEARCH
This invention was made with government support under Grant Numbers AI067353, AI124284, and AI100135, and contract number HHSN272201400052C, awarded by the National Institutes of Health. The Government has certain rights in the invention.

Signed and Sealed this
Twenty-eighth Day of November, 2023

Katherine Kelly Vidal
*Director of the United States Patent and Trademark Office*